(12) United States Patent
Min et al.

(10) Patent No.: US 11,465,160 B2
(45) Date of Patent: Oct. 11, 2022

(54) BLOOD SEPARATION SYSTEMS AND METHODS EMPLOYING CENTRIFUGAL AND SPINNING MEMBRANE SEPARATION TECHNIQUES

(71) Applicant: Fenwal, Inc., Lake Zurich, IL (US)

(72) Inventors: Kyungyoon Min, Kildeer, IL (US); Benjamin E. Kusters, Pleasant Prairie, WI (US); Richard I. Brown, Northbrook, IL (US); Mark J. Brierton, Cary, IL (US)

(73) Assignee: Fenwal, Inc., Lake Zurich, IL (US)

( * ) Notice: Subject to any disclaimer, the term of this patent is extended or adjusted under 35 U.S.C. 154(b) by 831 days.

(21) Appl. No.: 16/327,358

(22) PCT Filed: Sep. 15, 2017

(86) PCT No.: PCT/US2017/051695
§ 371 (c)(1),
(2) Date: Feb. 22, 2019

(87) PCT Pub. No.: WO2018/053217
PCT Pub. Date: Mar. 22, 2018

(65) Prior Publication Data
US 2019/0201916 A1  Jul. 4, 2019

Related U.S. Application Data

(60) Provisional application No. 62/395,536, filed on Sep. 16, 2016, provisional application No. 62/447,478, filed on Jan. 18, 2017.

(51) Int. Cl.
*B04B 5/04* (2006.01)
*A61M 1/36* (2006.01)
(Continued)

(52) U.S. Cl.
CPC ............ *B04B 5/0442* (2013.01); *A61M 1/02* (2013.01); *A61M 1/029* (2013.01); *A61M 1/265* (2014.02);
(Continued)

(58) Field of Classification Search
CPC . B04B 5/0442; B04B 11/02; B04B 2013/006; A61M 1/02; A61M 1/029;
(Continued)

(56) References Cited

U.S. PATENT DOCUMENTS

| 4,776,964 A | 10/1988 | Schoendorfer et al. |
| 5,194,145 A | 3/1993 | Schoendorfer |

(Continued)

FOREIGN PATENT DOCUMENTS

| EP | 1946784 B1 | 10/2012 |
| WO | WO2012/091720 A1 | 7/2012 |

(Continued)

OTHER PUBLICATIONS

International Search Report for counterpart PCT Application No. PCT/US2017/051695 (dated Nov. 16, 2017) (12 pages).

*Primary Examiner* — Walter D. Griffin
*Assistant Examiner* — Shuyi S. Liu
(74) *Attorney, Agent, or Firm* — Cook Alex Ltd.

(57) ABSTRACT

Systems and methods are provided for separating blood into two or more components. A blood separation system includes a blood separation device and a fluid flow circuit configured to be mounted to the blood separation device. The blood separation device includes a centrifugal separator and a spinning membrane separator drive unit incorporated into a common case, which allows for fluid separation by two different methods. Depending on the separation procedure to be carried out, the fluid flow circuit paired with the blood separation device may include only one separation (Continued)

chamber configured to be mounted to the centrifugal separator or spinning membrane separator drive unit or two separation chambers, with one being mounted to the centrifugal separator and the other to the spinning membrane separator drive unit. The system may be used to separate and collect any combination of red blood cells, plasma, and platelets.

20 Claims, 35 Drawing Sheets

(51) Int. Cl.
  *A61M 1/02* (2006.01)
  *A61M 1/26* (2006.01)
  *B01D 36/04* (2006.01)
  *B01D 63/16* (2006.01)
  *B04B 11/02* (2006.01)
  *B04B 13/00* (2006.01)

(52) U.S. Cl.
  CPC ......... *A61M 1/3693* (2013.01); *B01D 36/045* (2013.01); *B01D 63/16* (2013.01); *B04B 11/02* (2013.01); *A61M 2205/3306* (2013.01); *B04B 2013/006* (2013.01)

(58) Field of Classification Search
  CPC ............. A61M 1/265; A61M 1/3693; A61M 2205/3306; A61M 1/3603; B01D 36/045; B01D 63/16
  USPC ........... 435/2; 210/96.1, 142, 749, 767, 805, 210/806; 494/4
  See application file for complete search history.

(56) References Cited

U.S. PATENT DOCUMENTS

| | | | |
|---|---|---|---|
| 5,632,893 A | 5/1997 | Brown et al. |
| 5,868,696 A | 2/1999 | Giesier et al. |
| 6,419,822 B2 | 7/2002 | Muller et al. |
| 6,471,855 B1 | 10/2002 | Odak et al. |
| 6,579,219 B2 | 6/2003 | Dolecek et al. |
| 6,582,386 B2 | 6/2003 | Min et al. |
| 6,629,919 B2 | 10/2003 | Egozy et al. |
| 6,706,008 B2 | 3/2004 | Vishnoi et al. |
| 6,770,883 B2 | 8/2004 | McNeal et al. |
| 6,808,503 B2 | 10/2004 | Farrell et al. |
| 6,866,826 B2 | 3/2005 | Moore et al. |
| 6,884,228 B2 | 4/2005 | Brown et al. |
| 7,049,622 B1 | 5/2006 | Weiss |
| 7,081,082 B2 | 7/2006 | Scholz et al. |
| 7,150,834 B2 | 12/2006 | Mueth et al. |
| 7,186,230 B2 | 3/2007 | Briggs et al. |
| 7,186,231 B2 | 3/2007 | Takagi et al. |
| 7,211,037 B2 | 5/2007 | Briggs et al. |
| 7,294,513 B2 | 11/2007 | Wyatt |
| 7,347,948 B2 | 3/2008 | Dolecek et al. |
| 7,354,515 B2 | 4/2008 | Coull et al. |
| 7,381,291 B2 | 6/2008 | Tobe et al. |
| 7,422,693 B2 | 9/2008 | Carter et al. |
| 7,485,084 B2 | 2/2009 | Borgstrom et al. |
| 7,563,376 B2 | 7/2009 | Oishi |
| 7,648,639 B2 | 1/2010 | Holmes et al. |
| 7,806,845 B2 | 10/2010 | Arm et al. |
| 7,906,771 B2 | 3/2011 | Carter et al. |
| 7,951,059 B2 | 5/2011 | Sweat |
| 8,057,377 B2 | 11/2011 | Holmes et al. |
| 8,075,468 B2 | 12/2011 | Min et al. |
| 8,163,276 B2 | 4/2012 | Hedrick et al. |
| 8,287,742 B2 | 10/2012 | Holmes |
| 8,317,672 B2 | 11/2012 | Nash et al. |
| 8,337,379 B2 | 12/2012 | Fletcher et al. |
| 8,535,210 B2 | 9/2013 | Kolenbrander et al. |
| 8,556,793 B2 | 10/2013 | Foley et al. |
| 8,758,211 B2 | 6/2014 | Nash et al. |
| 8,974,362 B2 | 3/2015 | Nash et al. |
| 9,011,687 B2 | 4/2015 | Swift et al. |
| 9,156,039 B2 | 10/2015 | Holmes et al. |
| 9,302,042 B2 | 4/2016 | Pages |
| 9,302,276 B2 | 4/2016 | Pesetsky et al. |
| 9,370,615 B2 | 6/2016 | Ragusa et al. |
| 9,399,182 B2 | 7/2016 | Pesetsky et al. |
| 9,550,016 B2 | 1/2017 | Gifford |
| 9,610,590 B2 | 4/2017 | Hamandi |
| 9,789,235 B2 | 10/2017 | Gifford et al. |
| 10,086,128 B2 | 10/2018 | Kyle et al. |
| 10,166,322 B2 | 1/2019 | Sweat et al. |
| 10,238,787 B2 | 3/2019 | Takuwa |
| 10,293,097 B2 | 5/2019 | Murphy et al. |
| 10,399,881 B2 | 9/2019 | Donais et al. |
| 10,493,467 B2 | 12/2019 | Lundquist et al. |
| 10,518,007 B2 | 12/2019 | Kimura |
| 10,561,783 B2 | 2/2020 | Hamandi et al. |
| 2002/0128583 A1* | 9/2002 | Min ............... A61M 1/3687 604/6.01 |
| 2004/0195190 A1 | 10/2004 | Min et al. |
| 2009/0215602 A1* | 8/2009 | Min ............... B01D 21/302 494/4 |
| 2011/0003675 A1 | 1/2011 | Dolecek |
| 2011/0294641 A1 | 12/2011 | Dolecek et al. |
| 2014/0199680 A1* | 7/2014 | Min ............... A61M 1/0236 435/2 |
| 2014/0378292 A1 | 12/2014 | Igarashi |
| 2015/0068959 A1 | 3/2015 | Zheng |
| 2015/0104824 A1 | 4/2015 | Walker |
| 2015/0174313 A1* | 6/2015 | Kimura ........... A61M 1/3696 494/37 |
| 2015/0218517 A1 | 8/2015 | Kusters et al. |
| 2015/0219558 A1* | 8/2015 | Koudelka ......... G01N 21/59 356/39 |
| 2015/0367063 A1 | 12/2015 | Kimura |
| 2017/0153431 A1 | 6/2017 | Nguyen et al. |
| 2018/0043374 A1 | 2/2018 | Meinig et al. |
| 2018/0164141 A1 | 6/2018 | Bordignon et al. |
| 2018/0185772 A1 | 7/2018 | Karhiniemi et al. |
| 2019/0003873 A1 | 1/2019 | Araujo et al. |
| 2019/0030545 A1 | 1/2019 | Hamada et al. |
| 2019/0083696 A1 | 3/2019 | Igarashi |

FOREIGN PATENT DOCUMENTS

| | | |
|---|---|---|
| WO | 2013043433 A2 | 3/2013 |
| WO | 2014039091 A1 | 3/2014 |
| WO | WO2018/154115 A2 | 8/2018 |
| WO | WO2019/047498 A1 | 3/2019 |
| WO | WO2019/165478 A1 | 8/2019 |
| WO | WO2020/002059 A1 | 1/2020 |
| WO | WO2020/055958 A1 | 3/2020 |

* cited by examiner

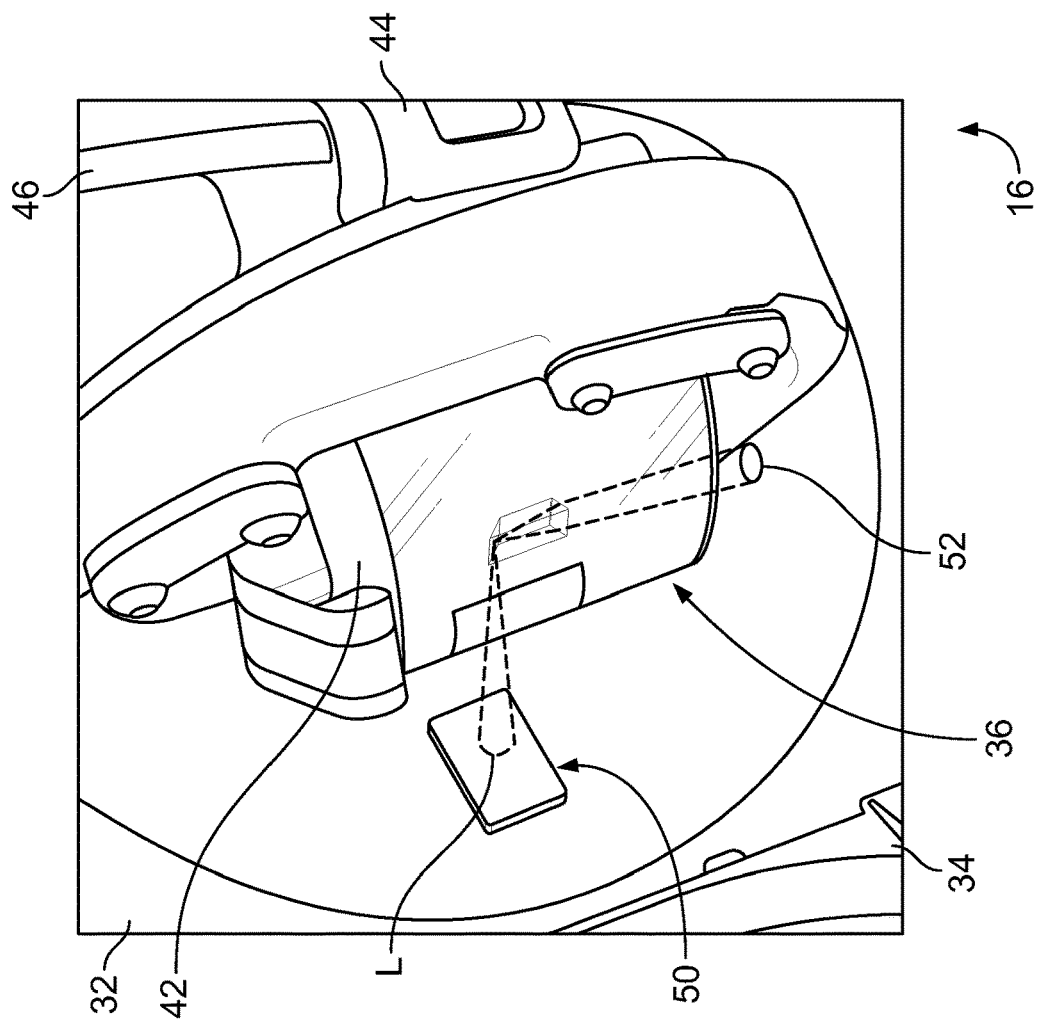
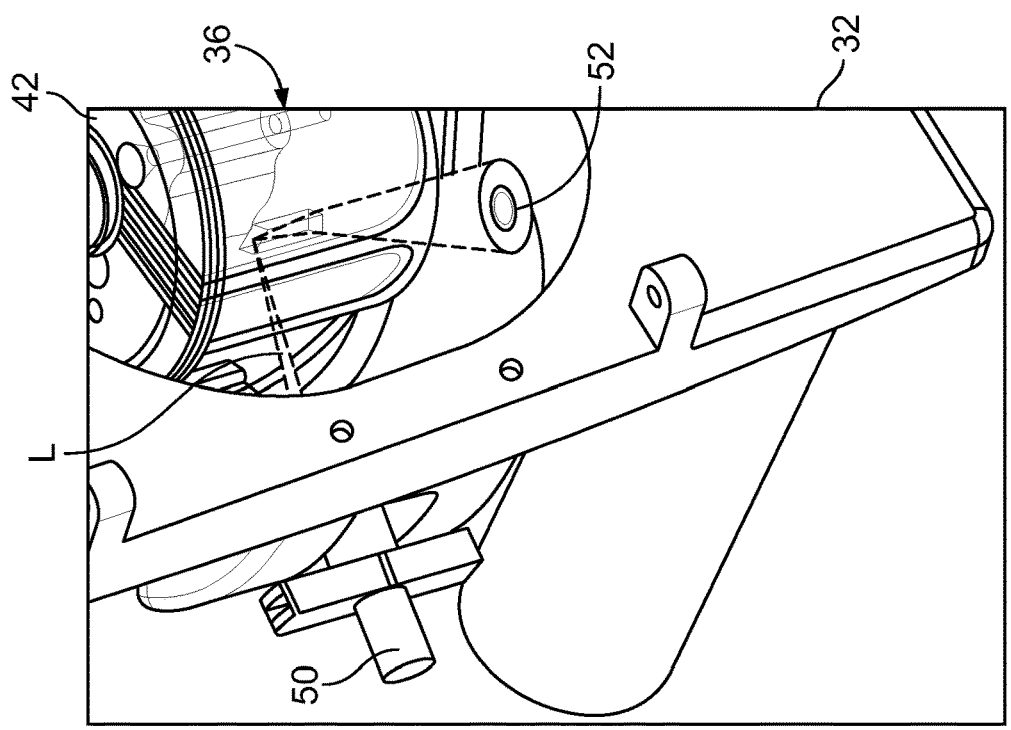
FIG. 12B
FIG. 12A

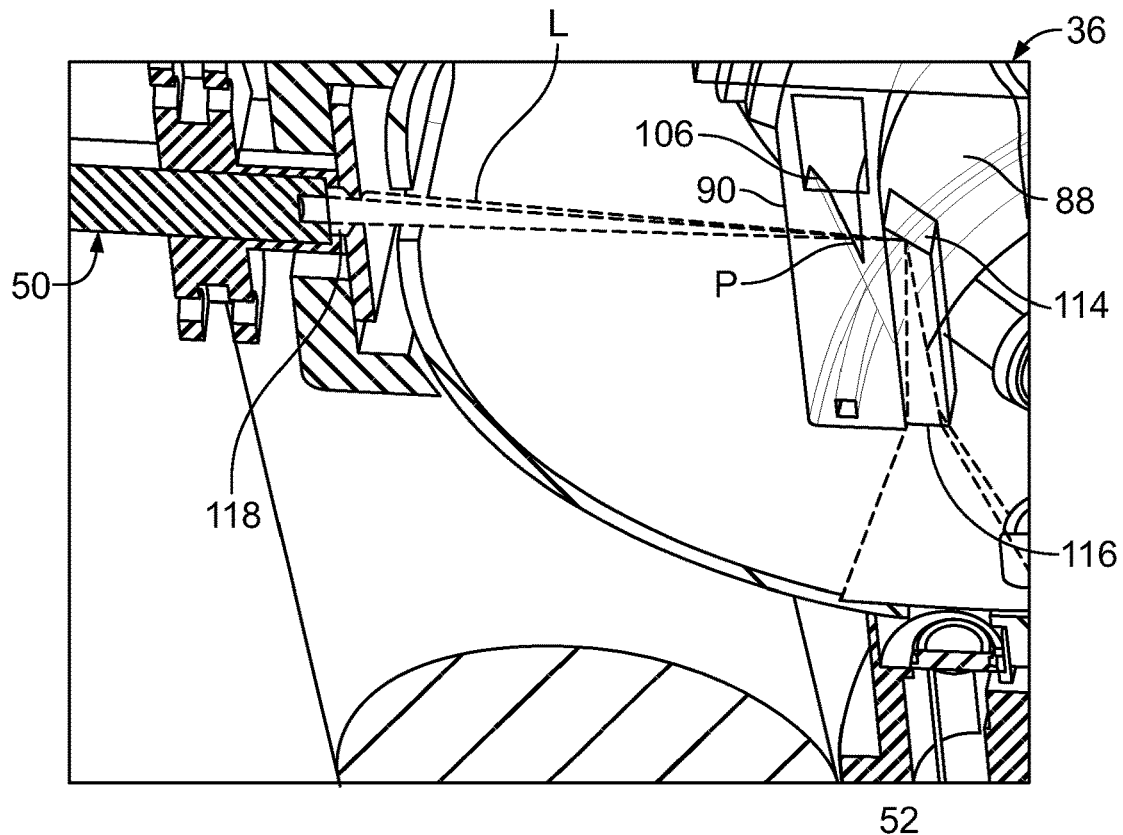
FIG. 12C
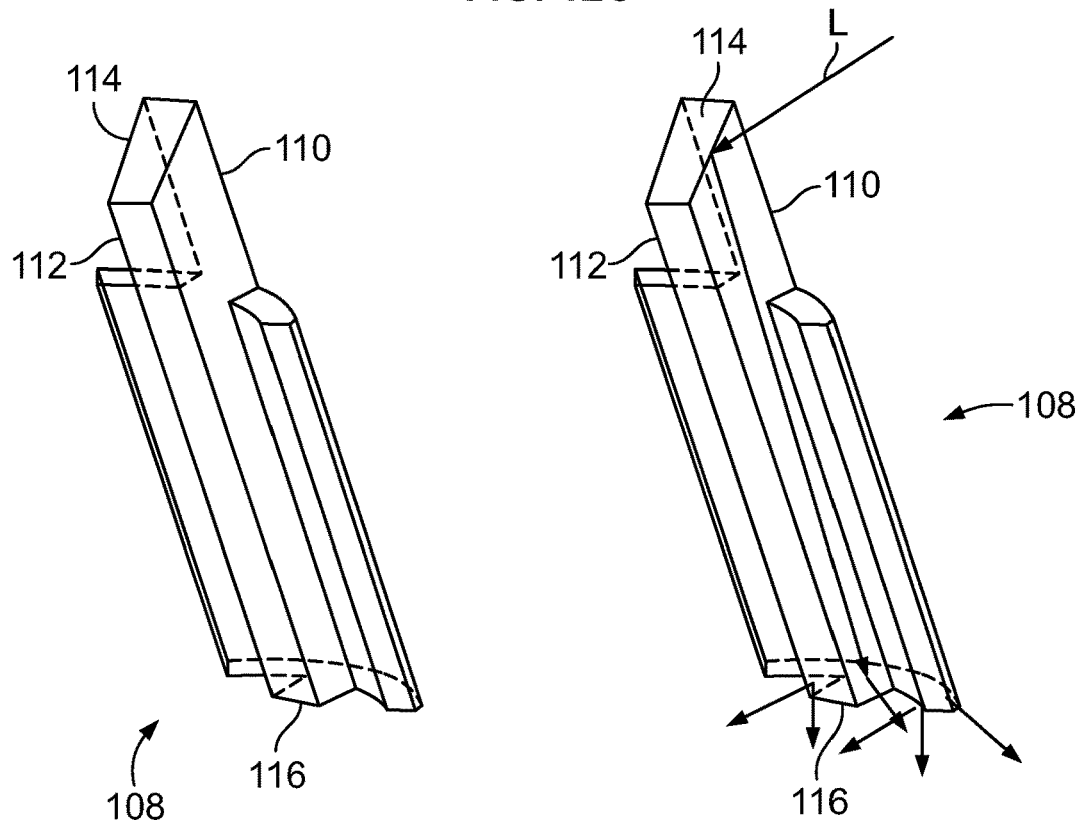
FIG. 22
FIG. 22A

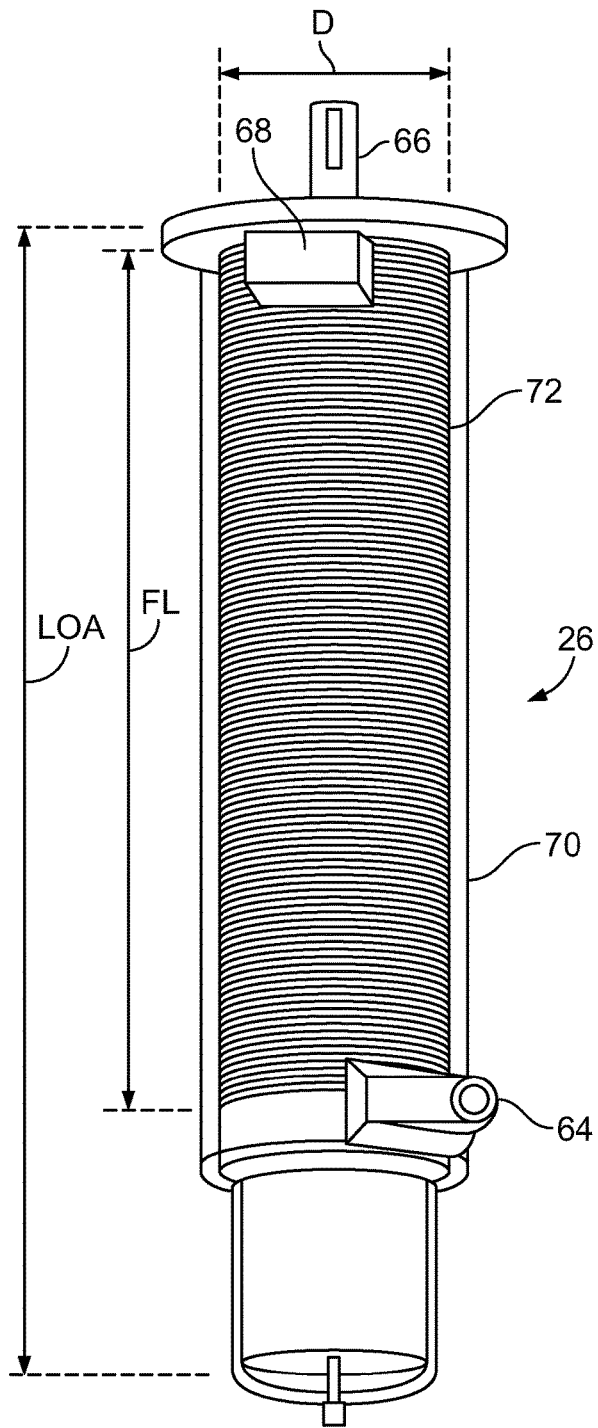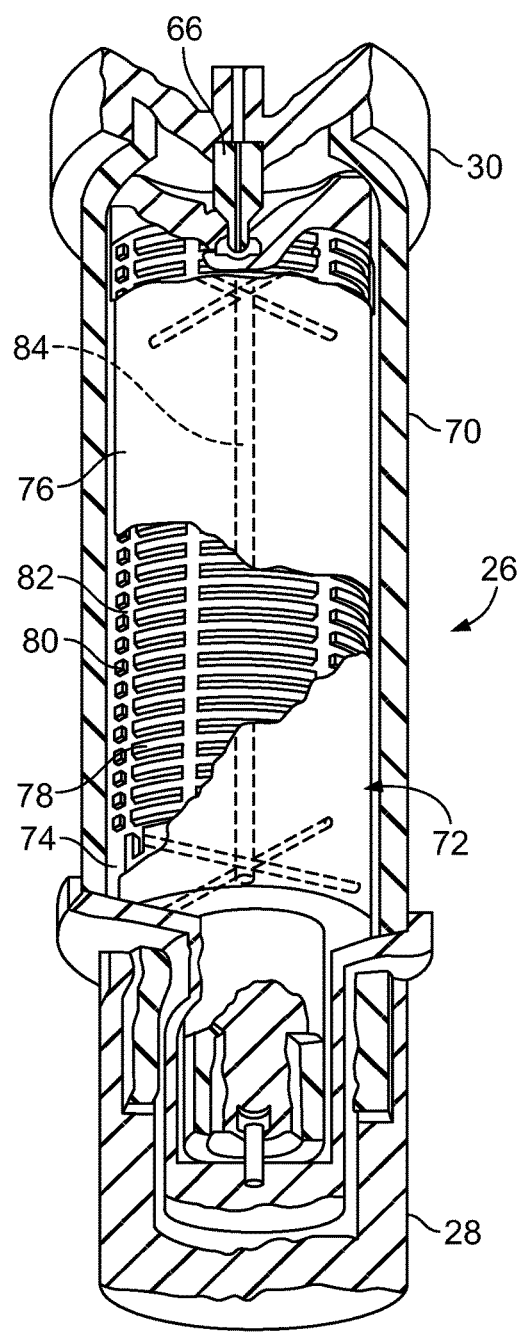
FIG. 14  FIG. 15

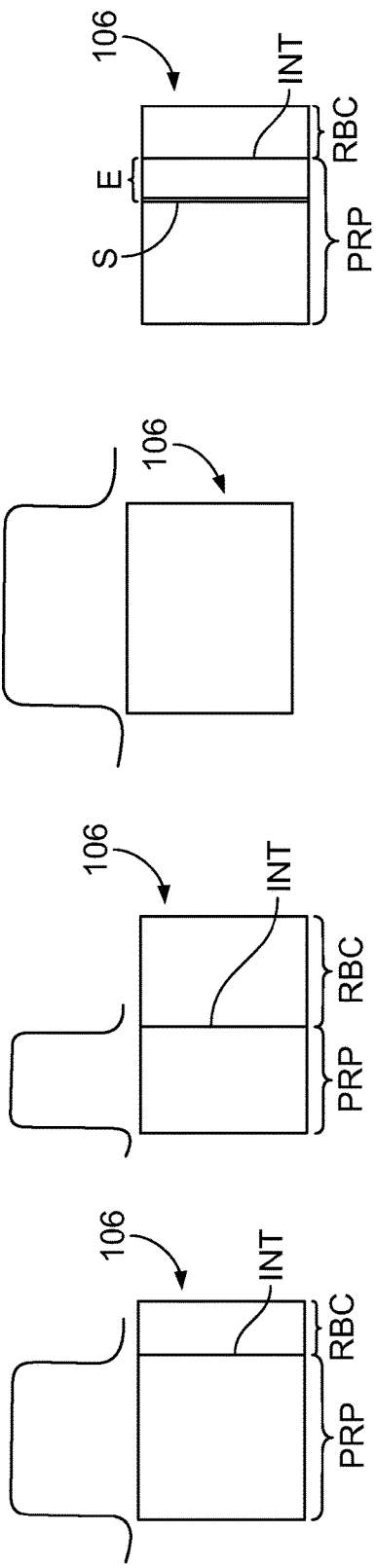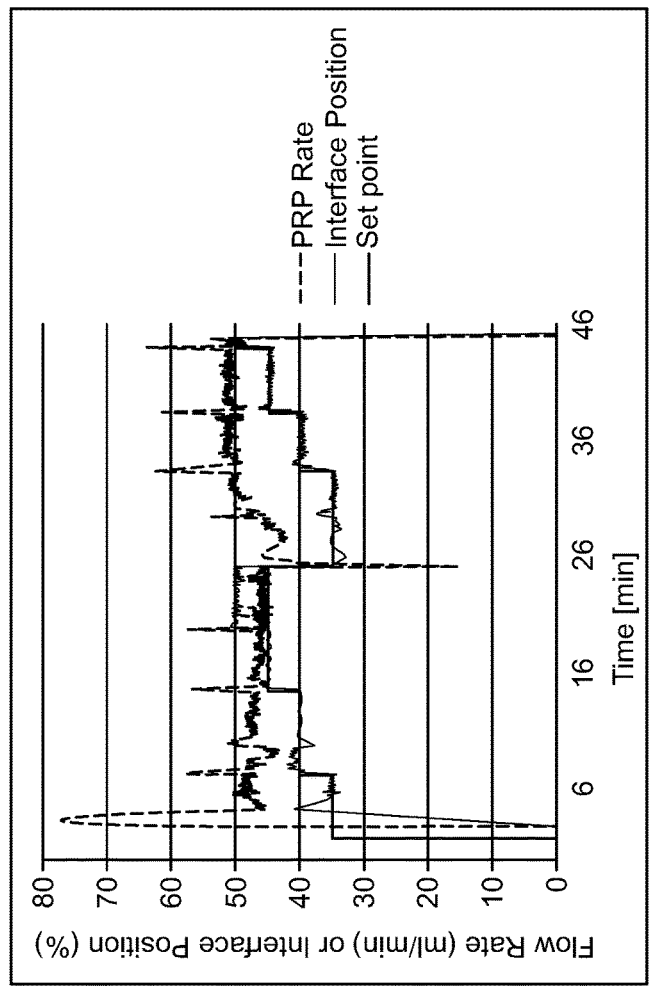
FIG. 29
FIG. 29A
FIG. 29C
FIG. 30
FIG. 31

BLOOD SEPARATION SYSTEMS AND METHODS EMPLOYING CENTRIFUGAL AND SPINNING MEMBRANE SEPARATION TECHNIQUES

RELATED APPLICATIONS

This application is a U.S. national stage application of PCT Patent Application Serial No. PCT/US2017/051695, which claims the benefit of and priority of U.S. Provisional Patent Application Ser. No. 62/395,536, filed Sep. 16, 2016, and U.S. Provisional Patent Application Ser. No. 62/447,478, filed Jan. 18, 2017, the contents of which are incorporated by reference herein.

DESCRIPTION

Technical Field

The present subject matter relates to systems and methods for processing and collecting blood, blood constituents, or other suspensions of cellular material. More particularly, the present subject matter relates to blood separation systems and methods employing both centrifugal and spinning membrane separation techniques.

BACKGROUND

Various blood processing systems now make it possible to collect particular blood constituents, instead of whole blood, from a blood source. Typically, in such systems, whole blood is drawn from a blood source, the particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

According to one approach, whole blood may be separated into its constituents through centrifugation. This requires that the whole blood be passed through a centrifuge after it is withdrawn from, and before it is returned to, the blood source. To reduce contamination and possible infection (if the blood source is a human donor or patient), the blood is preferably processed within a sealed, sterile fluid flow circuit during the centrifugation process. The operator installs a fresh, sterile disposable flow circuit in the centrifuge before processing and removes and discards it afterwards. Typical disposable flow circuits are sealed and sterile, and include a separation chamber portion, which is mounted in cooperation on a durable, reusable assembly containing the hardware (centrifuge, drive system, pumps, valve actuators, programmable controller, and the like) that rotates the separation chamber and controls the flow through the fluid circuit. The separation chamber may be formed of a generally rigid material (e.g., molded plastic), in which case the chamber itself defines a flow path or channel in which blood is separated into two or more components, or a more flexible material (e.g., in the form of a belt or annulus), which relies upon the system hardware to support the chamber and define the shape of the chamber as blood flows through it.

With a disposable circuit loaded onto the centrifuge (or just prior to or during loading) the operator typically enters, for example, by means of a touch screen or other user interface system, a particular processing protocol to be executed by the system (e.g., a procedure wherein platelets are separated from whole blood and collected) and other parameters (e.g., the weight of the donor, the desired volume of separated blood component to be collected, etc.). When the system has been programmed, the operator phlebotomizes a donor and the system carries out the procedure, under the supervision of the operator.

The centrifuge rotates the separation chamber of the disposable flow circuit during processing, causing the heavier (greater specific gravity) components of the whole blood in the separation chamber, such as red blood cells, to move radially outwardly away from the center of rotation toward the outer or "high-G" wall of the separation chamber. The lighter (lower specific gravity) components, such as plasma, migrate toward the inner or "low-G" wall of the separation chamber. The boundary that forms between the heavier and lighter components in the separation chamber is commonly referred to as the interface. Various ones of these components can be selectively removed from the whole blood by providing appropriately located channeling structures and outlet ports in the flow circuit. For example, in one blood separation procedure, plasma is separated from cellular blood components and collected, with the cellular blood components and a replacement fluid being returned to the blood source. Alternatively, red blood cells may be harvested from the separation chamber and the rest of the blood constituents returned to the donor. Other processes are also possible including, without limitation, platelet collection, red blood cell exchanges, plasma exchanges, etc.

While many blood separation systems and procedures have employed centrifugal separation principles, there is another class of devices, based on the use of a membrane, that has been used for plasmapheresis (i.e., separating plasma from whole blood). More specifically, this type of device employs relatively rotating surfaces, at least one or which carries a porous membrane. Typically, the device employs an outer stationary housing and an internal spinning rotor covered by a porous membrane.

Well-known plasmapheresis devices include the Autopheresis-C® and Aurora separators sold by Fenwal, Inc. of Lake Zurich, Ill., which is an affiliate of Fresenius Kabi AG of Bad Homburg, Germany. A detailed description of an exemplary spinning membrane separator may be found in U.S. Pat. No. 5,194,145, which is incorporated by reference herein. This patent describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection bag. The remaining blood components, primarily red blood cells, platelets, and white blood cells, move to the exit region between the spinner and the shell and then are typically returned to the donor.

Spinning membrane separators have been found to provide excellent plasma filtration rates, due primarily to the unique flow patterns ("Taylor vortices") induced in the gap between the spinning membrane and the shell. The Taylor vortices help to keep the blood cells from depositing on and fouling or clogging the membrane.

Both types of separators have their advantages, so it would be advantageous to provide an integrated system capable of harnessing the benefits of both centrifugal separation and spinning membrane separation.

SUMMARY

There are several aspects of the present subject matter which may be embodied separately or together in the devices, systems, and methods described and/or claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto or later amended.

In one aspect, a blood separation device comprises a centrifugal separator and a spinning membrane drive unit. A controller is configured and/or programmed to control the operation of the centrifugal separator and the spinning membrane separator drive unit. The blood separation device further includes a case, with the centrifugal separator and spinning membrane separator drive unit being incorporated into the case.

In another aspect, a fluid flow circuit for use in combination with a blood separation device comprises a centrifugal separation system and a spinning membrane separator in fluid communication with the centrifugal separation chamber.

In yet another aspect, a blood separation system comprises a blood separation device including a centrifugal separator and a spinning membrane separator drive unit incorporated into a case. The system also includes a fluid flow circuit with a centrifugal separation chamber configured to be mounted to the centrifugal separator and/or a spinning membrane separator configured to be mounted to the spinning membrane separator drive unit.

In another aspect, a blood separation method comprises providing a blood separation device including a centrifugal separator and a spinning membrane separator drive unit. A fluid flow circuit is mounted to the blood separation device and blood is conveyed through the fluid flow circuit. At least a portion of the blood in the fluid flow circuit is separated into two or more blood components using the centrifugal separator and/or the spinning membrane separator drive unit.

In yet another aspect, a method of controlling a blood separation procedure comprises providing a blood separation device including a pump, a centrifugal separator, and a spinning membrane separator drive unit. A fluid flow circuit is mounted to the blood separation device and the pump is controlled to convey blood through the fluid flow circuit. The centrifugal separator and/or the spinning membrane separator drive unit is controlled to separate at least a portion of the blood in the fluid flow circuit into two or more blood components.

In another aspect, a blood separation method comprises conveying blood through a fluid flow circuit and separating at least a portion of the blood into two or more blood components using a centrifugal separator. At least a portion of one of the separated blood components is further separated into two or more sub-components using a spinning membrane separator drive unit.

In yet another aspect, a method of controlling a blood separation procedure comprises controlling a pump to convey blood through a fluid flow circuit. A centrifugal separator is controlled to separate at least a portion of the blood in the fluid flow circuit into two or more blood components and a spinning membrane separator drive unit is controlled to further separate at least a portion of one of the separated blood components into two or more sub-components.

In another aspect, a blood separation method comprises mounting a fluid flow circuit to a blood separation device including a centrifugal separator and a spinning membrane separator drive unit and conveying blood through the fluid flow circuit. Red blood cells are separated from at least a portion of the blood in the fluid flow circuit using the spinning membrane separator drive unit, with at least a portion of the separated red blood cells being collected.

In yet another aspect, a method of controlling a blood separation procedure comprises mounting a fluid flow circuit including a fluid container to a blood separation device including a plurality of pumps, a centrifugal separator, and a spinning membrane separator drive unit. At least one of the pumps is controlled to convey blood through the fluid flow circuit and the spinning membrane separator drive unit is controlled to separate red blood cells from at least a portion of the blood in the fluid flow circuit, with at least one of the pumps being controlled to convey at least a portion of the separated red blood cells to the fluid container.

In another aspect, a blood separation method comprises mounting a fluid flow circuit to a blood separation device including a centrifugal separator and a spinning membrane separator drive unit and conveying blood through the fluid flow circuit. Red blood cells and plasma are separated from at least a portion of the blood in the fluid flow circuit using the spinning membrane separator drive unit, with at least a portion of the separated red blood cells and separated plasma being collected.

In yet another aspect, a method of controlling a blood separation procedure comprises mounting a fluid flow circuit including a plurality of fluid containers to a blood separation device including a plurality of pumps, a centrifugal separator, and a spinning membrane separator drive unit. At least one of the pumps is controlled to convey blood through the fluid flow circuit and the spinning membrane separator drive unit is controlled to separate red blood cells and plasma from at least a portion of the blood in the fluid flow circuit, with at least a portion of the separated red blood cells and separated plasma being conveyed to the fluid containers.

In another aspect, a blood separation method comprises mounting a fluid flow circuit to a blood separation device including a centrifugal separator and a spinning membrane separator drive unit and conveying blood through the fluid flow circuit. Plasma is separated from at least a portion of the blood in the fluid flow circuit using the spinning membrane separator drive unit, with at least a portion of the separated plasma being collected.

In yet another aspect, a method of controlling a blood separation procedure comprises mounting a fluid flow circuit including a fluid container to a blood separation device including a plurality of pumps, a centrifugal separator, and a spinning membrane separator drive unit. At least one of the pumps is controlled to convey blood through the fluid flow circuit and the spinning membrane separator drive unit is controlled to separate plasma from at least a portion of the blood in the fluid flow circuit, with at least one of the pumps being controlled to convey at least a portion of the separated plasma to the fluid container.

In another aspect, a blood separation method comprises conveying blood through a fluid flow circuit and separating at least a portion of the blood in the fluid flow circuit into first and second blood components, with at least a portion of the first blood component being conveyed into a container. At least a portion of the second blood component is further separated into first and second sub-components, with at least a portion of the first sub-component being conveyed into the container to form a mixture with the first blood component in the container. At least a portion of the second sub-component is collected. At least a portion of the mixture is separated into the first and second blood components, with at least a portion of the second blood component separated from the mixture being further separated into the first and second sub-components. At least a portion of the second sub-component separated from said at least a portion of the second blood component separated from the mixture is collected.

In yet another aspect, a method of controlling a blood separation procedure comprises controlling a pump to convey blood through a fluid flow circuit, controlling a first separator to separate at least a portion of the blood in the fluid flow circuit into first and second blood components, and conveying at least a portion of the first blood component into a container. A second separator is controlled to further separate at least a portion of the second blood component into first and second sub-components, with a second pump being controlled to convey at least a portion of the first sub-component into the container to form a mixture with the first blood component in the container. At least a portion of the second sub-component is collected. The first separator is controlled to separate at least a portion of the mixture into the first and second blood components and the second separator is controlled to separate at least a portion of the second blood component separated from the mixture into the first and second sub-components. At least a portion of the second sub-component separated from the second blood component separated from the mixture is collected.

In another aspect, a centrifugal separation chamber comprises a body including a low-g side wall portion and a high-g side wall portion extending circumferentially about a rotational axis in a spaced apart relationship to define therebetween a generally annular channel. A plurality of interior radial walls define an inlet and at least one outlet associated with the channel, while a ramp is defined by one of the side wall portions and extends across at least a portion of the channel to display an interface between separated fluid components within the channel. At least a portion of the ramp and at least a portion of the other side wall portion angularly aligned with the ramp are formed of a light-transmissive material.

In yet another aspect, a prismatic reflector for incorporation into a centrifugal separation chamber comprises inner and outer walls and first and second end walls. The prismatic reflector is formed of a light-transmissive material. The inner wall is configured to receive light traveling along an initial path and transmit the light to the first end wall, which is configured to receive the light and direct it toward the second end wall in a direction that is angled with respect to the initial path. The second end wall is configured to receive the light from the first end wall and transmit it out of the prismatic reflector.

In another aspect, an interface monitoring system for detecting the location of an interface between separated fluid components within a channel of a centrifugal separation chamber having a rotational axis comprises a light source and a light detector. The light source is configured to transmit a light along an initial path toward the rotational axis, into the centrifugal separation chamber, and through the channel of the centrifugal separation chamber. The light detector is configured to receive at least a portion of the light as it exits the centrifugal separation chamber and generate a signal indicative of the location of the interface between separated fluid components within the channel of the centrifugal separation chamber, with the light detector being oriented to receive light traveling in a direction generally perpendicular to the initial path of the light.

In yet another aspect, a blood separation system comprises a blood separation device and a fluid flow circuit. The blood separation device includes a centrifugal separator and an interface monitoring system. The fluid flow circuit includes a centrifugal separation chamber comprising a channel defined between a low-g side wall portion and a high-g side wall portion, with the chamber being configured to be mounted to the centrifugal separator. The interface monitoring system includes a light source and a light detector. The light source is configured to transmit a light along an initial path toward the rotational axis, into the centrifugal separation chamber, and through the channel of the centrifugal separation chamber. The light detector is configured to receive at least a portion of the light as it exits the centrifugal separation chamber, with the light detector being oriented to receive light traveling in a direction generally perpendicular to the initial path of the light.

In another aspect, a method of detecting the location of an interface between separated fluid components within a channel of a centrifugal separation chamber having a rotational axis comprises separating fluid in a channel of a centrifugal separation chamber into at least two fluid components. A light is directed along an initial path through the channel so as to intersect at least one of the fluid components. The light exiting the channel is directed out of the centrifugal separation chamber in a direction that is generally perpendicular to the initial path of the light. At least a portion of the light exiting the centrifugal separation chamber is detected, and a signal indicative of the location of an interface between the separated fluid components within the channel is generated.

In yet another aspect, a method of controlling a fluid separation procedure comprises controlling a pump to convey fluid into a channel of a centrifugal separation chamber. A centrifugal separator is controlled to rotate the centrifugal separation chamber about a rotational axis to separate the fluid in the channel into at least two fluid components. A light source is controlled to direct a light along an initial path through the channel so as to intersect at least one of the fluid components and direct the light exiting the channel out of the centrifugal separation chamber in a direction generally perpendicular to the initial path of the light. A light detector is controlled to detect at least a portion of the light exiting the centrifugal separation chamber and generate a signal indicative of the location of an interface between the separated fluid components within the channel.

BRIEF DESCRIPTION OF THE DRAWINGS

FIG. 12A is a perspective view of the centrifugal separator of FIG. 12, with selected portions thereof broken away to show a light source of an interface monitoring system;

FIG. 12B is a perspective view of the centrifugal separator of FIG. 12, with the light source operating to transmit a light beam to a light detector of the interface monitoring system;

FIG. 12C is a perspective view of the centrifugal separator of FIG. 12, with selected portions thereof broken away to show the light source and light detector of the interface monitoring system;

FIG. 14 is a perspective view of an exemplary spinning membrane separator of a fluid flow circuit;

FIG. 15 is a perspective view of the spinning membrane separator of FIG. 14 and a portion of a spinning membrane separator drive unit, with portions of both being cut away for illustrative purposes;

FIG. 22 is a perspective view of a prismatic reflector used in combination with any of the centrifugal separation chambers of FIGS. 16-18A;

FIG. 22A is a perspective view of the prismatic reflector of FIG. 22, showing light being transmitted therethrough;

FIGS. 29 and 29A are diagrammatic views of separated blood components on the ramp and the pulse widths of a signal generated by the light detector for each condition;

FIG. 29C is a diagrammatic view of saline on the ramp and the pulse width of a signal generated by the light detector for such a condition;

FIG. 30 is a diagrammatic view of the position of an interface between separated blood components on the ramp compared to a target interface position;

FIG. 31 is a chart that illustrates a control protocol for moving the interface between separated blood components on the ramp from a current position to the target interface position;

DETAILED DESCRIPTION OF THE ILLUSTRATED EMBODIMENTS

The embodiments disclosed herein are for the purpose of providing an exemplary description of the present subject matter. They are, however, only exemplary and not exclusive, and the present subject matter may be embodied in various forms. Therefore, specific details disclosed herein are not to be interpreted as limiting the subject matter as defined in the accompanying claims.

Figure 1:
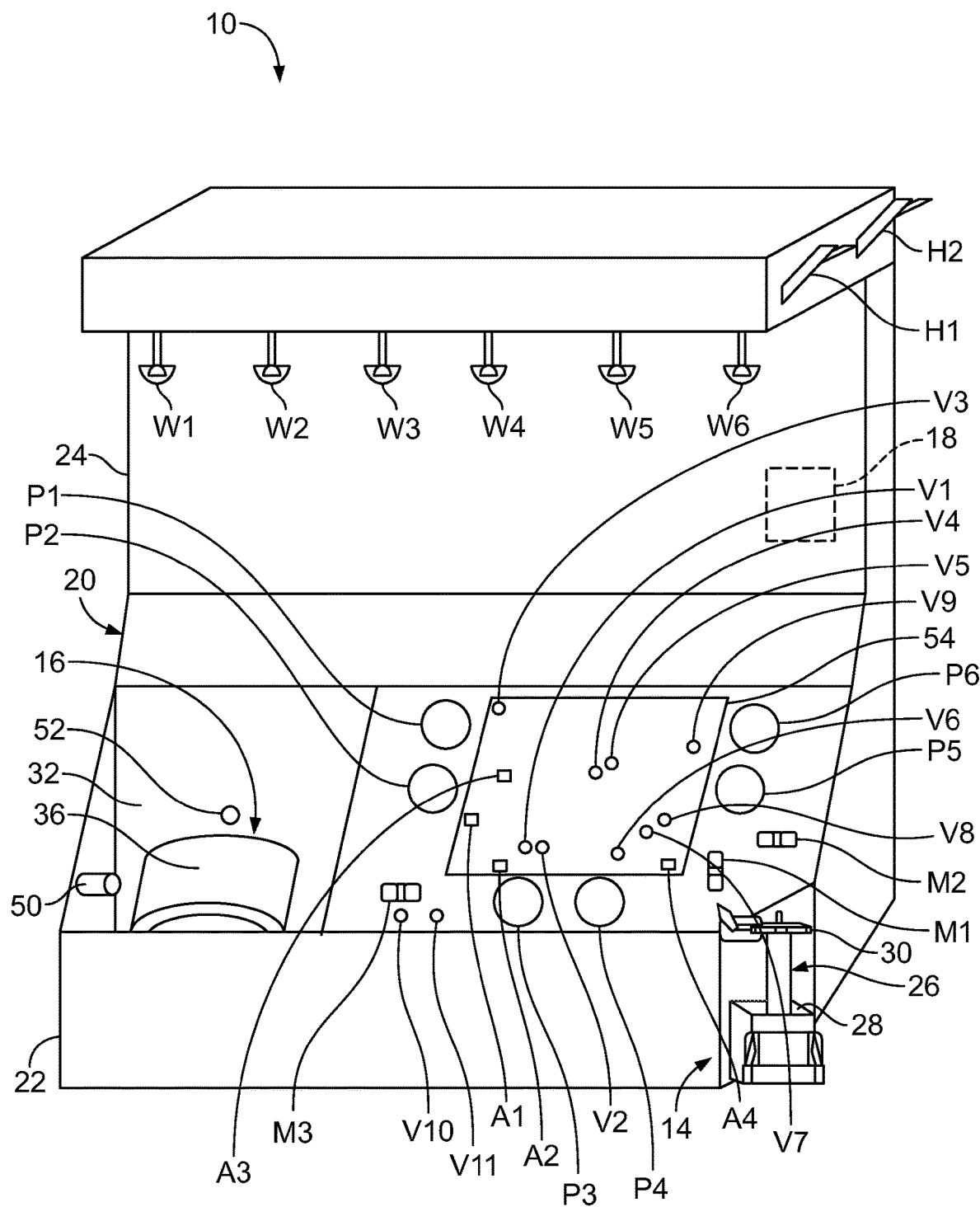
FIG. 1 is a perspective view of an exemplary blood separation device that comprises a component of a blood separation system according to an aspect of the present disclosure.
Figure 60:
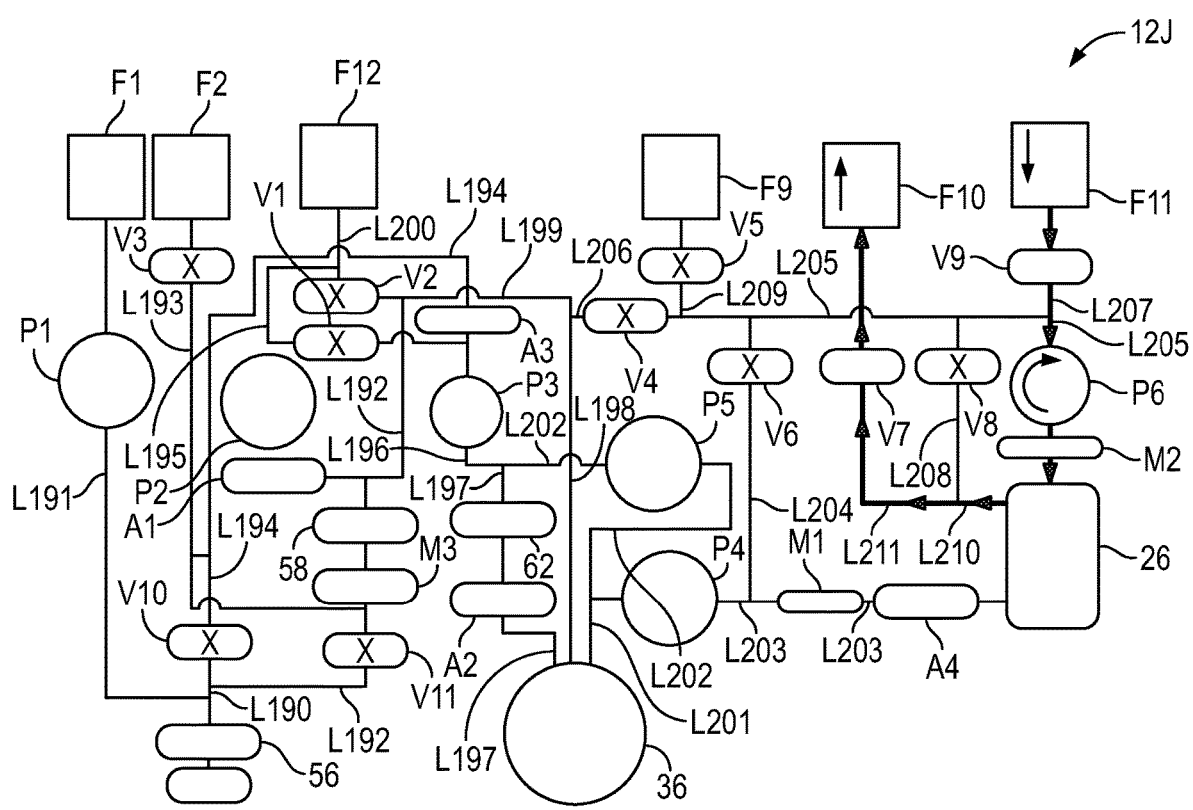

FIGS. 1-60 show components of a blood or fluid separation system that embodies various aspects of the present subject matter. While the system may be referred to herein as a "blood processing system" or a "blood separation system" and examples will be given of various ways in which the system may be used to separate blood into its component parts, it should be understood that systems according to the present disclosure can be used for processing a variety of fluids, which may include bodily fluids and non-bodily fluids.

Generally speaking, the system includes two principal components, a durable and reusable blood separation device 10 (FIG. 1) and a disposable fluid flow circuit 12A-12J (FIGS. 2-11, which may be collectively referenced herein as element 12). The blood separation device 10 includes a spinning membrane separator drive unit 14 (FIG. 1), a centrifuge or centrifugal separator 16 (FIG. 12), additional components that control fluid flow through the disposable flow circuit 12, and a controller 18 (FIG. 1), which governs the operation of the other components of the blood separation device 10 to perform a blood processing and collection procedure selected by the operator, as will be described in greater detail.

I. The Durable Blood Separation Device

The blood separation device 10 (FIG. 1) is configured as a durable item that is capable of long-term use. It should be understood that the blood separation device 10 of FIG. 1 is merely exemplary of one possible configuration and that blood separation devices according to the present disclosure may be differently configured.

In the illustrated embodiment, the blood separation device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24. The configuration and operation of the spinning membrane separator drive unit 14, the centrifugal separator 16, the controller 18, and selected other components of the blood separation device 10 will be described in greater detail.

In the illustrated embodiment, the generally horizontal portion 22 is intended to rest on an elevated, generally horizontal support surface (e.g., a countertop or a tabletop), but it is also within the scope of the present disclosure for the case 20 to include a support base to allow the case 20 to be appropriately positioned and oriented when placed onto a floor or ground surface. It is also within the scope of the present disclosure for the case 20 to be mounted to a generally vertical surface (e.g., a wall), by either fixedly or removably securing the generally vertical portion 24 of the case 20 to the surface.

The case 20 may be configured to assume only the position or configuration of FIG. 1 or may be configured to move between two or more positions or configurations. For example, in one embodiment, the generally horizontal and vertical portions 22 and 24 are joined by a hinge or pivot, which allows the case 20 to be moved between a functional or open configuration (FIG. 1) in which the generally vertical portion 24 is oriented at approximately 90 degrees to the generally horizontal portion 22 and a transport or closed configuration in which the generally vertical portion 24 is rotated about the hinge to approach the generally horizontal portion 22. In such a reconfigurable embodiment, the generally vertical portion 24 may be considered to be the lid of the case 20, while the generally horizontal portion 22 may be considered to be the base. If the case 20 is so reconfigurable, then it may include a latch for releasably locking the case 20 in its closed configuration and/or a handle, which the operator can grasp for transporting the case 20 in its closed configuration.

While it may be advantageous for the blood separation device 10 to be embodied in a compact, portable case 20, it is also within the scope of the present disclosure for the blood separation device to be embodied in a larger case or fixture that is intended to be installed in a single location and remain in that location for an extended period of time. If the blood separation device is provided as a fixture, it may be provided with more components and functionality than a more portable version.

A. Spinning Membrane Separator Drive Unit

The blood separation device 10 includes a spinner support or spinning membrane separator drive unit 14 (FIG. 1) for accommodating a generally cylindrical spinning membrane separator 26 of the fluid flow circuit 12 (FIGS. 14 and 15). U.S. Pat. No. 5,194,145 describes an exemplary spinning membrane separator drive unit that would be suitable for incorporation into the blood separation device 10, but it should be understood that the spinning membrane separator drive unit 14 may be differently configured without departing from the scope of the present disclosure.

The illustrated spinning membrane separator drive unit 14 has a base 28 configured to receive a lower portion of the spinning membrane separator 26 and an upper end cap 30 to receive an upper portion of the spinning membrane separator 26. Preferably, the upper end cap 30 is positioned directly above the base 28 to orient a spinning membrane separator 26 received by the spinning membrane separator drive unit 14 vertically and to define a vertical axis about which the spinning membrane separator 26 is spun. While it may be advantageous for the spinning membrane separator drive unit 14 to vertically orient a spinning membrane separator 26, it is also within the scope of the present disclosure for the spinning membrane separator 26 to be differently oriented when mounted to the blood separation device 10.

In one embodiment, one of the components of the spinning membrane separator drive unit 14 is movable with respect to the other component, which may allow differently sized spinning membrane separators 26 to be received by the spinning membrane separator drive unit 14. For example, the upper end cap 30 may be translated vertically with respect to the base 28 and locked in a plurality of different positions, with each locking position corresponding to a differently sized spinning membrane separator 26. As will be described in greater detail, a smaller spinning membrane separator 26 may be sufficient for selected separation procedures, while a larger spinning membrane separator 26 may be required or advantageous for other separation procedures (particularly when red blood cells are being separated from plasma).

At least one of the base 28 and the upper end cap 30 is configured to spin one or more components of the spinning membrane separator 26 about the axis defined by the spinning membrane separator drive unit 14. The mechanism by which the spinning membrane separator drive unit 14 spins one or more components of the spinning membrane separator 26 may vary without departing from the scope of the present disclosure. In one embodiment, a component of the spinning membrane separator 26 to be spun includes at least one element configured to be acted upon by a magnet (e.g., a metallic material), while the spinning membrane separator drive unit 14 includes a magnet (e.g., a series of magnetic coils or semi-circular arcs). By modulating the magnetic field acting upon the aforementioned element of the spinning membrane separator 26, the component or components of the spinning membrane separator 26 may be made to spin in different directions and at varying speeds. In other embodiments, different mechanisms may be employed to spin the component or components of the spinning membrane separator 26.

Regardless of the mechanism by which the spinning membrane separator drive unit 14 spins the component or components of the spinning membrane separator 26, the component or components of the spinning membrane separator 26 is preferably spun at a speed that is sufficient to create Taylor vortices in a gap between the spinning component and a stationary component of the spinning membrane separator 26 (or a component that spins at a different speed). Fluid to be separated within the spinning membrane separator 26 flows through this gap, and filtration may be dramatically improved by the creation of Taylor vortices.

B. Centrifugal Separator

Figure 12:
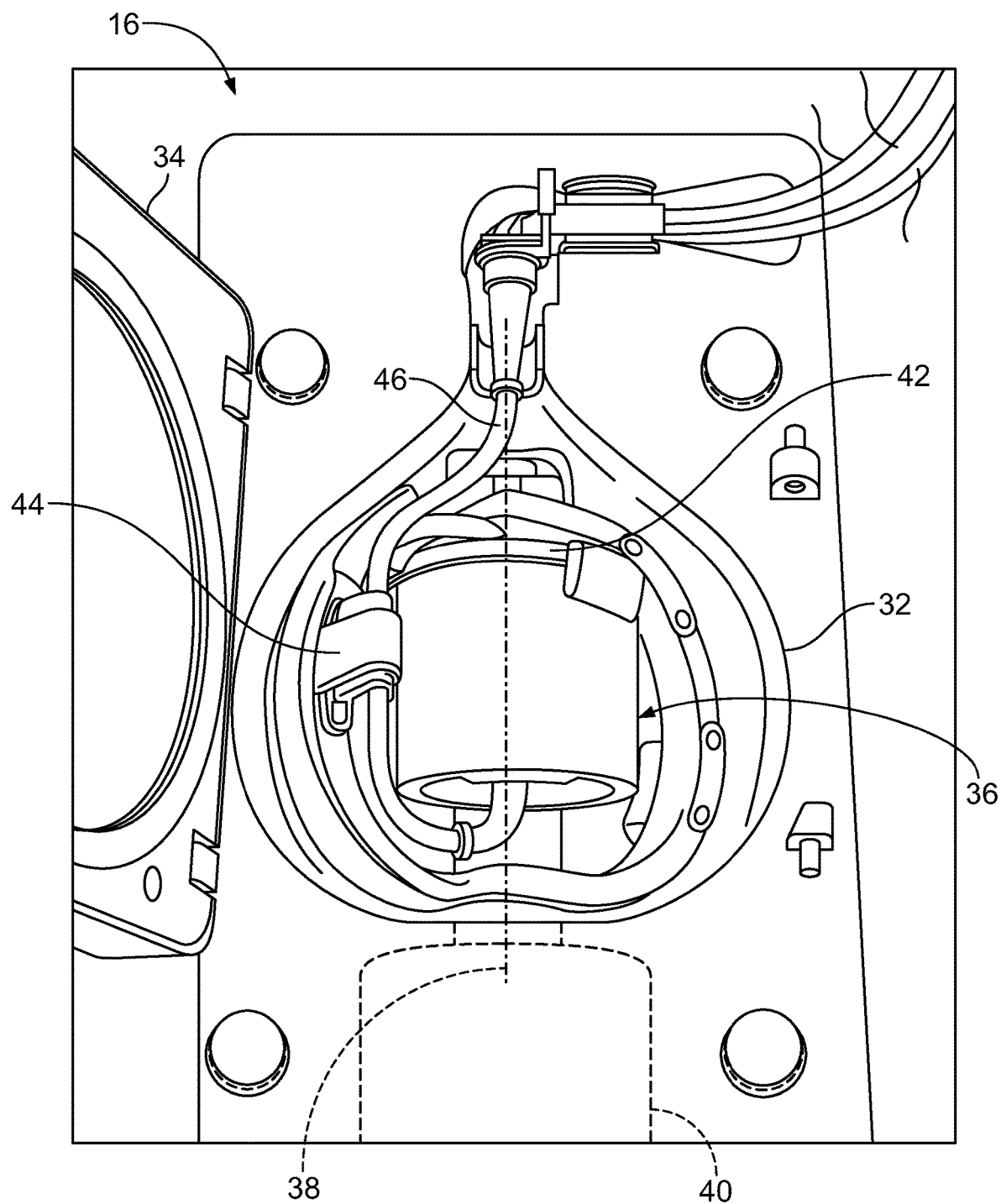
FIG. 12 is a perspective view of an exemplary centrifugal separator of the blood separation device of FIG. 1, with the centrifugal separation chamber of a fluid flow circuit mounted therein.

As for the centrifugal separator 16, it includes a centrifuge compartment 32 that may receive the other components of the centrifugal separator 16 (FIG. 12). The centrifuge compartment 32 may include a lid 34 that is opened to insert and remove a centrifugal separation chamber 36 of the fluid flow circuit 12. During a separation procedure, the lid 34 may be closed with the centrifugal separation chamber 36 positioned within the centrifuge compartment 32, as the centrifugal separation chamber 36 is spun or rotated about an axis 38 under the power of an electric drive motor or rotor 40 of the centrifugal separator 16.

Figure 13:
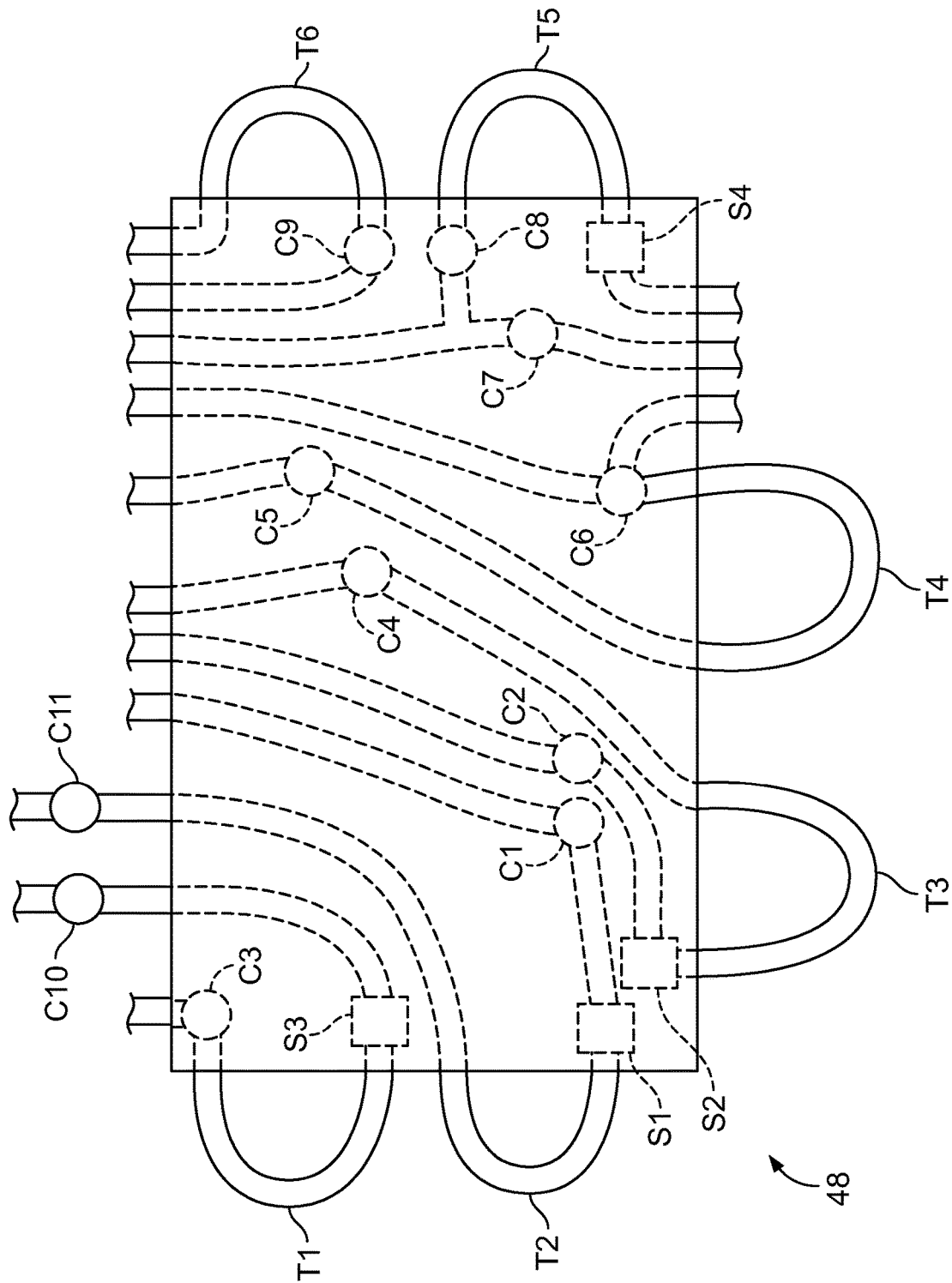
FIG. 13 is a top plan view of an exemplary cassette of a fluid flow circuit, which can be programmed to perform a variety of different blood processing procedures in association with the blood separation device shown in FIG. 1.

The particular configuration and operation of the centrifugal separator 16 depends upon the particular configuration of the centrifugal separation chamber 36 of the fluid flow circuit 12. In one embodiment, the centrifugal separator 16 is similar in structure and operation to that of the ALYX system manufactured by Fenwal, Inc. of Lake Zurich, Ill., which is an affiliate of Fresenius Kabi AG of Bad Homburg, Germany, as described in greater detail in U.S. Pat. No. 8,075,468, which is incorporated herein by reference. More particularly, the centrifugal separator 16 may include a carriage or support 42 that holds the centrifugal separation chamber 36 and a yoke member 44. The yoke member 44 engages an umbilicus 46 of the fluid flow circuit 12, which extends between the centrifugal separation chamber 36 and a cassette 48 of the fluid flow circuit 12 (FIG. 13). The yoke member 44 causes the umbilicus 46 to orbit around the centrifugal separation chamber 36 at a one omega rotational speed. The umbilicus 46 twists about its own axis as it orbits around the centrifugal separation chamber 36. The twisting of the umbilicus 46 about its axis as it rotates at one omega with the yoke member 44 imparts a two omega rotation to the centrifugal separation chamber 36, according to known design. The relative rotation of the yoke member 44 at a one omega rotational speed and the centrifugal separation chamber 36 at a two omega rotational speed keeps the umbilicus 46 untwisted, avoiding the need for rotating seals.

Blood is introduced into the centrifugal separation chamber 36 by the umbilicus 46, with the blood being separated (e.g., into a layer of less dense components, such as platelet-rich plasma, and a layer of more dense components, such as packed red blood cells) within the centrifugal separation chamber 36 as a result of centrifugal forces as it rotates. Components of an interface monitoring system may be positioned within the centrifuge compartment 32 to oversee separation of blood within the centrifugal separation chamber 36.

As shown in FIGS. 12A-12C, the interface monitoring system may include a light source 50 and a light detector 52, which is positioned and oriented to receive at least a portion of the light emitted by the light source 50. Preferably, the light source 50 and the light detector 52 are positioned on stationary surfaces of the centrifuge compartment 32, but it is also within the scope of the present disclosure for one or both to be mounted to a movable component of the centrifugal separator 16 (e.g., to the yoke member 44, which rotates at a one omega speed).

The orientation of the various components of the interface monitoring system depends at least in part on the particular configuration of the centrifugal separation chamber 36, which will be described in greater detail herein. In general, though, the light source 50 emits a light beam (e.g., a laser light beam) through the separated blood components within the centrifugal separation chamber 36 (which may be formed of a material that substantially transmits the light or at least a particular wavelength of the light without absorbing it). A portion of the light reaches the light detector 52, which transmits a signal to the controller 18 that is indicative of the location of an interface between the separated blood components. If the controller 18 determines that the interface is in the wrong location (which can affect the separation efficiency of the centrifugal separator 16 and/or the quality of the separated blood components), then it can issue commands to the appropriate components of the blood separation device 10 to modify their operation so as to move the interface to the proper location.

C. Other Components of the Blood Separation Device

In addition to the spinning membrane separator drive unit 14 and the centrifugal separator 16, the blood separation device 10 may include other components compactly arranged to aid blood processing.

The generally horizontal portion 22 of the case 20 of the illustrated blood separation device 10 includes a cassette station 54, which accommodates a cassette 48 of the fluid flow circuit 12 (FIG. 13). In one embodiment, the cassette station 54 is similarly configured to the cassette station of U.S. Pat. No. 5,868,696 (which is incorporated herein by reference), but is adapted to include additional components and functionality. The illustrated cassette station 54 includes a plurality of clamps or valves V1-V9 (FIG. 1), which move between a plurality of positions (e.g., between a retracted or lowered position and an actuated or raised position) to selectively contact or otherwise interact with corresponding valve stations C1-C9 of the cassette 48 of the fluid flow circuit 12 (FIGS. 2-11 and 13). Depending on the configuration of the fluid flow circuit 12, its cassette 48 may not include a valve station C1-C9 for each valve V1-V9 of the cassette station 54, in which case fewer than all of the valves V1-V9 will be used in a separation procedure, as will be described.

In the actuated position, a valve V1-V9 engages the associated valve station C1-C9 to prevent fluid flow through that valve station C1-C9 (e.g., by closing one or more ports associated with the valve station C1-C9, thereby preventing fluid flow through that port or ports). In the retracted position, a valve V1-V9 is disengaged from the associated valve station C1-C9 (or less forcefully contacts the associated valve station C1-C9 than when in the actuated position) to allow fluid flow through that valve station C1-C9 (e.g., by opening one or more ports associated with the valve station C1-C9, thereby allowing fluid flow through that port or ports). Additional clamps or valves V10 and V11 may be positioned outside of the cassette station 52 to interact with portions or valve stations C10 and C11 (which may be lengths of tubing) of the fluid flow circuit 12 to selectively allow and prevent fluid flow therethrough. The valves V1-V9 and corresponding valve stations C1-C9 of the cassette station 54 and cassette 48 may be differently configured and operate differently from the valves V10 and V11 and valve stations C10 and C11 that are spaced away from the cassette station 54.

The cassette station 54 may be provided with additional components, such as pressure sensors A1-A4, which interact with sensor stations S1-S4 of the cassette 48 to monitor the pressure at various locations of the fluid flow circuit 12. For example, if the blood source is a human donor, one or more of the pressure sensors A1-A4 may be configured to monitor the pressure of the donor's vein during blood draw and return. Other pressure sensors A1-A4 may monitor the pressure of the spinning membrane separator 26 and the centrifugal separation chamber 36. The controller 18 may receive signals from the pressure sensor A1-A4 that are indicative of the pressure within the fluid flow circuit 12 and, if a signal indicates a low- or high-pressure condition, the controller 18 may initiate an alarm or error condition to alert an operator to the condition and/or to attempt to bring the pressure to an acceptable level without operator intervention.

The blood separation device 10 may also include a plurality of pumps P1-P6 to cause fluid to flow through the fluid flow circuit 12. The pumps P1-P6 may be differently or similarly configured and/or function similarly or differently from each other. In the illustrated embodiment, the pumps P1-P6 are configured as peristaltic pumps, which may be generally configured as described in U.S. Pat. No. 5,868,696. Each pump P1-P6 engages a different tubing loop T1-T6 extending from a side surface of the cassette 48 (FIG. 13) and may be selectively operated under command of the controller 18 to cause fluid to flow through a portion of the fluid flow circuit 12, as will be described in greater detail. In one embodiment, all or a portion of the cassette station 54 may be capable of translational motion in and out of the case 20 to allow for automatic loading of the tubing loops T1-T6 into the associated pump P1-P6.

The illustrated blood separation device 10 also includes a spinner inlet sensor M1 for determining one or more properties of a fluid flowing into a spinning membrane separator 26 mounted within the spinning membrane separator drive unit 14. If the fluid flowing into the spinning membrane separator 26 is whole blood (which may include anticoagulated whole blood), the spinner inlet sensor M1 may be configured to determine the hematocrit of the blood flowing into the spinning membrane separator 26. If the fluid flowing into the spinning membrane separator 26 is platelet-rich plasma, the spinner inlet sensor M1 may be configured to determine the platelet concentration of platelet-rich plasma flowing into the spinning membrane separator 26. The spinner inlet sensor M1 may detect the one or more properties of a fluid by optically monitoring the fluid as it flows through tubing of the fluid flow circuit 12 or by any other suitable approach. The controller 18 may receive signals from the spinner inlet sensor M1 that are indicative of the one or more properties of fluid flowing into the spinning membrane separator 26 and use the signals to optimize the separation procedure based upon that property or properties. If the property or properties is/are outside of an acceptable range, then the controller 18 may initiate an alarm or error condition to alert an operator to the condition. A suitable device and method for monitoring hematocrit and/or platelet concentration is described in U.S. Pat. No. 6,419,822 (which is incorporated herein by reference), but it should be understood that a different approach may also be employed for monitoring hematocrit and/or platelet concentration of fluid flowing into the spinning membrane separator 26.

The illustrated blood separation device 10 further includes a spinner outlet sensor M2, which accommodates tubing of the fluid flow circuit 12 that flows a separated blood component out of the spinning membrane separator 26. The spinner outlet sensor M2 monitors the fluid to determine one or more properties of the fluid, and may do so by optically monitoring the fluid as it flows through the tubing or by any other suitable approach. In one embodiment, separated plasma flows through the tubing, in which case the spinner outlet sensor M2 may be configured to determine the amount of cellular blood components in the plasma and/or whether the plasma is hemolytic and/or lipemic. This may be done using an optical monitor of the type described in U.S. Pat. No. 8,556,793 (which is incorporated herein by reference) or by any other suitable device and/or method.

The illustrated blood separation device 10 also includes an air detector M3 (e.g., an ultrasonic bubble detector), which accommodates tubing of the fluid flow circuit 12 that flows fluid to a recipient. It may be advantageous to prevent air from reaching the recipient, whether a human recipient (e.g., the same human that serves as the blood source) or a non-human recipient (e.g., a storage bag or container), so the air detector M3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient (e.g., by reversing the flow of fluid through the tubing or diverting flow to a vent location).

The generally vertical portion 24 of the case 18 may include a plurality of weight scales W1-W6 (six are shown, but more or fewer may be provided), each of which may support one or more fluid containers F1-F12 of the fluid flow circuit 12 (FIGS. 2-11). The containers F1-F12 receive blood components separated during processing or intravenous fluids or additive fluids. Each weight scale W1-W6 transmits to the controller 18 a signal that is indicative of the weight of the fluid within the associated container F1-F12 to track the change of weight during the course of a procedure. This allows the controller 18 to process the incremental weight changes to derive fluid processing volumes and flow rates and subsequently generate signals to control processing events based, at least in part, upon the derived processing volumes. For example, the controller 18 may diagnose leaks and obstructions in the fluid flow circuit 12 and alert an operator.

The illustrated case 20 is also provided with a plurality of hooks or supports H1 and H2 that may support various components of the fluid flow circuit 12 or other suitably sized and configured objects.

D. Controller

According to an aspect of the present disclosure, the blood separation device 10 includes a controller 18, which is suitably configured and/or programmed to control operation of the blood separation device 10. In one embodiment, the controller 18 comprises a main processing unit (MPU), which can comprise, e.g., a Pentium™ type microprocessor made by Intel Corporation, although other types of conventional microprocessors can be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the blood separation device 10.

The controller 18 is configured and/or programmed to execute at least one blood processing application but, more advantageously, is configured and/or programmed to execute a variety of different blood processing applications. For example, the controller 18 may be configured and/or programmed to carry out one or more of the following: a double unit red blood cell collection procedure, a plasma collection procedure, a plasma/red blood cell collection procedure, a red blood cell/platelet/plasma collection procedure, a platelet collection procedure, and a platelet/plasma collection procedure. The details of various exemplary procedures that may be carried out by the controller 18 will be described in greater detail. Additional or alternative procedure applications can be included without departing from the scope of the present disclosure.

More particularly, in carrying out any one of these blood processing applications, the controller 18 is configured and/or programmed to control one or more of the following tasks: drawing blood into a fluid flow circuit 12 mounted to the blood separation device 10, conveying blood through the fluid flow circuit 12 to a location for separation (i.e., into a spinning membrane separator 26 or centrifugal separation chamber 36 of the fluid flow circuit 12), separating the blood into two or more components as desired, and conveying the separated components into storage containers, to a second location for further separation (e.g., into whichever of the spinning membrane separator 26 and centrifugal separation chamber 36 that was not used in the initial separation stage), or to a recipient (which may be a donor from which the blood was originally drawn).

This may include instructing the spinning membrane separator drive unit 14 and/or the centrifugal separator 16 to operate at a particular rotational speed and instructing a pump P1-P6 to convey fluid through a portion of the fluid flow circuit 12 at a particular flow rate. Hence, while it may be described herein that a particular component of the blood separation device 10 (e.g., the spinning membrane separator drive unit 14 or the centrifugal separator 16) performs a particular function, it should be understood that that component is being controlled by the controller 18 to perform that function.

As will be described, several procedures call for the use of both the centrifugal separator 16 and the spinning membrane separator drive unit 14, in which case a properly programmed controller 18 is especially important to coordinate the operation of these two components, along with the other components of the blood separation device 10 to ensure that flow to and from the centrifugal separator 16 and spinning membrane separator drive unit 14 is at the proper level and that the components are functioning properly to process the blood circulating through the fluid flow circuit 12.

Before, during, and after a procedure, the controller 18 may receive signals from various components of the blood separation device 10 (e.g., the pressure sensors A1-A4) to monitor various aspects of the operation of the blood separation device 10 and characteristics of the blood and separated blood components as they flow through the fluid flow circuit 12. If the operation of any of the components and/or one or more characteristics of the blood or separated blood components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 18 may include an interface control module, which receives signals from the light detector 52 of the interface monitoring system. The signals that the controller 18 receives from the light detector 52 are indicative of the location of an interface between the separated blood components within the centrifugal separation chamber 36. If the controller 18 determines that the interface is in the wrong location, then it can issue commands to the appropriate components of the blood separation device 10 to modify their operation so as to move the interface to the proper location. For example, the controller 18 may instruct one of the pumps P1-P6 to cause blood to flow into the centrifugal separation chamber 36 at a different rate and/or for a separated blood component to be removed from the centrifugal separation chamber 36 at a different rate and/or for the centrifugal separation chamber 36 to be spun at a different speed by the centrifugal separator 16. A particular protocol carried out by the interface control module in adjusting the position of the interface within the centrifugal separation chamber 36 will be described in greater detail with respect to an exemplary centrifugal separation chamber 36.

Such control typically occurs regardless of whether the blood originates from a container or directly from a donor, and regardless of whether the components are directed into storage containers or returned to a donor or another living recipient.

If provided, an operator interface station associated with the controller 18 allows the operator to view on a screen or display (in alpha-numeric format and/or as graphical images) information regarding the operation of the system. The operator interface station also allows the operator to select applications to be executed by the controller 18, as well as to change certain functions and performance criteria of the system. If configured as a touchscreen, the screen of the operator interface station can receive input from an operator via touch-activation. Otherwise, if the screen is not a touchscreen, then the operator interface station may receive input from an operator via a separate input device, such as a computer mouse or keyboard. It is also within the scope of the present disclosure for the operator interface station to receive input from both a touchscreen and a separate input device, such as a keypad.

II. The Disposable Fluid Flow Circuit

A. Overview

As for the fluid flow circuit or flow set 12 (FIGS. 2-11), it is intended to be a sterile, single use, disposable item. Before beginning a given blood processing and collection procedure, the operator loads various components of the fluid flow circuit 12 in the case 20 in association with the blood separation device 10. The controller 18 implements the procedure based upon preset protocols, taking into account other input from the operator. Upon completing the procedure, the operator removes the fluid flow circuit 12 from association with the blood separation device 10. The portions of the fluid flow circuit 12 holding the collected blood component or components (e.g., collection containers or bags) are removed from the case 20 and retained for storage, transfusion, or further processing. The remainder of the fluid flow circuit 12 is removed from the case 20 and discarded.

Figure 16:
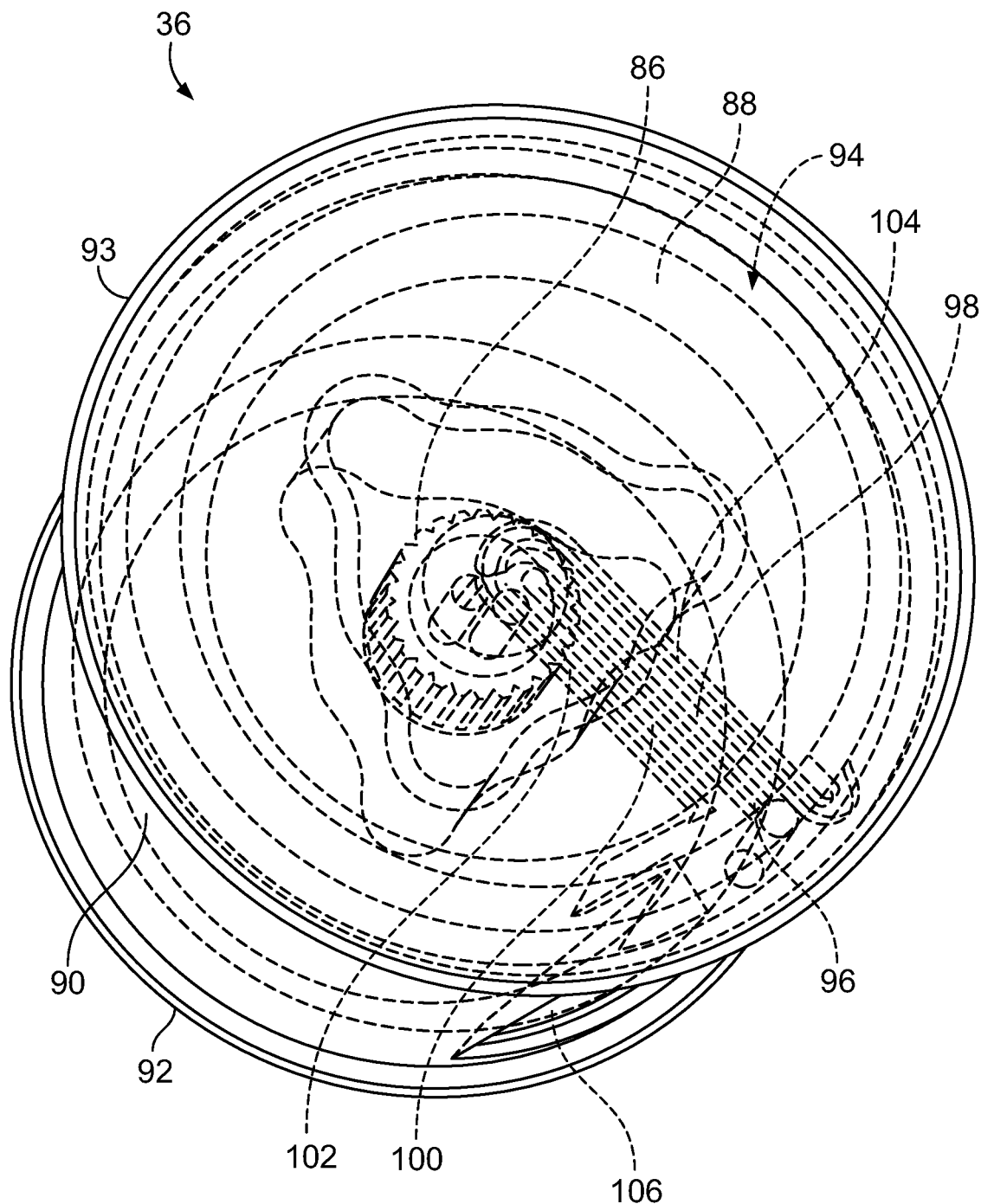
FIG. 16 is a perspective view of an exemplary centrifugal separation chamber of a fluid flow circuit.

A variety of different disposable fluid flow circuits 12A-12J may be used in combination with the blood separation device 10, with the appropriate fluid flow circuit depending on the separation procedure to be carried out using the system. Accordingly, different fluid flow circuits will be described in connection with particular separation procedures. Generally speaking, though, the fluid flow circuit 12 includes a cassette 48 (FIG. 13), to which the other components of the fluid flow circuit 12 are connected by flexible tubing. The other components may include a plurality of fluid containers F1-F12 (for holding blood, a separated blood component, an intravenous fluid, or an additive solution), one or more blood source access devices (e.g., a phlebotomy needle or a connector for accessing blood within a fluid container), and a spinning membrane separator 26 (FIGS. 14 and 15) and/or a centrifugal separation chamber 36 (FIG. 16).

B. Cassette and Tubing

The cassette 48 (FIG. 13) provides a centralized, programmable, integrated platform for all the pumping and many of the valving functions required for a given blood processing procedure. In one embodiment, the cassette 48 is similarly configured to the cassette of U.S. Pat. No. 5,868,696, but is adapted to include additional components (e.g., more tubing loops T1-T6) and functionality.

In use, the cassette 48 is mounted to the cassette station 54 of the blood separation device 10, with a flexible diaphragm of the cassette 48 placed into contact with the cassette station 54. The flexible diaphragm overlays an array of interior cavities formed by the body of the cassette 48. The different interior cavities define sensor stations S1-S4, valve stations C1-C9, and a plurality of flow paths. The side of the cassette 48 opposite the flexible diaphragm may be sealed by another flexible diaphragm or a rigid cover, thereby sealing fluid flow through the cassette 48 from the outside environment.

Each sensor station S1-S4 is aligned with an associated pressure sensor A1-A4 of the cassette station 54, with each pressure sensor A1-A4 capable of monitoring the pressure within the associated sensor station S1-S4. Each valve station C1-C9 is aligned with an associated valve V1-V9, and may define one or more ports that allow fluid communication between the valve station C1-C9 and another interior cavity of the cassette 48 (e.g., a flow path). As described above, each valve V1-V9 is movable under command of the controller 18 to move between a plurality of positions (e.g., between a retracted or lowered position and an actuated or raised position) to selectively contact the valve stations C1-C9 of the cassette 48. In the actuated position, a valve V1-V9 engages the associated valve station C1-C9 to close one or more of its ports to prevent fluid flow therethrough. In the retracted position, a valve V1-V9 is disengaged from the associated valve station C1-C9 (or less forcefully contacts the associated valve station C1-C9 than when in the actuated position) to open one or more ports associated with the valve station C1-C9, thereby allowing fluid flow therethrough.

As described, a plurality of tubing loops T1-T6 extend from the side surface of the cassette 48 to interact with pumps P1-P6 of the blood separation device 10. In the illustrated embodiment, six tubing loops T1-T6 extend from the cassette 48 to be received by a different one of six pumps P1-P6, but in other embodiments, a procedure may not require use of all of the pumps P1-P6, in which case the cassette 48 may include fewer than six tubing loops. The different pumps P1-P6 may interact with the tubing loops T1-T6 of the cassette 48 to perform different tasks during a separation procedure (as will be described in greater detail), but in one embodiment, a different one of the pumps P1-P6 may be configured to serve as a source pump, an anticoagulant pump, a spinner pump, a separated component pump, an additive pump, and a replacement fluid pump. As will be described, certain procedures require fewer than all of the sensor stations, valve stations, and/or tubing loops illustrated in the exemplary cassette 48 of FIG. 13, such that it should be understood that the cassettes of different fluid flow circuits 12 may be differently configured (e.g., with fewer sensor stations, valve stations, and/or tubing loops) without departing from the scope of the present disclosure.

Additional tubing extends from the side surface of the cassette 48 to connect to the other components of the fluid flow circuit 12, such as the various fluid containers F1-F12, the spinning membrane separator 26 (if provided), and the centrifugal separation chamber 36 (if provided). The number and content of the various fluid containers F1-F12 depends upon the procedure for which the fluid flow circuit 12 is used, so they will be described in greater detail with respect to the particular procedures. If the fluid flow circuit 12 includes a centrifugal separation chamber 36, then the tubing connected to it (which includes one inlet tube and two outlet tubes) may be aggregated into an umbilicus 46 (FIG. 12) that is engaged by the yoke member 44 of the centrifugal separator 16 (as described above) to cause the umbilicus 46 to orbit around and spin or rotate the centrifugal separation chamber 36 during a separation procedure.

Various additional components may be incorporated into the tubing leading out of the cassette 48 or into one of the cavities of the cassette 48. For example, as shown in FIGS. 2-11, a manual clamp 56 may be associated with a line or lines leading to the blood source and/or fluid recipient, a return line filter 58 (e.g., a microaggregate filter) may be associated with a line leading to a fluid recipient, filters 60 may be positioned upstream of one or more of the fluid containers to remove a substance (e.g., leukocytes) from a separated component (e.g., red blood cells or platelets) flowing into the fluid container (as in FIGS. 2-5 and 8), and/or an air trap 62 may be positioned on a line upstream of the centrifugal separation chamber 36 (as in FIGS. 8-11).

C. Spinning Membrane Separator

Turning to FIGS. 14 and 15, a spinning membrane separator 26 is shown. As will be described in greater detail, the spinning membrane separator 26 is used to separate plasma from cellular blood components of whole blood obtained from blood source or from some other plasma-containing fluid (e.g., platelet-rich plasma). The spinning membrane separator 26 (if provided) is associated with the remainder of the fluid flow circuit 12 by an inlet port 64 and two outlet ports 66 and 68. The inlet port 64 is shown as being associated with a bottom end or portion of the spinning membrane separator 26, while the outlet ports 66 and 68 are associated with an upper end or portion of the spinning membrane separator 26, but it is within the scope of the present disclosure for the spinning membrane separator 26 to be inverted, with fluid entering an upper end or portion of the spinning membrane separator 26 and fluid exiting a lower end or portion of the spinning membrane separator 26.

The illustrated spinning membrane separator 26 includes a generally cylindrical housing 70 mounted concentrically about a longitudinal vertical central axis. An internal member or rotor 72 is mounted concentrically with the central axis. The housing 70 and rotor 72 are relatively rotatable, as described above with respect to the spinning membrane separator drive unit 14. In a preferred embodiment, the housing 70 is stationary and the rotor 72 is a rotating spinner that is rotatable concentrically within the cylindrical housing 70. In such an embodiment, the housing 70 (or at least its upper and lower ends) are formed of non-magnetic material, while the rotor 72 includes an element (e.g., a metallic material) that interacts with a magnet of the spinning membrane separator drive unit 14 to rotate the rotor 72 within the housing 70, as described above.

The boundaries of the blood flow path are generally defined by the gap 74 between the interior surface of the housing 70 and the exterior surface of the rotor 72, which is sometimes referred to as the shear gap. A typical shear gap 74 may be approximately 0.025-0.050 inches (0.067-0.127 cm) and may be of a uniform dimension along the axis, for example, where the axis of the housing 70 and rotor 72 are coincident. Alternatively, the width of the shear gap 74 also may vary along the axial direction, for example with the width of the gap 74 increasing in the direction of flow to limit hemolysis. Such a gap width may range from about 0.025 to about 0.075 inches (0.06-0.19 cm). For example, in one embodiment, the axes of the housing 70 and rotor 72 are coincident, with the outer diameter of the rotor 72 decreasing in the direction of flow, while the inner diameter of the housing 70 remaining constant. In other embodiments, the inner diameter of the housing 70 may increase while the outer rotor diameter remains constant or both surfaces may vary in diameter. In one exemplary embodiment, the gap width may be about 0.035 inches (0.088 cm) at the upstream or inlet end of the gap 74 and about 0.059 inches (0.15 cm) at the downstream end or terminus of the gap 74. The gap width could change linearly or stepwise or in some other manner as may be desired. In any event, the width dimension of the gap 74 is preferably selected so that at the desired relative rotational speed, Taylor-Couette flow, such as Taylor vortices, are created in the gap 74 and hemolysis is limited.

Plasma-containing fluid is fed into the gap 74 by the inlet port 64 (FIG. 14), which directs the fluid into the blood flow entrance region at or adjacent to the bottom end of the spinning membrane separator 26. The spinning membrane separator drive unit 14 causes relative rotation of the housing 70 and rotor 72, creating Taylor vortices within the gap 74. The outer surface of the rotor 72 and/or the inner surface of the housing 70 is at least partially (and more preferably, substantially or entirely) covered by a cylindrical porous membrane 76 (shown in FIG. 15 as being mounted to the outer surface of the rotor 72). It should be, thus, understood that the term "spinning membrane separator" does not necessarily require that the membrane 76 is mounted to a component of the spinning membrane separator 26 that spins, but may also include a device in which the membrane 76 is mounted to a stationary component that includes another component that rotates with respect to the stationary membrane 76.

The membrane 76 typically has a nominal pore size of 0.65-0.8 microns, but other pore sizes may alternatively be used. Membranes useful in the methods described herein may be fibrous mesh membranes, cast membranes, track-etched membranes or other types of membranes that will be known to those of skill in the art. For example, in one embodiment, the membrane 76 may have a polyester mesh (substrate) with nylon particles solidified thereon, thereby creating a tortuous path through which only certain sized components will pass. In another embodiment, the membrane 76 may be made of a thin (approximately 15 micron thick) sheet of, for example, polycarbonate with pores or holes defined therein that are sized and configured to allow passage of only a selected one or more blood components.

In an embodiment in which the rotor 72 spins within the housing 70 and the membrane 76 is mounted to the outer surface of the rotor 72, the outer surface of the rotor 72 may be shaped to define a series of spaced-apart circumferential grooves or ribs 78 separated by annular lands 80 (FIG. 15). The surface channels defined by the circumferential grooves 78 are interconnected by longitudinal grooves 82. At one or both ends of the rotor 72, these grooves 78 are in communication with a central orifice or manifold 84. Pumping fluid into and out of the spinning membrane separator 26 causes plasma to flow through the membrane 76 and grooves 78, while the cellular blood components remain within the gap 74 as fluid flows from the inlet port 64 at the bottom portion of the spinning membrane separator 26 toward the upper portion. Relative rotation of the rotor 72 and housing 70 causes a particular flow pattern within the gap 74 (described above) that enables filtration of the cellular blood components from the plasma without clogging the membrane 76.

At the upper portion of the spinning membrane separator 26, plasma exits the spinning membrane separator 26 via an outlet port 66 that is concentric with the rotational axis and in fluid communication with the central orifice 84 of the rotor 72 (FIG. 15), with the plasma flowing into a line associated with the outlet port 66.

The separated cellular blood components exit the gap 74 via an outlet port 68 defined in the upper end or portion of the housing 70 and oriented generally tangentially to the gap 74 (FIG. 14), with the cellular blood components flowing into a line associated with the outlet port 68.

As described above, it may be advantageous to use differently sized spinning membrane separators 26 depending on the particular blood separation procedure being carried out. FIG. 14 shows a spinning membrane separator 26 having a rotor 72 with a spinner diameter D, a filtration length FL, and an overall length LOA. An exemplary smaller spinning membrane separator may have a spinner diameter D of approximately 1.1", a filtration length FL of approximately 3", and an overall length LOA of approximately 5.0". By comparison, an exemplary larger spinning membrane separator may have a spinner diameter D of approximately 1.65", a filtration length FL of approximately 5.52", and an overall length LOA of approximately 7.7". An exemplary smaller spinning membrane separator is described in greater detail in U.S. Pat. No. 5,194,145, while an exemplary larger spinning membrane separator is described in greater detail in U.S. Patent Application Publication No. 2015/0218517, which is incorporated herein by reference.

D. Centrifugal Separation Chamber

Figure 16A:
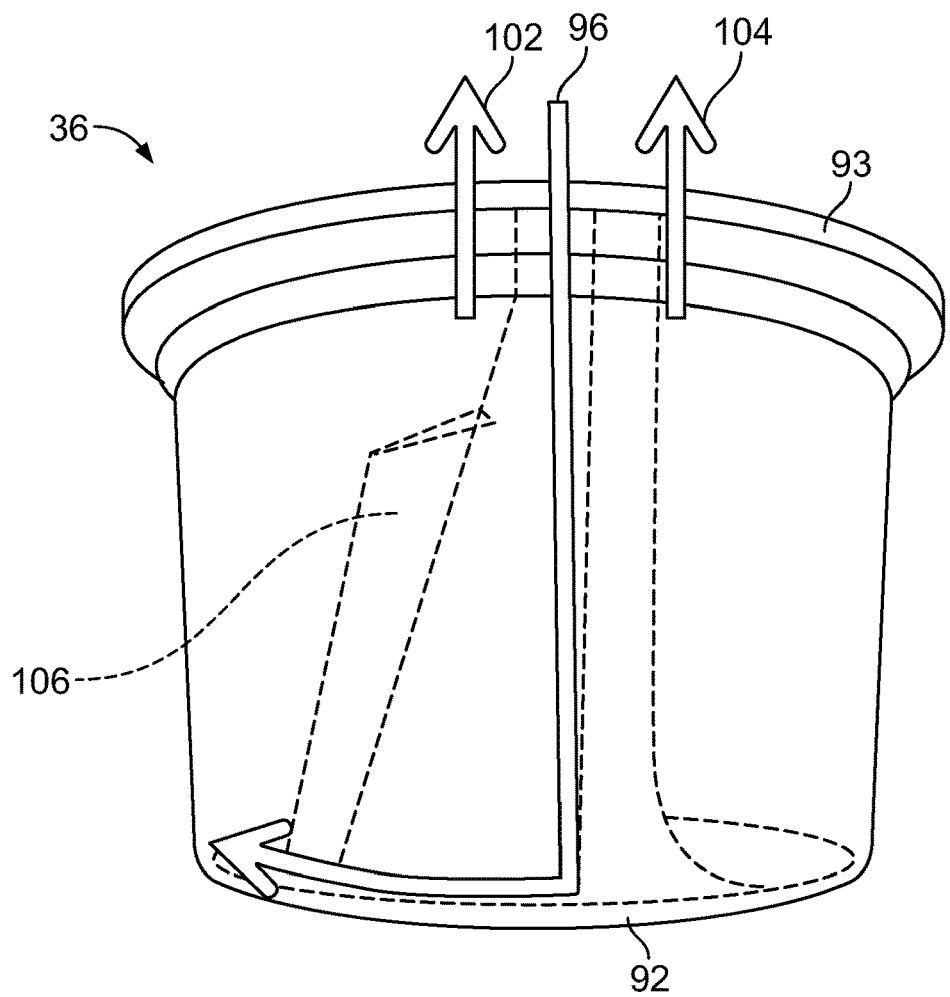
FIG. 16A is a front elevational view of the centrifugal separation chamber of FIG. 16.
Figure 16B:
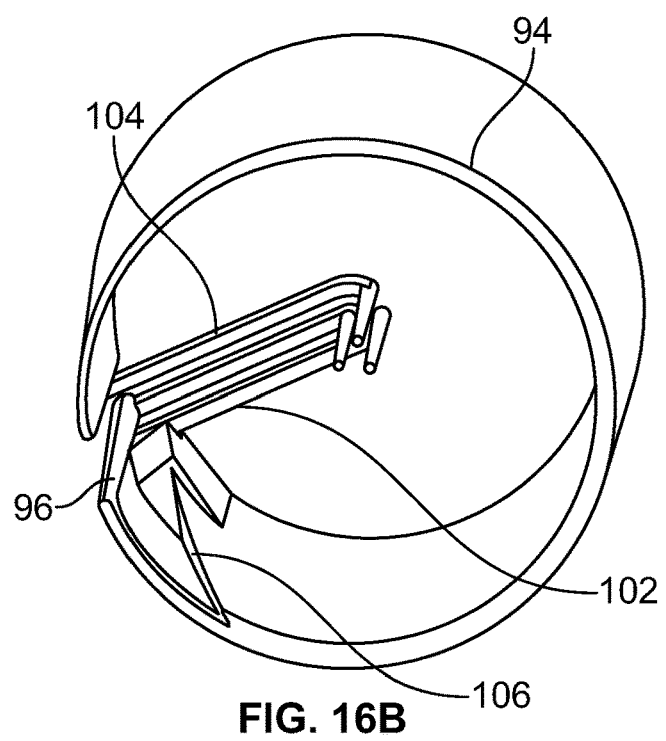
FIG. 16B is a bottom perspective view of the fluid flow path through the centrifugal separation chamber of FIG. 16.

A fluid flow circuit 12 may be provided with a centrifugal separation chamber 36 if platelets and/or white blood cells are to be separated and collected. An exemplary centrifugal separation chamber 36 is shown in FIGS. 16 and 16A, while FIG. 16B illustrates the fluid flow path defined by the centrifugal separation chamber 36. In the illustrated embodiment, the body of the centrifugal separation chamber 36 is pre-formed in a desired shape and configuration (e.g., by injection molding) from a rigid, biocompatible plastic material, such as a non-plasticized medical grade acrylonitrile-butadiene-styrene (ABS). All contours, ports, channels, and walls that affect the blood separation process are preformed in a single, injection molded operation. Alternatively, the centrifugal separation chamber 36 can be formed by separate molded parts, either by nesting cup-shaped subassemblies or two symmetric halves.

The underside of the centrifugal separation chamber 36 includes a shaped receptacle 86 that is suitable for receiving an end of the umbilicus 46 of the fluid flow circuit 12 (FIG. 12). A suitable receptacle 86 and the manner in which the umbilicus 46 may cooperate with the receptacle 86 to deliver fluid to and remove fluid from the centrifugal separation chamber 36 are described in greater detail in U.S. Pat. No. 8,075,468.

The illustrated centrifugal separation chamber 36 has radially spaced apart inner (low-g) and outer (high-g) side wall portions 88 and 90, a bottom or first end wall portion 92, and a cover or second end wall portion 93. The cover 93 comprises a simple flat part that can be easily welded or otherwise secured to the body of the centrifugal separation chamber 36. Because all features that affect the separation process are incorporated into one injection molded component, any tolerance differences between the cover 93 and the body of the centrifugal separation chamber 36 will not affect the separation efficiencies of the centrifugal separation chamber 36. The wall portions 88 and 90, the bottom 92, and the cover 93 together define an enclosed, generally annular channel 94 (FIG. 16B).

The (whole blood) inlet 96 communicating with the channel 94 is defined between opposing interior radial walls 98 and 100. One of the interior walls 98 joins the outer (high-g) wall portion 90 and separates the upstream and downstream ends of the channel 94. The interior walls 98 and 100 define the inlet passageway 96 of the centrifugal separation chamber 36 which, in one flow configuration, allows fluid to flow from the umbilicus 46 to the upstream end of the channel 94.

The illustrated centrifugal separation chamber 36 further includes first and second outlets 102 and 104, respectively, which may be defined by opposing surfaces of interior radial walls. Both the first and second outlets 102 and 104 extend radially inward from the channel 94. The first (platelet-rich plasma) outlet 102 extends radially inward from an opening which, in the illustrated embodiment, is located at the inner side wall portion 88, while the second (red blood cell) outlet 104 extends radially inward from an opening that is associated with the outer side wall portion 90. The illustrated first outlet 102 is positioned adjacent to the inlet 96 (near the upstream end of the channel 94), while the second outlet 104 may be positioned at the opposite, downstream end of the channel 94.

Figure 17:
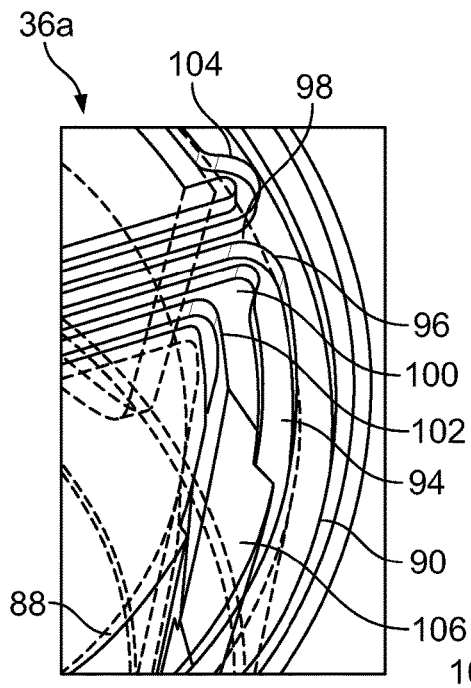
FIG. 17 is a perspective view of another embodiment of a centrifugal separation chamber of a fluid flow circuit.
Figure 17A:
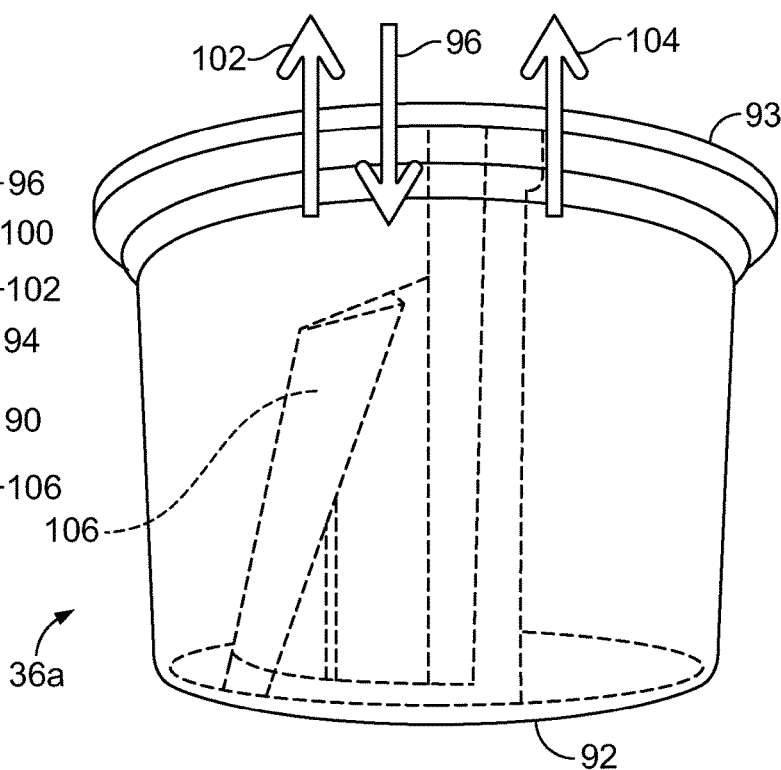
FIG. 17A is a front elevational view of the centrifugal separation chamber of FIG. 17.
Figure 17B:
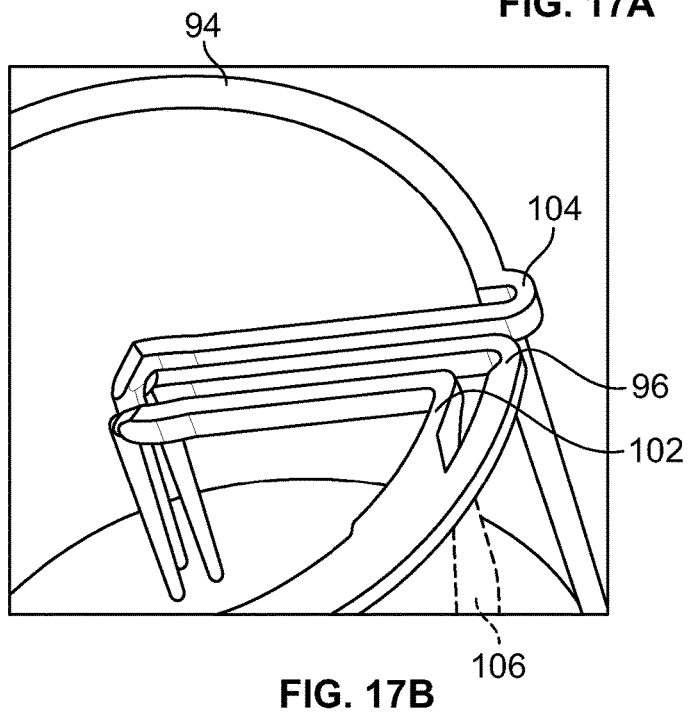
FIG. 17B is a top perspective view of the fluid flow path through the centrifugal separation chamber of FIG. 17.

It should be understood that the centrifugal separation chamber 36 illustrated in FIG. 16 is merely exemplary and that the centrifugal separation chamber may be differently configured without departing from the scope of the present disclosure. For example, FIGS. 17 and 17A show an alternative embodiment of a centrifugal separation chamber 36a, while FIG. 17B illustrates the fluid flow path defined by the centrifugal separation chamber 36a. The centrifugal separation chamber 36a is similar to the centrifugal separation chamber 36 except for the location at which the inlet 96 opens into the channel 94. In the centrifugal separation chamber 36 of FIG. 16, the inlet 96 opens into the channel 94 adjacent to the first end wall portion 92 (while the outlets 102 and 104 open into the channel 94 adjacent to the second end wall portion 93), as best shown in FIGS. 16A and 16B. In contrast, the inlet 96 of the centrifugal separation chamber 36a of FIG. 17 opens into the channel 94 adjacent to the second end wall portion 93 (along with the outlets 102 and 104), as best shown in FIGS. 17A and 17B. The location at which the inlet 96 opens into the channel 94 may affect the separation of fluid within the channel 94, so the centrifugal separation chamber 36 of FIG. 16 may be preferable for certain procedures or for use in combination with certain blood separation devices, while the centrifugal separation chamber 36a of FIG. 17 may be preferable for other procedures or for use in combination with other blood separation devices.

Figure 18:
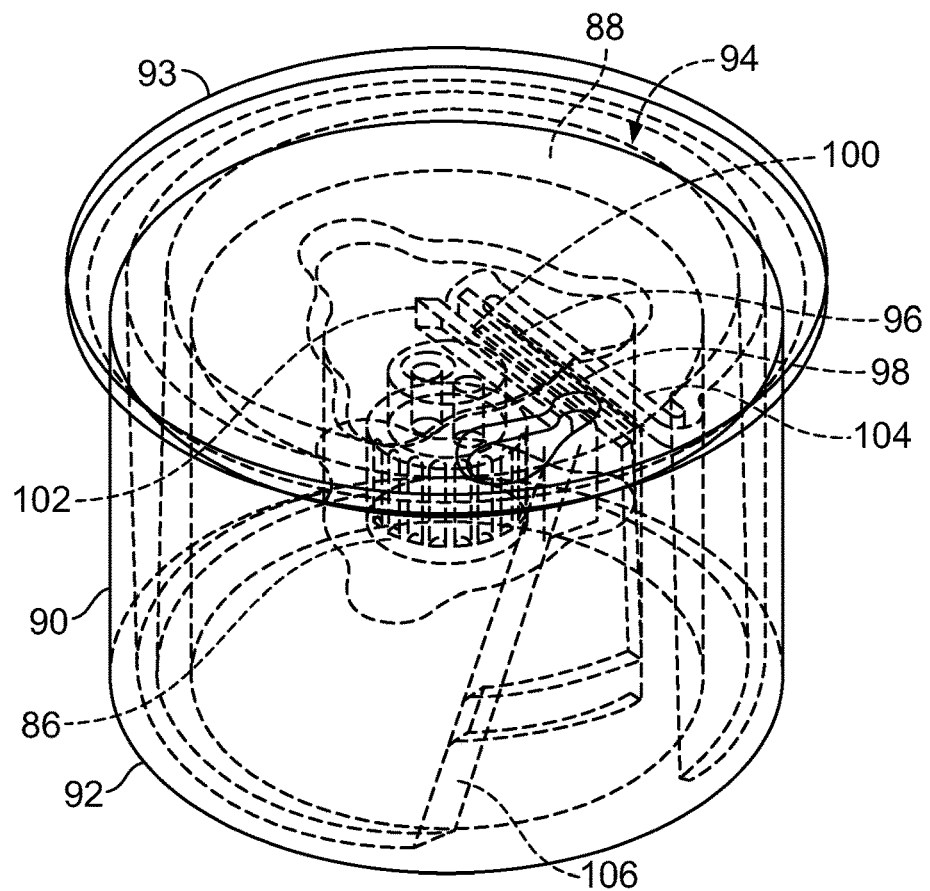
FIG. 18 is a perspective view of a third embodiment of a centrifugal separation chamber of a fluid flow circuit.
Figure 18A:
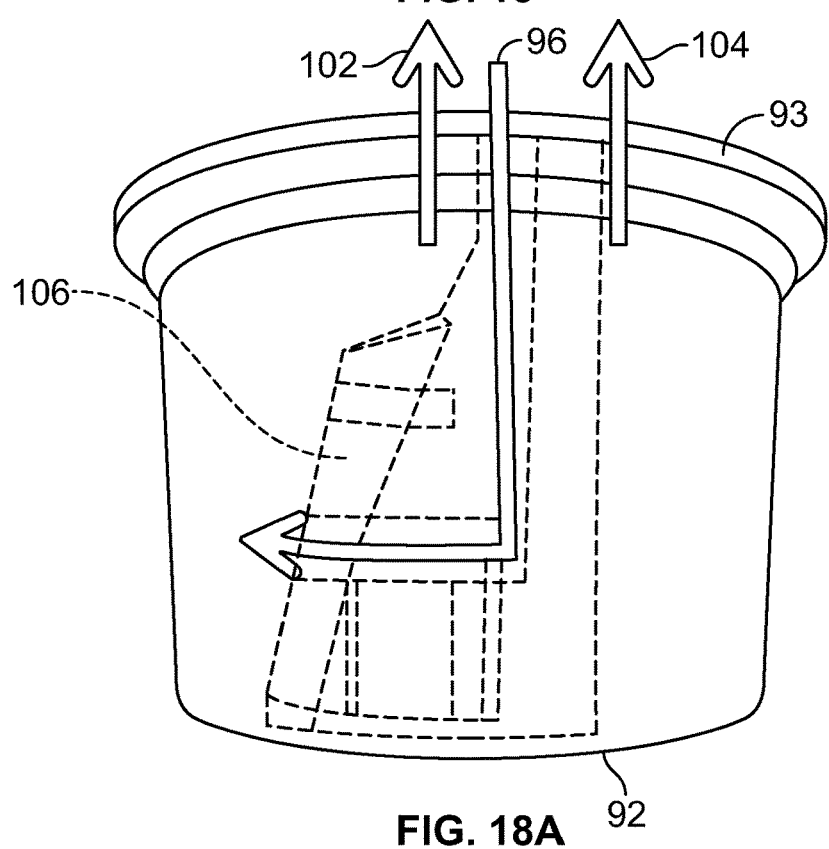
FIG. 18A is a front elevational view of the centrifugal separation chamber of FIG. 18.

FIGS. 18 and 18A show another exemplary embodiment of a centrifugal separation chamber 36b suitable for incorporation into a fluid flow circuit 12. The centrifugal separation chamber 36b is similar to the centrifugal separation chambers 36 and 36a of FIGS. 16 and 17 except for the location at which the inlet 96 opens into the channel 94. In contrast to the inlets 96 of the centrifugal separation chambers 36 and 36a of FIGS. 16 and 17, the inlet 96 of the centrifugal separation chamber 36b of FIG. 18 opens into the channel 94 at an intermediate axial location that is spaced from the first and second end wall portion 92 and 93 (while the outlets 102 and 104 open into the channel adjacent to the second end wall portion 93), as best shown in FIG. 18A. The inlet 96 may open into the channel 94 at a location that is closer to the first end wall portion 92 than to the second end wall portion 93, at a location that is closer to the second end wall portion 93 than to the first end wall portion 92, or at a location that is equally spaced between the first and second end wall portions 92 and 93. The axial location at which the inlet 96 opens into the channel 94 may affect the separation of fluid within the channel 94, so the preferred location at which the inlet 96 opens into the channel 94 (which may also depend upon the nature of the blood separation device paired with the centrifugal separation chamber 36b) may be experimentally determined.

1. Centrifugal Separation and Interface Detection Principles

Blood flowed into the channel 94 separates into an optically dense layer RBC and a less optically dense layer PRP (FIGS. 19-21) as the centrifugal separation chamber 36 is rotated about the rotational axis 38. The optically dense layer RBC forms as larger and/or heavier blood particles move under the influence of centrifugal force toward the outer (high-g) wall portion 90. The optically dense layer RBC will typically include red blood cells (and, hence, may be referred to herein as the "RBC layer") but, depending on the speed at which the centrifugal separation chamber 36 is rotated, other cellular components (e.g., larger white blood cells) may also be present in the RBC layer RBC.

The less optically dense layer PRP typically includes platelet-rich plasma (and, hence, will be referred to herein as the "PRP layer"). Depending on the speed at which the centrifugal separation chamber 36 is rotated and the length of time that the blood is resident therein, other components (e.g., smaller white blood cells and anticoagulant) may also be present in the PRP layer PRP.

In one embodiment, blood introduced into the channel 94 via the inlet 96 will travel in a generally clockwise direction (in the orientation of FIG. 16) as the RBC layer RBC separates from the PRP layer PRP. The RBC layer RBC continues moving in the clockwise direction as it travels the length of the channel 94 along the outer side wall portion 90, from the upstream end to the downstream end, where it exits the channel 94 via the second outlet 104. The PRP layer PRP separated from the RBC layer RBC reverses direction, moving counterclockwise along the inner side wall portion 88 to the first outlet 102, adjacent to the inlet 96.

The inner side wall portion 88 may be tapered inward as it approaches the second outlet 104 to force the plasma liberated at or adjacent to the downstream end of the channel 94 to drag the interface back towards the upstream end of the channel 94, where the lower surface hematocrit will resuspend any platelets settled on the interface.

Figure 19:
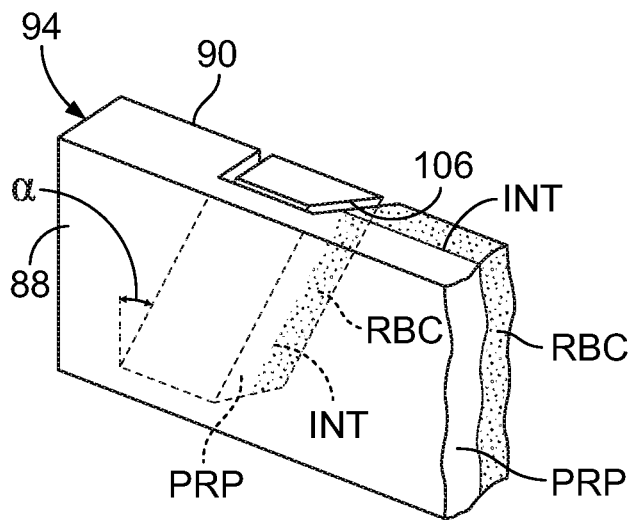
FIG. 19 is an enlarged perspective view of a portion of a channel of any of the centrifugal separation chambers of FIGS. 16-18A, with an interface between separated blood components being positioned at a desired location on a ramp defined within the channel.
Figure 20:
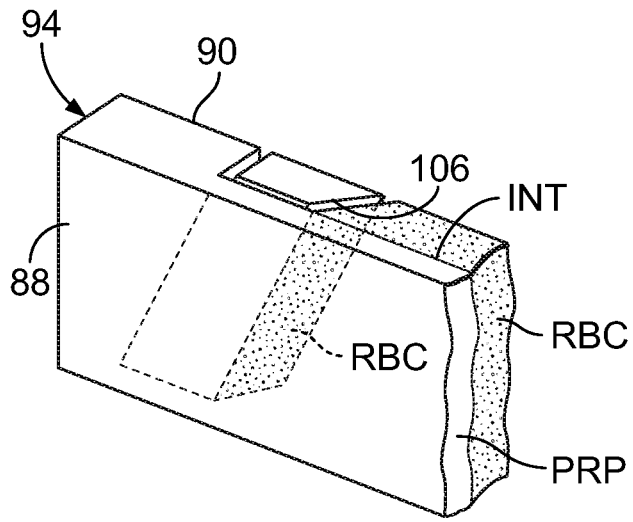
FIG. 20 is an enlarged perspective view of the channel and ramp of FIG. 19, with the interface being at an undesired high location on the ramp.
Figure 21:
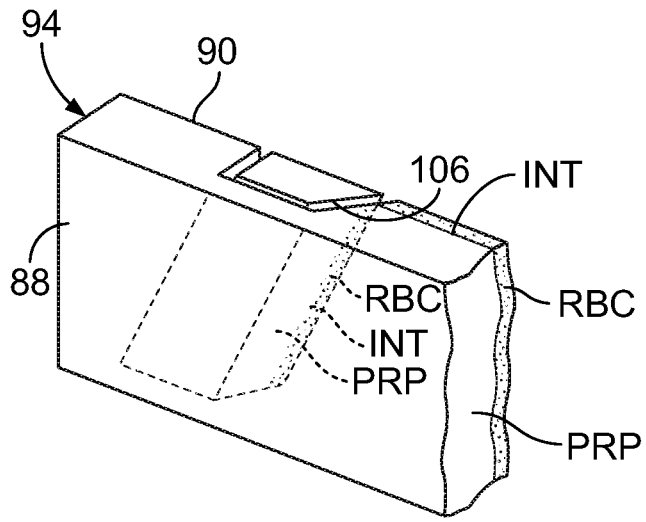
FIG. 21 is an enlarged perspective view of the channel and ramp of FIG. 19, with the interface being at an undesired low location on the ramp.

As described above, the transition between the RBC layer RBC and the PRP layer PRP may be referred to as the interface INT. The location of the interface INT within the channel 94 of the centrifugal separation chamber 36 can dynamically shift during blood processing, as FIGS. 19-21 show. If the location of the interface INT is too high (that is, if it is too close to the inner side wall portion 88 and the first outlet 102, as in FIG. 20), red blood cells can flow into the first outlet 102, potentially adversely affecting the quality of the low density components (platelet-rich plasma). On the other hand, if the location of the interface INT is too low (that is, if it resides too far away from the inner wall portion 88, as FIG. 21 shows), the collection efficiency of the system may be impaired.

The ideal or target interface INT may be experimentally determined, which may vary depending on any of a number of factors (e.g., the configuration of the centrifugal separation chamber 36, the rate at which the centrifugal separation chamber 36 is rotated about the rotational axis 38, etc.).

As described above, the blood separation device 10 may include an interface monitoring system and a controller 18 with an interface control module to monitor and, as necessary, correct the position of the interface INT. In one embodiment, the centrifugal separation chamber 36 is formed with a ramp 106 extending from the high-g wall portion 90 at an angle α across at least a portion of the channel 94 (FIGS. 16 and 19-21). The angle α, measured with respect to the rotational axis 38 is about 25° in one embodiment. FIGS. 19-21 show the orientation of the ramp 106 when viewed from the low-g side wall portion 88 of the centrifugal separation chamber 36. Although it describes a flexible separation chamber, the general structure and function of the ramp 106 may be better understood with reference to U.S. Pat. No. 5,632,893, which is incorporated herein by reference. The ramp 106 may be positioned at any of a number of locations between the upstream and downstream ends of the channel 94, but in one embodiment, the ramp 106 may be positioned generally adjacent to the first outlet 102, in the path of fluid and/or a fluid component moving from the inlet 96 to the first outlet 102.

The ramp 106 makes the interface INT between the RBC layer RBC and the PRP layer PRP more discernible for detection, displaying the RBC layer RBC, PRP layer PRP, and interface INT for viewing through a light-transmissive portion of the centrifugal separation chamber 36. To that end, the ramp 106 and at least the portion of the centrifugal separation chamber 36 angularly aligned with the ramp 106 may be formed of a light-transmissive material, although it may be advantageous for the entire centrifugal separation chamber 36 to be formed of the same light-transmissive material.

In the illustrated embodiment, the light source 50 of the interface monitoring system is secured to a fixture or wall of the centrifuge compartment 32 and oriented to emit a light that is directed toward the rotational axis 38 of the centrifugal separator 16, as shown in FIGS. 12A-12C. If the light detector 52 is positioned at an angle with respect to the light source 50 (as in the illustrated embodiment), the light L emitted by the light source 50 must be redirected from its initial path before it will reach the light detector 52. In the illustrated embodiment, the light L is redirected by a reflector that is associated with a light-transmissive portion of the inner side wall portion 88, as shown in FIGS. 12A and 12B. The reflector may be a separate piece that is secured to the inner side wall portion 88 (e.g., by being bonded thereto) or may be integrally formed with the body of the centrifugal separation chamber 36.

In one embodiment, the reflector may be a reflective surface, such as a mirror, that is oriented (e.g., at a 45° angle) to direct light L emitted by the light source 50 to the light detector 52. In another embodiment, the reflector is provided as a prismatic reflector 108 (FIGS. 12C, 22, and 22A), which is formed of a light-transmissive material (e.g., a clear plastic material) and has inner and outer walls 110 and 112 and first and second end walls 114 and 116 (FIG. 22). The inner wall 110 is positioned against the inner side wall portion 88 of the centrifugal separation chamber 36 and is oriented substantially perpendicular to the initial path of the light L from the light source 50. This allows light L from the light source 50 to enter into the prismatic reflector 108 via the inner wall 110 while continuing along its initial path. The light L continues through the prismatic reflector 108 along its initial path until it encounters the first end wall 114. The first end wall 114 is oriented at an angle (e.g., an approximately 45° angle) with respect to the first surface 110 and the second end wall 116, causing the light to be redirected within the prismatic reflector 108, rather than exiting the prismatic reflector 108 via the first end wall 114.

The first end wall 114 directs the light L at an angle to its initial path (which may be an approximately 90° angle, directing it from a path toward the rotational axis 38 to a path that is generally parallel to the rotational axis 38) toward the second end wall 116 (FIG. 22A). The first end wall 114 and the inner and outer walls 110 and 112 of the prismatic reflector 108 may be configured to transmit the redirected light L from the first end wall 114 to the second end wall 116 by total internal reflection. The second end wall 116 is oriented substantially perpendicular to the redirected path of the light L through the prismatic reflector 108, such that the light L will exit the prismatic reflector 108 via the second end wall 116, continuing along its redirected path. In one embodiment, the second end wall 116 is roughened or textured or otherwise treated or conditioned to diffuse the light L as it exits the prismatic reflector 108, which may better ensure that the light L reaches the light detector 52 (FIG. 12C).

The prismatic reflector 108 may be angularly aligned with the ramp 106, such that the light L from the light source 50 will only enter into the prismatic reflector 108 when the ramp 106 has been rotated into the path of the light L. At all other times (when the ramp 106 is not in the path of the light L), the light L will not reach the prismatic reflector 108 and, thus, will not reach the light detector 52.

Figure 23:
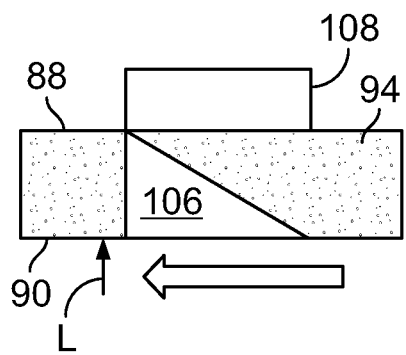
FIGS. 23-23C are diagrammatic views of the ramp and prismatic reflector of the centrifugal separation chamber passing through the path of light from the light source during a calibration phase.
Figure 24:
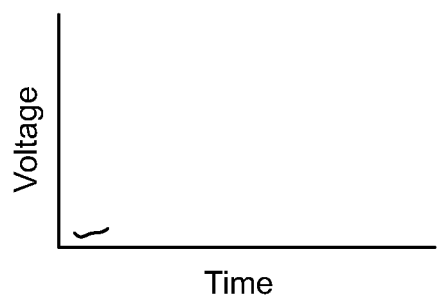
FIGS. 24-24C are diagrammatic views of the voltage output or signal transmitted by the light detector during the conditions shown in FIGS. 23-23C, respectively.
Figure 23A:
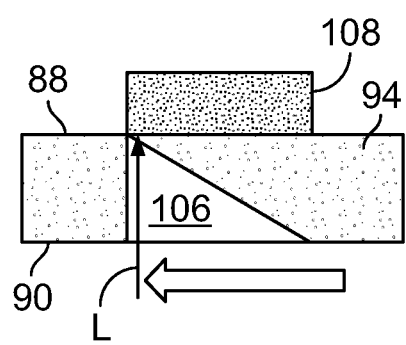
Figure 23B:
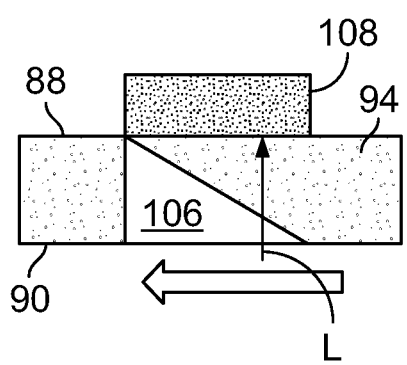
Figure 23C:
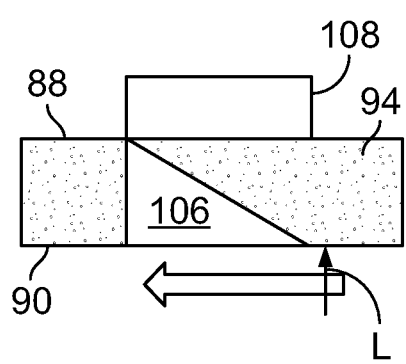

This is illustrated in FIGS. 23-23C, which show the ramp 106 and prismatic reflector 108 as the centrifugal separation chamber 36 is rotated about the rotational axis 38 (while the light source 50 remains in a fixed location). In FIG. 23, the ramp 106 and prismatic reflector 108 have not yet been rotated into the initial path of the light L from the light source 50. At this time, no light is transmitted to the light detector 52, such that the output voltage of the light detector 52 (i.e., the signal transmitted from the light detector 52 to the controller 18) is in a low- or zero-state (FIG. 24).

Figure 24A:
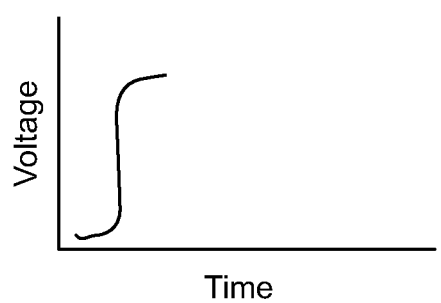

Upon the ramp 106 first being rotated into the initial path of the light L from the light source 50 (FIG. 23A), the light L will begin to reach the prismatic reflector 108, which directs the light L to the light detector 52. This causes the voltage output of the light detector 52 (i.e., the signal transmitted from the light detector 52 to the controller 18) to increase to a non-zero value or state, as shown in FIG. 24A.

Figure 24B:
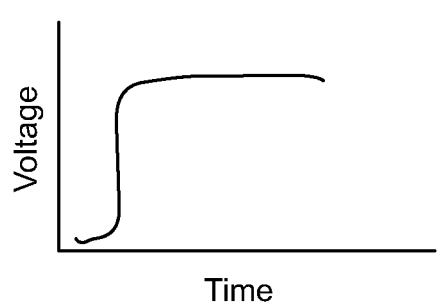

During a calibration phase, the channel 94 is filled with a fluid that will transmit the light L rather than absorbing or reflecting the light or otherwise preventing the light L from reaching the prismatic reflector 108, such that the voltage output of the light detector 52 will remain generally constant as the ramp 106 and prismatic reflector 108 are rotated through the initial path of the light L from the light source 50 (FIGS. 23B and 24B). Such a calibration phase may coincide with a priming phase during which saline is pumped through the fluid flow circuit 12 to prime the fluid flow circuit 12 or may comprise a separate phase. A calibration phase may be useful in ensuring the proper operation of the light source 50 and the light detector 52, standardizing the readings taken during a separation procedure in case of any irregularities or imperfections of the centrifugal separation chamber 36, and establishing a baseline value for the signal transmitted from the light detector 52 to the controller 18 when the ramp 106 and prismatic reflector 108 are aligned with the light source 50. As will be described in greater detail, the voltage output of the light detector 52 will typically not remain constant as the ramp 106 and prismatic reflector 108 are rotated through the initial path of the light L from the light source 50 because the different fluid layers displayed on the ramp 106 will allow different amounts of light L to reach the prismatic reflector 108.

Figure 24C:
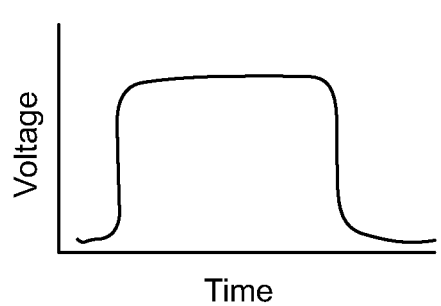

The ramp 106 and prismatic reflector 108 are eventually rotated out of alignment with the light source 50 (FIG. 23C), at which time no light L will reach the prismatic reflector 108 and the voltage output of the light detector 52 will return to its low- or zero-state (FIG. 24C).

Figure 25:
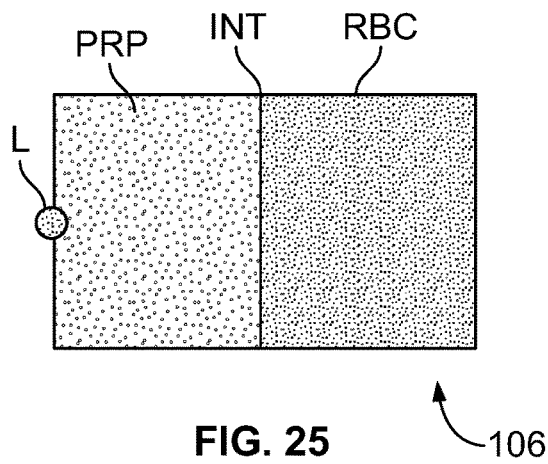
FIG. 25 is a diagrammatic view of the ramp being rotated into alignment with a small-diameter light beam from the light source.
Figure 26:
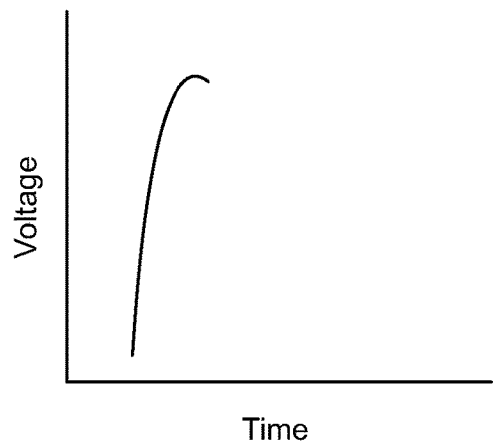
FIG. 26 is a diagrammatic view of the voltage output or signal transmitted by the light detector during the condition shown in FIG. 25.
Figure 25A:
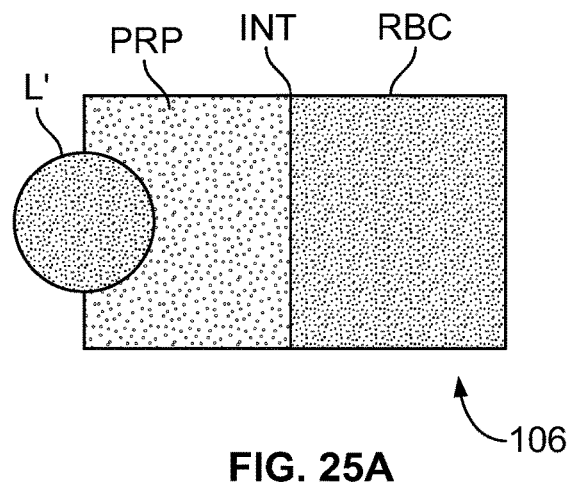
FIG. 25A is a diagrammatic view of the ramp being rotated into alignment with a large-diameter light beam from the light source.
Figure 26A:
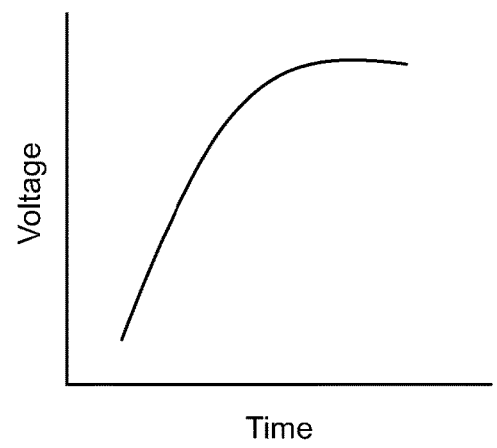
FIG. 26A is a diagrammatic view of the voltage output or signal transmitted by the light detector during the condition shown in FIG. 25A.

It may be advantageous for the light L to have a relatively small diameter for improved resolution of the signal that is generated by the light detector 52. For example, FIG. 25 illustrates a ramp 106 displaying separated blood components being rotated into the path of a small-diameter light L, while FIG. 25A illustrates the ramp 106 being rotated into the path of a large-diameter light L'. Ideally, the voltage output of the light detector 52 (i.e., the signal that it transmits to the controller 18) instantaneously increases from its zero-state to a higher state as soon as the ramp 106 and prismatic reflector 108 are rotated into the initial path of the light L from the light source 50. When a small-diameter light L is employed (FIG. 25), the entirety of the light L will be aligned with the ramp 106 and prismatic reflector 108 very quickly, resulting in a very rapid change in the voltage output of the light detector 52 (FIG. 26). In contrast, when a large-diameter light L' is employed (FIG. 25A), it will take a longer time for the entirety of the light L' to be aligned with the ramp 106 and the prismatic reflector 108, resulting in a slower change in the voltage output of the light detector 52 (FIG. 26A). Thus, it will be seen by comparing FIGS. 26 and 26A that a smaller diameter light will better approximate the idealized instantaneous change in the voltage output of the light detector 52.

The diameter of the light L may be decreased by providing a light source 50 that emits a focused light L having a relatively small diameter, such as by providing the light source 50 as a laser instead of as a typical light-emitting diode. To effectively decrease the diameter of the light L, the light source 50 may include a lens 118 (FIG. 12C) that focuses the light L on a point P (which may be only a few thousandths of an inch in diameter) within the centrifugal separation chamber 36. In one embodiment, this focal point P is the approximate midpoint of surface of the ramp 106 upon which the interface INT will be displayed (i.e., the inclined surface of the ramp 106 facing the inner side wall portion 88 or the last surface of the ramp 106 that the light L passes through before exiting the ramp 106). The circumferential displacement of the ramp 106 may be approximately 0.25 inch as the ramp 106 is rotated past the light L, in which case the resolution may be approximately 0.5%.

2. Exemplary Interface Detection and Correction Procedure

During separation of blood within the channel 94, the light L from the light source 50 travels through a light-transmissive portion of the outer side wall portion 90 and the ramp 106 to intersect the separated blood components thereon when the ramp 106 has been rotated into the initial path of the light L. After passing through the ramp 106, the light continues through the channel 94 and the fluids in the channel 94. At least a portion of the light L (i.e., the portion not absorbed or reflected by the fluids) exits the channel 94 by striking and entering a light-transmissive portion of the inner side wall portion 88. The light L passes through the inner side wall portion 88 and enters the prismatic reflector 108, which redirects the light L from its initial path to the light detector 50, as described above. Thus, it will be seen that the light L reaches the light detector 52 after intersecting and traveling through the separated blood components in the channel 94 only once, in contrast to known systems in which light from a light source travels through a ramp and a fluid-filled channel before being reflected back through the channel to reach a light detector. Requiring the light L to traverse the fluid-filled channel 94 only once before reaching the light detector 52 instead of twice may be advantageous in that it tends to increase the intensity of the light L that reaches the light detector 52, which may improve monitoring and correction of the interface location.

The light detector 52 generates a signal that is transmitted to the interface control module of the controller 18, which can determine the location of the interface INT on the ramp 106. In one embodiment, the location of the interface INT is associated with a change in the amount of light L that is transmitted through the PRP layer PRP and the RBC layer RBC. For example, the light source 50 may be configured to emit a light L that is more readily transmitted by platelet-rich plasma than by red blood cells, such as red visible light (from a laser or a differently configured light source 50), which is substantially absorbed by red blood cells. The PRP layer PRP and the RBC layer RBC each occupy a certain portion of the ramp 106, with the light detector 52 receiving different amounts of light L depending on whether the light L travels through the PRP layer PRP on the ramp 106 or the RBC layer RBC on the ramp 106. The percentage of the ramp 106 occupied by each layer is related to the location of the interface INT in the channel 94. Thus, by measuring the amount of time that the voltage output or signal from the light detector 52 is relatively high (corresponding to the time during which the light L is passing through only the PRP layer PRP on the ramp 106), the controller 18 may determine the location of the interface INT and take steps to correct the location of the interface INT, if necessary.

Figure 27:
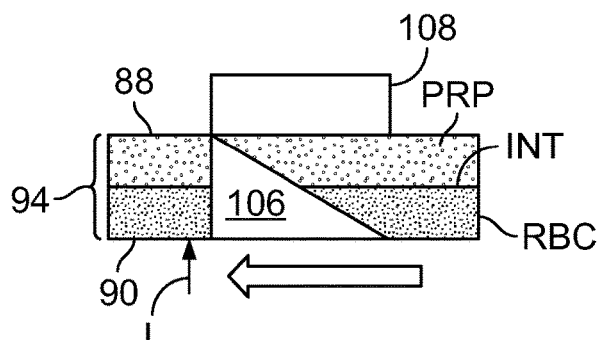
FIGS. 27-27C are diagrammatic views of the ramp and prismatic reflector passing through the path of light from the light source during a separation procedure.
Figure 28:
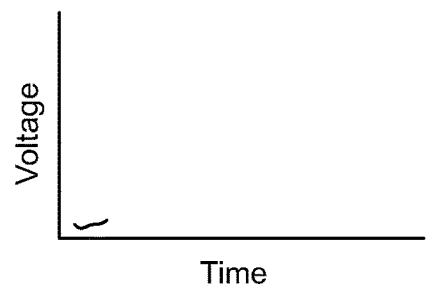
FIGS. 28-28C are diagrammatic views of the voltage output or signal transmitted by the light detector during the conditions shown in FIGS. 27-27C, respectively.
Figure 27A:
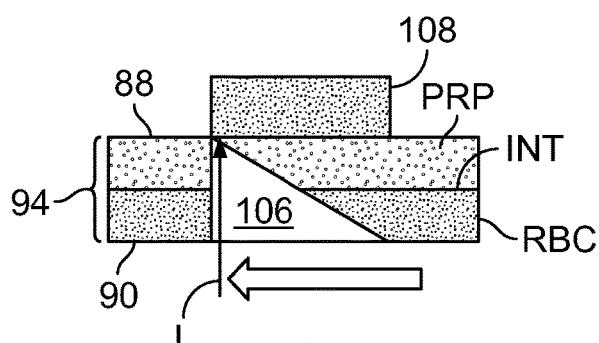
Figure 28A:
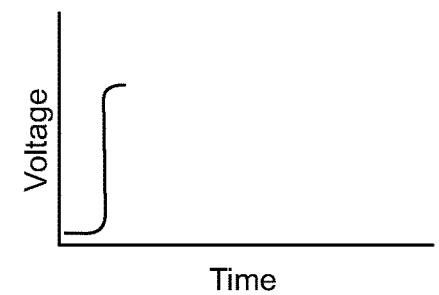
Figure 27B:
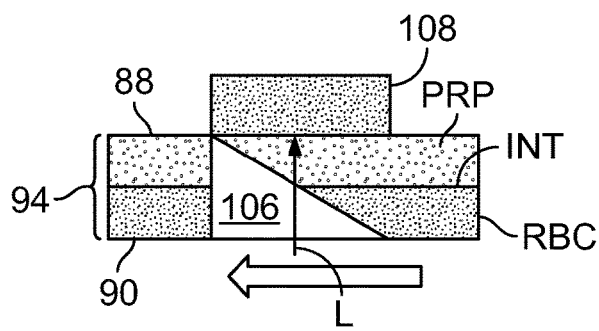
Figure 28B:
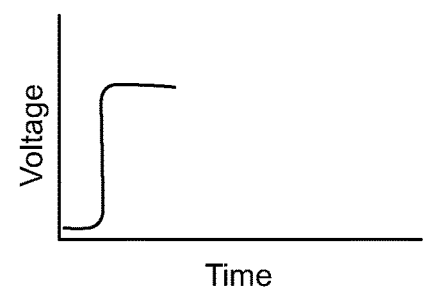
Figure 27C:
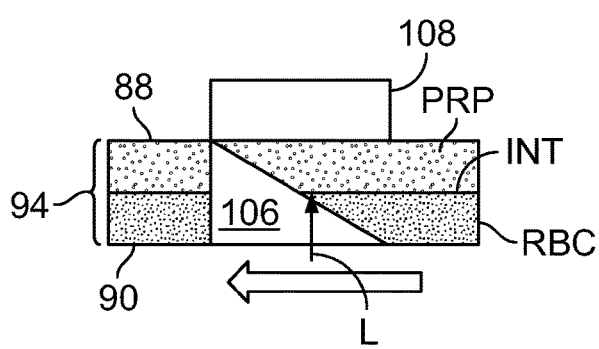
Figure 28C:
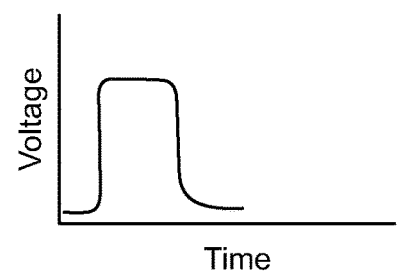

FIGS. 27-27C show a portion of the ramp 106 being rotated into and through the initial path of the light L from the light source 50. Four specific events are shown: just before the ramp 106 is rotated into the path of the light L (FIG. 27), the ramp 106 first being rotated into the path of the light L (FIG. 27A), just before the interface INT displayed on the ramp 106 is rotated into the path of the light L (FIG. 27B), and just after the interface INT is rotated into the path of the light L (FIG. 27C). FIGS. 28-28C illustrate the voltage output of the light detector 52 (corresponding to the signal that it transmits to the controller 18) during each of these events.

As described above, the light detector 52 will receive no light L from the light source 50 when the prismatic reflector 108 is out of alignment with the initial path of the light L from the light source 50, as shown in FIG. 27. FIG. 28 shows that the output voltage of the light detector 52 (i.e., the signal transmitted from the light detector 52) to the controller 18) at this time is in a low- or zero-state.

When the ramp 106 is first rotated into the path of light L from the light source 50 (FIG. 27A), the light detector 52 may begin receiving light L. The amount of light L received by the light detector 52 depends upon the fluid on the ramp 106 encountered by the light L (i.e., the fluid in the channel 94 between the ramp 106 and the inner side wall portion 88 that the light L must traverse before being directed to the light detector 52). As described above, the PRP layer PRP occupies a certain percentage of the channel 94 adjacent to the inner side wall portion 88, while the RBC layer RBC occupies a certain percentage of the channel 94 adjacent to the outer side wall portion 90 (with the interface INT positioned at the transition between the two separated blood component layers). The illustrated ramp 106 is closest to the inner side wall portion 88 at its left end (in the orientation of FIGS. 27-27C), while being farther spaced from the inner side wall portion 88 at its right end. At and adjacent to its left end, the ramp 106 will display only the fluid positioned closest to the inner side wall portion 88 (i.e., the PRP layer PRP), while the ramp 106 will display only the fluid positioned closest to the outer side wall portion 90 (i.e., the RBC layer RBC) at and adjacent to its right end, as shown in FIGS. 27-27C. At some point between its ends, the angled ramp 106 will be at a radial position where it will display the transition between the PRP layer PRP and the RBC layer RBC (i.e., the interface INT). Hence, the location of the interface INT on the ramp 106 is dependent upon the percentage of the width of the ramp 106 that displays the PRP layer PRP (which is indicative of the percentage of the channel 94 occupied by the PRP layer PRP) and the percentage of the width of the ramp 106 that displays the RBC layer RBC (which is indicative of the percentage of the channel 94 occupied by the RBC layer RBC).

It should be understood that the percentage of the ramp 106 occupied by the PRP layer PRP and by the RBC layer RBC is not necessarily equal to the percentage of the channel 94 occupied by the PRP layer PRP and by the RBC layer RBC, but that the percentage of the ramp 106 occupied by a separated blood component layer may be merely indicative of the percentage of the channel 94 occupied by that separated blood component layer.

In such an embodiment, as the ramp 106 is rotated into the path of the light L from the light source 50, the light L will first encounter the portion of the ramp 106 that is positioned closest to the inner side wall portion 88 (i.e., the section of the ramp 106 that most restricts the channel 94), as shown in FIG. 27A. As described above, the PRP layer PRP will be positioned adjacent to the inner side wall portion 88 as it separates from the RBC layer RBC, such that the fluid displayed on this radially innermost section of the ramp 106 (i.e., the fluid present in the channel 94 between the ramp 106 and the inner side wall portion 88) will be the PRP layer PRP. The light is substantially transmitted through the PRP layer PRP to the inner side wall portion 88, and through the light-transmissive inner side wall portion 88 to the prismatic reflector 108, which redirects the light L to the light detector 52. This causes the voltage output of the light detector 52 (i.e., the signal transmitted from the light detector 52 to the controller 18) to increase to a non-zero value or state, as shown in FIG. 28A. Depending on the nature of the light L, the amount of light L received by the light detector 52 (and, hence, the magnitude of the voltage output) after the light L has passed through the PRP layer PRP may be greater than, less than, or equal to the amount of light L received by the light detector 52 after passing through saline during the calibration phase described above.

Further rotation of the ramp 106 through the path of light L from the light source 50 exposes the light L to portions of the ramp 106 that are increasingly spaced from the inner side wall portion 88 (i.e., the light L travels through portions of the channel 94 that are less restricted by the ramp 106 as the ramp 106 is rotated through the path of the light L). Up until the time that the interface INT on the ramp 106 is rotated into the path of the light L (as shown in FIG. 27B), the only fluid in the channel 94 that the light L will have passed through will be the PRP layer PRP, such that a generally uniform level of light reaches the light detector 52 between the conditions shown in FIGS. 27A and 27B. Accordingly, the voltage output of the light detector 52 will be generally uniform (at an elevated level) the whole time that the ramp 106 passes through the path of the light L before being exposed to the interface INT, as shown in FIG. 28B. The controller 18 may be programmed and/or configured to consider a signal that deviates from a maximum signal level (e.g., a 10% decrease) to be part of the elevated signal for purposes of calculating the pulse width of the signal. The controller 18 will treat a greater deviation (i.e., a greater decrease in the magnitude of the signal) as the end of the elevated signal for purposes of calculating the pulse width of the signal.

Just after the interface INT has been rotated into the path of light L from the light source 50, the light L will begin to encounter the RBC layer RBC in the channel 94, as shown in FIG. 27C). As described above, the RBC layer RBC will be positioned adjacent to the outer side wall portion 90 as it separates from the PRP layer PRP, such that the RBC layer RBC will not be displayed on the ramp 106 until the ramp 106 is spaced a greater distance away from the inner side wall portion 88 (i.e., toward the right end of the ramp 106 in the orientation of FIGS. 27-27C). Less light L is transmitted through the RBC layer RBC than through the PRP layer PRP (which may include all or substantially all of the light L being absorbed by the RBC layer RBC), such that the amount of light L that reaches the light detector 52 will decrease compared to the amount of light L that reaches the light detector 52 while traveling through only the PRP layer PRP in the channel 94 (FIGS. 27A and 27B).

When receiving less light L, the voltage output or signal from the light detector 52 will decrease to a lower level than when the light L was passing through only the PRP layer PRP in the channel 94, as shown in FIG. 28C. When the light L encounters the RBC layer RBC in the channel 94, the light detector 52 may be generating a signal or voltage output that is approximately equal to its zero-state (as in FIG. 28, when the light detector 52 is receiving no light L) or a signal or voltage output that is some degree less than the magnitude of the signal or voltage output generated while the light L encounters only the PRP layer PRP in the channel 94. The controller 18 may be programmed and/or configured to recognize this lower level signal as representing the presence of the RBC layer RBC on the ramp 106 (and in the portion of the channel 94 being traversed by the light L) and treat this lower level signal as the end point of the elevated signal generated by the light detector 52 while light L passes through only the PRP layer PRP in the channel 94.

Thus, the pulse width of the elevated signal from the light detector 52 to the controller 18 (i.e., the time during which light L is traversing only the PRP layer PRP in the channel 94) is determined by the percentages of the ramp 106 that are occupied by the PRP layer PRP and the RBC layer RBC. Accordingly, a greater pulse width of the signal from the light detector 52 to the controller 18 is associated with the PRP layer PRP occupying a larger portion of the ramp 106 (as shown in FIG. 29 from the point of view of the light source 50, which may correspond to the condition shown in FIG. 20) and will be indicative of a thinner RBC layer RBC on the ramp 106 (and in the channel 94). Conversely, a signal from the light detector 52 to the controller 18 having a narrower pulse width is associated with the PRP layer PRP occupying a smaller portion of the ramp 106 (as shown in FIG. 29A) and will be indicative of a thicker RBC layer RBC on the ramp 106 (and in the channel 94).

The controller 18 may compare the pulse width of the signal to the pulse width generated during the calibration phase (described above and shown in FIG. 29C), which corresponds to the pulse width when light L is transmitted to the light detector 52 over the entire width of the ramp 106. The pulse width of the signal generated by the light detector 52 during the calibration phase may be referred to as the saline calibration signal. Comparing these two pulse widths will indicate the percentage of the ramp 106 that is occupied by the PRP layer PRP and by the RBC layer RBC, which information the controller 18 may use to determine the location of the interface INT within the channel 94. In particular, the interface position may be calculated as follows:

$$\text{Interface position (\%)} = ((\text{saline calibration pulse width} - \text{current plasma pulse width})/\text{saline calibration pulse width}) * 100 \quad \text{[Equation 1]}$$

It will be seen that Equation 1 effectively calculates the percentage of the ramp 106 that is occupied by the RBC layer RBC, as the difference between the two pulse widths corresponds to the length of time that the ramp 106 is rotated through the path of the light L without the light detector 52 received an elevated level of light L (i.e., the amount of time that the ramp 106 is rotated through the path of the light L while the RBC layer RBC is present on the ramp 106).

When the location of the interface INT on the ramp 106 has been determined, the interface control module compares the actual interface location with a desired interface location, which may be referred to as the setpoint S. The difference between the setpoint S and the calculated interface position may be referred to as the error signal E, which is shown in FIG. 30. It should be understood that so expressing the error signal E in terms of a targeted red blood cell percentage value (i.e., the percentage of the ramp 106 that is actually occupied by the RBC layer RBC vs. the percentage of the ramp 106 which should be occupied by the RBC layer RBC) is merely exemplary, and that the error signal E may be expressed or calculated in any of a number of other ways.

When the control value is expressed in terms of a targeted red blood cell percentage value, a negative error signal E indicates that the RBC layer RBC on the ramp 106 is too large (as FIG. 20 shows). The interface control module of the controller 18 generates a signal to adjust an operational parameter accordingly, such as by reducing the rate at which platelet-rich plasma is removed through the first outlet 102 under action of a pump of the blood separation device 10. The interface INT moves toward the desired control position (as FIG. 19 shows), where the error signal is zero.

A positive error signal indicates that the RBC layer RBC on the ramp 106 is too small (as FIGS. 21 and 30 show). The interface control module of the controller 18 generates a signal to adjust an operational parameter accordingly, such as by increasing the rate at which platelet-rich plasma is removed through the first outlet 102 under action of a pump of the blood separation device 10. The interface INT moves toward the desired control position (FIG. 19), where the error signal is again zero.

The exact change in the rate at which platelet-rich plasma is removed from the channel 94 may be calculated using a control algorithm of the interface control module. The control algorithm may take any of a number of forms, including a proportional-integral-derivative ("PID") control system, which works to minimize the difference between the target position of the interface INT on the ramp 106 and the actual position of the interface INT on the ramp 106. The PID control system considers the present difference between the two interface positions ("the P term"), differences between the two interface positions in the past ("the I term"), and a prediction of future differences between the two interface positions ("the D term"). Alternatively, the interface control module of the controller 18 may operate in a proportional-integral ("PI") control mode in which the D term is not a factor, which may provide better (i.e., smoother) interface control than a PID control system. FIG. 31 illustrates how the rate of removal of platelet-rich plasma from the channel 94 may be changed to move the interface INT toward the target interface location or setpoint S. The fluctuations in the interface position are indicative of repeatedly executing a control loop, which comprises: (1) calculating the interface position, (2) calculating the error signal, (3) inputting the error signal into the control algorithm of the interface control module, (4) calculating the control signal, (5) transmitting the control signal to a pump of the blood separation device 10 to cause platelet-rich plasma to be removed from the channel 94 at a different rate, and (6) returning to step (1) of the control loop. As shown in FIG. 31, the setpoint S may change during the course of a procedure, with the interface control module working to first quickly move the interface INT toward the setpoint S and then carry out finer adjustments to the location of the interface INT once it is in the vicinity of the setpoint S. FIG. 31 shows the setpoint S changing as a step function, but it is also within the scope of the present disclosure for the setpoint S to change in other ways during the course of a separation procedure or to remain the same during an entire separation procedure.

It should be understood that this system for controlling the location of the interface INT is merely exemplary and that differently configured and/or functioning systems may be employed without departing from the scope of the present disclosure.

III. Exemplary Separation Procedures

Exemplary blood separation procedures that may be carried out using systems and techniques according to the present disclosure will now be described.

Depending on the blood separation objectives, there is a suitable procedure for separating and collecting any combination of red blood cells, platelets, white blood cells, and (substantially cell-free) plasma. Accordingly, prior to processing, an operator selects the desired protocol (e.g., using an operator interface station, if provided), which informs the controller 18 of the manner in which it is to control the other components of the blood separation device 10 during the procedure.

If the blood source is a donor, the operator may proceed to enter various parameters, such as the donor gender/height/weight. In one embodiment, the operator also enters the target yield for the various blood components (which may also include entering a characteristic of the blood, such as a platelet pre-count) or some other collection control system (e.g., the amount of whole blood to be processed).

If there are any fluid containers (e.g., a platelet storage solution container) that are not integrally formed with the fluid flow circuit 12, they may be connected to the fluid flow circuit 12 (e.g., by piercing a septum of a tube of the fluid flow circuit 12 or via a luer connector), with the fluid flow circuit 12 then being mounted to the blood separation device 10 (including the fluid containers F1-F12 being hung from the weight scales W1-W6, as appropriate). An integrity check of the fluid flow circuit 12 may be executed by the controller 18 to ensure the various components are properly connected and functioning. Following a successful integrity check, the blood source is connected to the fluid flow circuit 12 (e.g., by phlebotomizing a donor), and the fluid flow circuit 12 may be primed (e.g., by saline pumped from a saline bag F2 by operation of one or more of the pumps P1-P6 of the blood separation device 10).

When the fluid flow circuit 12 has been primed, blood separation may begin. The stages of blood separation vary depending on the particular procedure, and will be described in greater detail below.

A. Red Blood Cell Collection

According to one aspect of the present disclosure, the blood separation device 10 may be used to separate and collect red blood cells from blood. If the blood source is a donor, it is typically safe to collect two units of red blood cells (a total of approximately 400 ml), but it is also within the scope of the present disclosure for a different amount of red blood cells to be collected.

A blood separation device 10 according to the present disclosure may be used in combination with a fluid flow circuit 12 having a single blood access device (e.g., a single needle that draws blood from and returns a separated blood component to the same location) or two blood access devices (e.g., one needle that draws blood from a source and a second needle that flows a separated blood component to the same source or to a different recipient). An exemplary fluid flow circuit 12A, 12B and procedure will be described for each arrangement.

1. Single Needle Fluid Flow Circuit and Procedure a. Fluid Flow Circuit

Figure 2:
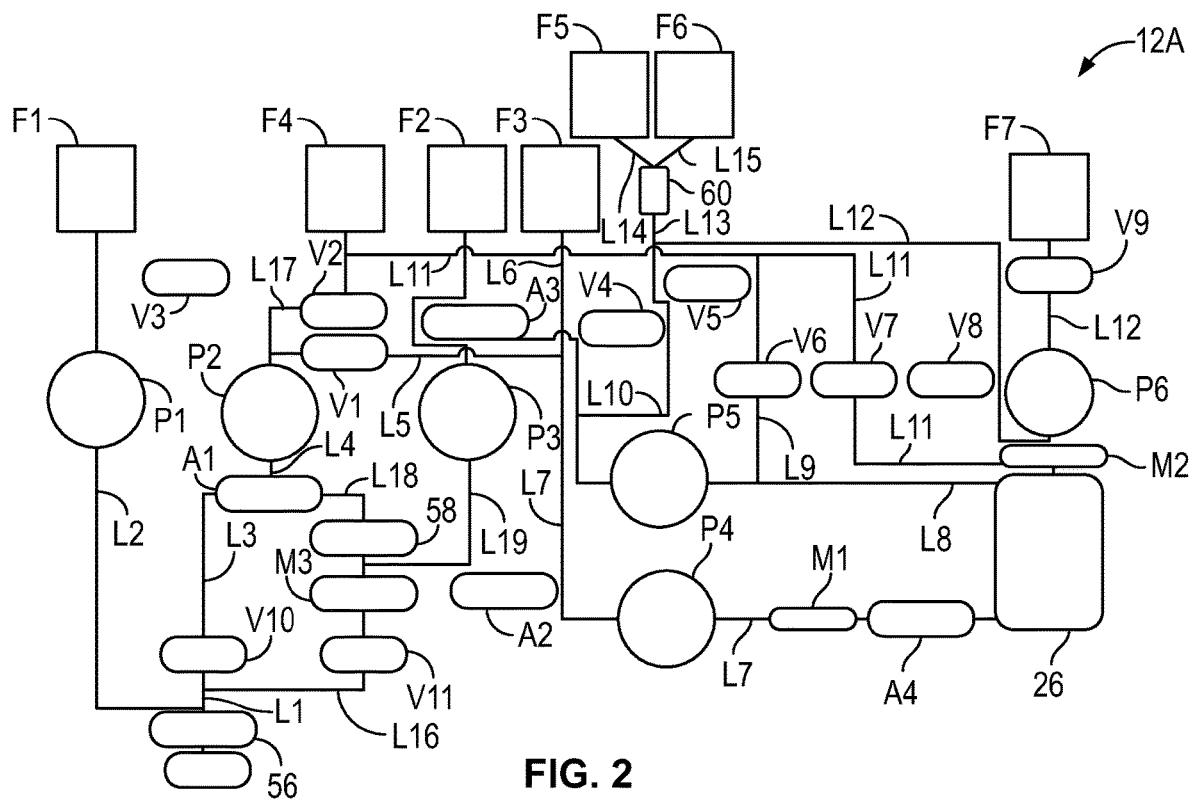
FIGS. 2-11 are schematic views of exemplary disposable fluid flow circuits that may be mounted to the blood separation device of FIG. 1 to complete a blood separation system according to an aspect of the present disclosure.

FIG. 2 is a schematic view of an exemplary fluid flow circuit 12A having a single blood access device (e.g., a needle) for separating and collecting red blood cells from blood. The fluid flow circuit 12A includes a cassette 48 of the type described above and illustrated in FIG. 13, which connects the various components of the fluid flow circuit 12A. The various connections amongst the components of the fluid flow circuit 12 are shown in FIG. 2, which also shows the fluid flow circuit 12A mounted to the blood separation device 10.

Components of the fluid flow circuit 12A interact with many of the components of the blood separation device 10, as will be described, but there are selected components of the blood separation device 10 that are not used in separating and collecting red blood cells using the fluid flow circuit 12A of FIG. 2.

Most notably, the centrifugal separator 16 is not used, but only the spinning membrane separator drive unit 14. There are also selected valves V3, V4, V5, V8 and a pressure sensor A2 of the blood separation device 10 that are not used in the procedure described herein.

b. Draw Phase

Figure 32:
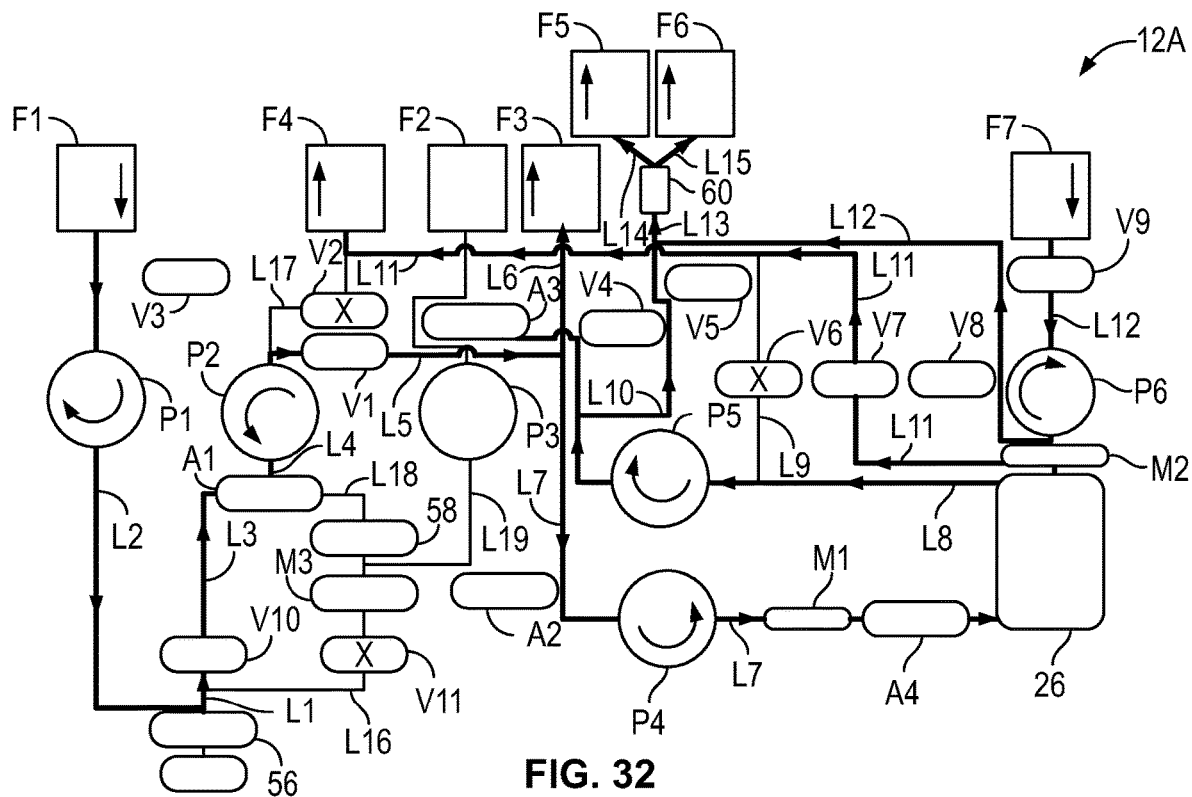
FIGS. 32 and 33 are schematic views of the fluid flow circuit of FIG. 2 mounted on the blood separation device of FIG. 1, showing the system carrying out different fluid flow tasks in connection with separation and collection of red blood cells from blood.

In a first phase (FIG. 32), blood is drawn into the fluid flow circuit 12A from a blood source. If the blood source is a donor, then blood may be drawn into the fluid flow circuit 12A through a single needle that is connected to the cassette 48 by line L1. The line L1 may include a manual clamp 56 that may initially be in a closed position to prevent fluid flow through the line L1. When processing is to begin, an operator may move the manual clamp 56 from its closed position to an open position to allow fluid flow through the line L1. The term "line" is used herein to refer to any fluid flow conduit, whether a flexible tube that is connected to the cassette 48 or a rigidly defined flow path of the cassette 48, and a particular line is not limited to a flexible conduit or a rigidly defined conduit unless stated to the contrary.

The blood is drawn into the line L1 by a pump P2 of the blood separation device 10, which may be referred to as the donor pump. As described above, the donor pump P2 may be a peristaltic pump that interacts with a tubing loop T2 extending from the cassette 48 of the fluid flow circuit 12A.

Anticoagulant may be added to the blood (such that the term "blood" as used herein should be understood to encompass blood with or without anticoagulant added thereto) via line L2 under action of a pump P1 of the blood separation device 10 (which may be referred to as the anticoagulant pump). The anticoagulant pump P1 may be a peristaltic pump that interacts with a tubing loop T1 of the fluid flow circuit 12A to draw anticoagulant from a fluid container F1 (which may be referred to as an anticoagulant bag), through line L2, and through a junction of lines L1 and L2, where it is mixed with blood flowing into the fluid flow circuit 12A.

In the illustrated embodiment, the valve station C10 associated with valve V10 is open to allow blood to flow through lines L3 and L4 and a sensor station S1 associated with pressure sensor A1 of the blood separation device 10. If the blood source is a living body (e.g., a donor), the pressure sensor A1 may communicate with the controller 18 to monitor the pressure within the vein of the blood source.

The cassette 48 includes two valve stations C1 and C2 downstream of the donor pump P2, which are associated with valves V1 and V2 (respectively) of the blood separation device 10. One valve V2 is closed to prevent fluid flow through the associated valve station C2, while the other valve V1 is open to allow fluid flow through the associated valve station C1. The blood flows through the line L5 associated with the open valve V1 to a junction, where a portion of the blood is directed through line L6 to a fluid container F3 (which may be referred to as an in-process bag) and the remainder is directed through line L7 toward the spinning membrane separator 26. The line L7 is associated with a pump P4 (which may be referred to as a spinner pump), which controls the amount of blood that is directed to the spinning membrane separator 26 instead of the in-process bag F3. In particular, the flow rate of the donor pump P2 is greater than the flow rate of the spinner pump P4, with the difference therebetween being equal to the flow rate of blood into the in-process bag F3. The flow rates may be selected such that the in-process bag F3 is partially or entirely filled with blood at the end of the draw phase.

The blood flowing through line L7 toward the spinning membrane separator 26 passes through a spinner inlet sensor M1 and sensor station S4 associated with pressure sensor A4 (which monitors the pressure of the spinning membrane separator 26). The spinner inlet sensor M1 may detect the hematocrit of the blood entering the spinning membrane separator 26, which may be used to set the flow rate of a pump P5 (which may be referred to as a red blood cell pump) to achieve a desired packed red blood cell hematocrit.

The spinning membrane separator drive unit 14 of the blood separation device 10 manipulates the spinning membrane separator 26 to separate plasma from the cellular blood components (i.e., red blood cells, platelets, and white blood cells). In one embodiment, the spinning membrane separator 26 is a larger spinning membrane separator (as described above), with a stationary housing 70 and a rotatable rotor 72 with a membrane 76 mounted thereon. In such an embodiment, the spinning membrane separator drive unit 14 may rotate the rotor 72 at approximately 2,500-3,000 rpm to separate blood entering the bottom portion of the spinning membrane separator 26 into plasma and cellular blood components (as described above).

The cellular blood components are pumped out of the spinning membrane separator 26 via line L8 by the red blood cell pump P5. Valve V6 is closed to prevent fluid flow through associated valve station C6 and line L9, thereby directing the flow of cellular blood components through line L10 toward a leukocyte removal filter 60. Pressure sensor A3 may interact with sensor station S3 of the cassette 48 to monitor the pressure of the leukocyte removal filter 60.

The valve V6 associated with valve station C6 may be selectively opened to allow fluid flow through lines L9 and L11 to a fluid container F4, which may be referred to as a return bag. This may be advantageous if the controller 18 determines that sufficient red blood cells have been collected and that further red blood cells may be conveyed to a recipient.

Prior to the cellular blood components reaching the leukocyte removal filter 60, they may be mixed with an additive solution, such as Adsol. The additive solution may be drawn out of a fluid container F7 (which may be referred to as an additive bag) via line L12 (with open valve V9) under action of a pump P6 of the blood separation device 10 (which may be referred to as the additive pump). The additive pump P6 conveys additive solution through line L12 and open valve station C9 to a junction where it is mixed with the cellular blood components flowing through line L10.

The mixture of cellular blood components and additive solution is conveyed through line L13 and the leukocyte removal filter 60, which removes the majority of the platelets and white blood cells from the mixture. The leukoreduced red blood cells are conveyed through lines L14 and L15 to fluid containers F5 and F6 (which may be referred to as red blood cell bags), respectively.

Cell-free plasma exits the spinning membrane separator 26 via line L11 and travels through spinner outlet sensor M2, the valve station C7 associated with open valve V7, and into the return bag F4. The spinner outlet sensor M2 cooperates with the controller 18 to determine one or more characteristics of the plasma, such as the amount of cellular blood components in the plasma and/or whether the plasma is hemolytic and/or lipemic.

There is no pump associated with line L11, so instead the flow rate at which the plasma exits the spinning membrane separator 26 is equal to the difference between the flow rates of the spinner pump P4 and red blood cell pump P5. In one embodiment, the spinner pump P4 is set to a constant flow rate and the red blood cell pump P5 is set to a flow rate that will produce a desired hematocrit for the separated cellular blood components, which may be in the range of approximately 75-85%. The additive pump P6 may be commanded to operate at a flow rate that will reduce or dilute the hematocrit of the separated cellular blood components to a specific level prior to entering the leukocyte removal filter 60, which may be in the range of approximately 60-70%. In one embodiment, the flow rates of the red blood cell pump P5 and the additive pump P6 may be calculated as follows:

Red blood cell pump flow rate=(spinner pump flow rate*hematocrit of blood entering the spinning membrane separator)/target hematocrit of the separated cellular blood components [Equation 2]

Additive pump flow rate=((red blood cell pump flow rate*target hematocrit of the separated cellular blood components)/target hematocrit after dilution)−red blood cell pump flow rate [Equation 3]

The draw phase may continue until the amount of blood drawn from the blood source reaches a target amount or the in-process bag F3 is filled to a particular level (as determined by a weight scale from which the in-process bag F3 is hung) or until some other condition is satisfied.

c. Return Phase

Figure 33:
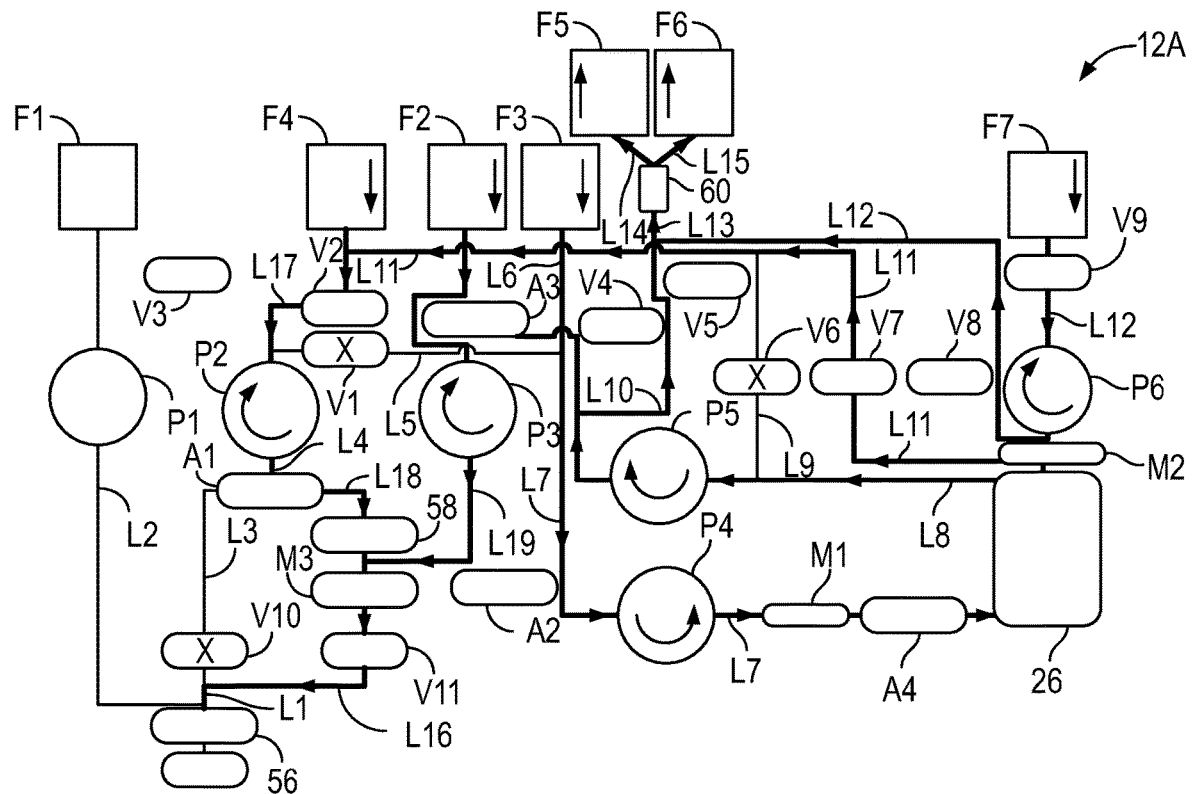

When the system transitions to the return phase (FIG. 33), the anticoagulant pump P1 will stop drawing anticoagulant from the anticoagulant bag F1. The valve V10 associated with valve station C10 will close to prevent fluid flow through line L3, and valve V11 associated with valve station C11 is opened to allow fluid flow through line L16. The valve V2 associated with valve station C2 also opens to allow flow through line L17, while the valve V1 associated with valve station C1 closes to prevent flow through line L5.

With the valves so situated, the donor pump P2 will reverse direction to allow the contents of the return bag F4 (typically plasma, which may include cellular blood components if red blood cells are no longer being collected) to be conveyed to a recipient (which may be the same blood source) via the same needle used to draw blood into the fluid flow circuit 12A. The return fluid is pumped through line L17, the valve station C2 associated with open valve V2, lines L4 and L18, the sensor station S1 associated with pressure sensor A1, a return line filter 58, air detector M3, the valve station C11 associated with open valve V11, and lines L16 and L1 on its way to the recipient. Depending on user preference, saline or another replacement fluid may be drawn from the saline bag F2 via line L19 by a pump P3 of the blood separation device 10 (which may be referred to as a saline pump) to a junction, where it mixes with fluid being conveyed to the recipient.

While fluid is being conveyed to the recipient, the blood in the in-process bag F3 acts as the blood supply for the spinning membrane separator 26. When the system transitions to the return phase, the spinner pump P4 remains unchanged and separation continues in the same manner as described for the draw phase (i.e., with blood being separated into plasma and cellular components, the plasma flowing to the return bag F4, and the cellular blood components being diluted, filtered, and collected as leukoreduced red blood cells) until the in-process bag F3 is emptied. Therefore, the system components downstream from the spinner pump P4 are "blinded" as to whether the system is in a draw or return phase. It will be appreciated that a method as described herein is preferable to a batch process (by which blood is only separated during a draw phase and not during a return phase) because separation and collection may be continuous, thereby decreasing the time required to complete the procedure.

It will be seen that plasma is conveyed to the return bag F4 at the same time that the contents of the return bag F4 are being conveyed to the recipient. The rate at which the donor pump P2 operates may be greater than the rate at which plasma exits the spinning membrane separator 26 to allow the return bag F4 to empty during the return phase, even as separation continues. Once the return bag F4 and/or in-process bag F3 is empty, the system may transition back to the draw phase if the target amount of red blood cells has not yet been collected.

2. Double Needle Fluid Flow Circuit and Procedure a. Fluid Flow Circuit

Figure 3:
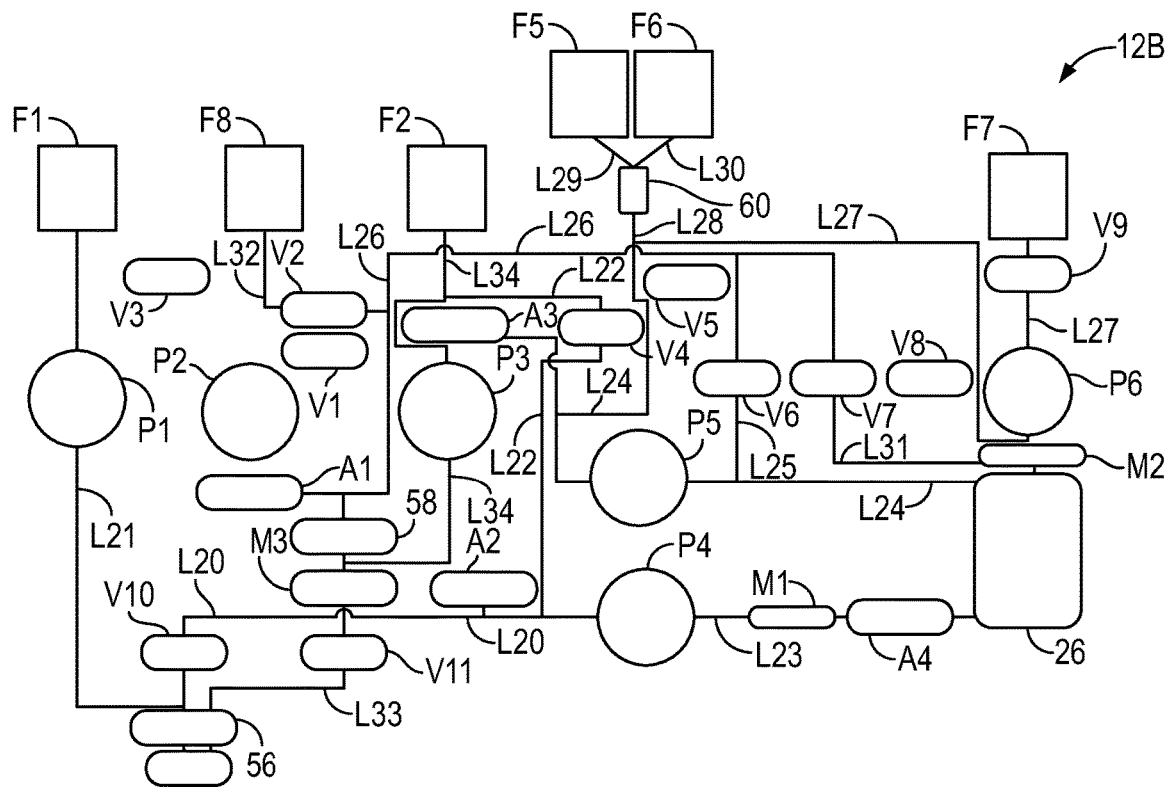

FIG. 3 is a schematic view of an exemplary fluid flow circuit 12B having a pair of blood access devices (e.g., needles) for separating and collecting red blood cells from blood. The fluid flow circuit 12B includes a cassette 48 of the type described above and illustrated in FIG. 13, which connects the various components of the fluid flow circuit 12B. The various connections amongst the components of the fluid flow circuit 12B are shown in FIG. 3, which also shows the fluid flow circuit 12B mounted to the blood separation device 10.

Components of the fluid flow circuit 12B interact with many of the components of the blood separation device 10, as will be described, but there are selected components of the blood separation device 10 that are not used in separating and collecting red blood cells using the fluid flow circuit 12B of FIG. 3. Most notably, the centrifugal separator 16 is not used, but only the spinning membrane separator drive unit 14. There are also selected valves V1, V3, V5, V8 and the donor pump P2 of the blood separation device 10 that are not used in the procedure described herein. The fluid flow circuit 12B includes a fluid container F8 (which may be referred to as a waste bag) that, in the illustrated procedure of FIG. 34, is only used during the pre-processing priming phase, in which saline from the saline bag F2 is pumped through the fluid flow circuit 12B to prime it, before being conveyed to the waste bag F8 for disposal at the end of the procedure.

b. Procedure

Figure 34:
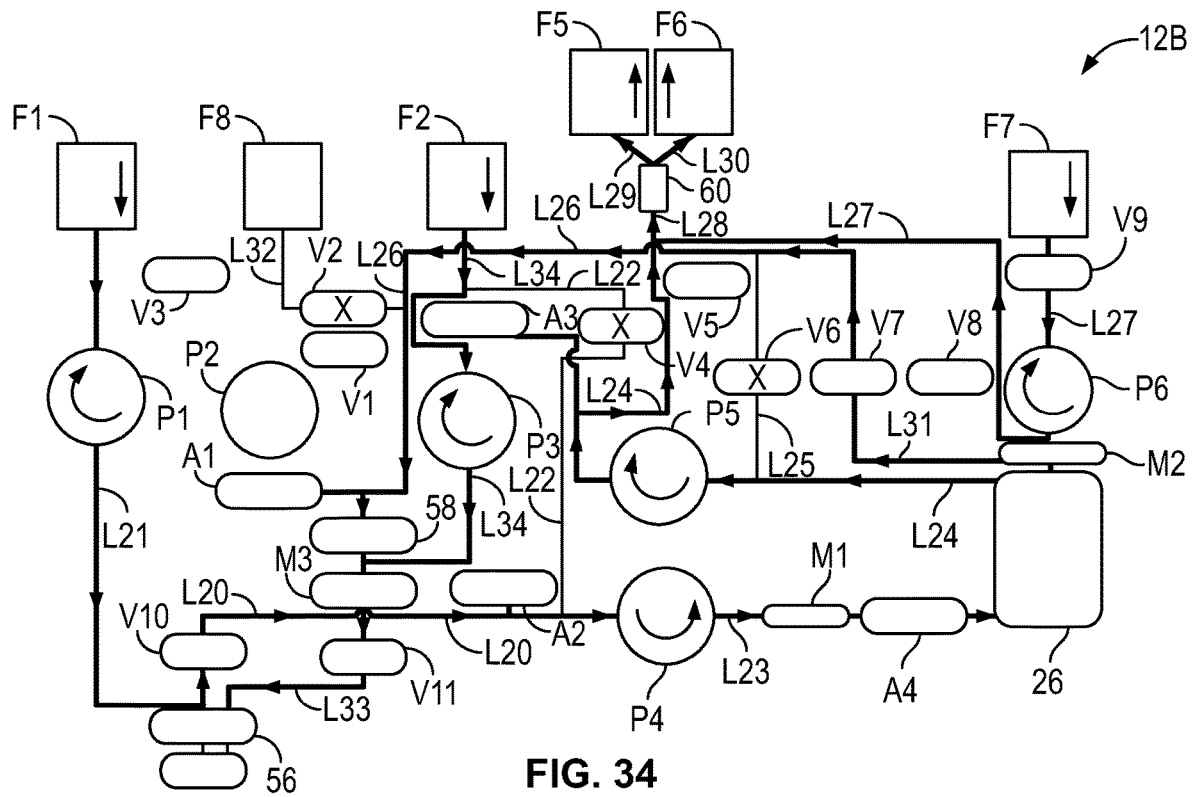
FIG. 34 is a schematic view of the fluid flow circuit of FIG. 3 mounted on the blood separation device of FIG. 1, showing the system carrying out different fluid flow tasks in connection with separation and collection of red blood cells from blood.

In contrast to the separation procedure described above with respect to the fluid flow circuit 12A of FIG. 2, the fluid flow circuit 12B of FIG. 3 allows for a single phase during which blood is simultaneous drawn and processed, with a portion of at least one separated component being conveyed to a recipient (FIG. 34). Blood is drawn into the fluid flow circuit 12B from a blood source (e.g., using a needle) via line L20. The line L20 may include a manual clamp 56 that may initially be in a closed position to prevent fluid flow through the line L20. When processing is to begin, an operator may move the manual clamp 56 from its closed position to an open position to allow fluid flow through the line L20.

The blood is drawn into the line L20 by the spinner pump P4, rather than the donor pump P2 (which is inactive in this procedure). Anticoagulant from the anticoagulant bag F1 may be added to the blood via line L21 by action of the anticoagulant pump P1. The valve V10 associated with valve station C10 is open to allow flow through line L20, while the valve V4 associated with valve station C4 is closed to prevent flow through line L22, thereby directing the blood toward the spinning membrane separator 26 via line L23. Prior to reaching the spinning membrane separator 26, the blood may pass through the sensor station S2 associated with pressure sensor A2 (which may be upstream of the spinner pump P4 and may monitor vein pressure if the blood source is a living donor), the spinner inlet sensor M1, and the sensor station S4 associated with pressure sensor A4. The spinner inlet sensor M1 may detect the hematocrit of the blood entering the spinning membrane separator 26 (which may be used to set the flow rate of the red blood cell pump P5 to achieve a desired packed red blood cell hematocrit), while the pressure sensor A4 may monitor the pressure of the spinning membrane separator 26.

The spinning membrane separator drive unit 14 of the blood separation device 10 manipulates the spinning membrane separator 26 to separate plasma from the cellular blood components (i.e., red blood cells, platelets, and white blood cells). In one embodiment, the spinning membrane separator 26 is a larger spinning membrane separator (as described above), with a stationary housing 70 and a rotatable rotor 72 with a membrane 76 mounted thereon. In such an embodiment, the spinning membrane separator drive unit 14 may rotate the rotor 72 at approximately 2,500-3,000 rpm to separate blood entering the bottom portion of the spinning membrane separator 26 into plasma and cellular blood components (as described above).

The cellular blood components are pumped out of the spinning membrane separator 26 via line L24 by the red blood cell pump P5. Valve V6 associated with valve station C6 is closed to prevent fluid flow through the line L25, thereby directing the flow of cellular blood components through line L24 toward a leukocyte removal filter 60. A sensor station S3 associated with line L24 may interact with a pressure sensor A3 of the blood separation device 10 to monitor the pressure of the leukocyte removal filter 60. The valve V6 associated with valve station C6 may be selectively opened to allow fluid flow through lines L25 and L26 to a recipient, which may be advantageous if the controller 18 determines that sufficient red blood cells have been collected.

Prior to the cellular blood components reaching the leukocyte removal filter 60, they may be mixed with an additive solution, such as Adsol. The additive solution may be drawn out of the additive bag F7 via line L27 (with valve V9 open to allow flow through valve station C9) under action of the additive pump P6. The additive pump P6 conveys additive solution through line L27 to a junction where it is mixed with the cellular blood components flowing through line L24.

The mixture of cellular blood components and additive solution is conveyed through line L28 and to the leukocyte removal filter 60, which removes the majority of the platelets and white blood cells from the mixture. The leukoreduced red blood cells are conveyed through lines L29 and L30 to red blood cell bags F5 and F6, respectively.

Cell-free plasma exits the spinning membrane separator 26 via line L31 and travels through spinner outlet sensor M2, the valve station C7 associated with open valve V7, and into line L26. The spinner outlet sensor M2 cooperates with the controller 18 to determine one or more characteristics of the plasma, such as the amount of cellular blood components in the plasma and/or whether the plasma is hemolytic and/or lipemic. There is no pump associated with line L31, so instead the flow rate at which the plasma exits the spinning membrane separator 26 is equal to the difference between the flow rates of the spinner pump P4 and red blood cell pump P5. In one embodiment, the spinner pump P4 is set to a constant flow rate and the red blood cell pump P5 is set to a flow rate that will produce a desired hematocrit for the separated cellular blood components, which may be in the range of approximately 75-85%. The additive pump P6 may be commanded to operate at a flow rate that will reduce or dilute the hematocrit of the separated cellular blood components to a specific level prior to entering the leukocyte removal filter 60, which may be in the range of approximately 60-70%. The flow rates of the red blood cell pump P5 and the additive pump P6 may be determined using above Equations 2 and 3.

Valve V2 associated with valve station C2 is closed to prevent flow through line L32 to the waste bag F8, thereby directing the plasma along line L26, through the sensor station S1 associated with pressure sensor A1 (which may monitor vein pressure if the fluid recipient is a living donor), a return line filter 58, air detector M3, the valve station C11 associated with open valve V11, and line L33 on its way to the recipient (which may be the same as the blood source) via the second needle or blood access device. Depending on user preference, saline or another replacement fluid may be drawn from the saline bag F2 via line L34 by the saline pump P3 to a junction, where it mixes with fluid being conveyed to the recipient.

This single-phase procedure continues until the target amount of red blood cells has been collected.

B. Red Blood Cell and Plasma Collection

According to one aspect of the present disclosure, the blood separation device 10 may be used to separate and collect red blood cells and plasma from blood. In contrast to the preceding applications in which only red blood cells are collected, it is typical for only a single unit of red blood cells to be collected, along with a target amount of plasma. However, other amounts of red blood cells and plasma may be separated and collected without departing from the scope of the present disclosure.

A blood separation device 10 according to the present disclosure may be used in combination with a fluid flow circuit 12 having a single blood access device (e.g., a single needle that draws blood from and returns a separated blood component to the same location) or two blood access devices (e.g., one needle that draws blood from a source and a second needle that flows a separated blood component to the same source or to a different recipient). An exemplary fluid flow circuit 12C, 12D and procedure will be described for each arrangement.

1. Single Needle Fluid Flow Circuit and Procedure a. Fluid Flow Circuit

Figure 4:
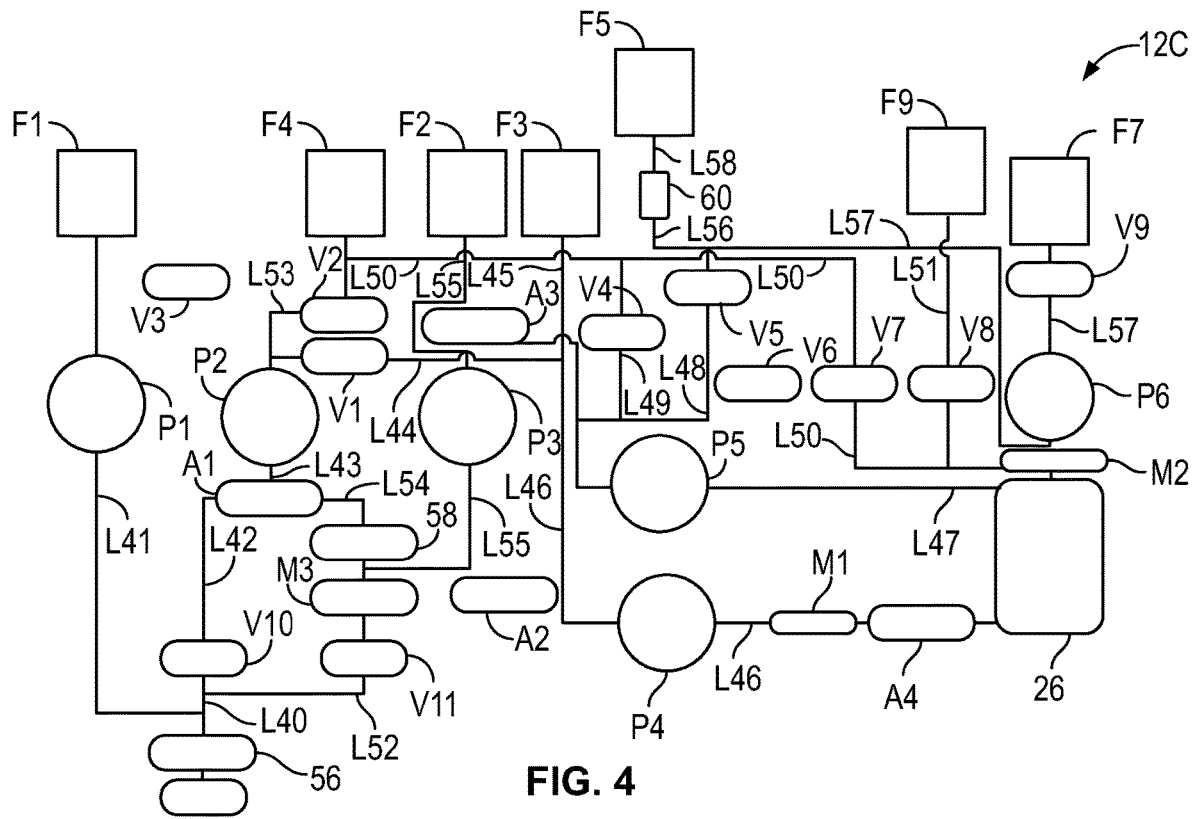

FIG. 4 is a schematic view of an exemplary fluid flow circuit 12C having a single blood access device (e.g., a needle) for separating and collecting red blood cells and plasma from blood. The fluid flow circuit 12C includes a cassette 48 of the type described above and illustrated in FIG. 13, which connects the various components of the fluid flow circuit 12C. The various connections amongst the components of the fluid flow circuit 12C are shown in FIG. 4, which also shows the fluid flow circuit 12C mounted to the blood separation device 10.

Components of the fluid flow circuit 12C interact with many of the components of the blood separation device 10, as will be described, but there are selected components of the blood separation device 10 that are not used in separating and collecting red blood cells and plasma using the fluid flow circuit 12C of FIG. 4. Most notably, the centrifugal separator 16 is not used, but only the spinning membrane separator drive unit 14. There are also selected valves V3 and V6 and a pressure sensor A2 of the blood separation device 10 that are not used in the procedure described herein.

b. Draw Phase—Plasma Collection Only

The volume of blood required to produce typical plasma product volumes is more than the volume of blood required to produce the corresponding red blood cell product volumes and, thus, there may be two draw phases. One phase only collects plasma (while conveying cellular blood components to a recipient) and the other phase collects plasma and red blood cells. Plasma-only collection occurs for a majority of the draw phases while plasma and red blood cell collection occurs near the end of the procedure. The plasma-only draw phase will continue until the collected plasma volume is within a specific amount of the target product volume and then the system will collect both plasma and red blood cells. The transition will occur when the collected plasma volume is within the volume of plasma that will be produced in order to obtain the target red blood cell product volume, typically 200 ml of red blood cells. For example, for blood having a hematocrit of 40%, 500 ml of blood will have to be processed in order to collect 200 ml of red blood cells. Assuming the separated cellular blood components exiting the spinning membrane separator 26 has a hematocrit of 80%, then 250 ml of plasma will be produced when processing the 500 ml of blood. Therefore, plasma-only collection would continue from the start of a procedure until the collected plasma volume is within 250 ml of the target plasma product volume.

Figure 35:
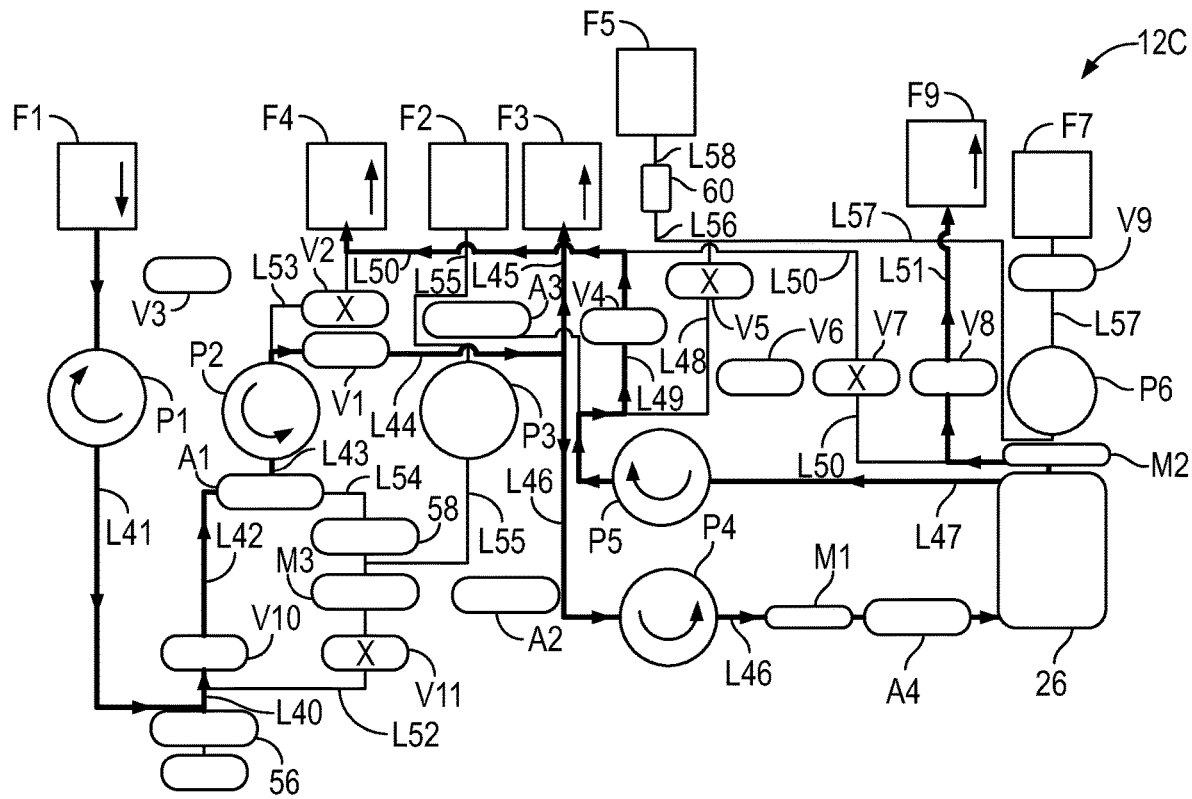
FIGS. 35-38 are schematic views of the fluid flow circuit of FIG. 4 mounted on the blood separation device of FIG. 1, showing the system carrying out different fluid flow tasks in connection with separation and collection of red blood cells and plasma from blood.

In the plasma-only draw phase (FIG. 35), blood is drawn into the fluid flow circuit 12C from a blood source. If the blood source is a donor, then blood may be drawn into the fluid flow circuit 12C through a single needle that is connected to the cassette 48 by line L40. The line L40 may include a manual clamp 56 that may initially be in a closed position to prevent fluid flow through the line L40.

When processing is to begin, an operator may move the manual clamp 56 from its closed position to an open position to allow fluid flow through the line L40.

The blood is drawn into the line L40 by the donor pump P2 of the blood separation device 10. Anticoagulant may be drawn from the anticoagulant bag F1 by the anticoagulant pump P1, which conveys the anticoagulant through line L41 to a junction, where it is mixed with blood flowing through line L40 into the fluid flow circuit 12C.

In the illustrated embodiment, the valve V10 associated with valve station C10 is open to allow blood to flow through line L42 and a sensor station S1 associated with pressure sensor A1. If the blood source is a living body (e.g., a donor), the pressure sensor A1 may communicates with the controller 18 to monitor the pressure within the vein of the blood source.

The cassette 48 includes two valve stations C1 and C2 downstream of the donor pump P2, with the valve V2 of one valve station C2 being closed and the valve V1 of the other valve station C1 being open. The blood is pumped through line L43 by the donor pump P2 to a junction, where it flows through the line L44 and the valve station C1 associated with the open valve V1 to another junction, where a portion of the blood is directed through line L45 to the in-process bag F3 and the remainder is directed through line L46 toward the spinning membrane separator 26. The spinner pump P4 is associated with line L46 and controls the amount of blood that is directed to the spinning membrane separator 26 instead of the in-process bag F3. In particular, the flow rate of the donor pump P2 is greater than the flow rate of the spinner pump P4, with the difference therebetween being equal to the flow rate of blood into the in-process bag F3. The flow rates may be selected such that the in-process bag F3 is partially or entirely filled with blood at the end of this draw phase.

The blood flowing through line L46 toward the spinning membrane separator 26 passes through a spinner inlet sensor M1 and a sensor station S4 associated with pressure sensor A4. The spinner inlet sensor M1 may detect the hematocrit of the blood entering the spinning membrane separator 26, which may be used to set the flow rate of the red blood cell pump P5 to achieve a desired packed red blood cell hematocrit. The pressure sensor A4 may function to monitor the pressure within the spinning membrane separator 26.

The spinning membrane separator drive unit 14 of the blood separation device 10 manipulates the spinning membrane separator 26 to separate plasma from the cellular blood components (i.e., red blood cells, platelets, and white blood cells). In one embodiment, the spinning membrane separator 26 is a larger spinning membrane separator (as described above), with a stationary housing 70 and a rotatable rotor 72 with a membrane 76 mounted thereon. In such an embodiment, the spinning membrane separator drive unit 14 may rotates the rotor 72 at approximately 2,500-3,000 rpm to separate blood entering the bottom portion of the spinning membrane separator 26 into plasma and cellular blood components (as described above).

The cellular blood components are pumped out of the spinning membrane separator 26 via line L47 by the red blood cell pump P5. Valve V5 associated with valve station C5 is closed to prevent fluid flow through the line L48, thereby directing the flow of cellular blood components through line L49 (and the valve station C4 associated with open valve V4), line L50, and into the return bag F4. Although associated with a sensor station S3 in communication with line L47, pressure sensor A3 may be inactive during this phase (while being active in another draw phase, as will be described herein).

Cell-free plasma exits the spinning membrane separator 26 via line L51. The valve V7 associated with valve station C7 is closed to prevent flow through line L50, while the valve V8 associated with valve station C8 is open, thereby causing the separated plasma to travel through spinner outlet sensor M2, the valve station C8 associated with open valve V8, and into a fluid container F9 that may be referred to as the plasma bag. The spinner outlet sensor M2 cooperates with the controller 18 to determine one or more characteristics of the plasma, such as the amount of cellular blood components in the plasma and/or whether the plasma is hemolytic and/or lipemic.

There is no pump associated with line L51, so instead the flow rate at which the plasma exits the spinning membrane separator 26 is equal to the difference between the flow rates of the spinner pump P4 and red blood cell pump P5. In one embodiment, the spinner pump P4 is set to a constant flow rate and the red blood cell pump P5 is set to a flow rate that will produce a desired hematocrit for the separated cellular blood components, which may be in the range of approximately 75-85%. In one embodiment, the flow rate of the red blood cell pump P5 may be determined according to above Equation 2.

As described above, the plasma-only draw phase may continue until the amount of blood drawn from the blood source reaches a target amount or the in-process bag F3 is filled to a particular level (as determined by a weight scale from which the in-process bag F3 is hung) or until some other condition is satisfied.

c. Return Phase

Figure 36:
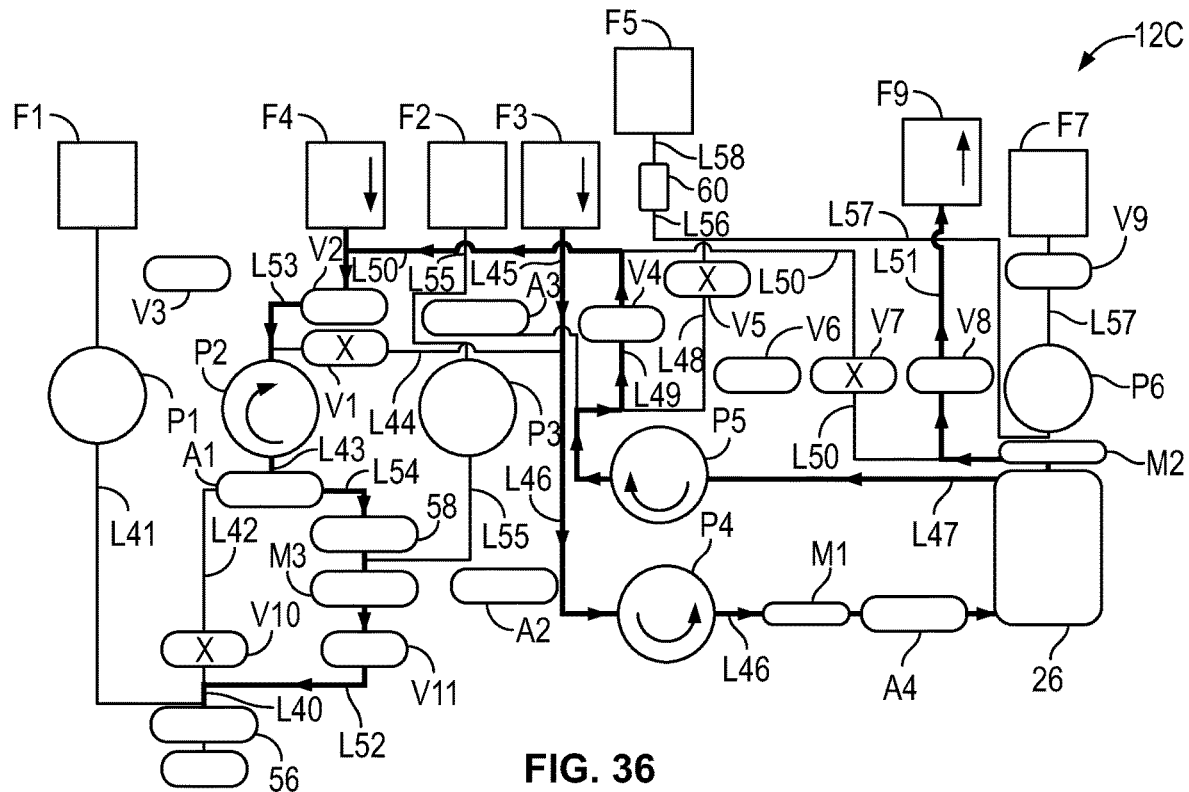

When the system transitions to the return phase (FIG. 36), the anticoagulant pump P1 will stop drawing anticoagulant from the anticoagulant bag F1. The valve V10 associated with valve station C10 will close to prevent fluid flow through line L42, and the valve V11 associated with valve station C11 is opened to allow fluid flow through line L52. The valve V2 associated with valve station C2 also opens to allow flow through line L53, while the valve V1 associated with valve station C1 closes to prevent flow through line L44.

With the valves so situated, the donor pump P2 will reverse direction to allow the contents of the return bag F4 (typically cellular blood components) to be conveyed to a recipient (which may be the same blood source) via the same needle used to draw blood into the fluid flow circuit 12C. The return fluid is pumped through line L53, the valve station C2 associated with open valve V2, line L43, the sensor station S1 associated with pressure sensor A1, line L54, a return line filter 58, air detector M3, the valve station C11 associated with open valve V11, and lines L52 and L40 on its way to the recipient. Saline or another replacement fluid may be drawn from the saline bag F2 via line L55 by the saline pump P3 to a junction, where it mixes with fluid being conveyed to the recipient, although it may be more typical for replacement fluid to not be conveyed to the recipient until plasma collection is complete.

While fluid is being conveyed to the recipient, the blood in the in-process bag F3 acts as the blood supply for the spinning membrane separator 26. When the system transitions to the return phase, the spinner pump P4 remains unchanged and separation continues in the same manner as described for the plasma-only draw phase (i.e., with blood being separated into plasma and cellular components, the cellular blood components flowing to the return bag F4, and the plasma being collected in the plasma bag F9) until the in-process bag F3 is emptied. Therefore, the system components downstream from the spinner pump P4 are "blinded" as to whether the system is in the plasma-only draw phase or the return phase. It will be appreciated that a method as described herein is preferable to a batch process (by which blood is only separated during a draw phase and not during a return phase) because separation and collection may be continuous, thereby decreasing the time required to complete the procedure.

It will be seen that cellular blood components are conveyed to the return bag F4 at the same time that the contents of the return bag F4 are being conveyed to the recipient. The rate at which the donor pump P2 operates may be greater than the rate at which the red blood cell pump P5 operates to allow the return bag F4 to empty during the return phase, even as separation continues. Once the return bag F4 is empty, the system may transition back to the plasma-only draw phase (FIG. 35) and subsequently alternate between the plasma-only draw phase and return phase until enough plasma has been collected to begin red blood cell collection.

d. Draw Phase—Red Blood Cell and Plasma Collection

Figure 37:
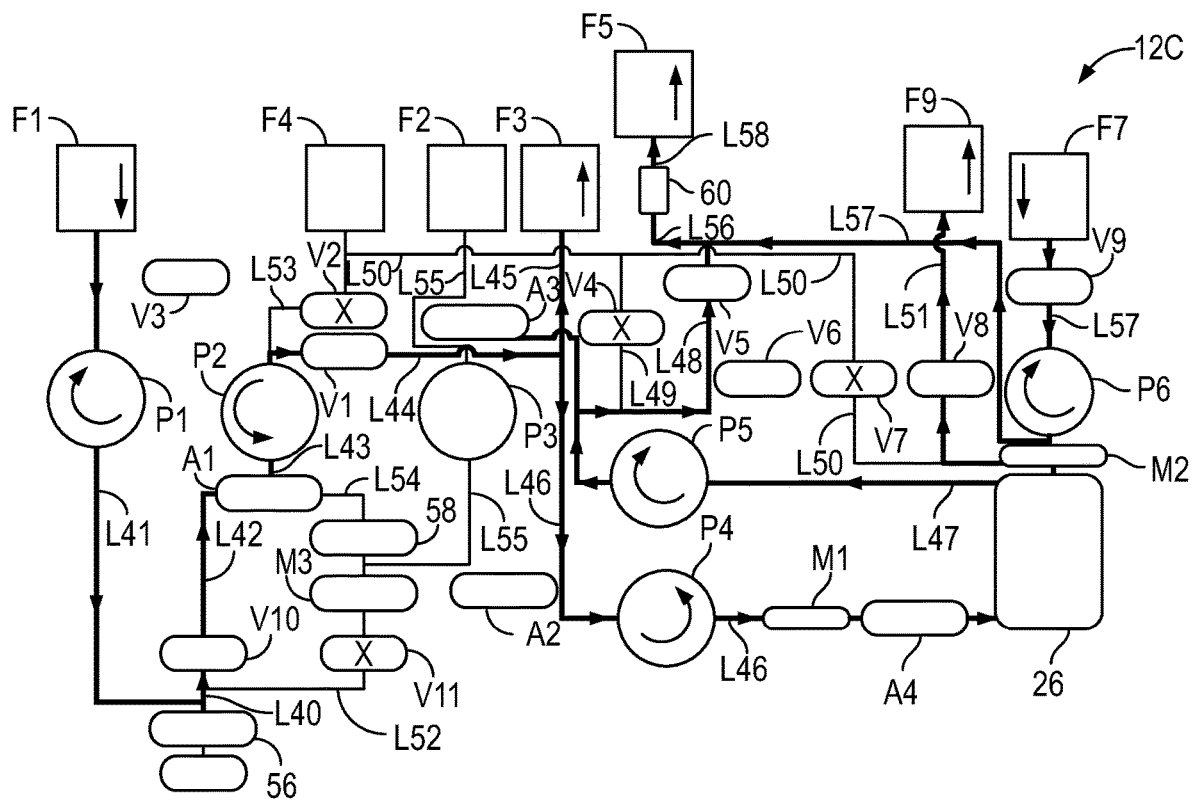

Once the plasma collection volume in plasma bag F9 is within a specific amount of the target (as explained above), the system will transition into a draw phase during which both plasma and red blood cells are collected, as shown in FIG. 37. This is the last draw phase of the procedure and will collect the red blood cell product and the remaining plasma volume. This draw phase is the same as the plasma-only draw phase until the cellular blood components exit the red blood cell pump P5. In this phase, the valve V4 associated with valve station C4 closes to prevent flow through line L49 (to the return bag F4) and the valve V5 associated with valve station C5 opens to allow the separated cellular blood components to flow through lines L48 and L56 toward the leukocyte removal filter 60.

Prior to the cellular blood components reaching the leukocyte removal filter 60, they may be mixed with an additive solution, such as Adsol. The additive solution may be drawn out of the additive bag F7 via line L57 (with the valve V9 associated with valve station C9 open) under action of the additive pump P6 of the blood separation device 10. The additive pump P6 conveys additive solution through line L57 to a junction where it is mixed with the cellular blood components flowing through line L48.

The mixture of cellular blood components and additive solution is conveyed through line L56 and the leukocyte removal filter 60, which removes the majority of the platelets and white blood cells from the mixture. A pressure sensor A3 associated with a sensor station S3 of the cassette 48 may monitor the pressure of the leukocyte removal filter 60. The leukoreduced red blood cells are conveyed through line L58 to the red blood cell bag F5.

As in the plasma-only draw phase, cell-free plasma exits the spinning membrane separator 26 via line L51 and travels through spinner outlet sensor M2, the valve station C8 associated with open valve V8, and into the plasma bag F9. There is no pump associated with line L51, so instead the flow rate at which the plasma exits the spinning membrane separator 26 is equal to the difference between the flow rates of the spinner pump P4 and red blood cell pump P5. In one embodiment, the spinner pump P4 is set to a constant flow rate and the red blood cell pump P5 is set to a flow rate that will produce a desired hematocrit for the separated cellular blood components, which may be in the range of approximately 75-85%. The additive pump P6 may be commanded to operate at a flow rate that will reduce or dilute the hematocrit of the separated cellular blood components to a specific level prior to entering the leukocyte removal filter 60, which may be in the range of approximately 60-70%. In one embodiment, the flow rates of the red blood cell pump P5 and the additive pump P6 may be calculated using above Equations 2 and 3.

e. Final Phase

At a point during the draw phase of FIG. 37, the donor pump P2 will have pumped enough blood into the fluid flow circuit 12C to allow for the targeted red blood cell and plasma product volumes to be reached. However, a specific volume of blood in the in-process bag F3 will have yet to be processed. At this point, the donor pump P2 will stop drawing blood and the valve V10 associated with valve station C10 will close to prevent fluid flow through line L42. The blood remaining in the in-process bag F3 will then be processed by the spinning membrane separator drive unit 26 to complete the procedure, as shown in FIG. 38.

Figure 38:
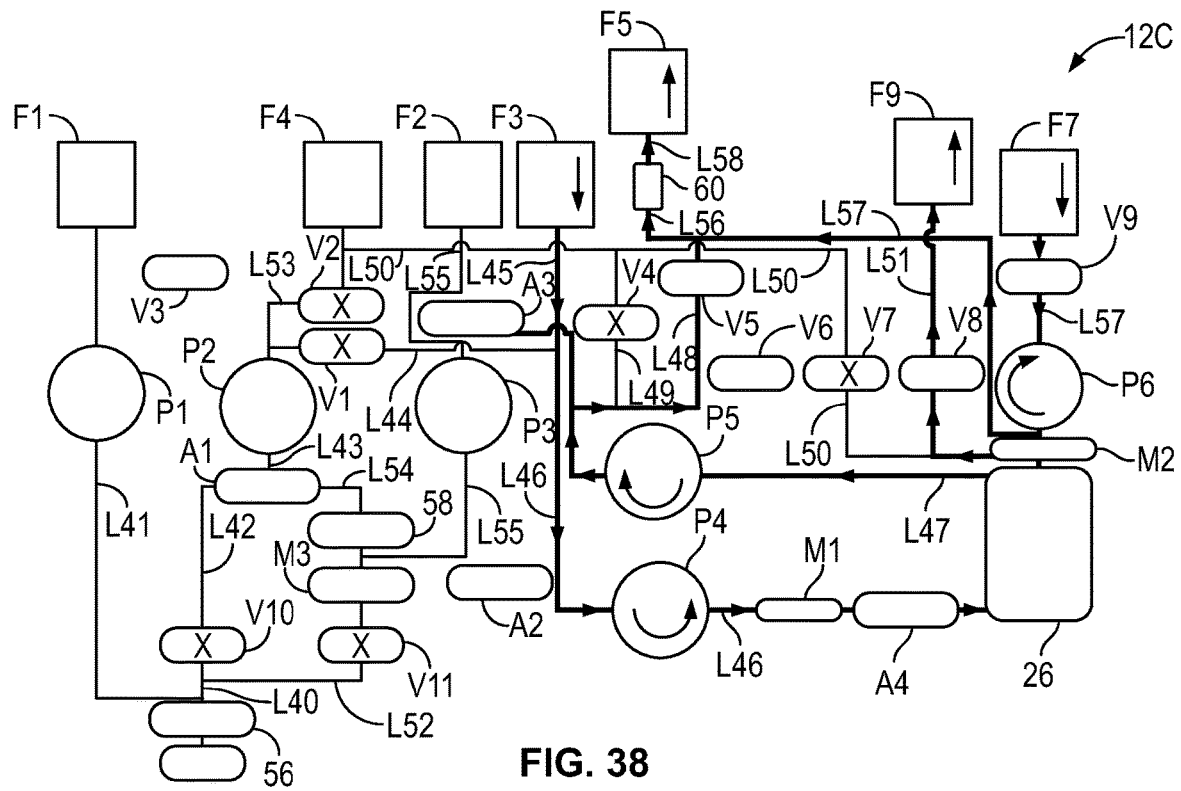

With the valve stations situated as shown in FIG. 38, the blood in the in-process bag F3 acts as the blood supply for the spinning membrane separator 26. Other than the blood entering the spinning membrane separator 26 from a different origin, this phase proceeds in the same manner as described for the final draw phase (i.e., with blood being separated into plasma and cellular components, the plasma flowing to the plasma bag F9, and the cellular blood components being diluted, filtered, and collected as leukoreduced red blood cells) until the in-process bag F3 is emptied. Upon emptying the in-process bag F3, the targeted amounts of red blood cell product and plasma product should be contained within the respective collection containers F5 and F9, which may be confirmed by the weight scales from which the containers F5 and F9 may be hung during the procedure.

2. Double Needle Fluid Flow Circuit and Procedure a. Fluid Flow Circuit

Figure 5:
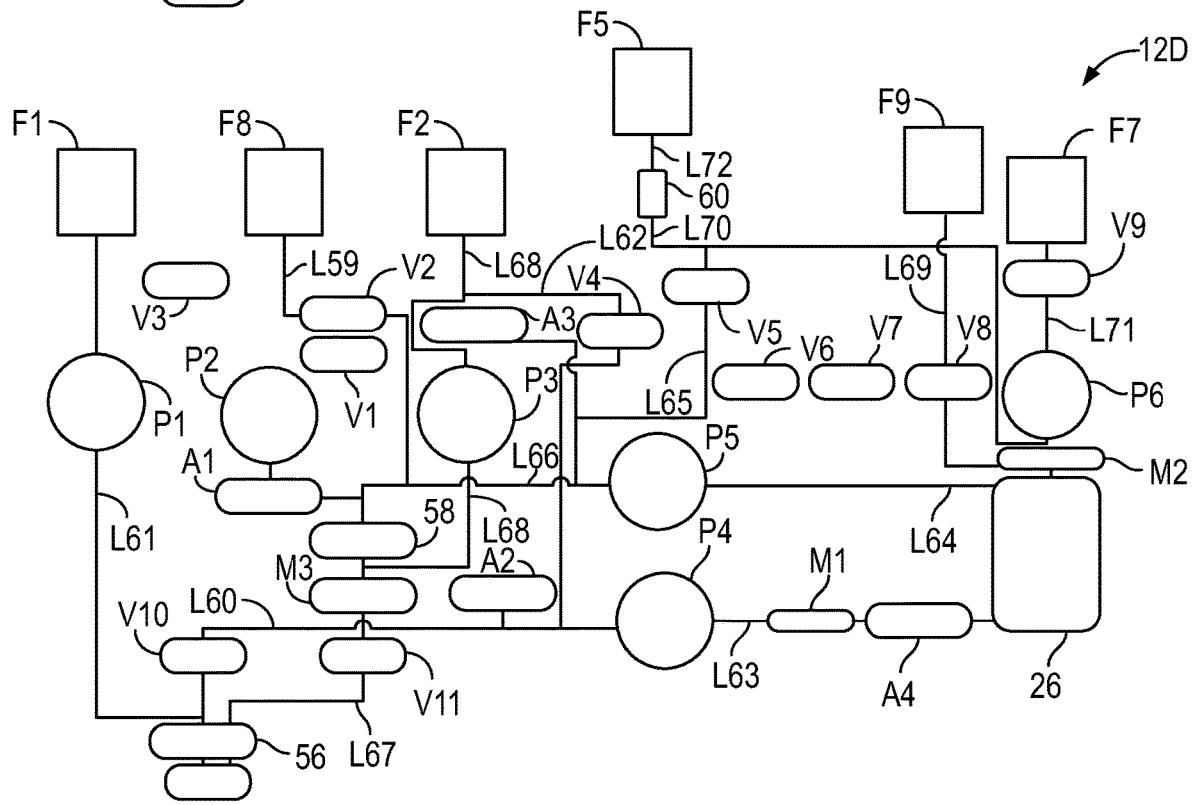

FIG. 5 is a schematic view of an exemplary fluid flow circuit 12D having a pair of blood access devices (e.g., needles) for separating and collecting red blood cells and plasma from blood. The fluid flow circuit 12D includes a cassette 48 of the type described above and illustrated in FIG. 13, which connects the various components of the fluid flow circuit 12D. The various connections amongst the components of the fluid flow circuit 12D are shown in FIG. 5, which also shows the fluid flow circuit 12D mounted to the blood separation device 10.

Components of the fluid flow circuit 12D interact with many of the components of the blood separation device 10, as will be described, but there are selected components of the blood separation device 10 that are not used in separating and collecting red blood cells and plasma using the fluid flow circuit 12D of FIG. 5. Most notably, the centrifugal separator 16 is not used, but only the spinning membrane separator drive unit 14. There are also selected valves V1, V3, V6, V7 and the donor pump P2 of the blood separation device 10 that are not used in the procedure described herein. In the procedure illustrated in FIGS. 39 and 40, valve V2 (along with a waste bag F8 and associated line L59 of the fluid flow circuit 12D) is only used during the pre-processing priming phase, in which saline from the saline bag F2 is pumped through the fluid flow circuit 12D to prime it, before being conveyed to the waste bag F8 for disposal at the end of the procedure.

b. Plasma Only Phase

Figure 39:
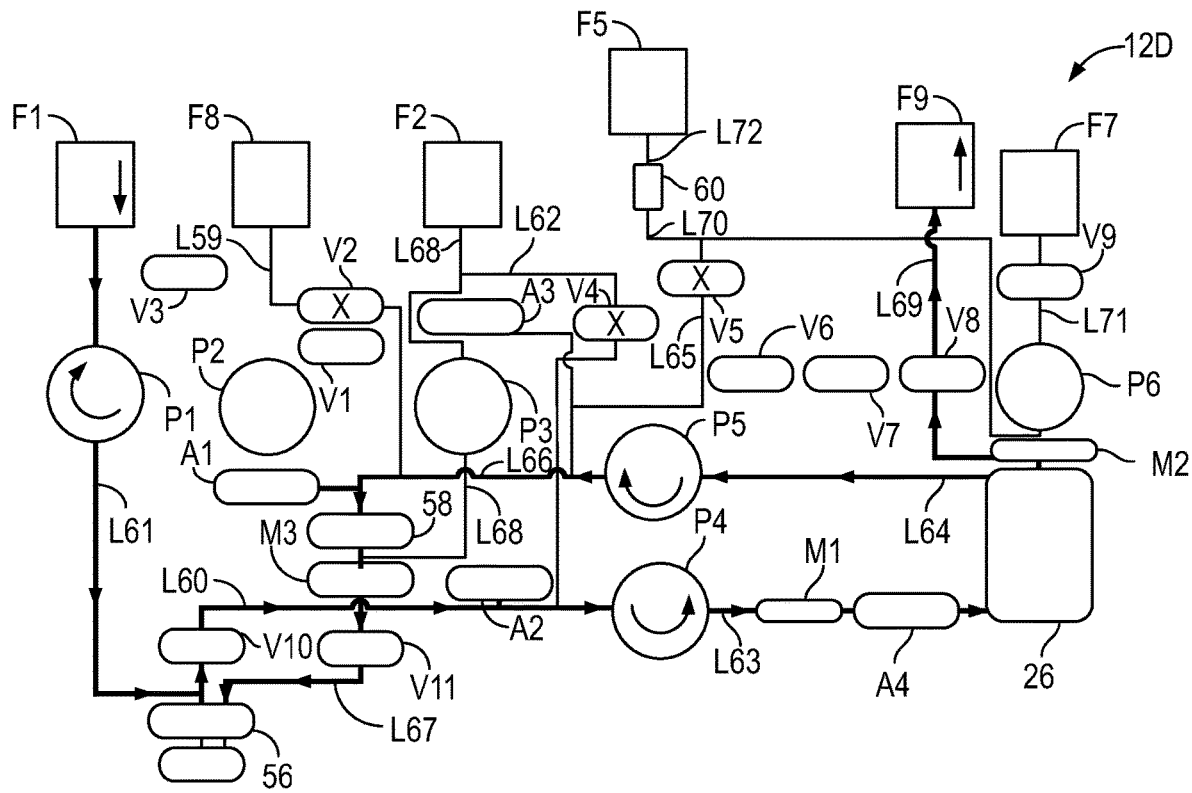
FIGS. 39 and 40 are schematic views of the fluid flow circuit of FIG. 5 mounted on the blood separation device of FIG. 1, showing the system carrying out different fluid flow tasks in connection with separation and collection of red blood cells and plasma from blood.

In the same manner as the single blood access device or needle procedure, the double blood access device or needle procedure collects only plasma for a specific duration from the start of the procedure until the collected plasma volume is within the specific amount of the target volume. FIG. 39 shows this plasma-only phase of the procedure.

Blood is drawn into the fluid flow circuit 12D from a blood source (e.g., using a needle) via line L60. The line L60 may include a manual clamp 56 that may initially be in a closed position to prevent fluid flow through the line L60. When processing is to begin, an operator may move the manual clamp 56 from its closed position to an open position to allow fluid flow through the line L60.

The blood is drawn into the line L60 by the spinner pump P4, rather than the donor pump P2 (which is inactive in this procedure). Anticoagulant from the anticoagulant bag F1 may be added to the blood via line L61 by action of the anticoagulant pump P1. The valve V10 associated with valve station C10 is open to allow flow through line L60, while the valve V4 associated with valve station C4 is closed to prevent flow through line L62, thereby directing the blood toward the spinning membrane separator 26 via line L63. Prior to reaching the spinning membrane separator 26, the blood may pass through the sensor station S2 associated with pressure sensor A2 (which may be upstream of the spinner pump P4 and may monitor vein pressure if the blood source is a living donor), the spinner inlet sensor M1, and the sensor station S4 associated with pressure sensor A4. The spinner inlet sensor M1 may detect the hematocrit of the blood entering the spinning membrane separator 26 (which may be used to set the flow rate of the red blood cell pump P5 to achieve a desired packed red blood cell hematocrit), while the pressure sensor A4 may monitor the pressure of the spinning membrane separator 26.

The spinning membrane separator drive unit 14 of the blood separation device 10 manipulates the spinning membrane separator 26 to separate plasma from the cellular blood components (i.e., red blood cells, platelets, and white blood cells). In one embodiment, the spinning membrane separator 26 is a larger spinning membrane separator (as described above), with a stationary housing 70 and a rotatable rotor 72 with a membrane 76 mounted thereon. In such an embodiment, the spinning membrane separator drive unit 14 may rotate the rotor 72 at approximately 2,500-3,000 rpm to separate blood entering the bottom portion of the spinning membrane separator 26 into plasma and cellular blood components (as described above).

The cellular blood components are pumped out of the spinning membrane separator 26 via line L64 by the red blood cell pump P5. Valve V5 associated with valve station C5 is closed to prevent fluid flow through the line L65, thereby directing the flow of cellular blood components through line L66, the sensor station S1 associated with pressure sensor A1 (which may monitor vein pressure if the fluid recipient is a living donor), a return line filter 58, air detector M3, the valve station C11 associated with open valve V11, and line L67 on its way to the recipient (which may be the same as the blood source) via the second needle or blood access device. Saline or another replacement fluid may be drawn from the saline bag F2 via line L68 by the saline pump P3 to a junction, where it mixes with fluid being conveyed to the recipient, although it may be more typical for replacement fluid to not be conveyed to the recipient until plasma collection is complete. Although sensor station S3 is in communication with line L64, the pressure sensor A3 associated with sensor station S3 may be inactive during this phase (while being active in a second phase, as will be described herein).

Cell-free plasma exits the spinning membrane separator 26 via line L69 and travels through spinner outlet sensor M2, the valve station C8 associated with open valve V8, and into plasma bag F9. The spinner outlet sensor M2 operates with the controller 18 to determine one or more characteristics of the plasma, such as the amount of cellular blood components in the plasma and/or whether the plasma is hemolytic and/or lipemic. There is no pump associated with line L69, so instead the flow rate at which the plasma exits the spinning membrane separator 26 is equal to the difference between the flow rates of the spinner pump P4 and red blood cell pump P5.

c. Red Blood Cell and Plasma Phase

Figures 40, 41:
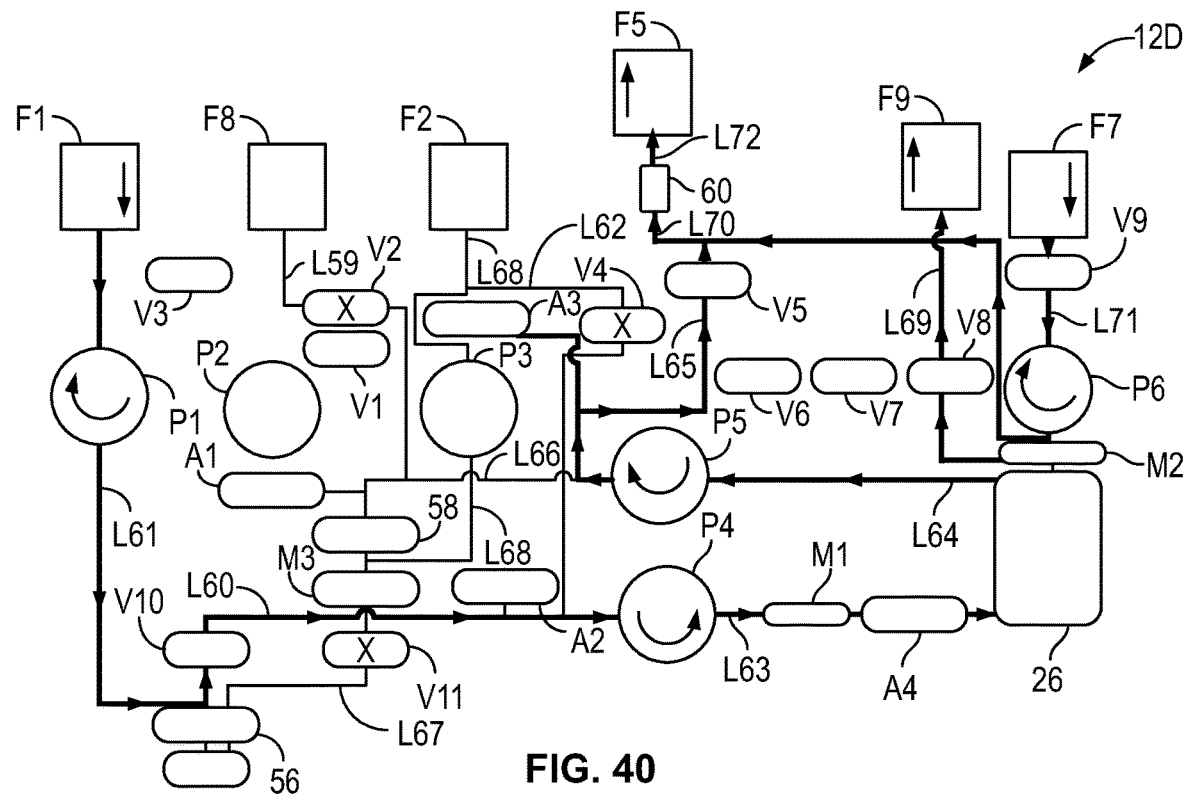
FIGS. 41 and 42 are schematic views of the fluid flow circuit of FIG. 6 mounted on the blood separation device of FIG. 1, showing the system carrying out different fluid flow tasks in connection with separation and collection of plasma from blood.

Once the plasma collection volume in plasma bag F9 is within a specific amount of the target (as explained above), the system will transition into a phase during which both plasma and red blood cells are collected, as shown in FIG. 40.

In this phase, the valve V11 associated with valve station C11 closes (to prevent the separated cellular blood components from being conveyed through line L67 to the recipient), while the valve V5 associated with valve station C5 opens to allow flow through line L65. With the valves so situated, separated plasma continues being conveyed to the plasma bag F9, while the separated cellular components are conveyed through line L65 (instead of line L66), the valve station C5 associated with open valve V5, and line L70 toward a leukocyte removal filter 60.

Prior to the cellular blood components reaching the leukocyte removal filter 60, they may be mixed with an additive solution, such as Adsol. The additive solution may be drawn out of the additive bag F7 via line L71 (with the valve V9 associated with valve station C9 being open) under action of the additive pump P6 of the blood separation device 10. The additive pump P6 conveys additive solution through line L71 to a junction where it is mixed with the cellular blood components flowing through line L65.

The mixture of cellular blood components and additive solution is conveyed through line L70 and the leukocyte removal filter 60, which removes the majority of the platelets and white blood cells from the mixture. A pressure sensor A3 associate with sensor station S3 (which communicates with line L65) may monitor the pressure of the leukocyte removal filter 60. The leukoreduced red blood cells are conveyed through line L72 to the red blood cell bag F5.

There is no pump associated with line L69 leading to the plasma bag F9, so instead the flow rate at which the plasma exits the spinning membrane separator 26 is equal to the difference between the flow rates of the spinner pump P4 and red blood cell pump P5. In one embodiment, the spinner pump P4 is set to a constant flow rate and the red blood cell pump P5 is set to a flow rate that will produce a desired hematocrit for the separated cellular blood components, which may be in the range of approximately 75-85%. The additive pump P6 may be commanded to operate at a flow rate that will reduce or dilute the hematocrit of the separated cellular blood components to a specific level prior to entering the leukocyte removal filter 60, which may be in the range of approximately 60-70%. In one embodiment, the flow rates of the red blood cell pump P5 and the additive pump P6 may be calculated using above Equations 2 and 3.

This phase will continue until the red blood cell and plasma product target volumes are achieved.

C. Plasma Collection

According to one aspect of the present disclosure, the blood separation device 10 may be used to separate and collect substantially cell-free plasma from blood. A blood separation device 10 according to the present disclosure may be used in combination with a fluid flow circuit 12 having a single blood access device (e.g., a single needle that draws blood from and returns a separated blood component to the same location) or two blood access devices (e.g., one needle that draws blood from a source and a second needle that flows a separated blood component to the same source or to a different recipient). An exemplary fluid flow circuit 12E, 12F and procedure will be described for each arrangement.

1. Single Needle Fluid Flow Circuit and Procedure a. Fluid Flow Circuit

Figure 6:
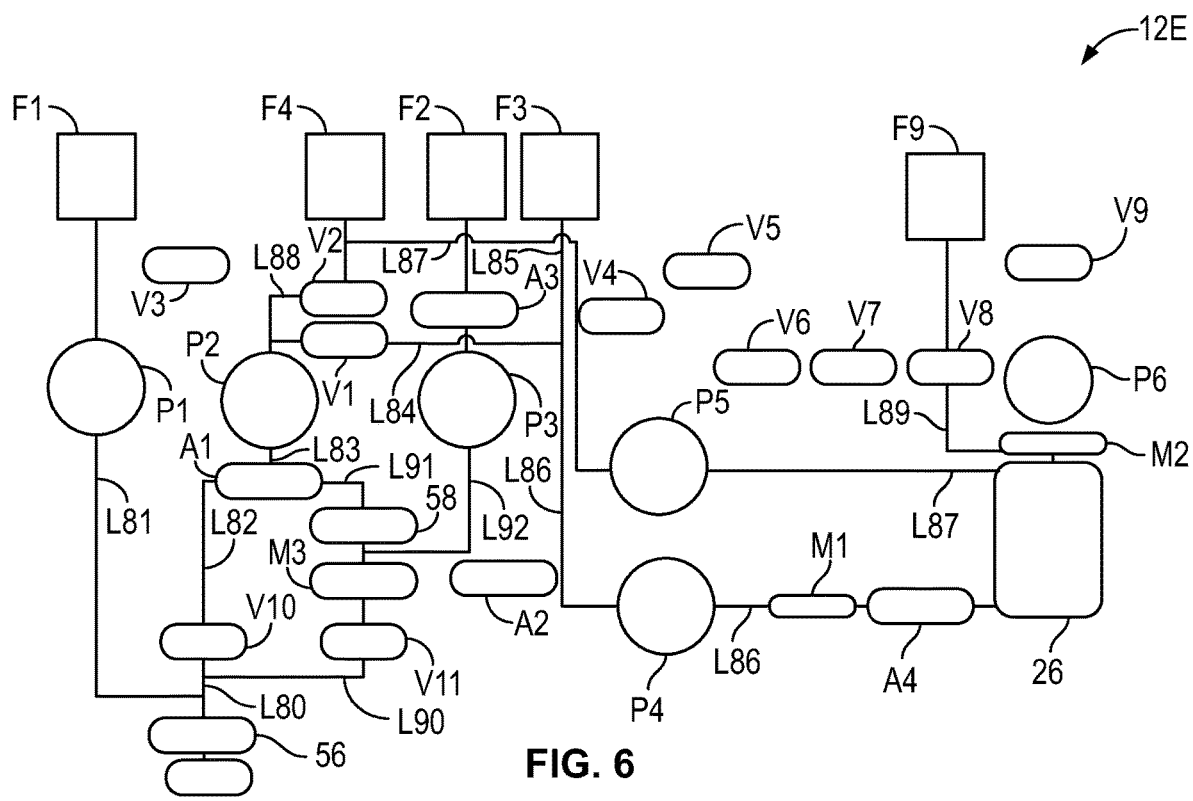

FIG. 6 is a schematic view of an exemplary fluid flow circuit 12E having a single blood access device (e.g., a needle) for separating and collecting plasma from blood. The fluid flow circuit 12E includes a cassette 48 of the type described above and illustrated in FIG. 13, which connects the various components of the fluid flow circuit 12E. The various connections amongst the components of the fluid flow circuit 12E are shown in FIG. 6, which also shows the fluid flow circuit 12E mounted to the blood separation device 10.

Components of the fluid flow circuit 12E interact with many of the components of the blood separation device 10, as will be described, but there are selected components of the blood separation device 10 that are not used in separating and collecting plasma using the fluid flow circuit 12E of FIG. 6. Most notably, the centrifugal separator 16 is not used, but only the spinning membrane separator drive unit 14. There are also selected valves V3, V4, V5, V6, V7, V9, a pressure sensor A2, and the additive pump P6 of the blood separation device 10 that are not used in the procedure described herein.

b. Draw Phase

In a first phase (FIG. 41), blood is drawn into the fluid flow circuit 12E from a blood source. If the blood source is a donor, then blood may be drawn into the fluid flow circuit 12E through a single needle that is connected to the cassette 48 by line L80. The line L80 may include a manual clamp 56 that may initially be in a closed position to prevent fluid flow through the line L80. When processing is to begin, an operator may move the manual clamp 56 from its closed position to an open position to allow fluid flow through the line L80.

The blood is drawn into the line L80 by the donor pump P2 of the blood separation device 10. Anticoagulant from the anticoagulant bag F1 may be drawn through line L81 under action of the anticoagulant pump P1 and added to the blood at a junction of lines L80 and L81. Valve V10 associated with valve station C10 is open to allow blood to flow through lines L80 and L82 and a sensor station S1 associated with pressure sensor A1. If the blood source is a living body (e.g., a donor), the pressure sensor A1 may monitor the pressure within the vein of the blood source.

The cassette 48 includes two valve stations C1 and C2 downstream of the donor pump P2 and line L83, with the valve V2 associated with one of the valve stations C2 being closed and the valve V1 associated with the other valve station C1 being open. The blood flows through the line L84 associated with the open valve V1 to a junction, where a portion of the blood is directed through line L85 to the in-process bag F3, with the remainder being directed through line L86 toward the spinning membrane separator 26. The spinner pump P4 associated with line L86 controls the amount of blood that is directed to the spinning membrane separator 26 instead of the in-process bag F3. In particular, the flow rate of the donor pump P2 is greater than the flow rate of the spinner pump P4, with the difference therebetween being equal to the flow rate of blood into the in-process bag F3. The flow rates may be selected such that the in-process bag F3 is partially or entirely filled with blood at the end of the draw phase.

The blood flowing through line L86 toward the spinning membrane separator 26 passes through a spinner inlet sensor M1 and a sensor station S4 associated with pressure sensor A4. The spinner inlet sensor M1 may detect the hematocrit of the blood entering the spinning membrane separator 26, which may be used to set the flow rate of the red blood cell pump P5 to achieve a desired packed red blood cell hematocrit. The pressure sensor A4 monitors the pressure of the spinning membrane separator 26.

The spinning membrane separator drive unit 14 of the blood separation device 10 manipulates the spinning membrane separator 26 to separate plasma from the cellular blood components (i.e., red blood cells, platelets, and white blood cells). The spinning membrane separator 26 may be either a smaller or larger spinning membrane separator, as described above. In one embodiment, the spinning membrane separator 26 has a stationary housing 70 and a rotatable rotor 72 with a membrane 76 mounted thereon. In such an embodiment, the spinning membrane separator drive unit 14 may rotate the rotor 72 at approximately 2,500-3,000 rpm to separate blood entering the bottom portion of the spinning membrane separator 26 into plasma and cellular blood components (as described above).

The cellular blood components are pumped out of the spinning membrane separator 26 via line L87 by the red blood cell pump P5. As described above, the valve V2 associated with valve station C2 is closed to prevent fluid flow through the line L88, thereby directing the flow of cellular blood components through line L87 and into the return bag F4.

Cell-free plasma exits the spinning membrane separator 26 via line L89 and travels through spinner outlet sensor M2, the valve station C8 associated with open valve V8, and into the plasma bag F9. The spinner outlet sensor M2 cooperates with the controller 18 to determine one or more characteristics of the plasma, such as the amount of cellular blood components in the plasma and/or whether the plasma is hemolytic and/or lipemic.

There is no pump associated with line L89, so instead the flow rate at which the plasma exits the spinning membrane separator 26 is equal to the difference between the flow rates of the spinner pump P4 and red blood cell pump P5. In one embodiment, the spinner pump P4 is set to a constant flow rate and the red blood cell pump P5 is set to a flow rate that will produce a desired hematocrit for the separated cellular blood components, which may be in the range of approximately 75-85%. In one embodiment, the flow rate of the red blood cell pump P5 may be determined according to above Equation 2.

The draw phase may continue until the amount of blood drawn from the blood source reaches a target amount or the in-process bag F3 is filled to a particular level or until some other condition is satisfied.

c. Return Phase

Figure 42:
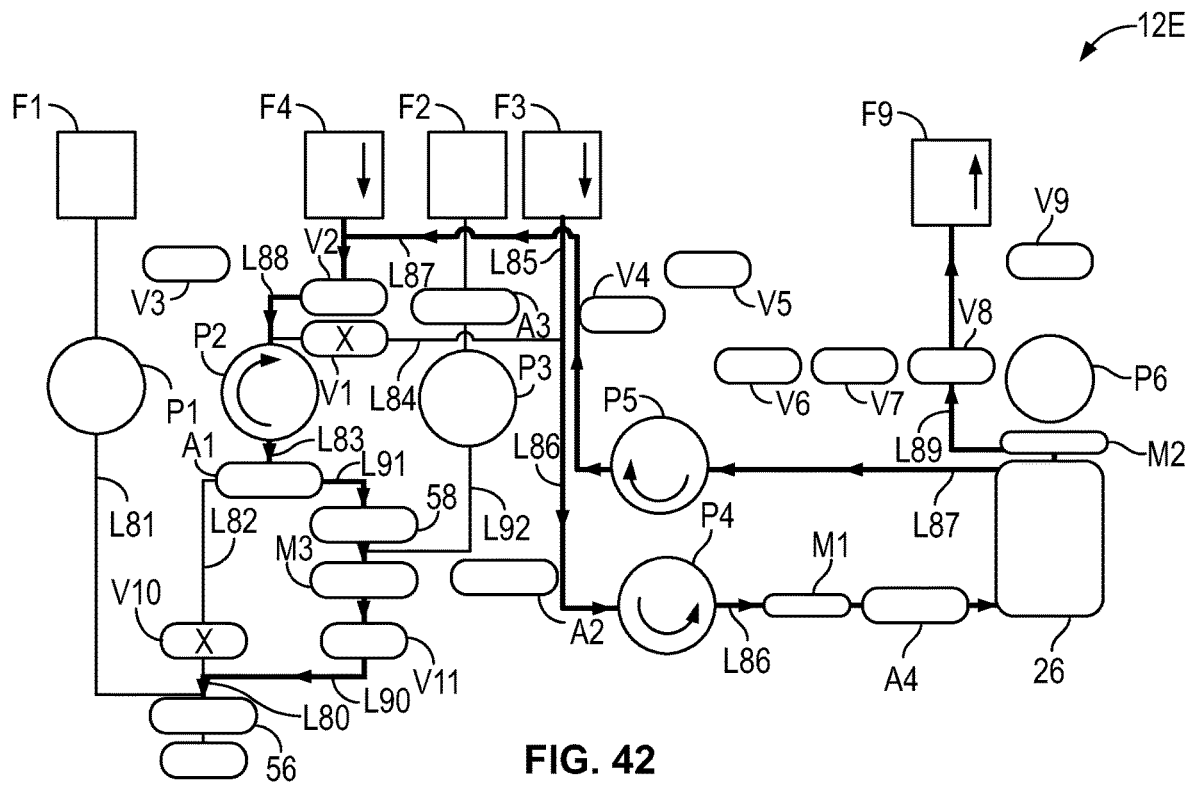

When the system transitions to the return phase (FIG. 42), the anticoagulant pump P1 will stop drawing anticoagulant from the anticoagulant bag F1. The valve V10 associated with valve station C10 closes to prevent fluid flow through line L82 and the valve V11 associated with valve station C11 is opened to allow fluid flow through line L90. The valve V2 associated with valve station C2 opens to allow flow through line L88, while the valve V1 associated with valve station C1 closes to prevent flow through line L84.

With the valves so situated, the donor pump P2 will reverse direction to allow the contents of the return bag F4 (typically cellular blood components) to be conveyed to a recipient (which may be the same blood source) via the same needle used to draw blood into the fluid flow circuit 12E. The return fluid is pumped through line L88, the valve station C2 associated with open valve V2, line L83, the sensor station S1 associated with pressure sensor A1, line L91 a return line filter 58, air detector M3, the valve station C11 associated with open valve V11, and lines L90 and L80 on its way to the recipient. Saline or another replacement fluid may be drawn from the saline bag F2 and through the sensor station S3 associated with pressure sensor A3 via line L92 by the saline pump P3 to a junction, where it mixes with fluid being conveyed to the recipient, although it may be more typical for replacement fluid to not be conveyed to the recipient until plasma collection is complete.

While fluid is being conveyed to the recipient, the blood in the in-process bag F3 acts as the blood supply for the spinning membrane separator 26. When the system transitions to the return phase, the spinner pump P4 remains unchanged and separation continues in the same manner as described for the draw phase (i.e., with blood being separated into plasma and cellular components, the separated cellular components flowing to the return bag F4, and the separated plasma being collected in the plasma bag F9) until the in-process bag F3 is emptied. Therefore, the system components downstream from the spinner pump P4 are "blinded" as to whether the system is in a draw or return phase. It will be appreciated that a method as described herein is preferable to a batch process (by which blood is only separated during a draw phase and not during a return phase) because separation and collection may be continuous, thereby decreasing the time required to complete the procedure.

It will be seen that separated cellular blood components are conveyed to the return bag F4 at the same time that the contents of the return bag F4 are being conveyed to the recipient. The rate at which the donor pump P2 operates may be greater than the rate at which cellular blood components exit the spinning membrane separator 26 to allow the return bag F4 to empty during the return phase, even as separation continues. Once the return bag F4 is empty, the system may transition back to the draw phase if the target amount of plasma has not yet been collected.

2. Double Needle Fluid Flow Circuit and Procedure a. Fluid Flow Circuit

Figure 7:
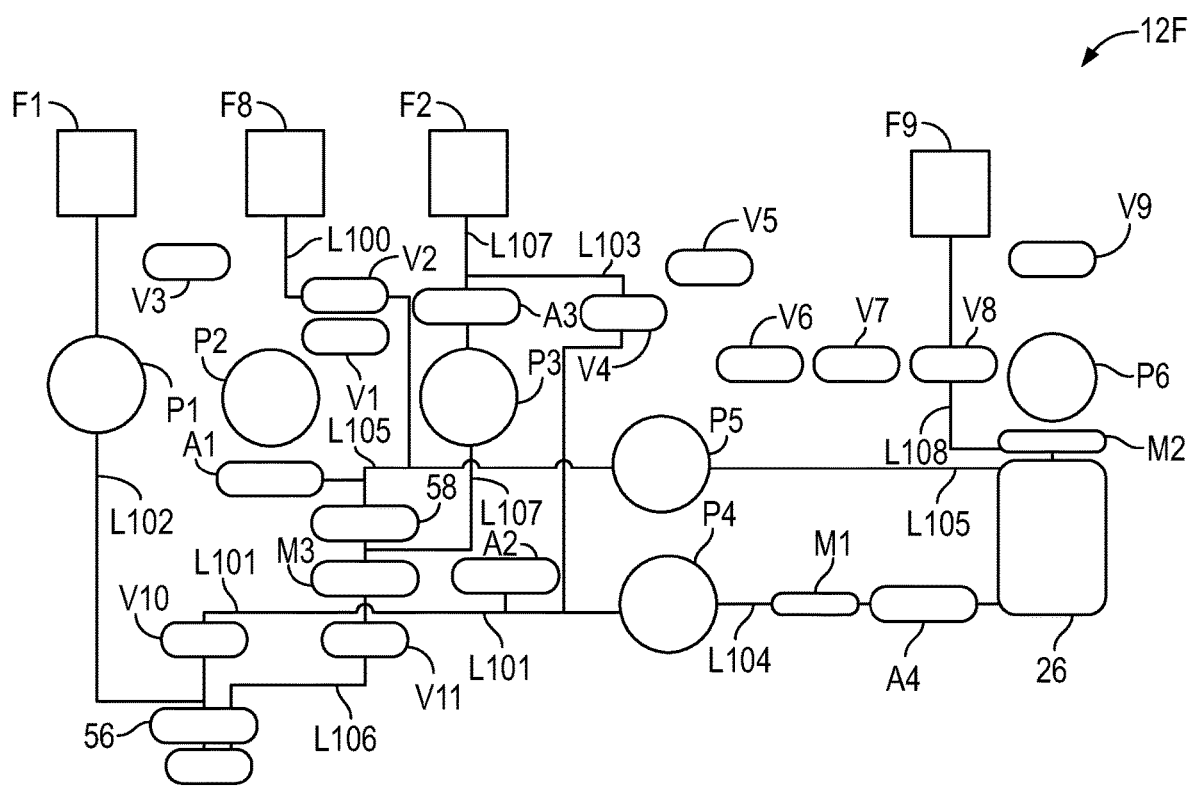

FIG. 7 is a schematic view of an exemplary fluid flow circuit 12F having a pair of blood access devices (e.g., needles) for separating and collecting plasma from blood. The fluid flow circuit 12F includes a cassette 48 of the type described above and illustrated in FIG. 13, which connects the various components of the fluid flow circuit 12F. The various connections amongst the components of the fluid flow circuit 12F are shown in FIG. 7, which also shows the fluid flow circuit 12F mounted to the blood separation device 10.

Components of the fluid flow circuit 12F interact with many of the components of the blood separation device 10, as will be described, but there are selected components of the blood separation device 10 that are not used in separating and collecting plasma using the fluid flow circuit 12F of FIG. 7. Most notably, the centrifugal separator 16 is not used, but only the spinning membrane separator drive unit 14. There are also selected valves V1, V3, V5, V6, V7, V9 and the donor and additive pumps P2 and P6 of the blood separation device 10 that are not used in the procedure described herein. The fluid flow circuit 12F includes a waste bag F8 and line L100 that, in the illustrated procedure of FIG. 43, is only used during the pre-processing priming phase, in which saline from the saline bag F2 is pumped through the fluid flow circuit 12F to prime it, before being conveyed to the waste bag F8 for disposal at the end of the procedure.

b. Procedure

Figure 43:
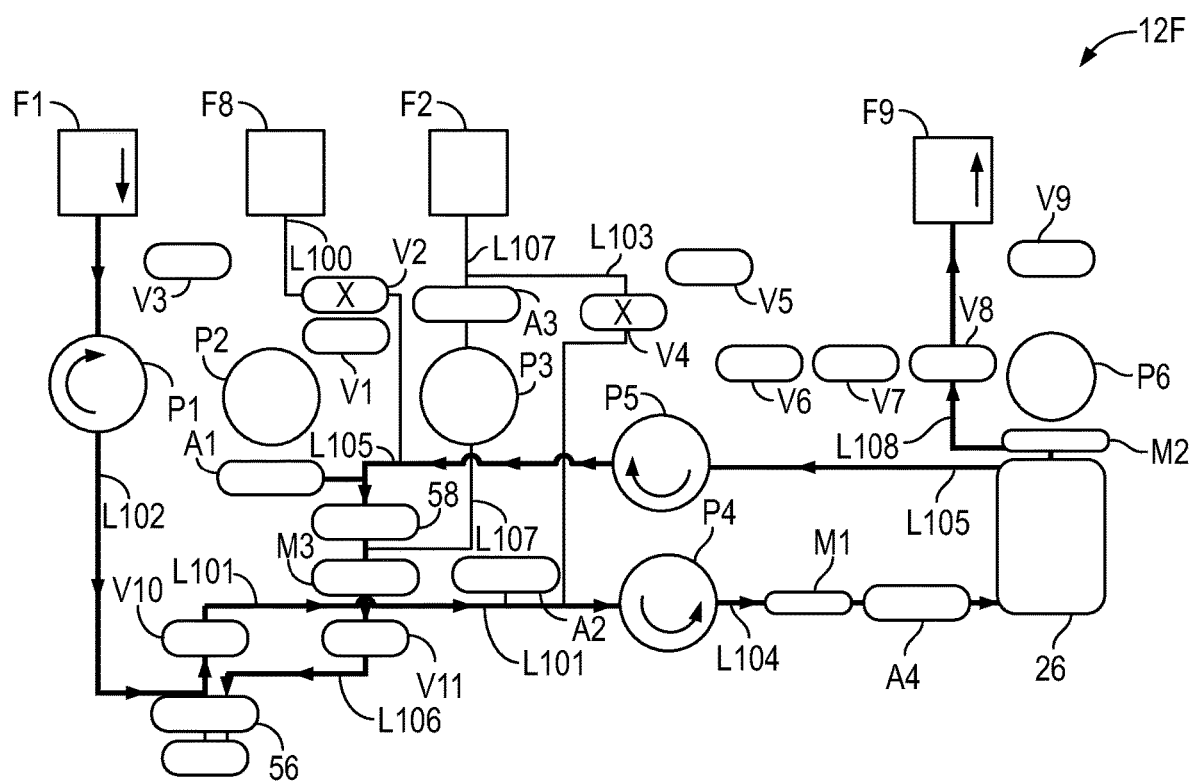
FIG. 43 is a schematic view of the fluid flow circuit of FIG. 7 mounted on the blood separation device of FIG. 1, showing the system carrying out different fluid flow tasks in connection with separation and collection of plasma from blood.

In contrast to the separation procedure described above with respect to the fluid flow circuit 12E of FIG. 6, the fluid flow circuit 12F of FIG. 7 allows for a single phase during which blood is simultaneous drawn and processed, with a portion of at least one separated component being conveyed to a recipient (FIG. 43). Blood is drawn into the fluid flow circuit 12F from a blood source (e.g., using a needle) via line L101. The line L101 may include a manual clamp 56 that may initially be in a closed position to prevent fluid flow through the line L101. When processing is to begin, an operator may move the manual clamp 56 from its closed position to an open position to allow fluid flow through the line L101.

The blood is drawn into the line L101 by the spinner pump P4, rather than the donor pump P2 (which is inactive in this procedure). Anticoagulant from the anticoagulant bag F1 may be added to the blood via line L102 by action of the anticoagulant pump P1. The valve V10 associated with valve station C10 is open to allow flow through line L101, while the valve V4 associated with valve station C4 is closed to prevent flow through line L103, thereby directing the blood toward the spinning membrane separator 26 via line L104. Prior to reaching the spinning membrane separator 26, the blood may pass through the sensor station S2 associated with pressure sensor A2 (which may be upstream of the spinner pump P4 and may monitor vein pressure if the blood source is a living donor), the spinner inlet sensor M1, and the sensor station S4 associated with pressure sensor A4. The spinner inlet sensor M1 may detect the hematocrit of the blood entering the spinning membrane separator 26 (which may be used to set the flow rate of the red blood cell pump P5 to achieve a desired packed red blood cell hematocrit), while the pressure sensor A4 may monitor the pressure of the spinning membrane separator 26.

The spinning membrane separator drive unit 14 of the blood separation device 10 manipulates the spinning membrane separator 26 to separate plasma from the cellular blood components (i.e., red blood cells, platelets, and white blood cells). The spinning membrane separator 26 may be a smaller or larger spinning membrane separator, as described above. In one embodiment, the spinning membrane separator 26 has a stationary housing 70 and a rotatable rotor 72 with a membrane 76 mounted thereon. In such an embodiment, the spinning membrane separator drive unit 14 may rotate the rotor 72 at approximately 2,500-3,000 rpm to separate blood entering the bottom portion of the spinning membrane separator 26 into plasma and cellular blood components (as described above).

The cellular blood components are pumped out of the spinning membrane separator 26 via line L105 by the red blood cell pump P5. The valve V2 associated with valve station C2 is closed to prevent fluid flow through line L100 to the waste bag F8, thereby directing the cellular blood components along line L105, through the sensor station S1 associated with pressure sensor A1 (which may monitor vein pressure if the fluid recipient is a living donor), a return line filter 58, air detector M3, the valve station C11 associated with open valve V11, and line L106 on its way to the recipient (which may be the same as the blood source) via the second needle or blood access device. Saline or another replacement fluid may be drawn from the saline bag F2 and through the sensor station S3 associated with pressure sensor A3 via line L107 by the saline pump P3 to a junction, where it mixes with fluid being conveyed to the recipient, although it may be more typical for replacement fluid to not be conveyed to the recipient until plasma collection is complete.

Cell-free plasma exits the spinning membrane separator 26 via line L108 and travels through spinner outlet sensor M2, the valve station C8 associated with open valve V8, and into plasma bag F9. The spinner outlet sensor M2 cooperates with the controller 18 to determine one or more characteristics of the plasma, such as the amount of cellular blood components in the plasma and/or whether the plasma is hemolytic and/or lipemic. There is no pump associated with line L108, so instead the flow rate at which the plasma exits the spinning membrane separator 26 is equal to the difference between the flow rates of the spinner pump P4 and red blood cell pump P5. In one embodiment, the spinner pump P4 is set to a constant flow rate and the red blood cell pump P5 is set to a flow rate that will produce a desired hematocrit for the separated cellular blood components, which may be in the range of approximately 75-85%. The flow rate of the red blood cell pump P5 may be determined using above Equation 2.

This single-phase procedure continues until the target amount of plasma has been collected.

Figure 8:
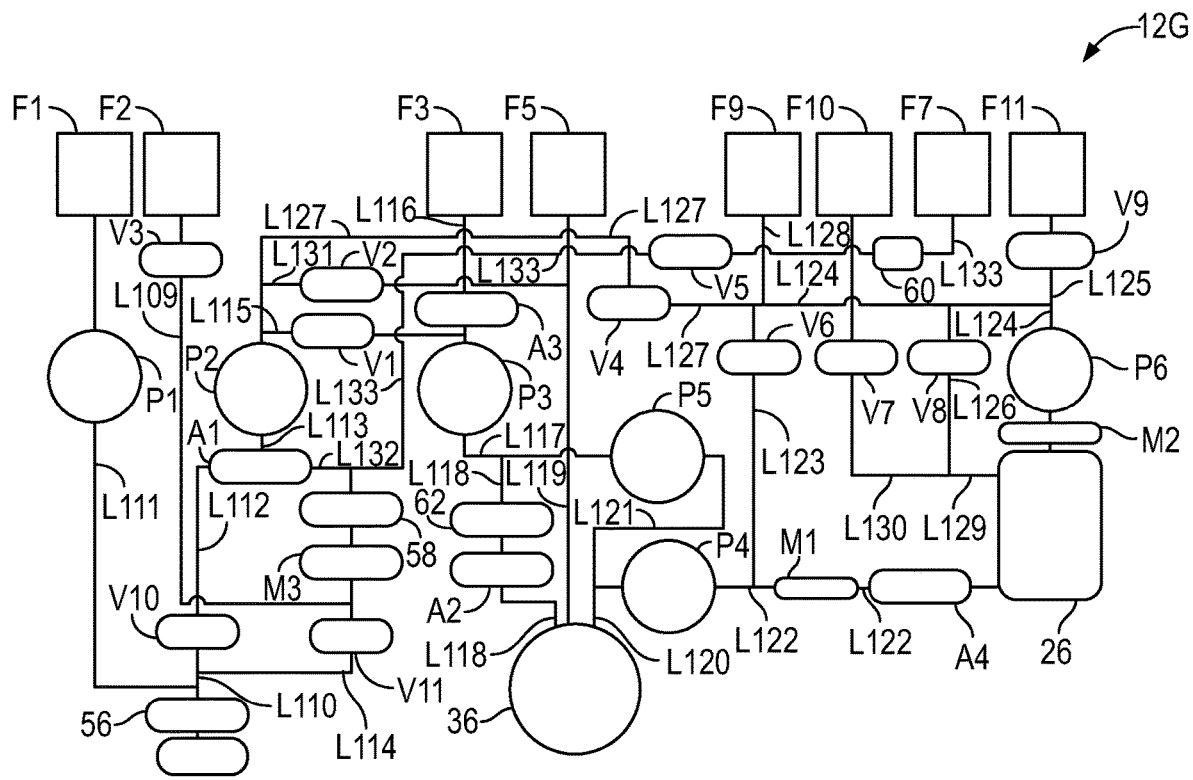

D. Platelet, Plasma, and Red Blood Cell Collection Fluid Flow Circuit and Procedure 1. Fluid Flow Circuit According to one aspect of the present disclosure, the blood separation device 10 may be used to separate and collect platelets, plasma, and red blood cells from blood. A blood separation device 10 according to the present disclosure may be used in combination with a fluid flow circuit 12 having a single blood access device (e.g., a single needle that draws blood from and returns a separated blood component to the same location). FIG. 8 is a schematic view of an exemplary fluid flow circuit 12G that may be used to separate and collect platelets, plasma, and red blood cells. The fluid flow circuit 12G includes a cassette 48 of the type described above and illustrated in FIG. 13, which connects the various components of the fluid flow circuit 12G. The various connections amongst the components of the fluid flow circuit 12G are shown in FIG. 8, which also shows the fluid flow circuit 12G mounted to the blood separation device 10.

All of the various valves V1-V11 and pressure sensors A1-A4 of the blood separation device 10, except for pressure sensor A3, are used in collecting platelets, plasma, and red blood cells. As will be described, fluid may flow through the sensor station S3 associated with pressure sensor A3, but the pressure sensor A3 does not communicate with the controller 18 to monitor the pressure at any location within the fluid flow circuit 12G. Additionally, valve V3 is typically only opened during the pre-processing priming phase, in which saline from the saline bag F2 is pumped through the flow circuit 12G to prime it. As will be described, both the centrifugal separator 16 and the spinning membrane separator drive unit 14 are used in separating blood into platelets, plasma, and red blood cells for collection.

2. Draw Phase

Figure 44:
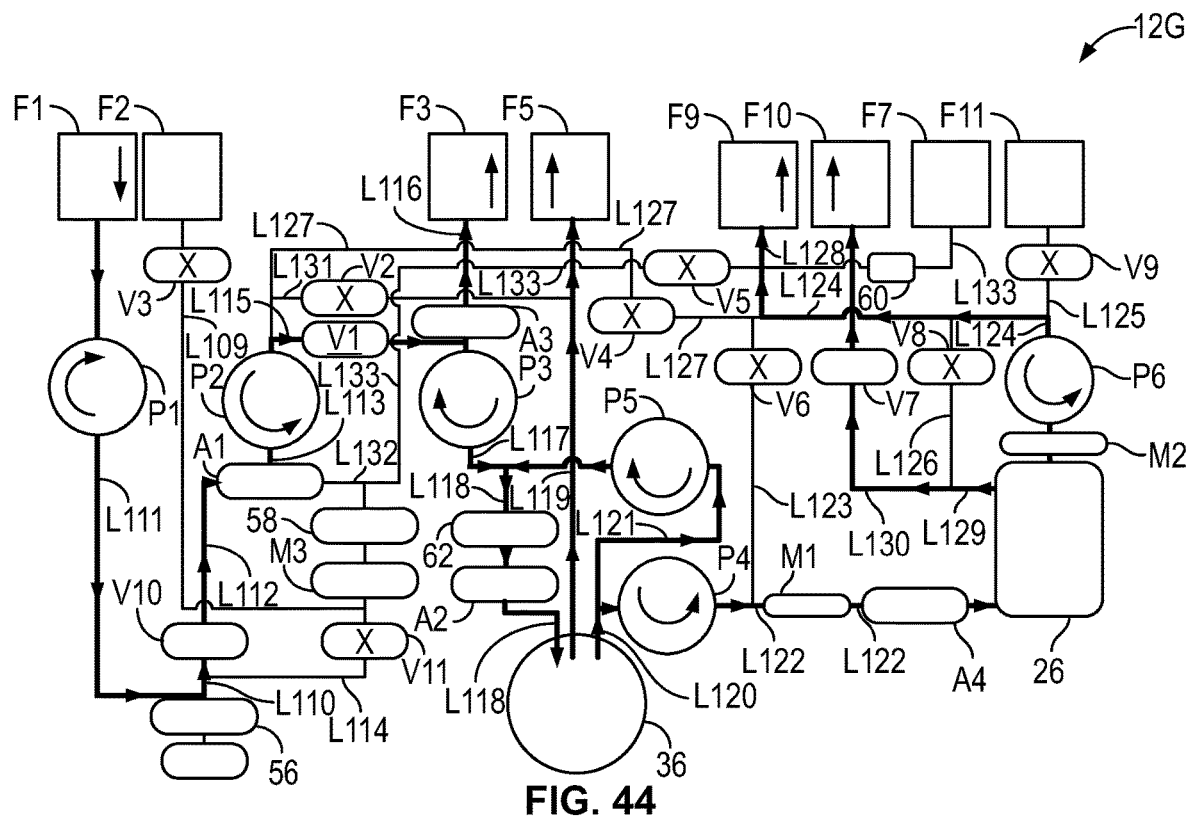
FIGS. 44-49 are schematic views of the fluid flow circuit of FIG. 8 mounted on the blood separation device of FIG. 1, showing the system carrying out different fluid flow tasks in connection with separation and collection of platelets, plasma, and red blood cells from blood.

In a first phase (FIG. 44), blood is drawn into the fluid flow circuit 12G from a blood source. If the blood source is a donor, then blood may be drawn into the fluid flow circuit 12G through a single needle that is connected to the cassette 48 by line L110. The line L110 may include a manual clamp 56 that may initially be in a closed position to prevent fluid flow through the line L110. When processing is to begin, an operator may move the manual clamp 56 from its closed position to an open position to allow fluid flow through the line L110.

The blood is drawn into the line L110 by the donor pump P2 of the blood separation device 10. Anticoagulant from the anticoagulant bag F1 may be drawn through line L111 under action of the anticoagulant pump P1 and added to the blood at a junction of lines L110 and L111.

In the illustrated embodiment, the valve V10 associated with valve station C10 is open to allow blood to flow through lines L110 and L112, the sensor station S1 associated with pressure sensor A1, and line L113, while the valve V11 associated with valve station C11 is closed to prevent fluid flow through line L114.

If the blood source is a living body (e.g., a donor), the pressure sensor A1 may communicate with the controller 18 to monitor the pressure within the vein of the blood source.

The cassette 48 includes three valve stations C1, C2, and C4 downstream of the donor pump P2, with the valves V2 and V4 associated with valve stations C2 and C4 being closed and the valve V1 associated with the other valve station C1 being open. The blood flows through the line L115 associated with the open valve V1 to a junction, where a portion of the blood is directed through line L116 and the sensor station S3 associated with inactive pressure sensor A3 to the in-process bag F3 and the remainder is directed through line L117 toward a centrifuge pump P3 (which is the same pump referred to above as the saline pump), which controls the amount of blood that is directed to the centrifugal separation chamber 36 instead of the in-process bag F3. In particular, the flow rate of the donor pump P2 is greater than the flow rate of the centrifuge pump P3, with the difference therebetween being equal to the flow rate of blood into the in-process bag F3. The flow rates may be selected such that the in-process bag F3 is partially or entirely filled with blood at the end of the draw phase.

The blood pumped through line L117 by the centrifuge pump P3 passes through line L118, an air trap 62, and the sensor station S2 associated with pressure sensor A2 (which works in combination with the controller 18 of the blood separation device 10 to monitor the pressure in the centrifugal separation chamber 36).

The centrifugal separator 16 of the blood separation device 10 manipulates the centrifugal separation chamber 36 of the fluid flow circuit 12G to separate the blood in the centrifugal separation chamber 36 into platelet-rich plasma and packed red blood cells, as described above. In one embodiment, the centrifugal separation chamber 36 is rotated nominally at 4,500 rpm, but the particular rotational speed may vary depending on the flow rates of fluids into and out of the centrifugal separation chamber 36.

The packed red blood cells exit the centrifugal separation chamber 36 via line L119 and flow directly into red blood cell bag F5. White blood cells may be retained within the centrifugal separation chamber 36 or may exit with the red blood cells.

Platelet-rich plasma is drawn out of the centrifugal separation chamber 36 via line L120 by the combined operation of two pumps P4 and P5 of the blood separation device 10. The platelet-rich plasma travels through line L120 until it reaches a junction, which splits into lines L121 and L122. One of the pumps P5 (which may be referred to as the recirculation pump and is the same pump that is referred to above as the red blood cell pump) is associated with line L121 and redirects a portion of the platelet-rich plasma to a junction, where it mixes with blood in line L118 that is being conveyed into the centrifugal separation chamber 36 by the centrifuge pump P3. Recirculating a portion of the platelet-rich plasma into the centrifugal separation chamber 36 with inflowing blood decreases the hematocrit of the blood entering the centrifugal separation chamber 36, which may improve separation efficiency. By such an arrangement, the flow rate of the fluid entering the centrifugal separation chamber 36 is equal to the sum of the flow rates of the centrifuge pump P3 and the recirculation pump P5.

As the platelet-rich plasma drawn out of the centrifugal separation chamber 36 into line L121 by the recirculation pump P5 is immediately added back into the centrifugal separation chamber 36, the bulk or net platelet-rich plasma flow rate out of the centrifugal separation chamber 36 is equal to the flow rate of the other pump P4 (which may be referred to as the PRP pump and is the same pump that is referred to above as the spinner pump). Before reaching the spinning membrane separator 26, the portion of the platelet-rich plasma conveyed through line L122 by the PRP pump P4 passes through the spinner inlet sensor M1 and the sensor station S4 associated with pressure sensor A4. The spinner inlet sensor M1 may detect the concentration of platelets in the platelet-rich plasma entering the spinning membrane separator 26, while the pressure sensor A4 may monitor the pressure of the spinning membrane separator 26.

Line L122 has a junction, where it joins with line L123. A valve V6 associated with valve station C6 is closed to prevent fluid flow through the line L123, thereby directing the separated platelet-rich plasma to the spinning membrane separator 26. Valve V6 may be selectively opened to divert all or a portion of the platelet-rich plasma through line L123 and to the plasma bag F9, if necessary. An example would be at the start of a procedure when separation is initializing and platelets are not yet exiting the centrifugal separation chamber 36, in which case the fluid conveyed through line L122 by the PRP pump P4 could be diverted to the plasma bag F9.

The spinning membrane separator drive unit 14 of the blood separation device 10 manipulates the spinning membrane separator 26 to separate the platelet-rich plasma into two sub-components (i.e., platelet-poor plasma and platelet concentrate). It should be understood that the term "platelet concentrate" as used herein is not limited to a platelet-containing fluid that is separated from the plasma of a quantity of platelet-rich plasma, but may include any platelet-dense fluid (e.g., a fluid containing the platelets derived from a buffy coat fluid separated from platelet-poor plasma and red blood cells in a centrifugal separation chamber 36).

In one embodiment, the spinning membrane separator 26 is a smaller spinning membrane separator (as described above), with a stationary housing 70 and a rotatable rotor 72 with a membrane 76 mounted thereon. In such an embodiment, the spinning membrane separator drive unit 14 may rotate the rotor 72 at approximately 1,500 rpm (or at a different speed, depending on the flow rates of fluid into and out of the spinning membrane separator 26 and/or the material composition of the membrane 76) to separate platelet-rich plasma entering the bottom portion of the spinning membrane separator 26 into plasma and platelets, according to the principles described above.

Plasma is pumped out of the spinning membrane separator 26 via line L124 by the sixth pump P6 of the blood separation device 10 (which may be referred to as the plasma pump and is the same pump referred to above as the additive pump). Valves V9, V8, V6, and V4 associated with valve stations C9, C8, C6, and C4 (respectively) are closed to prevent fluid flow through lines L125, L126, L123, and L127, thereby directing the separated plasma along lines L124 and L128 and into the plasma bag F9. On the way to the plasma bag F9, the plasma passes through spinner outlet sensor M2, which may cooperate with the controller 18 to determine one or more characteristics of the plasma, such as the amount of cellular blood components in the plasma and/or whether the plasma is hemolytic and/or lipemic.

The platelet concentrate is conveyed out of the spinning membrane separator 26 via line L129. There is no pump associated with line L129, so instead the flow rate at which the platelets exit the spinning membrane separator 26 is equal to the difference between the flow rates of the PRP pump P4 and plasma pump P6. The concentration of platelets in the platelet concentrate may be calculated as follows:

Concentration of platelets in the platelet concentrate=(concentration of platelets in the platelet-rich plasma entering the spinning membrane separator*flow rate of the PRP pump)/(flow rate of the PRP pump–flow rate of the plasma pump) [Equation 4]

The valve V8 associated with valve station C8 is closed to prevent fluid flow through the line L126, thereby directing the flow of platelets along lines L129 and L130, through the valve station C7 associated with open valve V7, and into a fluid container F10 (which may be referred to as the platelet concentrate bag). The valve V8 associated with valve station C8 may be selectively opened to allow fluid flow through line L126 and to a junction, where it joins the plasma flowing through line L124 to the plasma bag F9, if necessary.

The draw phase may continue until the amount of blood drawn from the blood source reaches a target amount or the in-process bag F3 is filled to a particular level (as determined by a weight scale from which the in-process bag F3 may be hung during the procedure) or until some other condition is satisfied.

3. Red Blood Cell Return Phase

Figure 45:
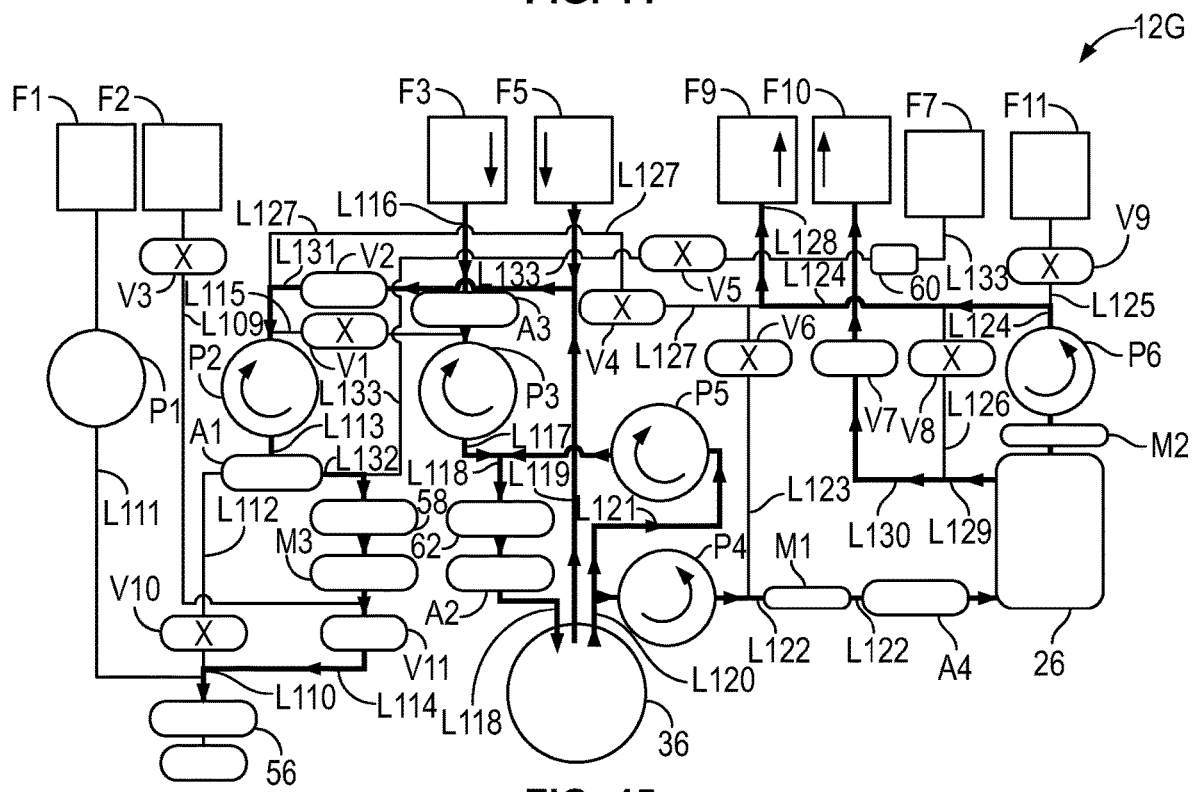

When the draw phase ends, the system transitions to one of two return phases (FIGS. 45 and 46), during which at least a portion of one of the separated blood components is conveyed to a recipient (which may be the blood source). In particular red blood cells (FIG. 45) and plasma (FIG. 46) may be conveyed to a recipient throughout the procedure until the amount of collected platelets reaches a target amount, at which time red blood cells and plasma will no longer be removed from their respective collection containers.

During a red blood cell return phase (FIG. 45), the anticoagulant pump P1 will stop drawing anticoagulant from the anticoagulant bag F1. The valve V10 associated with valve station C10 closes to prevent fluid flow through line L112 and the valve V11 associated with valve station C11 is opened to allow fluid flow through line L114. The valve V2 associated with valve station C2 opens to allow flow through line L131, while the valve V1 associated with valve station C1 is closed and the valve V3 associated with valve station C3 remains closed to prevent flow through lines L115 and L109, respectively.

With the valves so situated, the donor pump P2 will reverse direction to allow the contents of the red blood cell bag F5 to be conveyed to a recipient via the same needle used to draw blood into the fluid flow circuit 12G. The return fluid (red blood cells) is pumped through line L131, the valve station C2 associated with open valve V2, line L113, the sensor station S1 associated with pressure sensor A1, line L132, a return line filter 58, air detector M3, the valve station C11 associated with open valve V11, and lines L114 and L110 on its way to the recipient.

While fluid is being conveyed to the recipient, the blood in the in-process bag F3 acts as the blood supply for the centrifugal separator 16. When the system transitions to this return phase, the centrifuge pump P3 remains unchanged and separation continues in the same manner as described for the draw phase (i.e., with blood being separated in the centrifugal separation chamber 36 into red blood cells and platelet-rich plasma, the red blood cells flowing out of the centrifugal separation chamber 36 to the red blood cell bag F5, the platelet-rich plasma flowing to and being separated in the spinning membrane separator 26, and the separated platelets and plasma being collected in their respective containers) until the in-process bag F3 is emptied. Therefore, the system components downstream from the centrifuge pump P3 are "blinded" as to whether the system is in a draw or return phase. It will be appreciated that a method as described herein is preferable to a batch process (by which blood is only separated during a draw phase and not during a return phase) because separation and collection may be continuous, thereby decreasing the time required to complete the procedure. Additionally, by continuously processing blood in the centrifugal separation chamber 36, the interface between the separated red blood cells and platelet-rich plasma is maintained, whereas the location of the interface is lost during the return phase of a batch procedure, which requires the interface to be reestablished during every draw/separation phase and further increases the duration of the procedure.

It will be seen that the separated red blood cells are conveyed to the red blood cell bag F5 at the same time that the contents of the red blood cell bag F5 are being conveyed to the recipient. The rate at which the donor pump P2 operates may be greater than the rate at which red blood cells exit the centrifugal separation chamber 36 to allow the red blood cell bag F5 to empty during this return phase, even as separation continues. Once the red blood cell bag F5 is empty, the system may transition back to the draw phase or to the plasma return phase or to a different phase.

4. Plasma Return Phase

Figure 46:
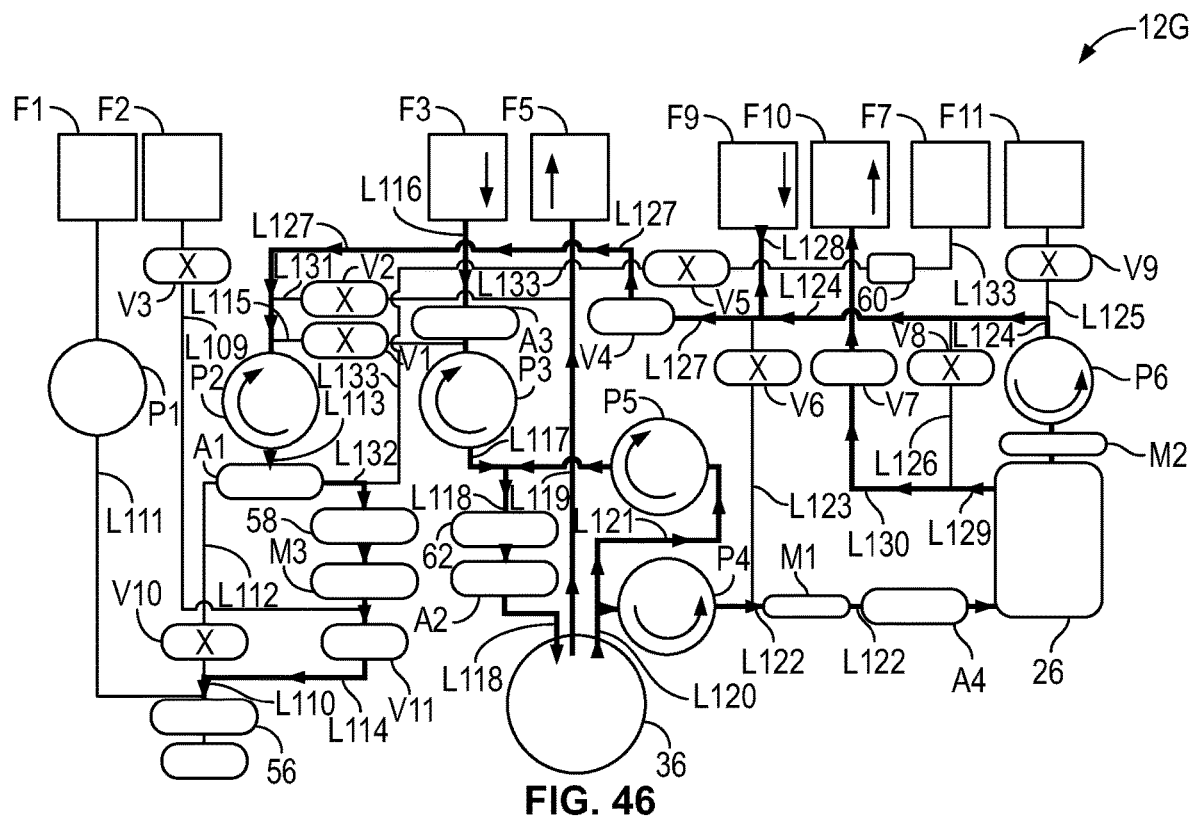

Similar to the red blood cell return phase (FIG. 45), the anticoagulant pump P1 will stop drawing anticoagulant from the anticoagulant bag F1 during a plasma return phase (FIG. 46). Depending on whether the plasma return phase is initiated from the draw phase or red blood cell return phase, selected valve stations may or may not need to move between their open and closed conditions to allow plasma to be conveyed to a recipient. In particular, the valves V10 and V3 associated with valve stations C10 and C3 (respectively) are closed to prevent fluid flow through lines L112 and L109, while the valve V11 associated with valve station C11 is open to allow fluid flow through line L114. The valves V1 and V2 associated with valve stations C1 and C2 (respectively) are closed to prevent flow through lines L115 and L131, while the valve V4 associated with valve station C4 is open to allow flow through line L127.

With the valves so situated, the donor pump P2 will operate in the same direction as in the red blood cell return phase (or in the opposite direction of its operation in the draw phase) to allow the contents of the plasma bag F9 to be conveyed to a recipient via the same needle used to draw blood into the fluid flow circuit 12G. The return fluid (cell-free plasma) is pumped through lines L128 and L127, the valve station C4 associated with open valve V4, line L113, the sensor station S1 associated with pressure sensor A1, line L132, a return line filter 58, air detector M3, the valve station C11 associated with open valve V11, and lines L114 and L110 on its way to the recipient.

While fluid is being conveyed to the recipient, the blood in the in-process bag F3 acts as the blood supply for the centrifugal separator 16. When the system transitions to this return phase, the centrifuge pump P3 remains unchanged and separation continues in the same manner as described for the draw phase and the red blood cell return phase (i.e., with blood being separated in the centrifugal separation chamber 36 into red blood cells and platelet-rich plasma, the red blood cells flowing out of the centrifugal separation chamber 36 to the red blood cell bag F5, the platelet-rich plasma flowing to and being separated in the spinning membrane separator 26, and the separated platelets and plasma being collected in their respective containers) until the in-process bag F3 is emptied. Therefore, the system components downstream from the centrifuge pump P3 are "blinded" as to whether the system is in a draw or return phase. It will be appreciated that a method as described herein is preferable to a batch process (by which blood is only separated during a draw phase and not during a return phase) because separation and collection may be continuous, thereby decreasing the time required to complete the procedure. Additionally, by continuously processing blood in the centrifugal separation chamber 36, the interface between the separated red blood cells and platelet-rich plasma is maintained, whereas the location of the interface is lost during the return phase of a batch procedure, which requires the interface to be reestablished during every draw/separation phase and further increases the duration of the procedure.

It will be seen that the separated plasma is conveyed to the plasma bag F9 at the same time that the contents of the plasma bag F9 are being conveyed to the recipient. The rate at which the donor pump P2 operates to draw plasma out of the plasma bag F9 may be greater than the rate at which the plasma pump P6 operates to convey plasma into the plasma bag F9 to allow the plasma bag F9 to empty during this return phase, even as separation continues. Once the plasma bag F9 is empty, the system may transition back to the draw phase or to the red blood cell return phase or to a different phase.

5. Final Phase

Figure 47:
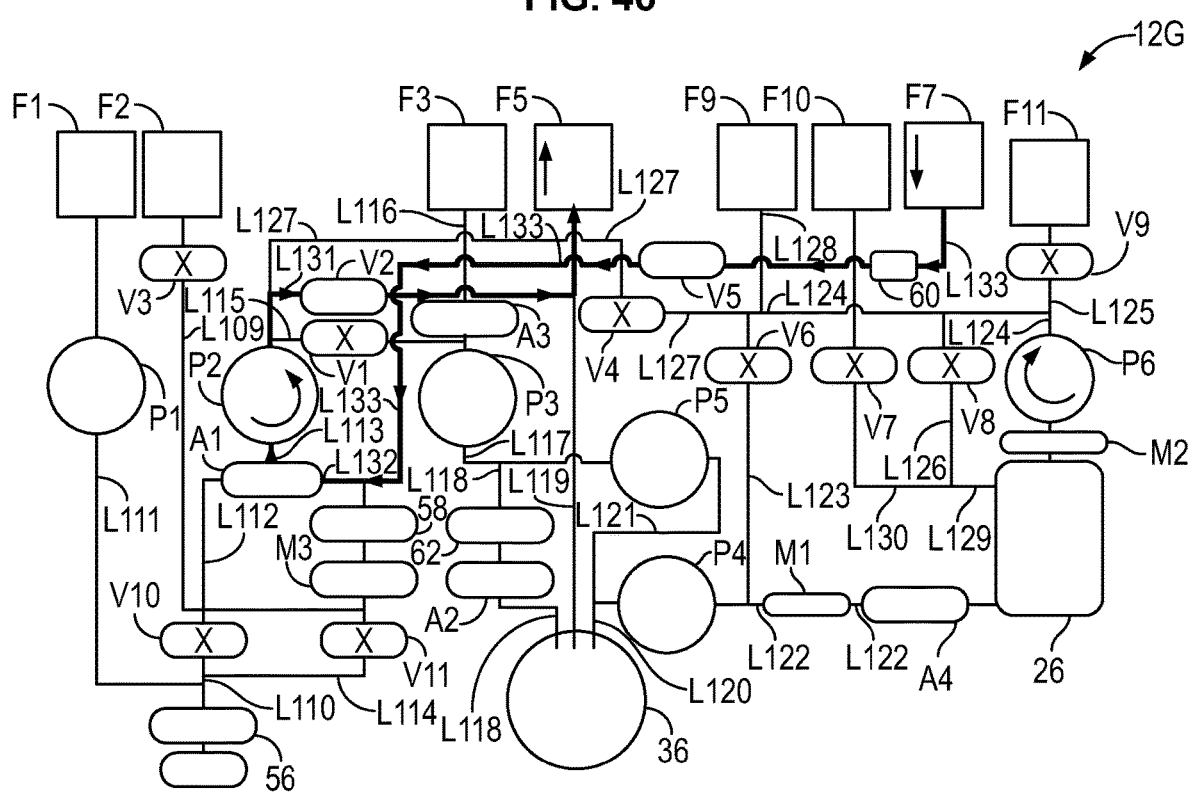
Figure 48:
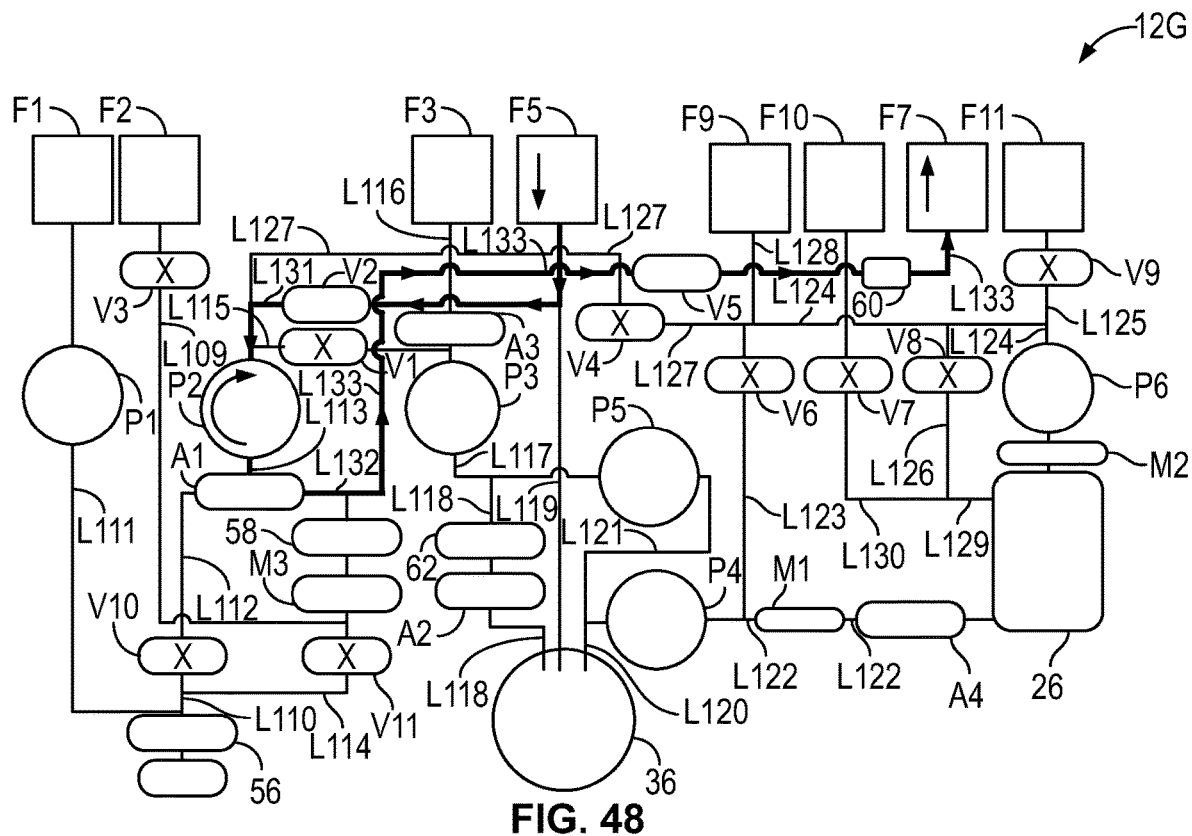
Figure 49:
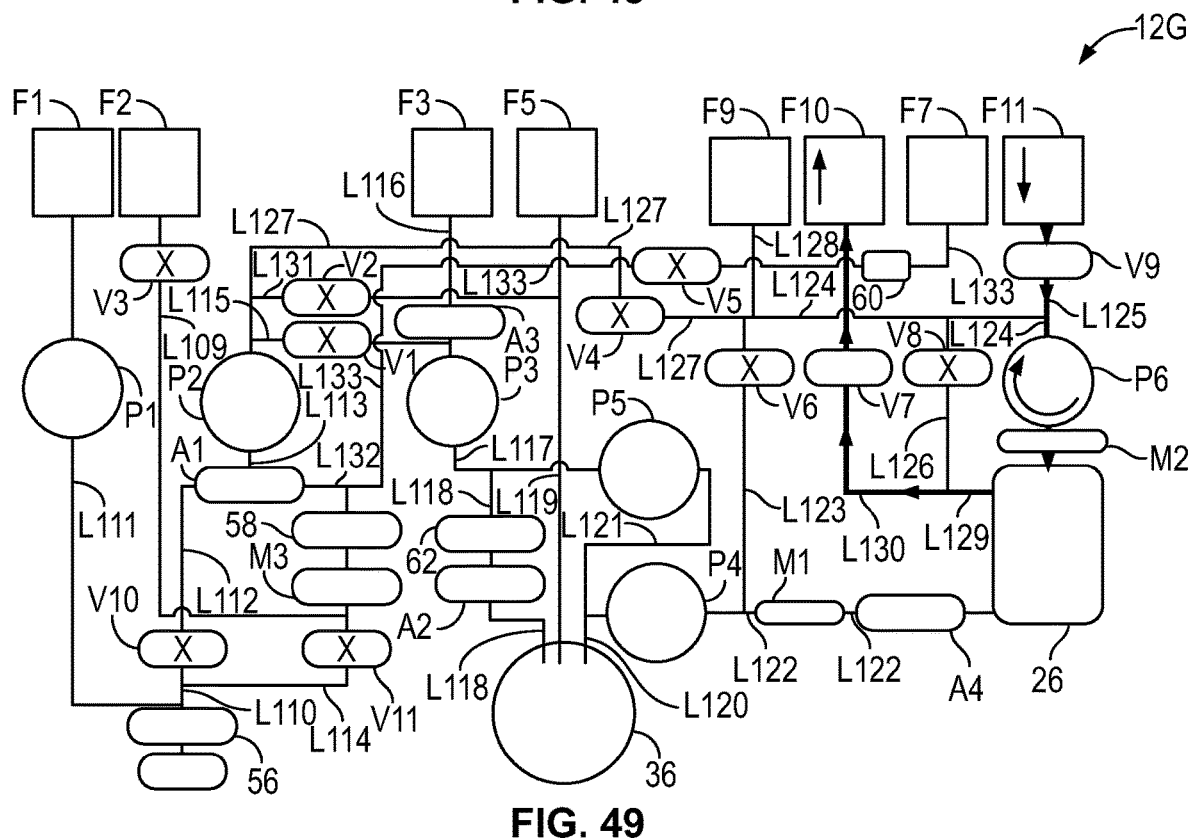

When the targeted amounts of platelets, plasma, and red blood cells have been collected, the blood source/recipient may be disconnected from the fluid flow circuit 12G and the system may transition to a final phase, which is represented by FIGS. 47-49.

During the final phase, an additive solution (such as Adsol) may be added to the collected red blood cells, as shown in FIG. 47. This may be carried out by opening the valves V5 and V2 associated with valve stations C5 and C2 (respectively) to allow flow through lines L133 and line L131, while the valves V11, V3, V10, V1, and V4 associated with valve stations C11, C3, C10, C1, and C4 (respectively) are closed to prevent flow through lines L114, L109, L112, L115, and L127. The donor pump P2 operates in the same direction as in the draw phase to draw additive solution from the additive bag F7, through line L133, leukocyte removal filter 60, the valve station C5 associated with open valve V5, line L132, the sensor station S1 associated with pressure sensor A1, lines L113 and L131, the valve station C2 associated with open valve V2, and line L119 to the red blood cell bag F5.

The mixture of red blood cells and additive solution may then be leukoreduced, as shown in FIG. 48. This may be carried out by maintaining the valves as in FIG. 47, but reversing the direction in which the donor pump P2 operates. The mixture of red blood cells and additive solution thus reverses the path traversed by the additive solution in the process of FIG. 47, thereby conveying the mixture through the leukocyte removal filter 60 and into the additive bag F7 (which may alternatively be referred to as the red blood cell product bag) as a leukoreduced red blood cell product. During this phase, the pressure sensor A1 associated with sensor station S1 may be used to monitor the pressure of the leukocyte removal filter 60 instead of a donor vein pressure (as in the draw phase).

Finally, a platelet additive solution ("PAS") may be added to the collected platelets, as shown in FIG. 49. This may be carried out with the valves V9 and V7 associated with valve stations C9 and C7 (respectively) in an open condition to allow flow through lines L125 and L130 and the valves V4, V8, and V6 associated with valve stations C4, C8, and C6 (respectively) in a closed condition to prevent flow through lines L127, L126, and L123. With the valves so situated, the plasma pump P6 may operate to draw the platelet additive solution from a fluid container F11 (which may be referred to as a PAS bag) via line L125, through the valve station C9 associated with open valve V9, line L124, spinner outlet sensor M2, the spinning membrane separator 26, lines L129 and L130, the valve station C7 associated with open valve V7, and into the platelet concentrate bag F10.

E. Platelet or Platelet and Plasma Collection

According to one aspect of the present disclosure, the blood separation device 10 may be used to separate and collect platelets or both platelets and substantially cell-free plasma from blood. A blood separation device 10 according to the present disclosure may be used in combination with a fluid flow circuit 12 having a single blood access device (e.g., a single needle that draws blood from and returns a separated blood component to the same location) or two blood access devices (e.g., one needle that draws blood from a source and a second needle that flows a separated blood component to the same source or to a different recipient). An exemplary fluid flow circuit 12H, 12I and procedure will be described for each arrangement.

1. Single Needle Fluid Flow Circuit and Procedure a. Fluid Flow Circuit

Figure 9:
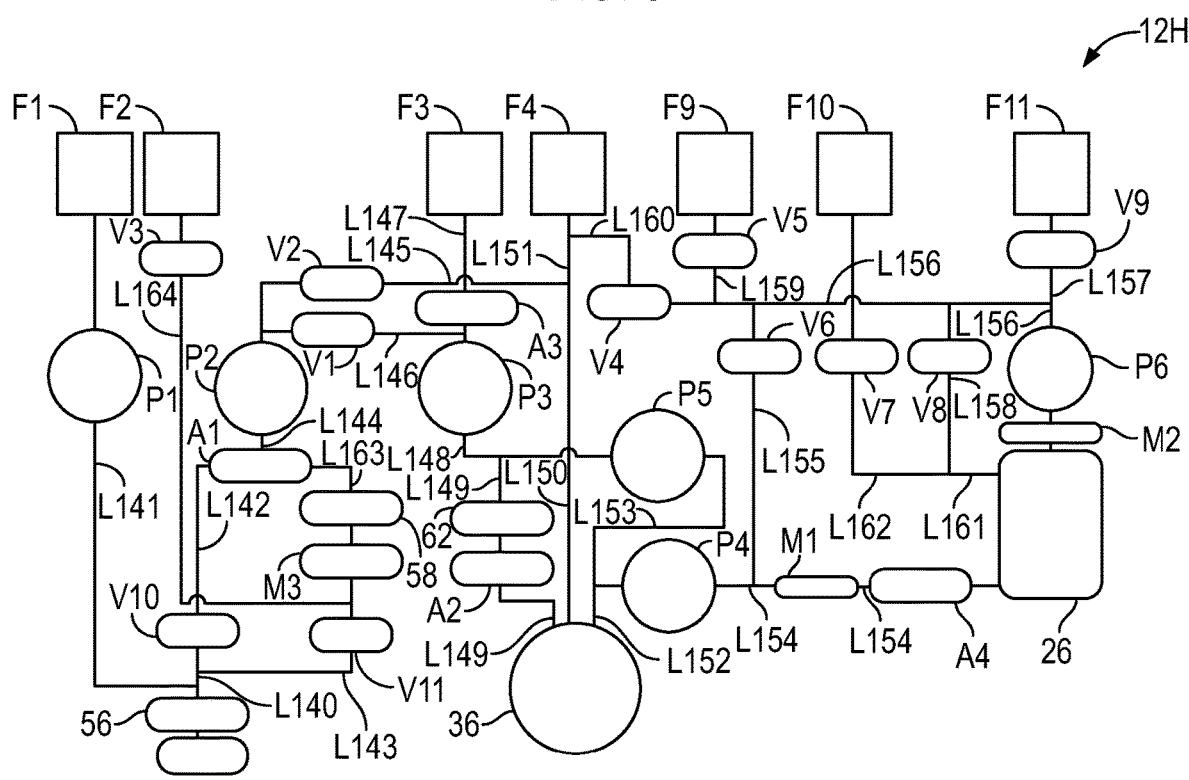

FIG. 9 is a schematic view of an exemplary fluid flow circuit 12H having a single blood access device (e.g., a single needle that draws blood from and returns a separated blood component to the same location) that may be used to separate and collect only platelets or both platelets and plasma. The fluid flow circuit 12H includes a cassette 48 of the type described above and illustrated in FIG. 13, which connects the various components of the fluid flow circuit 12H. The various connections amongst the components of the fluid flow circuit 12H are shown in FIG. 9, which also shows the fluid flow circuit 12H mounted to the blood separation device 10.

All of the various valves V1-V11 and pressure sensors A1-A4 of the blood separation device 10 are used in combination with the fluid flow circuit 12H of FIG. 9 for separating and collecting platelets or platelets and plasma, except for pressure sensor A3. As will be described, fluid may flow through the sensor station S3 associated with pressure sensor A3, but the pressure sensor A3 does not communicate with the controller 18 to monitor the pressure at any location within the fluid flow circuit 12G. Additionally, as will be described, both the centrifugal separator 16 and the spinning membrane separator drive unit 14 are used in separating blood into platelets or platelets and plasma for collection.

b. Draw Phase

Figure 50:
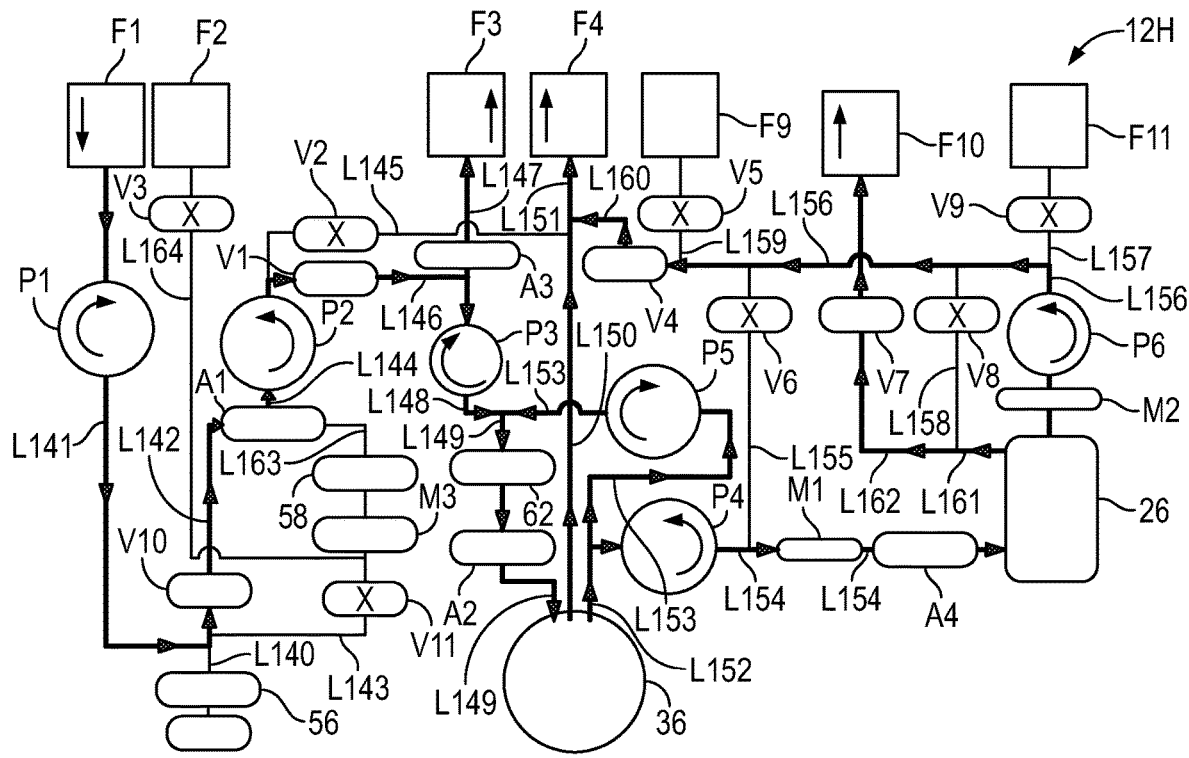
FIGS. 50-53 are schematic views of the fluid flow circuit of FIG. 9 mounted on the blood separation device of FIG. 1, showing the system carrying out different fluid flow tasks in connection with separation and collection of platelets or platelets and plasma from blood.

In a first phase (FIG. 50), blood is drawn into the fluid flow circuit 12H from a blood source. If the blood source is a donor, then blood may be drawn into the fluid flow circuit 12H through a single needle that is connected to the cassette 48 by line L140. The line L140 may include a manual clamp 56 that may initially be in a closed position to prevent fluid flow through the line L140. When processing is to begin, an operator may move the manual clamp 56 from its closed position to an open position to allow fluid flow through the line L140.

The blood is drawn into the line L140 by the donor pump P2 of the blood separation device 10. Anticoagulant from the anticoagulant bag F1 may be drawn through line L141 under action of the anticoagulant pump P1 and added to the blood at a junction of lines L140 and L141.

In the illustrated embodiment, the valve V10 associated with valve station C10 of the fluid flow circuit 12H is open to allow blood to flow through lines L140 and L142 and a sensor station S1 associated with pressure sensor A1, while the valve V11 associated with valve station C11 is closed to prevent fluid flow through line L143. If the blood source is a living body (e.g., a donor), the pressure sensor A1 may communicate with the controller 18 to monitor the pressure within the vein of the blood source.

The cassette 48 includes two valve stations C1 and C2 downstream of the donor pump P2 and line L144, with the valve V2 associated with valve station C2 being closed to prevent flow through line L145 and the valve V1 associated with valve station C1 being open to allow flow through line L146. The blood flows through the line L146 associated with the open valve V1 to a junction, where a portion of the blood is directed through line L147 and the sensor station S3 associated with inactive pressure sensor A3 to the in-process bag F3 and the remainder is directed through line L148 toward the centrifuge pump P3, which controls the amount of blood that is directed to the centrifugal separation chamber 36 instead of the in-process bag F3. In particular, the flow rate of the donor pump P2 is greater than the flow rate of the centrifuge pump P3, with the difference therebetween being equal to the flow rate of blood into the in-process bag F3.

The flow rates may be selected such that the in-process bag F3 is partially or entirely filled with blood at the end of the draw phase.

The blood pumped through line L148 by the centrifuge pump P3 passes through line L149, an air trap 62, and the sensor station S2 associated with pressure sensor A2 (which works in combination with the controller 18 of the blood separation device 10 to monitor the pressure in the centrifugal separation chamber 36) before reaching the centrifugal separation chamber 36 of the fluid flow circuit 12H. The centrifugal separator 16 of the blood separation device 10 manipulates the centrifugal separation chamber 36 to separate the blood in the centrifugal separation chamber 36 into platelet-rich plasma and packed red blood cells, as described above. In one embodiment, the centrifugal separation chamber 36 is rotated nominally at 4,500 rpm, but the particular rotational speed may vary depending on the flow rates of fluids into and out of the centrifugal separation chamber 36.

The packed red blood cells exit the centrifugal separation chamber 36 via line L150 and flow through line L151 into the return bag F4. White blood cells may be retained within the centrifugal separation chamber 36 or may exit with the red blood cells.

Platelet-rich plasma is drawn out of the centrifugal separation chamber 36 via line L152 by the combined operation of the recirculation and PRP pumps P5 and P4 of the blood separation device 10. The platelet-rich plasma travels through line L152 until it reaches a junction, which splits into lines L153 and L154. The recirculation pump P5 is associated with line L153 and redirects a portion of the platelet-rich plasma to a junction, where it mixes with blood in line L148 that is being conveyed into the centrifugal separation chamber 36 by the centrifuge pump P3. Recirculating a portion of the platelet-rich plasma into the centrifugal separation chamber 36 with inflowing blood decreases the hematocrit of the blood entering the centrifugal separation chamber 36, which may improve separation efficiency. By such an arrangement, the flow rate of the fluid entering the centrifugal separation chamber 36 is equal to the sum of the flow rates of the centrifuge pump P3 and the recirculation pump P5.

As the platelet-rich plasma drawn out of the centrifugal separation chamber 36 into line L153 by the recirculation pump P5 is immediately added back into the centrifugal separation chamber 36, the bulk or net platelet-rich plasma flow rate out of the centrifugal separation chamber 36 is equal to the flow rate of the PRP pump P4. Before reaching the spinning membrane separator 26, the portion of the platelet-rich plasma conveyed through line L154 by the PRP pump P4 passes through the spinner inlet sensor M1 and the sensor station S4 associated with pressure sensor A4. The spinner inlet sensor M1 may detect the concentration of platelets in the platelet-rich plasma entering the spinning membrane separator 26, while the pressure sensor A4 may monitor the pressure of the spinning membrane separator 26.

Line L154 has a junction, where it joins with line L155. The valve V6 associated with valve station C6 is closed to prevent fluid flow through the line L155, thereby directing the separated platelet-rich plasma to the spinning membrane separator 26. The valve V6 may be selectively opened to divert all or a portion of the platelet-rich plasma through line L155 and to the return bag F4, if necessary. An example would be at the start of a procedure when separation is initializing and platelets are not yet exiting the centrifugal separation chamber 36, in which case the fluid conveyed through line L154 by the PRP pump P4 could be diverted to the return bag F4.

The spinning membrane separator drive unit 14 of the blood separation device 10 manipulates the spinning membrane separator 26 to separate the platelet-rich plasma into two sub-components (i.e., platelet-poor plasma and platelet concentrate). In one embodiment, the spinning membrane separator 26 is a smaller spinning membrane separator (as described above), with a stationary housing 70 and a rotatable rotor 72 with a membrane 76 mounted thereon. In such an embodiment, the spinning membrane separator drive unit 14 may rotate the rotor 72 at approximately 1,500 rpm (or at a different speed, depending on the flow rates of fluid into and out of the spinning membrane separator 26) to separate platelet-rich plasma entering the bottom portion of the spinning membrane separator 26 into plasma and platelets, according to the principles described above.

Plasma is pumped out of the spinning membrane separator 26 via line L156 by the plasma pump P6 of the blood separation device 10. Valves V9, V8, V6, and V5 associated with valve stations C9, C8, C6, and C5 (respectively) are closed to prevent flow through lines L157, L158, L155, and L159, thereby directing the separated plasma along lines L156 and L160, through the valve station C4 associated with open valve V4, and into the return bag F4 (with the separated red blood cells). On the way to the return bag F4, the plasma passes through spinner outlet sensor M2, which may cooperate with the controller 18 to determine one or more characteristics of the plasma, such as the amount of cellular blood components in the plasma and/or whether the plasma is hemolytic and/or lipemic.

The platelet concentrate is conveyed out of the spinning membrane separator 26 via line L161. There is no pump associated with line L161, so instead the flow rate at which the platelets exit the spinning membrane separator 26 is equal to the difference between the flow rates of the PRP pump P4 and plasma pump P6. The concentration of platelets in the platelet concentrate may be calculated according to above Equation 4.

The valve V8 associated with valve station C8 is closed to prevent fluid flow through the line L158, thereby directing the flow of platelets along lines L161 and L162, through the valve station C7 associated with open valve V7, and into the platelet concentrate bag F10. The valve V8 associated with valve station C8 may be selectively opened to allow fluid flow through line L158 and to a junction, where it joins the plasma flowing through line L156 to the return bag F4, if necessary.

The draw phase may continue until the amount of blood drawn from the blood source reaches a target amount or the in-process bag F3 is filled to a particular level (as determined by a weight scale from which the in-process bag F3 is hung during the procedure) or until some other condition is satisfied.

c. Return Phase—Platelet Collection Only

Figure 51:
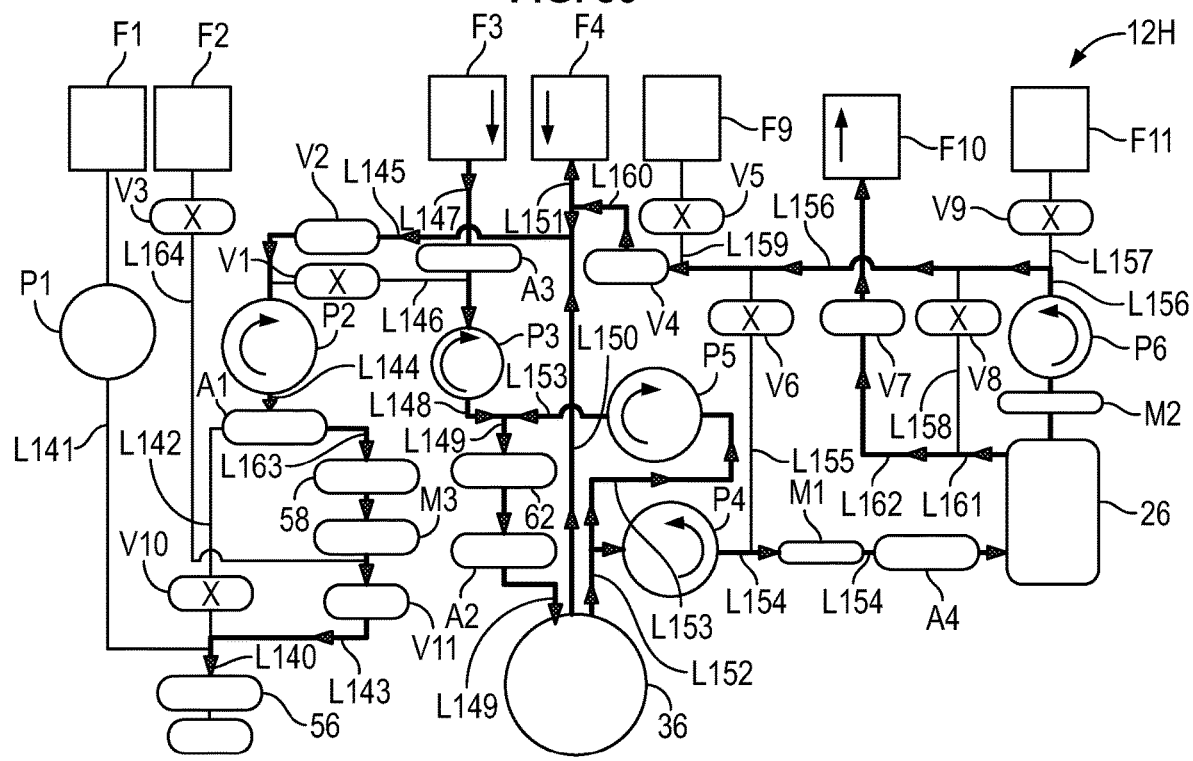
Figure 52:
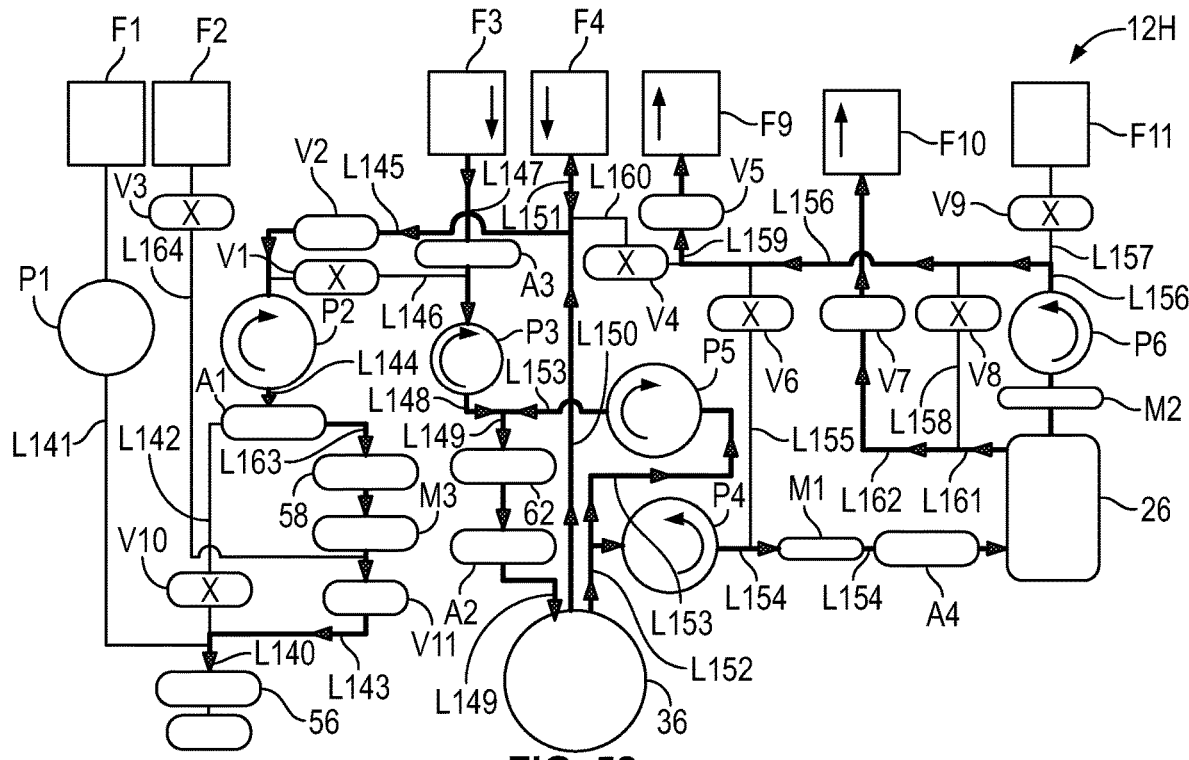

When the draw phase ends, the system transitions to one of two return phases (FIGS. 51 and 52), depending on whether only platelets are being collected (FIG. 51) or if both platelets and plasma are being collected (FIG. 52). At least a portion of one of the separated blood components is conveyed to a recipient (which may be the blood source), while the collection of either platelets (FIG. 51) or both platelets and plasma (FIG. 52) proceeds.

During the return phase of a procedure in which only platelets are being collected (FIG. 51), the anticoagulant pump P1 will stop drawing anticoagulant from the anticoagulant bag F1. The valve V10 associated with valve station C10 will close to prevent fluid flow through line L142 and the valve V11 associated with valve station C11 is opened to allow fluid flow through line L143. The valve V2 associated with valve station C2 also opens to allow flow through line L145, while the valve V1 associated with valve station C1 is closed to prevent flow through line L146.

With the valves so situated, the donor pump P2 will reverse direction to allow the contents of the return bag F4 to be conveyed to a recipient via the same needle used to draw blood into the fluid flow circuit 12H. The return fluid (red blood cells and plasma) is pumped through lines L151 and L145, the valve station C2 associated with open valve V2, line L144, the sensor station S1 associated with pressure sensor A1, and into line L163. The return fluid travels along line L163, through a return line filter 58 and air detector M3 until it reaches a junction, which joins lines L163 and L164 (which leads to the saline bag F2). The valve V3 associated with valve station C3 is closed, thereby preventing fluid flow through line L164 and directing the return fluid further along line L163, through the valve station C11 associated with open valve V11, and along lines L143 and L140 to the recipient.

While fluid is being conveyed to the recipient, the blood in the in-process bag F3 acts as the blood supply for the centrifugal separator 16. When the system transitions to this return phase, the centrifuge pump P3 remains unchanged and separation continues in the same manner as described for the draw phase (i.e., with blood being separated in the centrifugal separation chamber 36 into red blood cells and platelet-rich plasma, the red blood cells flowing out of the centrifugal separation chamber 36 to the return bag F4, the platelet-rich plasma flowing to and being separated in the spinning membrane separator 26, and the separated platelets being collected while plasma is directed to the return bag F4) until the in-process bag F3 is emptied. Therefore, the system components downstream from the centrifuge pump P3 are "blinded" as to whether the system is in the draw phase or this return phase. It will be appreciated that a method as described herein is preferable to a batch process (by which blood is only separated during a draw phase and not during a return phase) because separation and collection may be continuous, thereby decreasing the time required to complete the procedure. Additionally, by continuously processing blood in the centrifugal separation chamber 36, the interface between the separated red blood cells and platelet-rich plasma is maintained, whereas the location of the interface is lost during the return phase of a batch procedure, which requires the interface to be reestablished during every draw/separation phase and further increases the duration of the procedure.

It will be seen that the separated plasma and red blood cells are conveyed to the return bag F4 at the same time that the contents of the return bag F4 are being conveyed to the recipient. The rate at which the donor pump P2 operates may be greater than the rate at which plasma and red blood cells are conveyed into the return bag F4 to allow the return bag F4 to empty during this return phase, even as separation continues. Once the in-process and/or return bag F3, F4 is empty, the system may transition back to the draw phase (FIG. 50) or to a final phase (FIG. 53).

d. Return Phase—Platelet and Plasma Collection

The return phase when collecting platelets and plasma (FIG. 52) is similar to the return phase when only platelets are being collected (FIG. 51). The principal difference is that, when collecting platelets and plasma, the valve V5 associated with valve station C5 is open to allow flow through line L159, while the valve V4 associated with valve station C4 is closed to prevent flow through line L160, thereby directing the separated plasma exiting the spinning membrane separator 26 through the line L159 associated with open valve V5 to the plasma bag F9 instead of to the return bag F4. The valves may be so situated for the entire return phase or the conditions of valves V4 and V5 may be reversed for a portion of the phase (thereby directing separated plasma to the return bag F4 instead of the plasma bag F9), depending on the amount of plasma to be collected.

Figure 53:
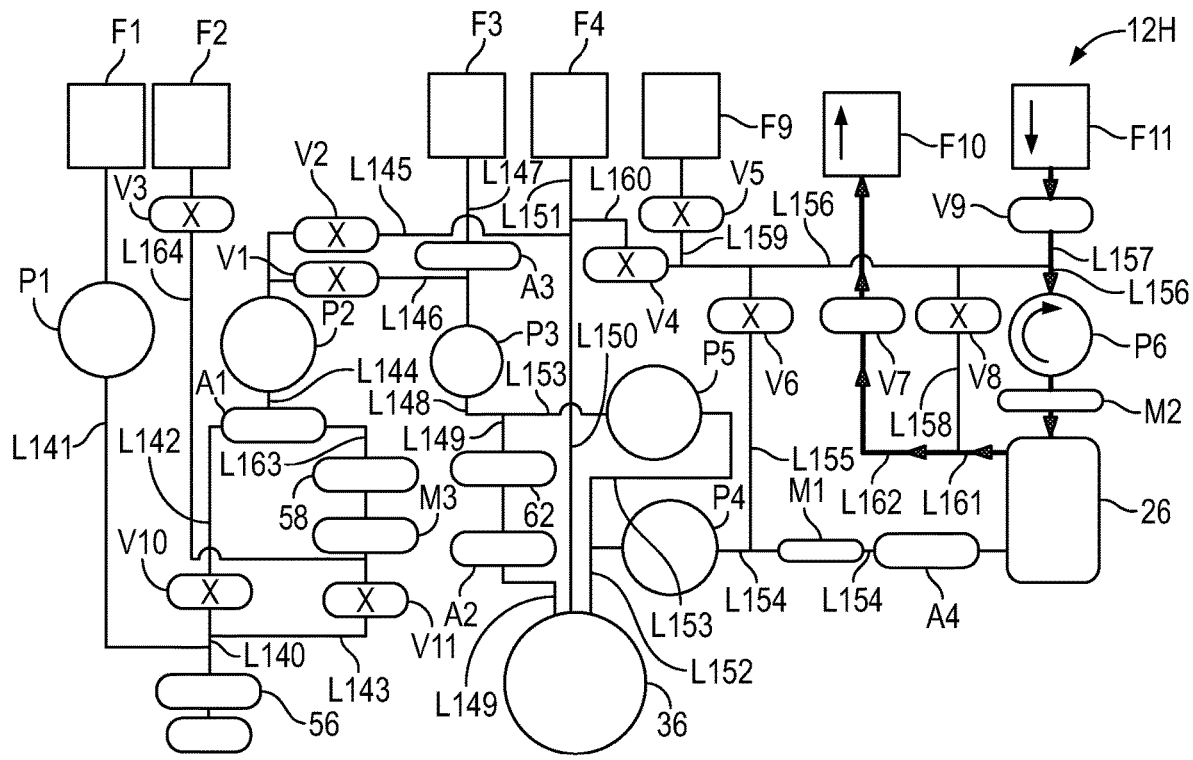

Once the in-process and/or return bag F3, F4 is empty, the system may transition back to the draw phase (FIG. 50) or to a final phase (FIG. 53).

e. Final Phase

When the targeted amount of platelets or the targeted amounts of platelets and plasma have been collected, the blood source/recipient may be disconnected from the fluid flow circuit 12H and the system may transition to a final phase in which a platelet additive solution is added to the collected platelets, as shown in FIG. 53. This may be carried out with the valves V9 and V7 associated with valve stations C9 and C7 (respectively) in an open condition to allow flow through lines L157 and L162, while the valves V8, V6, V5, and V4 associated with valve stations C8, C6, C5, and C4 (respectively) in a closed condition to prevent flow through lines L158, L155, L159, and L160. With the valves so situated, the plasma pump P6 may operate to draw the platelet additive solution from the PAS bag F11 via line L157, through the valve station C9 associated with open valve V9, line L156, spinner outlet sensor M2, the spinning membrane separator 26, lines L161 and L162, the valve station C7 associated with open valve V7, and into the platelet concentrate bag F10.

2. Double Needle Fluid Flow Circuit and Procedure a. Fluid Flow Circuit

Figure 10:
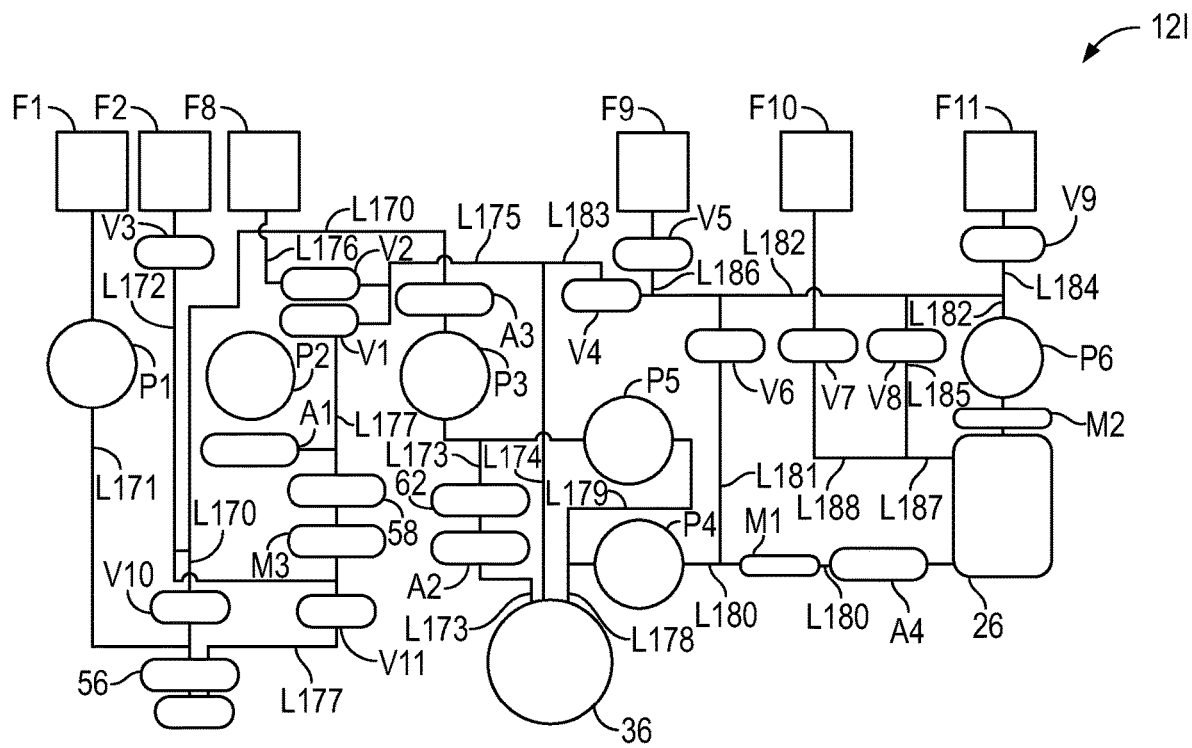

FIG. 10 is a schematic view of an exemplary fluid flow circuit 12I having a pair of blood access devices (e.g., needles) for separating and collecting platelets or both platelets and plasma from blood. The fluid flow circuit 12I includes a cassette 48 of the type described above and illustrated in FIG. 13, which connects the various components of the fluid flow circuit 12I. The various connections amongst the components of the fluid flow circuit 12I are shown in FIG. 10, which also shows the fluid flow circuit 12I mounted to the blood separation device 10.

All of the various valves V1-V11 and pressure sensors A1-A4 of the fluid flow circuit 12I of FIG. 10 are used in collecting platelets or platelets and plasma, along with all of the pumps P1-P6, except for the donor pump P2. Additionally, as will be described, both the centrifugal separator 16 and the spinning membrane separator drive unit 14 are used in separating blood into platelets or platelets and plasma for collection. The fluid flow circuit 12I includes a waste bag F8 that, in the illustrated procedure of FIGS. 54-56, is only used during the pre-processing priming phase, in which saline from the saline bag F2 is pumped through the fluid flow circuit 12I to prime it, before being conveyed to the waste bag F8 for disposal at the end of the procedure.

b. Separation and Collection—Platelets Only

Figure 54:
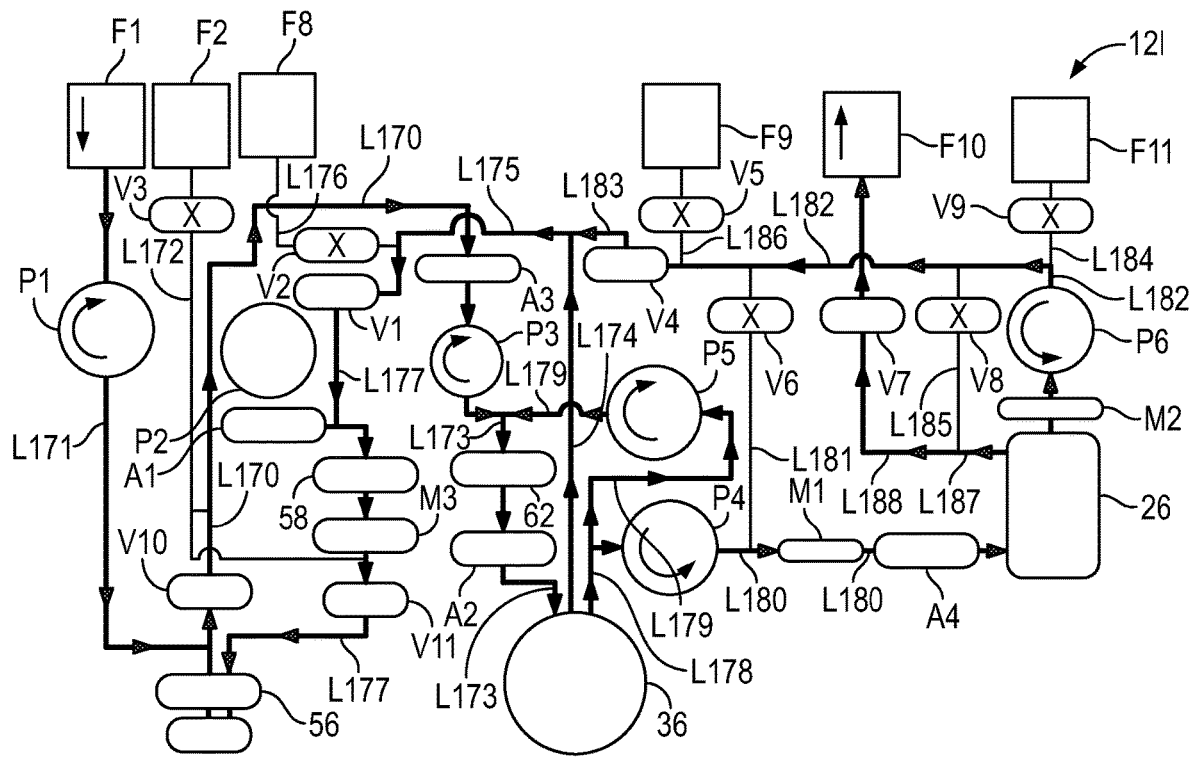
FIGS. 54-56 are schematic views of the fluid flow circuit of FIG. 10 mounted on the blood separation device of FIG. 1, showing the system carrying out different fluid flow tasks in connection with separation and collection of platelets or platelets and plasma from blood.
Figure 55:
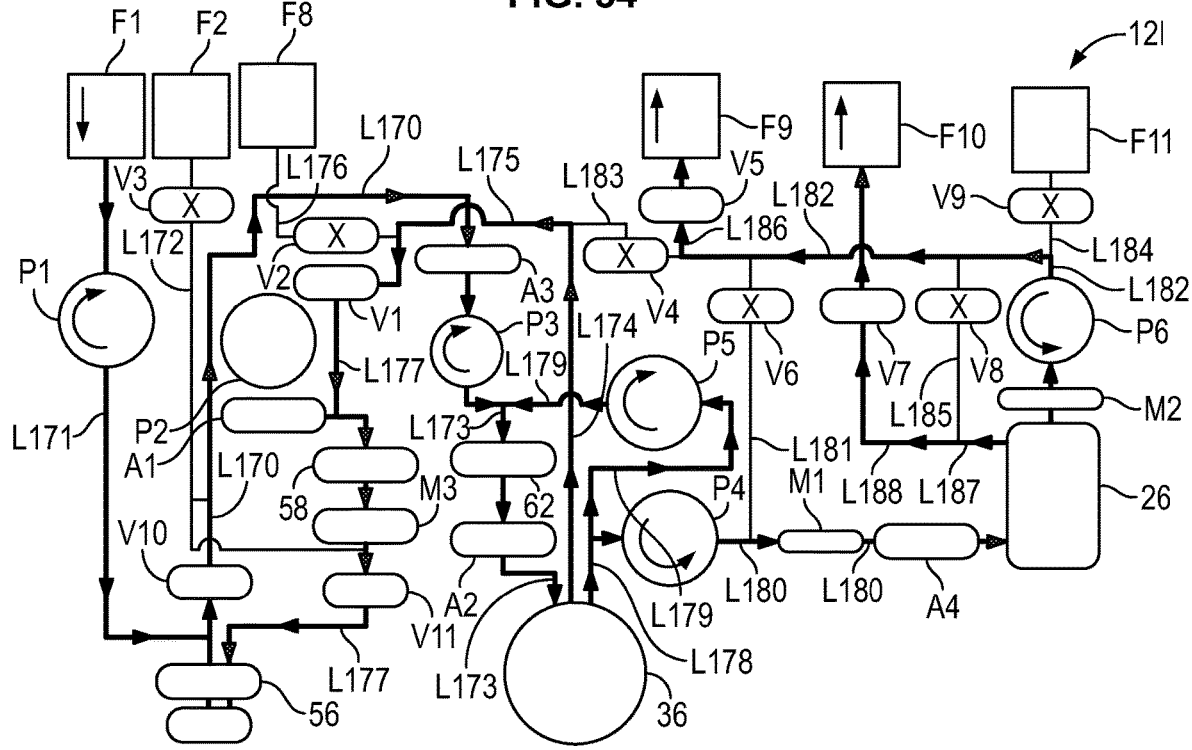
Figure 56:
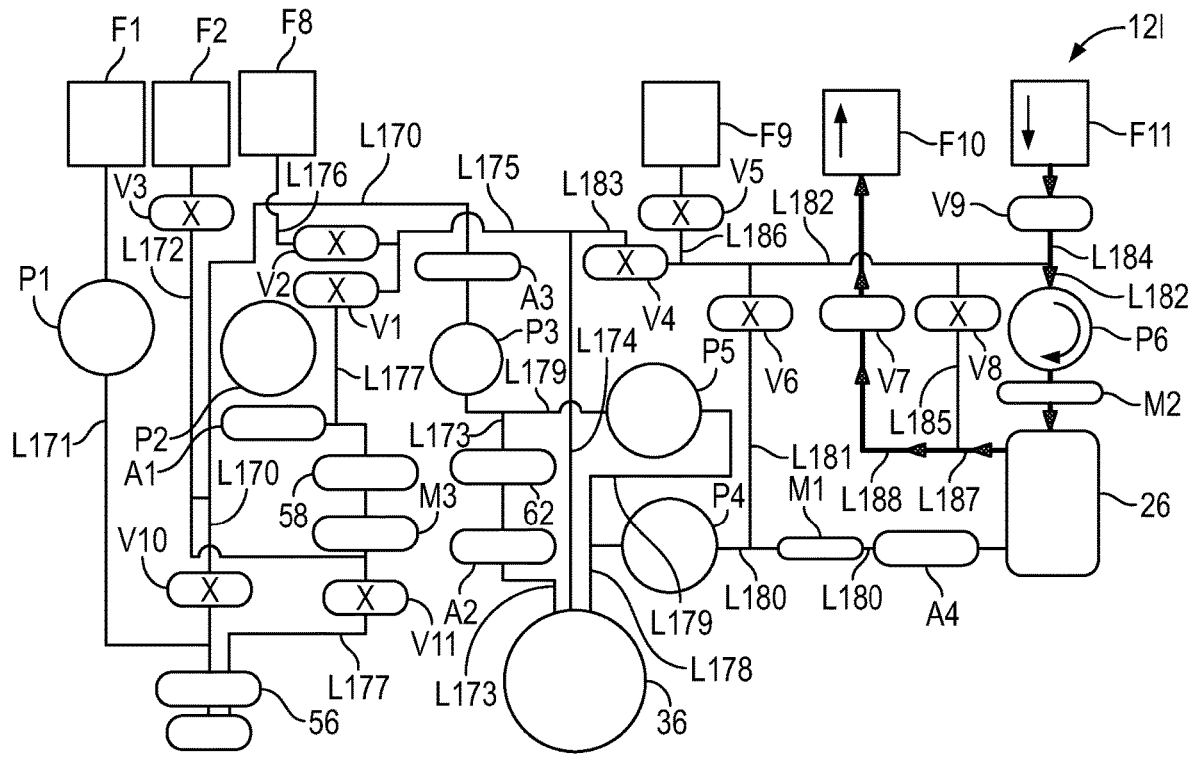

In contrast to the separation procedure described above with respect to the fluid flow circuit 12H of FIG. 9, the fluid flow circuit 12I of FIG. 10 allows for a single phase during which blood is simultaneous drawn from a blood source and processed, with a portion of at least one separated component being conveyed to a recipient (FIGS. 54 and 55). The valves V1-V11 of the blood separation device 10 are placed into different conditions depending on whether only platelets (FIG. 54) or both platelets and plasma (FIG. 55) are being collected.

When only platelets are being collected (FIG. 54), blood is drawn into the fluid flow circuit 12I from a blood source (e.g., using a needle) via line L170. The line L170 may include a manual clamp 56 that may initially be in a closed position to prevent fluid flow through the line L170. When processing is to begin, an operator may move the manual clamp 56 from its closed position to an open position to allow fluid flow through the line L170.

The blood is drawn into the line L170 by the centrifuge pump P3, rather than the donor pump P2 (which is inactive in this procedure). Anticoagulant from the anticoagulant bag F1 may be drawn through line L171 under action of the anticoagulant pump P1 and added to the blood at a junction of lines L170 and L171.

In the illustrated embodiment, the valve V10 associated with valve station C10 is open to allow blood to flow through line L170 and the sensor station S3 associated with pressure sensor A3, while the valve V3 associated with valve station C3 is closed to prevent fluid flow through line L172.

If the blood source is a living body (e.g., a donor), the pressure sensor A3 may communicate with the controller 18 to monitor the pressure within the vein of the blood source.

Continued action of the centrifuge pump P3 conveys the blood through line L173, an air trap 62, and the sensor station S2 associated with pressure sensor A2 (which works with the controller 18 to monitor the pressure in the centrifugal separation chamber 36) before the blood reaches the centrifugal separation chamber 36 of the fluid flow circuit 12I. The centrifugal separator 16 of the blood separation device 10 manipulates the centrifugal separation chamber 36 to separate the blood in the centrifugal separation chamber 36 into platelet-rich plasma and packed red blood cells, as described above. In one embodiment, the centrifugal separation chamber 36 is rotated nominally at 4,500 rpm, but the particular rotational speed may vary depending on the flow rates of fluids into and out of the centrifugal separation chamber 36.

The packed red blood cells (along with white blood cells, if they are not retained within the centrifugal separation chamber 36) exit the centrifugal separation chamber 36 via line L174 and flow through line L175 to a junction of lines L175 and L176. The valve V2 associated with valve station C2 is closed to prevent flow through line L176, while the valve V1 associated with valve station C1 is open to allow flow through line L177, thereby directing the red blood cells through line L177. The red blood cells pass through a return line filter 58, air detector M3, and the valve station C11 associated with open valve V11 on its way to the recipient. The pressure sensor A1 associated with sensor station S1 may monitor the pressure of the vein of a donor, if the fluid recipient is a living body.

Platelet-rich plasma is drawn out of the centrifugal separation chamber 36 via line L178 by the combined operation of the recirculation and PRP pumps P5 and P4 of the blood separation device 10. The platelet-rich plasma travels through line L178 until it reaches a junction, which splits into lines L179 and L180. The recirculation pump P5 is associated with line L179 and redirects a portion of the platelet-rich plasma to a junction, where it mixes with blood in line L170 that is being conveyed into the centrifugal separation chamber 36 via line L173 by the centrifuge pump P3. Recirculating a portion of the platelet-rich plasma into the centrifugal separation chamber 36 with inflowing blood decreases the hematocrit of the blood entering the centrifugal separation chamber 36, which may improve separation efficiency. By such an arrangement, the flow rate of the fluid entering the centrifugal separation chamber 36 is equal to the sum of the flow rates of the centrifuge pump P3 and the recirculation pump P5.

As the platelet-rich plasma drawn out of the centrifugal separation chamber 36 into line L179 by the recirculation pump P5 is immediately added back into the centrifugal separation chamber 36, the bulk or net platelet-rich plasma flow rate out of the centrifugal separation chamber 36 is equal to the flow rate of the PRP pump P4. Before reaching the spinning membrane separator 26, the portion of the platelet-rich plasma conveyed through line L180 by the PRP pump P4 passes through the spinner inlet sensor M1 and the sensor station S4 associated with pressure sensor A4. The spinner inlet sensor M1 may detect the concentration of platelets in the platelet-rich plasma entering the spinning membrane separator 26, while the pressure sensor A4 may monitor the pressure of the spinning membrane separator 26.

Line L180 has a junction, where it joins with line L181. The valve V6 associated with valve station C6 is closed to prevent fluid flow through the line L181, thereby directing the separated platelet-rich plasma to the spinning membrane separator 26. If necessary, the valve V6 may be selectively opened to divert all or a portion of the platelet-rich plasma to line L182 and through line L183 and the valve station C4 associated with open valve V4, where the platelet-rich plasma arrives at a junction with lines L174 and L175 and joins the separated red blood cells being conveyed to a recipient.

The spinning membrane separator drive unit 14 of the blood separation device 10 manipulates the spinning membrane separator 26 to separate the platelet-rich plasma into two sub-components (i.e., platelet-poor plasma and platelet concentrate). In one embodiment, the spinning membrane separator 26 is a smaller spinning membrane separator (as described above), with a stationary housing 70 and a rotatable rotor 72 with a membrane 76 mounted thereon. In such an embodiment, the spinning membrane separator drive unit 14 may rotate the rotor 72 at approximately 1,500 rpm (or at a different speed, depending on the flow rates of fluid into and out of the spinning membrane separator 26) to separate platelet-rich plasma entering the bottom portion of the spinning membrane separator 26 into plasma and platelets, according to the principles described above.

Plasma is pumped out of the spinning membrane separator 26 via line L182 by the plasma pump P6 of the blood separation device 10. The valves V9, V8, V6, and V5 associated with valve stations C9, C8, C6, and C5 (respectively) are closed to prevent flow through lines L184, L185, L181, and L186, thereby directing the separated plasma along lines L182 and L183 to a junction with lines L174 and L175, where it joins the red blood cells being conveyed to a recipient. On the way to the fluid recipient, the plasma passes through spinner outlet sensor M2, which may cooperate with the controller 18 to determine one or more characteristics of the plasma, such as the amount of cellular blood components in the plasma and/or whether the plasma is hemolytic and/or lipemic.

The platelet concentrate is conveyed out of the spinning membrane separator 26 via line L187. There is no pump associated with line L187, so instead the flow rate at which the platelets exit the spinning membrane separator 26 is equal to the difference between the flow rates of the PRP pump P4 and plasma pump P6. The concentration of platelets in the platelet concentrate may be calculated according to above Equation 4.

As described, the valve V8 associated with valve station C8 is closed to prevent fluid flow through the line L185, thereby directing the flow of platelets through lines L187 and L188 and the valve station C7 associated with open valve V7 and into the platelet concentrate bag F10. The valve V8 may be selectively opened to allow fluid flow through line L185 and to a junction with line L182, where it joins the plasma flowing to the fluid recipient, if necessary.

This phase may continue until the amount of collected platelets is equal to the targeted amount (as determined by a weight scale from which the platelet concentrate bag F10 may be hung during a procedure), at which time the system may transition to a final phase (FIG. 56).

c. Separation and Collection—Platelets and Plasma

The procedure when collecting platelets and plasma (FIG. 55) is similar to the procedure when only platelets are being collected (FIG. 54). The principal difference is that, when collecting platelets and plasma, the valve V5 associated with valve station C5 is open, while the valve V4 associated with valve station C5 is closed, which directs the separated plasma exiting the spinning membrane separator 26 through line L186 to be collected in the plasma bag F9 instead of being conveyed to a fluid recipient with the separated red blood cells. If the targeted amount of one component is collected before the targeted amount of the other component, then the component that has already been fully collected may be diverted to line L183, where it is conveyed to a fluid recipient with the separated red blood cells while collection of the other targeted component continues.

This phase may continue until the amounts of collected platelets and plasma are equal to the targeted amounts, at which time the system may transition to a final phase (FIG. 56).

d. Final Phase

When the targeted amount of platelets or the targeted amounts of platelets and plasma have been collected, the blood source/recipient may be disconnected from the fluid flow circuit 12I and the system may transition to a final phase in which a platelet additive solution is added to the collected platelets, as shown in FIG. 56. This may be carried out with the valves V9 and V7 associated with valve stations C9 and C7 (respectively) in an open condition and the valves V8, V6, V5, and V4 associated with valve stations C8, C6, C5, and C4 (respectively) in a closed condition. With the valves so situated, the plasma pump P6 may operate to draw the platelet additive solution from the PAS bag F11 via line L184, through the valve station C9 associated with open valve V9, line L182, spinner outlet sensor M2, the spinning membrane separator 26, lines L187 and L188, the valve station C7 associated with open valve V7, and into the platelet concentrate bag F10.

3. Low Processing Volume Circuit and Procedure

Figure 11:
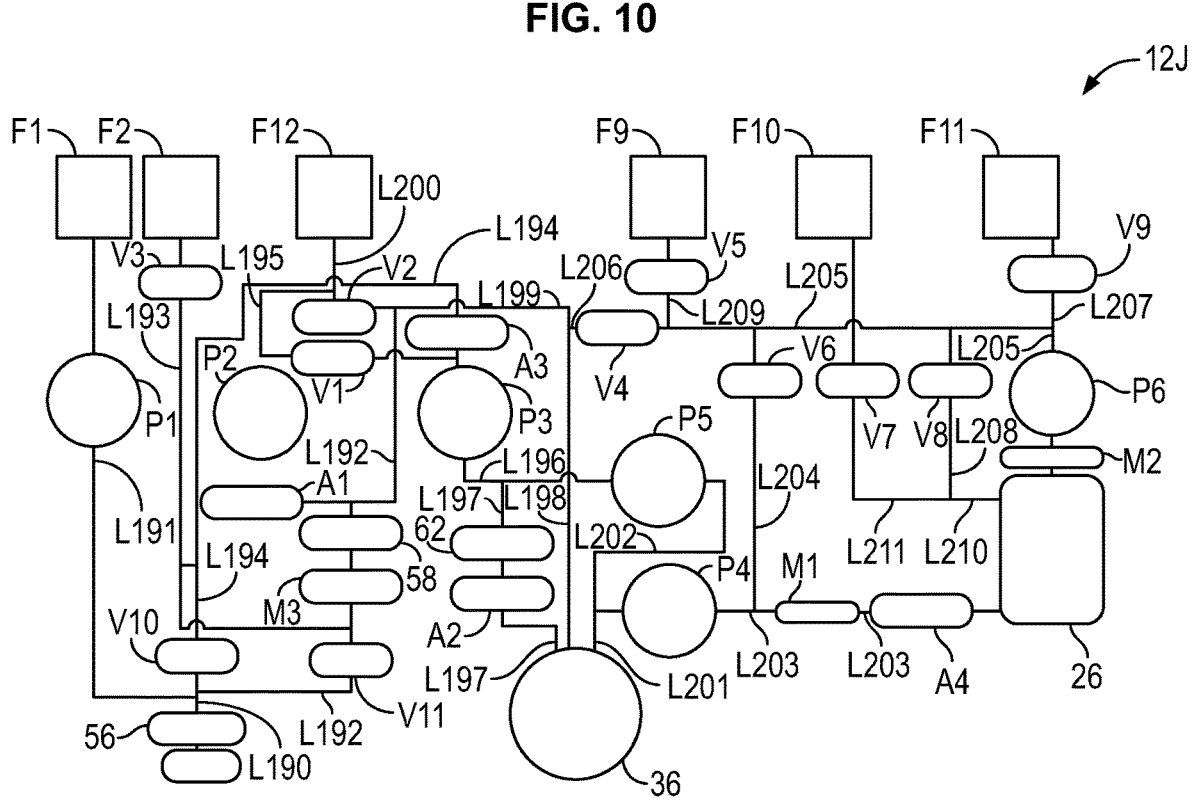

According to one aspect of the present disclosure, the blood separation device 10 may be used (e.g., in combination with a fluid flow circuit 12J of the type shown in FIG. 11) to separate and collect platelets or both platelets and substantially cell-free plasma from lower processing volumes of blood. This may be considered to be a variation of the single needle process of FIGS. 50-53, in which a portion of blood drawn from a source is processed while another portion of the blood is drawn into an in-process bag F3, to be processed while a separated component is conveyed to a fluid recipient. If equal amounts of blood are processed and accumulated in the in-process bag F3, then an extracorporeal volume of blood of approximately 200-300 ml may be typical to ensure that adequate amounts of blood are available for processing during both draw and return phases. The procedure of FIGS. 50-53 may not be preferable for a blood source having a relatively low amount of blood available for processing (e.g., a smaller human donor) such that, when collecting platelets or platelets and plasma from such a blood source, it may be preferred to use a fluid flow circuit 12J of the type shown in FIG. 11 and a procedure of the type shown in FIGS. 57-60.

Figure 57:
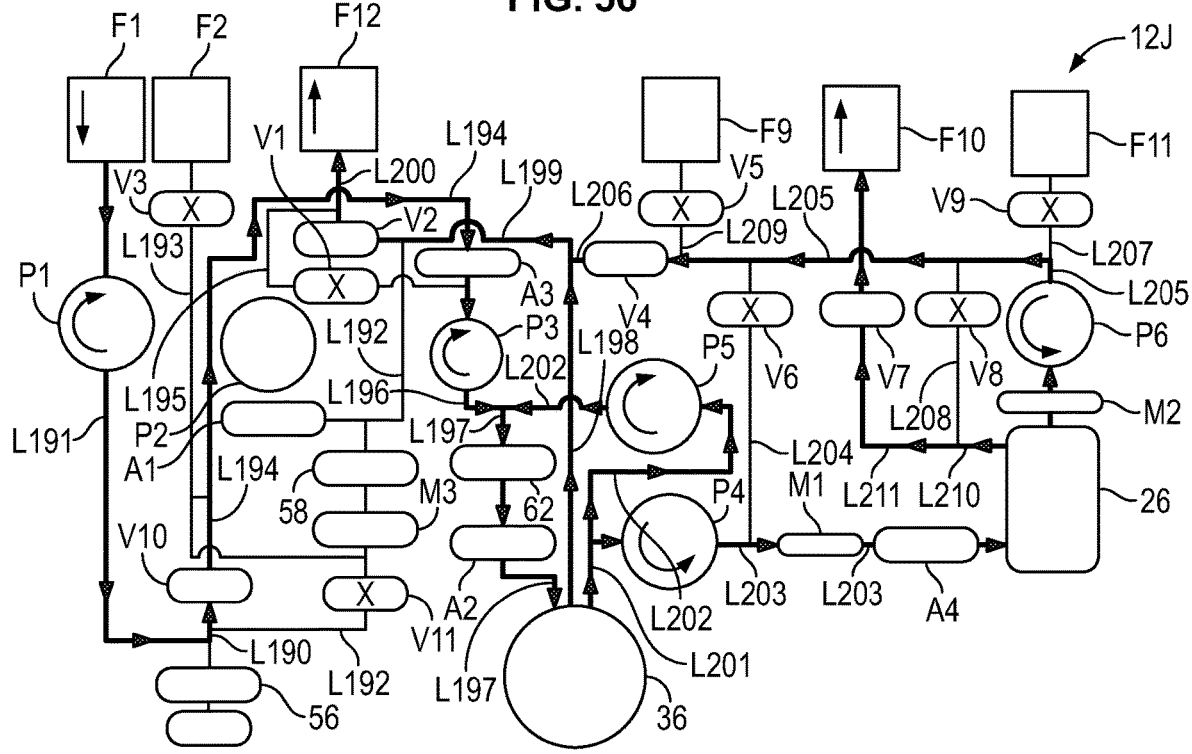
FIGS. 57-60 are schematic views of the fluid flow circuit of FIG. 11 mounted on the blood separation device of FIG. 1, showing the system carrying out different fluid flow tasks in collection with separation and collection of platelets or platelets and plasma from lower processing/extracorporeal volumes of blood.
Figure 58:
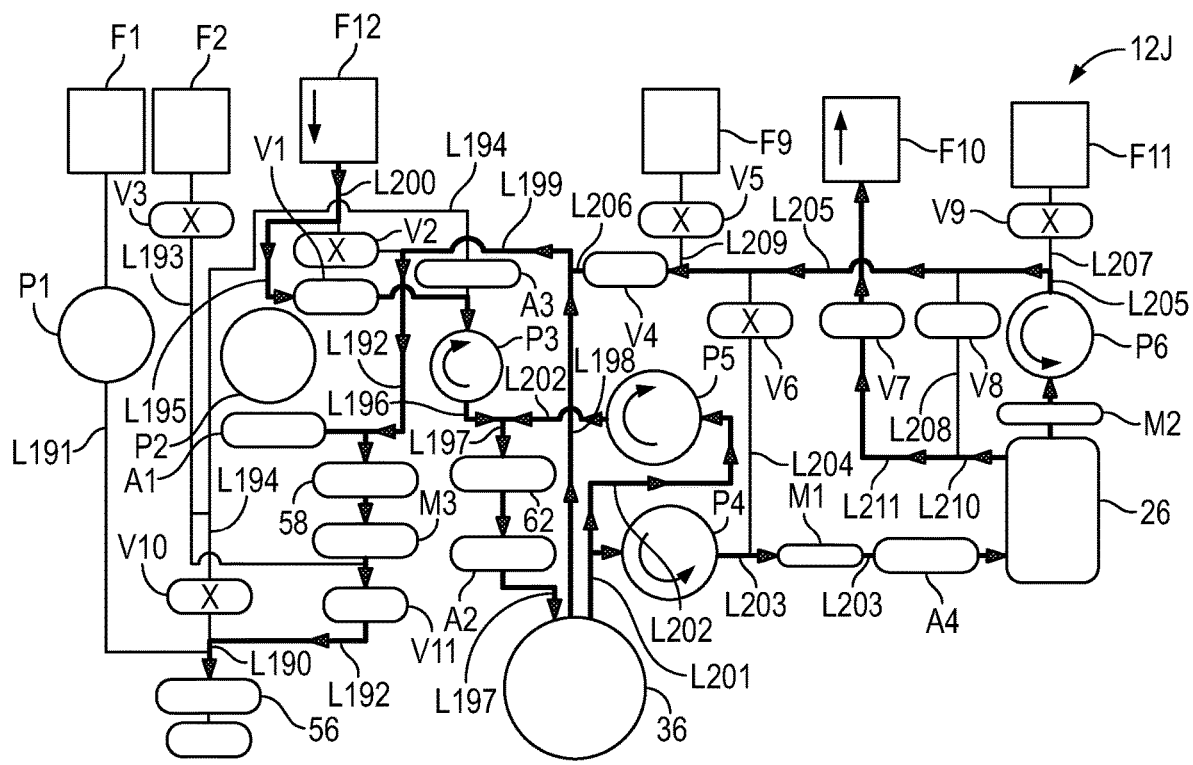

As will be described in greater detail, the procedure of FIGS. 57-60 is capable of collecting the same amounts of platelets or platelets and plasma as the procedure of FIGS. 50-53, but with lower processing volumes of blood. Rather than temporarily holding blood in an in-process bag F3, all of the blood is drawn into the centrifugal separation chamber 36 and separated into red blood cells and platelet-rich plasma during a draw phase (FIG. 57). The separated red blood cells are conveyed to a fluid container F12 (which may be referred to herein as the reprocess bag), while the platelet-rich plasma is separated into platelet concentrate and substantially cell-free plasma in the spinning membrane separator 26. The platelets are collected in the platelet concentrate bag F10, while the plasma is conveyed to the reprocess bag F12. During a return phase (FIG. 58 or 59), the contents of the reprocess bag F12 (primarily red blood cells and plasma) are processed using the centrifugal separation chamber 36 and the spinning membrane separator 26 to extract additional platelets from the fluid in the reprocess bag F12, while the separated red blood cells (FIG. 59) or the separated red blood cells and plasma (FIG. 58) are conveyed to a fluid recipient (e.g., the same blood source). By such a procedure, the interface may be maintained within the centrifugal separation chamber 36, while requiring lower processing/extracorporeal volumes of blood (e.g., approximately 100 ml instead of approximately 200-300 ml) and improving platelet collection efficiency for each amount of blood drawn.

a. Fluid Flow Circuit

FIG. 11 is a schematic view of an exemplary fluid flow circuit 12J having a single blood access device (e.g., a single needle that draws blood from and returns a separated blood component to the same location) that may be used to separate and collect only platelets or both platelets and plasma from lower processing volumes of blood. The fluid flow circuit 12J includes a cassette 48 of the type described above and illustrated in FIG. 13, which connects the various components of the fluid flow circuit 12J. The various connections amongst the components of the fluid flow circuit 12J are shown in FIG. 11, which also shows the fluid flow circuit 12J mounted to the blood separation device 10.

All of the various valves V1-V11 and pressure sensors A1-A4 of the blood separation device 10 are used in combination with the fluid flow circuit 12J of FIG. 11 for separating and collecting platelets or platelets and plasma, except for donor pump P2. Additionally, as will be described, both the centrifugal separator 16 and the spinning membrane separator drive unit 14 are used in separating blood into platelets or platelets and plasma for collection.

b. Draw Phase

In a first phase (FIG. 57), blood is drawn into the fluid flow circuit 12J from a blood source. If the blood source is a donor, then blood may be drawn into the fluid flow circuit 12J through a single needle that is connected to the cassette 48 by line L190. The line L190 may include a manual clamp 56 that may initially be in a closed position to prevent fluid flow through the line L190. When processing is to begin, an operator may move the manual clamp 56 from its closed position to an open position to allow fluid flow through the line L190.

The blood is drawn into the line L190 by the centrifuge pump P3 of the blood separation device 10. Anticoagulant from the anticoagulant bag F1 may be drawn through line L191 under action of the anticoagulant pump P1 and added to the blood at a junction of lines L190 and L191.

In the illustrated embodiment, the valve V10 associated with valve station C10 of the fluid flow circuit 12J is open, while the valves V11 and V3 associated with valve stations C11 and C3 (respectively) are closed to prevent fluid flow through lines L192 and L193, thereby directing blood to flow through lines L190 and L194 and a sensor station S3 associated with pressure sensor A3. If the blood source is a living body (e.g., a donor), the pressure sensor A3 may communicate with the controller 18 to monitor the pressure within the vein of the blood source.

The cassette 48 includes a junction downstream of the sensor station S3, where line L194 meets lines L195 and L196. The valve V1 associated with the valve station C1 is closed to prevent flow through line L195, which directs all of the blood through lines L196 and L197, an air trap 62, and the sensor station S2 associated with pressure sensor A2 (which works in combination with the controller 18 of the blood separation device 10 to monitor the pressure in the centrifugal separation chamber 36) before reaching the centrifugal separation chamber 36 of the fluid flow circuit 12J. The centrifugal separator 16 of the blood separation device 10 manipulates the centrifugal separation chamber 36 to separate the blood in the centrifugal separation chamber 36 into platelet-rich plasma and packed red blood cells, as described above. In one embodiment, the centrifugal separation chamber 36 is rotated nominally at 4,500 rpm, but the particular rotational speed may vary depending on the flow rates of fluids into and out of the centrifugal separation chamber 36.

The packed red blood cells exit the centrifugal separation chamber 36 via line L198 and flow through line L199 to a junction where line L199 meets lines L200 and L192. The valve V11 associated with valve station C11 (along with the valve V3 associated with valve station C3) is closed to prevent flow through line L192, thereby directed the separated red blood cells through line L200 and the valve station C2 associated with open valve V2 and into the reprocess bag F12. White blood cells may be retained within the centrifugal separation chamber 36 or may exit with the red blood cells.

Platelet-rich plasma is drawn out of the centrifugal separation chamber 36 via line L201 by the combined operation of the recirculation and PRP pumps P5 and P4 of the blood separation device 10. The platelet-rich plasma travels through line L201 until it reaches a junction, which splits into lines L202 and L203. The recirculation pump P5 is associated with line L202 and redirects a portion of the platelet-rich plasma to a junction, where it mixes with blood in line L197 that is being conveyed into the centrifugal separation chamber 36 by the centrifuge pump P3. Recirculating a portion of the platelet-rich plasma into the centrifugal separation chamber 36 with inflowing blood decreases the hematocrit of the blood entering the centrifugal separation chamber 36, which may improve separation efficiency. By such an arrangement, the flow rate of the fluid entering the centrifugal separation chamber 36 is equal to the sum of the flow rates of the centrifuge pump P3 and the recirculation pump P5.

As the platelet-rich plasma drawn out of the centrifugal separation chamber 36 into line L202 by the recirculation pump P5 is immediately added back into the centrifugal separation chamber 36, the bulk or net platelet-rich plasma flow rate out of the centrifugal separation chamber 36 is equal to the flow rate of the PRP pump P4. Before reaching the spinning membrane separator 26, the portion of the platelet-rich plasma conveyed through line L203 by the PRP pump P4 passes through the spinner inlet sensor M1 and the sensor station S4 associated with pressure sensor A4. The spinner inlet sensor M1 may detect the concentration of platelets in the platelet-rich plasma entering the spinning membrane separator 26, while the pressure sensor A4 may monitor the pressure of the spinning membrane separator 26.

Line L203 has a junction, where it joins with line L204. The valve V6 associated with valve station C6 is closed to prevent fluid flow through the line L204, thereby directing the separated platelet-rich plasma to the spinning membrane separator 26. If necessary, the valve V6 may be selectively opened to divert all or a portion of the platelet-rich plasma through lines L204, L205, and L206 and the valve station C4 associated with open valve V4 to a junction, where it joins separated red blood cells flowing through line L198 to the reprocess bag F12. An example would be at the start of a procedure when separation is initializing and platelets are not yet exiting the centrifugal separation chamber 36, in which case the fluid conveyed through line L203 by the PRP pump P4 could be diverted to the reprocess bag F12.

The spinning membrane separator drive unit 14 of the blood separation device 10 manipulates the spinning membrane separator 26 to separate the platelet-rich plasma into two sub-components (i.e., platelet-poor plasma and platelet concentrate). In one embodiment, the spinning membrane separator 26 is a smaller spinning membrane separator (as described above), with a stationary housing 70 and a rotatable rotor 72 with a membrane 76 mounted thereon. In such an embodiment, the spinning membrane separator drive unit 14 may rotate the rotor 72 between approximately 1,000-3,000 rpm (or at a different speed, depending on the flow rates of fluid into and out of the spinning membrane separator 26 and/or the material composition of the membrane 76) to separate platelet-rich plasma entering the bottom portion of the spinning membrane separator 26 into plasma and platelets, according to the principles described above.

Plasma is pumped out of the spinning membrane separator 26 via line L205 by the plasma pump P6 of the blood separation device 10. Valves V9, V8, V6, and V5 associated with valve stations C9, C8, C6, and C5 (respectively) are closed to prevent flow through lines L207, L208, L204, and L209, thereby directing the separated plasma along lines L205 and L206, through the valve station C4 associated with open valve V4, and to a junction where the plasma joins the red blood cells flowing through line L198 to the reprocess bag F12. On the way to the reprocess bag F12, the plasma passes through spinner outlet sensor M2, which may cooperate with the controller 18 to determine one or more characteristics of the plasma, such as the amount of cellular blood components in the plasma and/or whether the plasma is hemolytic and/or lipemic.

The platelet concentrate is conveyed out of the spinning membrane separator 26 via line L210. There is no pump associated with line L210, so instead the flow rate at which the platelets exit the spinning membrane separator 26 is equal to the difference between the flow rates of the PRP pump P4 and plasma pump P6. The concentration of platelets in the platelet concentrate may be calculated according to above Equation 4.

The valve V8 associated with valve station C8 is closed to prevent fluid flow through the line L208, thereby directing the flow of platelets along lines L210 and L211, through the valve station C7 associated with open valve V7, and into the platelet concentrate bag F10. The valve V8 associated with valve station C8 may be selectively opened to allow fluid flow through line L208 and to a junction, where it joins the plasma flowing through line L205 to the reprocess bag F12, if necessary.

The draw phase may continue until the amount of blood drawn from the blood source reaches a target amount (e.g., approximately 100 ml) or the reprocess bag F12 is filled to a particular level (as determined by a weight scale from which the reprocess bag F12 is hung during the procedure) or until some other condition is satisfied.

c. Return Phase—Platelet Collection Only

Figure 59:
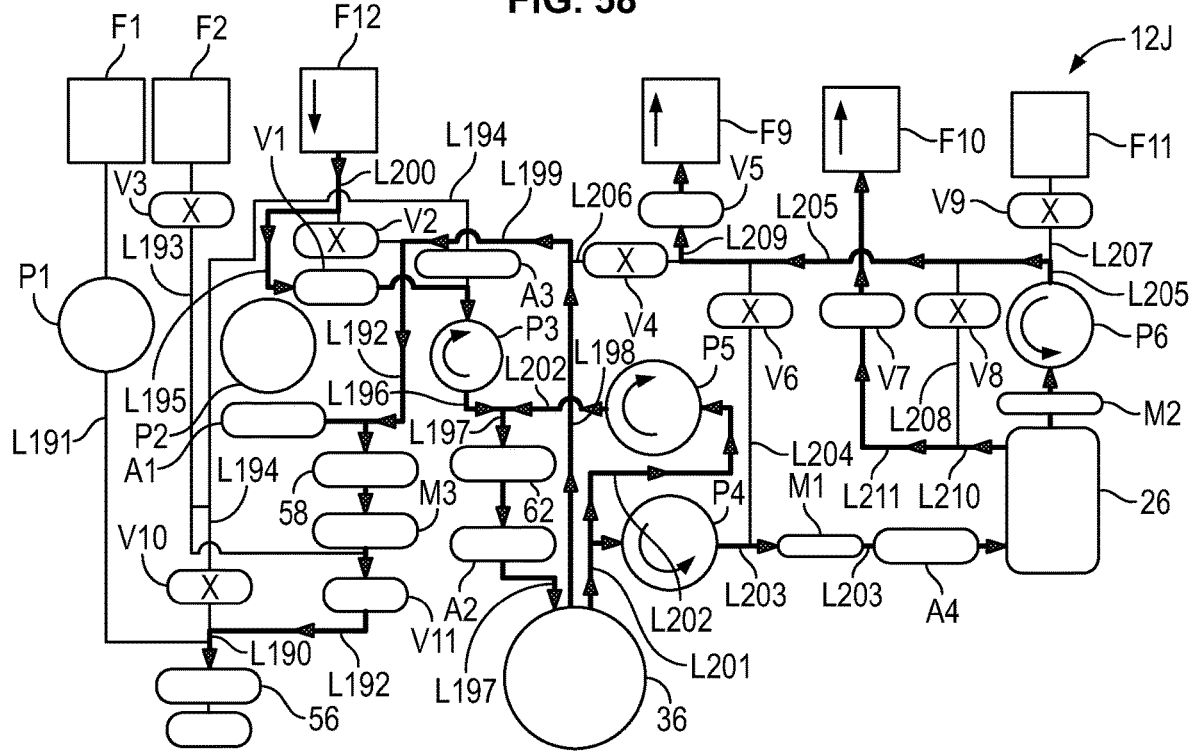

When the draw phase ends, the system transitions to one of two return phases (FIGS. 58 and 59), depending on whether only platelets are being collected (FIG. 58) or if both platelets and plasma are being collected (FIG. 59).

During the return phase of a procedure in which only platelets are being collected (FIG. 58), the anticoagulant pump P1 will stop drawing anticoagulant from the anticoagulant bag F1. The valve V10 associated with valve station C10 will close to prevent fluid flow through line L194 and the valve V11 associated with valve station C11 is opened to allow fluid flow through line L192. The valve V1 associated with valve station C1 also opens to allow flow through line L195, while the valve V2 associated with valve station C2 is closed to prevent flow therethrough.

The centrifuge pump P3 continues operating in the same direction as in the draw phase, but draws fluid (a mixture of red blood cells and plasma, typically) from the reprocess bag F12, rather than from the blood source. The fluid in the reprocess bag F12 thus acts as the fluid supply for the centrifugal separator 16.

When the system transitions to this return phase, separation continues in the same manner as described for the draw phase (i.e., with blood being separated in the centrifugal separation chamber 36 into red blood cells and platelet-rich plasma, the red blood cells flowing out of the centrifugal separation chamber 36, the platelet-rich plasma flowing to and being separated in the spinning membrane separator 26, and the separated platelets being collected) until the reprocess bag F12 is emptied.

With the valves so situated, the separated red blood cells and plasma will be conveyed to a fluid recipient, rather than flowing to the reprocess bag F12. In particular, the mixture of red blood cells and plasma flowing through line L199 is directed through line L192 instead of line L200 at the junction of lines L199, L192, and L200. The fluid flows through line L192, the sensor station S1 associated with pressure sensor A1 (which may monitor vein pressure if the recipient is a live body), a return line filter 58, and air detector M3 until it reaches a junction, which joins lines L192 and L193 (which leads to the saline bag F2). The valve V3 associated with valve station C3 is closed, thereby preventing fluid flow through line L193 and directing the return fluid further along line L192, through the valve station C11 associated with open valve V11, and along line L190 to the recipient.

Thus, it will be seen that most of the blood drawn from the blood source is processed twice before being conveyed to the fluid recipient (which may be the same blood source) as a mixture of separated red blood cells and plasma.

By continuously processing fluid in the centrifugal separation chamber 36, the interface between the separated red blood cells and platelet-rich plasma may be maintained. However, the fluid flowing through line L196 toward the centrifugal separation chamber 36 during this return phase (which typically comprises a mixture of red blood and plasma) will have a higher hematocrit than the blood flowing through line L196 during the draw phase due to the diversion of some plasma into the platelet concentrate bag F10. If the hematocrit of the fluid entering the centrifugal separation chamber 36 via line L197 during this return phase is the same as the hematocrit of the fluid entering the centrifugal separation chamber 36 during the draw phase and at the same volumetric flow rate, then the centrifugal separator 16 may continue rotating the centrifugal separation chamber 36 at the same speed in both phases to maintain the interface in the proper location. Accordingly, it may be advantageous for the controller 18 to make an adjustment to the operation of one or more of the components of the blood separation device 10 to cause the fluid entering the centrifugal separation chamber 36 during this return phase to be conveyed at the same volumetric flow rate and have the same hematocrit as the fluid entering the centrifugal separation chamber 36 in the draw phase.

According to an exemplary approach to adjusting the hematocrit of the fluid entering the centrifugal separation chamber 36, the controller 18 may slow down the centrifuge pump P3 (compared to its operation during the draw phase) to decrease the volumetric flow rate of fluid through line L196 while speeding up the recirculation pump P5 (compared to its operation during the draw phase) to increase the volumetric flow rate of platelet-rich plasma through line L202. The platelet-rich plasma pumped into line L197 by the recirculation pump P5 has a hematocrit of zero, which is lower than the hematocrit of the fluid pumped into line L197 by the centrifuge pump P3, so adjusting the rates of operation of the centrifuge and recirculation pumps P3 and P5 in this way will effectively decrease the hematocrit of the fluid entering the centrifugal separation chamber 36. The relative rates of operation of the centrifuge and recirculation pumps P3 and P5 may thus be adjusted to cause the hematocrit of fluid entering the centrifugal separation chamber 36 to be the same (or at least substantially or approximately the same) in this return phase as in the draw phase and at the same volumetric flow rate (or a volumetric flow rate that is at least substantially or approximately the same as in the draw phase), which allows the centrifugal separator 16 to rotate the centrifugal separation chamber 36 at the same speed in both phases to maintain the interface in the proper location.

More particularly, during the draw phase (FIG. 57), the centrifuge pump P3 operates to draw blood having a hematocrit Hdnr into the fluid flow circuit 12J at a volumetric flow rate Qin-wb. The recirculation pump P5 operates to convey separated platelet-rich plasma through line L202 at a volumetric rate Qrecirc-wb, which is set to achieve a target hematocrit of fluid entering the centrifugal separation chamber 36 (Hrecirc) and may be calculated as follows:

$$Qrecirc\text{-}wb = ((Qin\text{-}wb*Hdnr)/Hrecirc) - Qin\text{-}wb \quad \text{[Equation 5]}$$

As described above, the volumetric flow rate of fluid entering the centrifugal separation chamber 36 (which may be referred to as Qcent) is equal to the sum of the flow rates imparted by operation of the centrifuge pump P3 (Qin-wb) and the recirculation pump (Qrecirc-wb):

$$Qcent = Qin\text{-}wb + Qrecirc\text{-}wb \quad \text{[Equation 6]}$$

As described, it is preferred for the volumetric flow rate into the centrifugal separation chamber 36 (Qcent) and the hematocrit of that fluid (Hrecirc) to remain constant over the duration of a procedure to aid in control of the interface between red blood cells and platelet-rich plasma within the centrifugal separation chamber 36. This is easily accomplished in a typical batch-type platelet collection procedure (in which blood is only processed one time), because the source or inlet hematocrit is always equal to the hematocrit of the blood from the source (Hdnr), which allows a single recirculation rate Qrecirc-wb to be applied regardless of whether the system is in draw or return. However, during the procedure of FIGS. 57-60, the fluid being processed during the return phase will have a higher hematocrit than the blood drawn from the source during the draw phase due to the removal of plasma with the platelet concentrate. Thus, the operational rates of the centrifuge pump P3 and the recirculation pump P5 may be adjusted between the draw and return phases to maintain a constant volumetric flow rate (Qcent) and hematocrit (Hrecirc) into the centrifugal separation chamber 36. Setting the flow rates is straightforward for the draw phase because the operation rate of the centrifuge pump P3 to impart an inlet rate Qin-wb may be a constant set by the system and the operation rate of the recirculation pump P5 to impart the proper recirculation rate Qrecirc may be easily calculated using Equation 5 because the hematocrit of blood from the blood source (Hdnr) is known. To adjust these rates during return, the hematocrit of the fluid within the reprocess bag F12 (Hreproc) must be known as well, which requires a calculation.

Determining the hematocrit of the fluid within the reprocess bag F12 is independent of the recirculation rate applied during draw (FIG. 57), and the system can be simplified into inlet parameters (Qin-wb and Hdnr) and outlet parameters with and without red blood cells. Namely, these outlet parameters are the volumetric flow rate and hematocrit of fluid entering the reprocess bag F12 during the draw phase (Qout-reproc and Hreproc) and the volumetric flow rate of the platelet concentrate entering the platelet concentrate bag F10 during the draw phase (Qout-pc).

At a steady state, the amount of red blood cells entering the fluid flow circuit 12J must be equal to the amount of red blood cells exiting the fluid flow circuit 12J, so:

$$Qin\text{-}wb*Hdnr = Qout\text{-}reproc*Hreproc \quad \text{[Equation 7]},$$

in which the volumetric flow rate of fluid entering the reprocess bag F12 is the difference between the volumetric flow rate of blood drawn into the fluid flow circuit 12J and the volumetric flow rate of platelets entering the platelet concentrate bag 10:

$$Qout\text{-}reproc = Qin\text{-}wb - Qout\text{-}pc \quad \text{[Equation 8]}$$

Plugging Equation 8 into Equation 7 and solving for the hematocrit of the fluid entering the reprocess bag F12 yields:

$$Hreproc = (Qin\text{-}wb*Hdnr)/(Qin\text{-}wb - Qout\text{-}pc) \quad \text{[Equation 9]}$$

Thus, when the system transitions from the draw phase (FIG. 57) to the return phase (FIG. 58), the hematocrit of the fluid in the reprocess bag F12 (Hreproc) is known and can be used to set the operational rate of the centrifuge pump P3 required to achieve the proper volumetric flow rate of fluid out of the reprocess bag F12 (Qin-reproc). As the hematocrit of the fluid in the reprocess bag F12 (Hreproc) is greater than the hematocrit of blood from the blood source (Hdnr), the volumetric flow rate of fluid out of the reprocess bag F12 (Qin-reproc) applied during the return phase will be lower than the volumetric flow rate of blood into the fluid flow circuit F12 during the draw phase (Qin-wb), meaning that the centrifuge pump P3 will operate at a slower rate during the return phase than during the draw phase.

The goal is to adjust the volumetric flow rate out of the reprocess bag F12 (Qin-reproc) during return so that the red blood cell fraction flow rate Qreproc-rbc of the fluid being reprocessed equals the red blood cell fraction flow rate Qwb-rbc that was drawn from the source during the draw phase, where:

$$Qreproc\text{-}rbc = Qin\text{-}reproc*Hreproc \quad \text{[Equation 10] and}$$

$$Qwb\text{-}rbc = Qin\text{-}wb*Hdnr \quad \text{[Equation 11], with the goal being:}$$

$$Qreproc\text{-}rbc = Qwb\text{-}rbc \quad \text{[Equation 12]}$$

Thus, combining Equations 10, 11, and 12 and solving for Qin-reproc yields:

$$\text{Qin-reproc} = (\text{Qin-wb} \cdot \text{Hdnr})/\text{Hreproc} \quad [\text{Equation 13}]$$

To maintain the same volumetric flow rate (Qcent) and hematocrit (Hrecirc) for the fluid entering the centrifugal separation chamber 36 (Qcent) during both the draw and return phases, the operational rate of the recirculation pump P5 must increase to produce a greater volumetric flow rate Qrecirc-reproc to account for the decreased volumetric flow rate imparted by the slowed operation of the centrifuge pump P3 (which decreases from Qin-wb to Qin-reproc). The volumetric flow rate imparted by operation of the recirculation pump P5 during the return phase may be calculated as follows:

$$\text{Qrecirc-reproc} = ((\text{Qin-reproc} \cdot \text{Hreproc})/\text{Hrecirc}) - \text{Qin-reproc} \quad [\text{Equation 14}]$$

The lower volumetric flow rate out of the reprocess bag F12 imparted by the centrifuge pump P3 (Qin-reproc) is thus opposed by the higher volumetric flow rate imparted by the recirculation pump P5 (Qrecirc-reproc) to ensure that the volumetric flow rate of fluid into the centrifugal separation chamber 36 (Qcent) remains the same during the return phase (FIG. 58) as it was during the draw phase (FIG. 57):

$$\text{Qcent} = \text{Qin-reproc} + \text{Qrecirc-reproc} \quad [\text{Equation 15}]$$

By way of example, blood may be drawn from a source at a volumetric flow rate Qin-wb of 100 ml/min (which may be a system-defined constant), with the blood having a hematocrit Hdnr of 40% and a target hematocrit of fluid entering the centrifugal separation chamber 36 Hrecirc of 34%. Using above Equation 5, Qrecirc-wb=(100*0.40)/0.34)−100=17.6 ml/min. Using above Equation 6, Qcent=100+17.6=117.6 ml/min.

All of the parameters required to calculate the hematocrit of the fluid in the reprocess bag F12 (Qin-wb, Hdnr, and Qout-pc) are known, because the volumetric flow rate of platelets into the platelet concentrate bag F10 may be either a system-defined constant or determined by the controller 18 (e.g., by communicating with a weight scale from which the platelet concentrate bag F10 is hung during processing) and may be 8 ml/min. Using above Equation 9, Hreproc=(100*0.40)/(100−8)=43.5%. With this value, Qin-reproc may be calculated using above Equation 13: Qin-reproc=(100*0.40)/0.435=92 ml/min. Inserting the appropriate values into above Equations 10 and 11 confirms that the red blood cell fraction flow rate will be the same during return (Qreproc-rbc=92*0.435=40 ml/min) and draw (Qwb-rbc=100*0.40=40 ml/min).

As operation of the centrifuge pump P3 results in a lower volumetric flow rate during the return phase (Qin-reproc=92 ml/min) than during the draw phase (Qin-wb=100 ml/min), the speed of the recirculation pump P5 must increase to maintain the same volumetric flow rate into the centrifugal separation chamber (Qcent). Per above Equation 14, Qrecirc-reproc=((92*0.435)/0.34)−92=25.6 ml/min. Above Equation 15 may be used to confirm that the volumetric flow rate of fluid entering the centrifugal separation chamber 36 and the hematocrit of that fluid will be the same during draw and return (117.6 ml/min and 34%, respectively), thereby allowing the centrifugal separator 16 to operate the same in both phases.

In any event, once the reprocess bag F12 is empty, the system may transition back to the draw phase (FIG. 57) or to a final phase (FIG. 60).

d. Return Phase—Platelet and Plasma Collection

The return phase when collecting platelets and plasma (FIG. 59) is similar to the return phase when only platelets are being collected (FIG. 58), including the way in which the operation of the centrifuge and recirculation pumps P3 and P5 may be controlled to maintain the volumetric flow rate and hematocrit of the fluid entering the centrifugal separation chamber 36. The principal difference is that, when collecting platelets and plasma, the valve V5 associated with valve station C5 is open to allow flow through line L209, while the valve V4 associated with valve station C4 is closed to prevent flow through line L206, thereby directing the separated plasma exiting the spinning membrane separator 26 through the line L209 associated with open valve V5 to the plasma bag F9 instead of to the fluid recipient. The valves may be so situated for the entire return phase or the conditions of valves V4 and V5 may be reversed for a portion of the phase (thereby directing separated plasma to the fluid recipient instead of the plasma bag F9), depending on the amount of plasma to be collected.

Once the reprocess bag F12 is empty, the system may transition back to the draw phase (FIG. 57) or to a final phase (FIG. 60).

e. Final Phase

When the targeted amount of platelets or the targeted amounts of platelets and plasma have been collected, the blood source/recipient may be disconnected from the fluid flow circuit 12J and the system may transition to a final phase in which a platelet additive solution is added to the collected platelets, as shown in FIG. 60. This may be carried out with the valves V9 and V7 associated with valve stations C9 and C7 (respectively) in an open condition to allow flow through lines L207 and L211, while the valves V8, V6, V5, and V4 associated with valve stations C8, C6, C5, and C4 (respectively) in a closed condition to prevent flow through lines L208, L204, L209, and L206. With the valves so situated, the plasma pump P6 may operate to draw the platelet additive solution from the PAS bag F11 via line L207, through the valve station C9 associated with open valve V9, line L205, spinner outlet sensor M2, the spinning membrane separator 26, lines L210 and L211, the valve station C7 associated with open valve V7, and into the platelet concentrate bag F10.

IV. Other Possible Variations

While fluid flow circuits 12 having only a spinning membrane separator 26 (and not a centrifugal separation chamber 36) or both a spinning membrane separator 26 and a centrifugal separation chamber 36 and methods employing only the spinning membrane separator drive unit 14 (and not the centrifugal separator 16) or both the spinning membrane separator drive unit 14 and the centrifugal separator 16 are described, it should be understood that other variations are possible. For example, it is within the scope of the present disclosure for a fluid flow circuit including a centrifugal separation chamber and not a spinning membrane separator to be used in combination with the blood separation device 10 for a procedure using only the centrifugal separator 16 and not the spinning membrane separator drive unit 14 (e.g., a white blood cell collection procedure). Also, it is within the scope of the present disclosure for a fluid flow circuit including both a spinning membrane separator 26 and a centrifugal separation chamber 36 to be used in a procedure employing only one of them to separate a fluid.

Additionally, it should be understood that, while it may be advantageous to use a blood separation device 10 incorporating both a spinning membrane separator drive unit 14 and a centrifugal separator 16 into a common case 20, it is also within the scope of the present disclosure for a blood separation procedure to employ a spinning membrane separator drive unit and a centrifugal separator that are associated with different blood separation devices. If two such separate blood separation devices are used to carry out a multi-stage separation procedure according to the present disclosure, then it may be advantageous for the system to also include a controller that is capable of communicating with and controlling both blood separation devices to ensure that the procedure is successfully carried out. Such a controller may be programmed and configured generally in accordance with the preceding description of the controller 18 of the blood separation device 10 or may be differently programmed and configured. Furthermore, the controller may be incorporated into either blood separation device or be separately provided (e.g., being incorporated into a computer or control station) and communicate with the blood separation devices either via a physical connection (e.g., via a cable) or wirelessly.

V. Aspects

Aspect 1. A blood separation device comprising: a centrifugal separator; a spinning membrane separator drive unit; and a controller configured and/or programmed to control the operation of the centrifugal separator and the spinning membrane separator drive unit, wherein the centrifugal separator and the spinning membrane separator drive unit are incorporated into a case.

Aspect 2. The blood separation device of Aspect 1, wherein the controller is configured and/or programmed to control only one of the centrifugal separator and the spinning membrane separator drive unit or both of the centrifugal separator and the spinning membrane separator drive unit to separate blood into two or more blood components or to separate a blood component into two or more subcomponents.

Aspect 3. The blood separation device of any of Aspects 1-2, further comprising first and second pumps, wherein the controller is configured and/or programmed to control the centrifugal separator to separate blood into two or more blood components, control the first pump to recirculate a portion of one of the blood components into the centrifugal separator with blood entering the centrifugal separator, and control the second pump to convey another portion of said one of the blood components into the spinning membrane separator drive unit to separate said another portion of said one of the blood components into two or more sub-components.

Aspect 4. The blood separation device of any of Aspects 1-3, further comprising an interface monitoring system associated with the centrifugal separator and including a light source configured to emit light through separated blood components within the centrifugal separator, and a light detector configured to receive at least a portion of the light emitted by the light source and cooperate with the controller to determine the location of an interface between two separated blood components within the centrifugal separator, wherein the light source comprises a laser.

Aspect 5. The blood separation device of Aspect 4, wherein the centrifugal separator is positioned within a centrifuge compartment, and the light source and the light detector are mounted to stationary surfaces of the centrifuge compartment.

Aspect 6. The blood separation device of any of Aspects 4-5, wherein the light detector is positioned and oriented to receive light traveling in a direction that is generally perpendicular to the direction of the light emitted by the light source.

Aspect 7. The blood separation device of any of Aspects 1-6, wherein the spinning membrane separator drive unit comprises an upper end cap and a base, and at least one of the upper end cap and the base is movable with respect to the other one of the upper end cap and the base to accommodate differently sized spinning membrane separators.

Aspect 8. The blood separation device of any of Aspects 1-7, further comprising at least one pump, and an inlet sensor configured to optically detect a characteristic of a fluid to be separated by the spinning membrane separator drive unit, wherein the controller is configured and/or programmed to control the operation of said at least one pump based at least in part on said characteristic of the fluid to be separated by the spinning membrane separator drive unit.

Aspect 9. The blood separation device of Aspect 8, wherein the inlet sensor is configured to optically detect a hematocrit of the fluid to be separated by the spinning membrane separator drive unit.

Aspect 10. The blood separation device of Aspect 8, wherein the inlet sensor is configured to optically detect the concentration of platelets in the fluid to be separated by the spinning membrane separator drive unit.

Aspect 11. The blood separation device of any of Aspects 1-10, further comprising an outlet sensor configured to optically detect a characteristic of a fluid exiting the spinning membrane separator drive unit.

Aspect 12. The blood separation device of Aspect 11, wherein the outlet sensor is configured to optically detect whether the fluid exiting the spinning membrane separator drive unit is lipemic and/or hemolytic.

Aspect 13. The blood separation device of any of Aspects 1-12, wherein the controller is configured and/or programmed to simultaneously control both the centrifugal separator and the spinning membrane separator drive unit to separate blood into two or more blood components or to separate a blood component into two or more sub-components.

Aspect 14. A fluid flow circuit for use in combination with a blood separation device, comprising: a centrifugal separation chamber; and a spinning membrane separator in fluid communication with the centrifugal separation chamber.

Aspect 15. The fluid flow circuit of Aspect 14, further comprising an in-process container, wherein the in-process container is configured to receive a portion of blood conveyed into the fluid flow circuit from a blood source and the centrifugal separation chamber is configured to receive another portion of the blood conveyed into the fluid flow circuit.

Aspect 16. The fluid flow circuit of Aspect 15, further comprising a cassette in fluid communication with the centrifugal separation chamber, the spinning membrane separator, and the in-process container and including six tubing loops each configured to cooperate with a different peristaltic pump of the blood separation device.

Aspect 17. The fluid flow circuit of Aspect 14, further comprising a reprocess container configured to receive at least a portion of at least one blood component separated from blood by the centrifugal separation chamber and/or the spinning membrane separator and to supply said at least a portion of said at least one blood component to the centrifugal separation chamber for separation of said at least a portion of said at least one blood component into two or more blood components.

Aspect 18. The fluid flow circuit of Aspect 17, further comprising a cassette in fluid communication with the centrifugal separation chamber, the spinning membrane separator, and the in-process container and including five tubing loops each configured to cooperate with a different peristaltic pump of the blood separation device.

Aspect 19. The fluid flow circuit of any of Aspects 14-18, further comprising a single blood access device configured to allow blood to be conveyed into the fluid flow circuit and to allow fluid to be conveyed out of the fluid flow circuit.

Aspect 20. The fluid flow circuit of Aspect 14, further comprising first and second blood access devices, wherein the first blood access device is configured to allow blood to be conveyed into the fluid flow circuit and the second blood access device is configured to allow fluid to be conveyed out of the fluid flow circuit.

Aspect 21. The fluid flow circuit of Aspect 20, further comprising a cassette in fluid communication with the centrifugal separation chamber, the spinning membrane separator, and the first and second blood access devices and including five tubing loops each configured to cooperate with a different peristaltic pump of the blood separation device.

Aspect 22. A blood separation system comprising: a blood separation device including a centrifugal separator and a spinning membrane separator drive unit incorporated into a case; and a fluid flow circuit including a centrifugal separation chamber configured to be mounted to the centrifugal separator, and/or a spinning membrane separator configured to be mounted to the spinning membrane separator drive unit.

Aspect 23. The blood separation system of Aspect 22, wherein the blood separation device includes a controller is configured and/or programmed to control only one of the centrifugal separator and the spinning membrane separator drive unit or both of the centrifugal separator and the spinning membrane separator drive unit to separate blood within the fluid flow circuit into two or more blood components or to separate a blood component within the fluid flow circuit into two or more sub-components.

Aspect 24. The blood separation system of any of Aspects 22-23, wherein the blood separation device includes first and second pumps and a controller configured and/or programmed to control the centrifugal separator to separate blood into two or more blood components, control the first pump to recirculate a portion of one of the blood components through the fluid flow circuit into the centrifugal separator with blood entering the centrifugal separator, and control the second pump to convey another portion of said one of the blood components through the fluid flow circuit into the spinning membrane separator drive unit to separate said another portion of said one of the blood components into two or more sub-components.

Aspect 25. The blood separation system of any of Aspects 22-24, wherein the blood separation device includes an interface monitoring system associated with the centrifugal separator and including a light source configured to emit light through the centrifugal separation chamber and separated blood components within the centrifugal separation chamber, and a light detector configured to receive at least a portion of the light emitted by the light source and cooperate with the controller to determine the location of an interface between two separated blood components within the centrifugal separation chamber.

Aspect 26. The blood separation system of Aspect 25, wherein the light source comprises a laser.

Aspect 27. The blood separation system of any of Aspects 25-26, wherein the centrifugal separator is positioned within a centrifuge compartment, and the light source and the light detector are mounted to stationary surfaces of the centrifuge compartment.

Aspect 28. The blood separation system of any of Aspects 25-27, wherein the light detector is positioned and oriented to receive light traveling in a direction that is generally perpendicular to the direction of the light emitted by the light source.

Aspect 29. The blood separation system of any of Aspects 22-28, wherein the spinning membrane separator drive unit comprises an upper end cap and a base, and at least one of the upper end cap and the base is movable with respect to the other one of the upper end cap and the base to accommodate differently sized spinning membrane separators of the fluid flow circuit.

Aspect 30. The blood separation system of any of Aspects 22-29, wherein the blood separation device includes at least one pump, and an inlet sensor configured to optically detect a characteristic of a fluid in the fluid flow circuit to be separated in the spinning membrane separator, wherein the controller is configured and/or programmed to control the operation of said at least one pump based at least in part on said characteristic of the fluid to be separated in the spinning membrane separator.

Aspect 31. The blood separation system of Aspect 30, wherein the inlet sensor is configured to optically detect a hematocrit of the fluid to be separated in the spinning membrane separator.

Aspect 32. The blood separation system of Aspect 30, wherein the inlet sensor is configured to optically detect the concentration of platelets in the fluid to be separated in the spinning membrane separator.

Aspect 33. The blood separation system of any of Aspects 22-32, wherein the blood separation device includes an outlet sensor configured to optically detect a characteristic of a fluid exiting the spinning membrane separator.

Aspect 34. The blood separation system of Aspect 33, wherein the outlet sensor is configured to optically detect whether the fluid exiting the spinning membrane separator is lipemic and/or hemolytic.

Aspect 35. The blood separation system of any of Aspects 22-34, wherein the blood separation device includes a pump, the fluid flow circuit includes an in-process container, and the pump is configured to convey a portion of blood entering the fluid flow circuit from a blood source to the in-process container and another portion of the blood conveyed entering the fluid flow circuit to the centrifugal separation chamber.

Aspect 36. The blood separation system of Aspect 35, wherein the blood separation device includes six peristaltic pumps, and the fluid flow circuit includes a cassette in fluid communication with the centrifugal separation chamber, the spinning membrane separator, and the in-process container and including six tubing loops each configured to cooperate with a different one of said six peristaltic pumps.

Aspect 37. The blood separation system of any of Aspects 22-34, wherein the blood separation device includes first and second pumps, the fluid flow circuit includes a reprocess container, the first pump is configured to convey at least a portion of at least one blood component separated from blood by the centrifugal separation chamber and/or the spinning membrane separator, and the second pump is configured to convey said at least a portion of said at least one blood component to the centrifugal separation chamber for separation of said at least a portion of said at least one blood component into two or more blood components.

Aspect 38. The blood separation system of Aspect 37, wherein the blood separation device includes five peristaltic pumps, and the fluid flow circuit includes a cassette in fluid communication with the centrifugal separation chamber, the spinning membrane separator, and the in-process container and including five tubing loops each configured to cooperate with a different one of said five peristaltic pumps.

Aspect 39. The blood separation system of any of Aspects 22-37, wherein the fluid flow circuit includes a single blood access device configured to allow blood to be conveyed into the fluid flow circuit and to allow fluid to be conveyed out of the fluid flow circuit.

Aspect 40. The blood separation system of any of Aspects 22-34, wherein the fluid flow circuit includes first and second blood access devices, the first blood access device is configured to allow blood to be conveyed into the fluid flow circuit, and the second blood access device is configured to allow fluid to be conveyed out of the fluid flow circuit.

Aspect 41. The blood separation system of Aspect 40, wherein the blood separation device includes five peristaltic pumps, and the fluid flow circuit includes a cassette in fluid communication with the centrifugal separation chamber, the spinning membrane separator, and the first and second blood access devices and including five tubing loops each configured to cooperate with a different one of said five peristaltic pumps.

Aspect 42. The blood separation system of any of Aspects 22-41, wherein the centrifugal separator and the spinning membrane separator drive unit are configured to be operated simultaneously.

Aspect 43. A blood separation method comprising: providing a blood separation device including a centrifugal separator and a spinning membrane separator drive unit; mounting a fluid flow circuit to the blood separation device; conveying blood through the fluid flow circuit; and separating at least a portion of the blood in the fluid flow circuit into two or more blood components using the centrifugal separator and/or the spinning membrane separator drive unit.

Aspect 44. The method of Aspect 43, wherein said separating at least a portion of the blood in the fluid flow circuit into two or more blood components using the centrifugal separator and/or the spinning membrane separator drive unit includes using the spinning membrane separator drive unit to separate and collect red blood cells from blood.

Aspect 45. The method of Aspect 44, further comprising simultaneously separating and collecting red blood cells from blood and conveying fluid out of the fluid flow circuit.

Aspect 46. The method of any of Aspects 44-45, further comprising conveying blood into the fluid flow circuit and conveying fluid out of the fluid flow circuit at the same location.

Aspect 47. The method of any of Aspects 44-46, further comprising simultaneously conveying a portion of blood into an in-process container of the fluid flow circuit and another portion of the blood into the spinning membrane separator drive unit to separate and collect red blood cells from said another portion of the blood, and then conveying said portion of blood from the in-process container into the spinning membrane separator drive unit to separate and collect red blood cells from said portion of blood from the in-process container.

Aspect 48. The method of Aspect 44, further comprising simultaneously conveying blood into the fluid flow circuit and conveying fluid out of the fluid flow circuit.

Aspect 49. The method of any of Aspects 44 and 48, further comprising conveying blood into the fluid flow circuit and conveying fluid out of the fluid flow circuit at different locations.

Aspect 50. The method of Aspect 43, wherein said separating at least a portion of the blood in the fluid flow circuit into two or more blood components using the centrifugal separator and/or the spinning membrane separator drive unit includes using the spinning membrane separator drive unit to separate and collect red blood cells and plasma from blood.

Aspect 51. The method of Aspect 50, further comprising simultaneously separating and collecting plasma or red blood cells and plasma from blood and conveying fluid out of the fluid flow circuit.

Aspect 52. The method of any of Aspects 50-51, further comprising conveying blood into the fluid flow circuit and conveying fluid out of the fluid flow circuit at the same location.

Aspect 53. The method of any of Aspects 50-52, further comprising simultaneously conveying a portion of blood into an in-process container of the fluid flow circuit and another portion of the blood into the spinning membrane separator drive unit to separate and collect plasma or red blood cells and plasma from said another portion of the blood, and then conveying said portion of blood from the in-process container into the spinning membrane separator drive unit to separate and collect plasma or red blood cells and plasma from said portion of blood from the in-process container.

Aspect 54. The method of Aspect 50, further comprising simultaneously conveying blood into the fluid flow circuit and conveying fluid out of the fluid flow circuit.

Aspect 55. The method of any of Aspects 50 and 54, further comprising conveying blood into the fluid flow circuit and conveying fluid out of the fluid flow circuit at different locations.

Aspect 56. The method of Aspect 43, wherein said separating at least a portion of the blood in the fluid flow circuit into two or more blood components using the centrifugal separator and/or the spinning membrane separator drive unit includes using the spinning membrane separator drive unit to separate and collect plasma from blood.

Aspect 57. The method of Aspect 56, further comprising simultaneously separating and collecting plasma from blood and conveying fluid out of the fluid flow circuit.

Aspect 58. The method of any of Aspects 56-57, further comprising conveying blood into the fluid flow circuit and conveying fluid out of the fluid flow circuit at the same location.

Aspect 59. The method of any of Aspects 56-58, further comprising simultaneously conveying a portion of blood into an in-process container of the fluid flow circuit and another portion of the blood into the spinning membrane separator drive unit to separate and collect plasma from said another portion of the blood, and then conveying said portion of blood from the in-process container into the spinning membrane separator drive unit to separate and collect plasma from said portion of blood from the in-process container.

Aspect 60. The method of Aspect 56, further comprising simultaneously conveying blood into the fluid flow circuit and conveying fluid out of the fluid flow circuit.

Aspect 61. The method of any of Aspects 56 and 60, further comprising conveying blood into the fluid flow circuit and conveying fluid out of the fluid flow circuit at different locations.

Aspect 62. The method of Aspect 43, wherein said separating at least a portion of the blood in the fluid flow circuit into two or more blood components using the centrifugal separator and/or the spinning membrane separator drive unit includes using the centrifugal separator and the spinning membrane separator drive unit to separate and collect red blood cells, platelets, and plasma from blood.

Aspect 63. The method of Aspect 62, further comprising simultaneously separating and collecting plasma and platelets or red blood cells and platelets from blood and conveying fluid out of the fluid flow circuit.

Aspect 64. The method of any of Aspects 62-63, further comprising conveying blood into the fluid flow circuit and conveying fluid out of the fluid flow circuit at the same location.

Aspect 65. The method of any of Aspects 62-64, further comprising simultaneously conveying a portion of blood into an in-process container of the fluid flow circuit and another portion of the blood into the centrifugal separator and the spinning membrane separator drive unit to separate and collect red blood cells, platelets, and plasma from said another portion of the blood, and then conveying said portion of blood from the in-process container into the centrifugal separator and the spinning membrane separator drive unit to separate and collect plasma and platelets or red blood cells and platelets from said portion of blood from the in-process container.

Aspect 66. The method of Aspect 43, wherein said separating at least a portion of the blood in the fluid flow circuit into two or more blood components using the centrifugal separator and/or the spinning membrane separator drive unit includes using the centrifugal separator and the spinning membrane separator drive unit to separate and collect platelets or platelets and plasma from blood.

Aspect 67. The method of Aspect 66, further comprising simultaneously separating and collecting platelets or platelets and plasma from blood and conveying fluid out of the fluid flow circuit.

Aspect 68. The method of any of Aspects 66-67, further comprising conveying blood into the fluid flow circuit and conveying fluid out of the fluid flow circuit at the same location.

Aspect 69. The method of any of Aspects 66-68, further comprising simultaneously conveying a portion of blood into an in-process container of the fluid flow circuit and another portion of the blood into the centrifugal separator and the spinning membrane separator drive unit to separate and collect platelets or platelets and plasma from said another portion of the blood, and then conveying said portion of blood from the in-process container into the centrifugal separator and the spinning membrane separator drive unit to separate and collect platelets or platelets and plasma from said portion of blood from the in-process container.

Aspect 70. The method of any of Aspects 66-68, further comprising simultaneously separating and collecting platelets or platelets and plasma and conveying red blood cells or red blood cells and plasma separated from blood into a reprocess container of the fluid flow circuit, and then conveying said red blood cells or red blood cells and plasma from the reprocess container into the centrifugal separator and the spinning membrane separator drive unit to separate and collect platelets or platelets and plasma from said red blood cells or red blood cells and plasma from the reprocess container.

Aspect 71. The method of Aspect 66, further comprising simultaneously conveying blood into the fluid flow circuit and conveying fluid out of the fluid flow circuit.

Aspect 72. The method of any of Aspects 66 and 71, further comprising conveying blood into the fluid flow circuit and conveying fluid out of the fluid flow circuit at different locations.

Aspect 73. The method of any of Aspects 43-72, wherein said separating at least a portion of the blood in the fluid flow circuit into two or more blood components using the centrifugal separator and/or the spinning membrane separator drive unit includes simultaneously operating the centrifugal separator and the spinning membrane separator drive unit.

Aspect 74. A method of controlling a blood separation procedure comprising: providing a blood separation device including a pump, a centrifugal separator, and a spinning membrane separator drive unit; mounting a fluid flow circuit to the blood separation device; controlling the pump to convey blood through the fluid flow circuit; and controlling the centrifugal separator and/or the spinning membrane separator drive unit to separate at least a portion of the blood in the fluid flow circuit into two or more blood components.

Aspect 75. The method of Aspect 74, wherein said controlling the centrifugal separator and/or the spinning membrane separator drive unit to separate at least a portion of the blood in the fluid flow circuit into two or more blood components includes controlling the spinning membrane separator drive unit to separate and collect red blood cells from blood.

Aspect 76. The method of Aspect 75, further comprising simultaneously separating and collecting red blood cells from blood and conveying fluid out of the fluid flow circuit.

Aspect 77. The method of any of Aspects 75-76, further comprising conveying blood into the fluid flow circuit and conveying fluid out of the fluid flow circuit at the same location.

Aspect 78. The method of any of Aspects 75-77, further comprising simultaneously conveying a portion of blood into an in-process container of the fluid flow circuit and another portion of the blood into the spinning membrane separator drive unit to separate and collect red blood cells from said another portion of the blood, and then conveying said portion of blood from the in-process container into the spinning membrane separator drive unit to separate and collect red blood cells from said portion of blood from the in-process container.

Aspect 79. The method of Aspect 75, further comprising simultaneously conveying blood into the fluid flow circuit and conveying fluid out of the fluid flow circuit.

Aspect 80. The method of any of Aspects 75 and 79, further comprising conveying blood into the fluid flow circuit and conveying fluid out of the fluid flow circuit at different locations.

Aspect 81. The method of Aspect 74, wherein said controlling the centrifugal separator and/or the spinning membrane separator drive unit to separate at least a portion of the blood in the fluid flow circuit into two or more blood components includes controlling the spinning membrane separator drive unit to separate and collect red blood cells and plasma from blood.

Aspect 82. The method of Aspect 81, further comprising simultaneously separating and collecting plasma or red blood cells and plasma from blood and conveying fluid out of the fluid flow circuit.

Aspect 83. The method of any of Aspects 81-82, further comprising conveying blood into the fluid flow circuit and conveying fluid out of the fluid flow circuit at the same location.

Aspect 84. The method of any of Aspects 81-83, further comprising simultaneously conveying a portion of blood into an in-process container of the fluid flow circuit and another portion of the blood into the spinning membrane separator drive unit to separate and collect plasma or red blood cells and plasma from said another portion of the blood, and then conveying said portion of blood from the in-process container into the spinning membrane separator drive unit to separate and collect plasma or red blood cells and plasma from said portion of blood from the in-process container.

Aspect 85. The method of Aspect 81, further comprising simultaneously conveying blood into the fluid flow circuit and conveying fluid out of the fluid flow circuit.

Aspect 86. The method of any of Aspects 81 and 85, further comprising conveying blood into the fluid flow circuit and conveying fluid out of the fluid flow circuit at different locations.

Aspect 87. The method of Aspect 74, wherein said controlling the centrifugal separator and/or the spinning membrane separator drive unit to separate at least a portion of the blood in the fluid flow circuit into two or more blood components includes controlling the spinning membrane separator drive unit to separate and collect plasma from blood.

Aspect 88. The method of Aspect 87, further comprising simultaneously separating and collecting plasma from blood and conveying fluid out of the fluid flow circuit.

Aspect 89. The method of any of Aspects 87-88, further comprising conveying blood into the fluid flow circuit and conveying fluid out of the fluid flow circuit at the same location.

Aspect 90. The method of any of Aspects 87-89, further comprising simultaneously conveying a portion of blood into an in-process container of the fluid flow circuit and another portion of the blood into the spinning membrane separator drive unit to separate and collect plasma from said another portion of the blood, and then conveying said portion of blood from the in-process container into the spinning membrane separator drive unit to separate and collect plasma from said portion of blood from the in-process container.

Aspect 91. The method of Aspect 87, further comprising simultaneously conveying blood into the fluid flow circuit and conveying fluid out of the fluid flow circuit.

Aspect 92. The method of any of Aspects 87 and 91, further comprising conveying blood into the fluid flow circuit and conveying fluid out of the fluid flow circuit at different locations.

Aspect 93. The method of Aspect 74, wherein said controlling the centrifugal separator and/or the spinning membrane separator drive unit to separate at least a portion of the blood in the fluid flow circuit into two or more blood components includes controlling the centrifugal separator and the spinning membrane separator drive unit to separate and collect red blood cells, platelets, and plasma from blood.

Aspect 94. The method of Aspect 93 further comprising simultaneously separating and collecting plasma and platelets or red blood cells and platelets from blood and conveying fluid out of the fluid flow circuit.

Aspect 95. The method of any of Aspects 93-94, further comprising conveying blood into the fluid flow circuit and conveying fluid out of the fluid flow circuit at the same location.

Aspect 96. The method of any of Aspects 93-95, further comprising simultaneously conveying a portion of blood into an in-process container of the fluid flow circuit and another portion of the blood into the centrifugal separator and the spinning membrane separator drive unit to separate and collect red blood cells, platelets, and plasma from said another portion of the blood, and then conveying said portion of blood from the in-process container into the centrifugal separator and the spinning membrane separator drive unit to separate and collect plasma and platelets or red blood cells and platelets from said portion of blood from the in-process container.

Aspect 97. The method of Aspect 74, wherein said controlling the centrifugal separator and/or the spinning membrane separator drive unit to separate at least a portion of the blood in the fluid flow circuit into two or more blood components includes controlling the centrifugal separator and the spinning membrane separator drive unit to separate and collect platelets or platelets and plasma from blood.

Aspect 98. The method of Aspect 97, further comprising simultaneously separating and collecting platelets or platelets and plasma from blood and conveying fluid out of the fluid flow circuit.

Aspect 99. The method of any of Aspects 97-98, further comprising conveying blood into the fluid flow circuit and conveying fluid out of the fluid flow circuit at the same location.

Aspect 100. The method of any of Aspects 97-99, further comprising simultaneously conveying a portion of blood into an in-process container of the fluid flow circuit and another portion of the blood into the centrifugal separator and the spinning membrane separator drive unit to separate and collect platelets or platelets and plasma from said another portion of the blood, and then conveying said portion of blood from the in-process container into the centrifugal separator and the spinning membrane separator drive unit to separate and collect platelets or platelets and plasma from said portion of blood from the in-process container.

Aspect 101. The method of any of Aspects 97-99, further comprising simultaneously separating and collecting platelets or platelets and plasma and conveying red blood cells or red blood cells and plasma separated from blood into a reprocess container of the fluid flow circuit, and then conveying said red blood cells or red blood cells and plasma from the reprocess container into the centrifugal separator and the spinning membrane separator drive unit to separate and collect platelets or platelets and plasma from said red blood cells or red blood cells and plasma from the reprocess container.

Aspect 102. The method of Aspect 97, further comprising simultaneously conveying blood into the fluid flow circuit and conveying fluid out of the fluid flow circuit.

Aspect 103. The method of any of Aspects 97 and 102, further comprising conveying blood into the fluid flow circuit and conveying fluid out of the fluid flow circuit at different locations.

Aspect 104. The method of any of Aspects 74-103, wherein said controlling the centrifugal separator and/or the spinning membrane separator drive unit to separate at least a portion of the blood in the fluid flow circuit into two or more blood components includes simultaneously controlling the centrifuge separator and the spinning membrane separator drive unit to separate said at least a portion of the blood in the fluid flow circuit into two or more blood components.

Aspect 105. A blood separation method comprising: conveying blood through a fluid flow circuit; separating at least a portion of the blood in the fluid flow circuit into two or more blood components using a centrifugal separator; and further separating at least a portion of one of said separated blood components into two or more sub-components using a spinning membrane separator drive unit.

Aspect 106. The method of Aspect 105, wherein said separating at least a portion of the blood in the fluid flow circuit into two or more blood components using the centrifugal separator includes separating the blood into red blood cells and platelet-rich plasma, and said further separating at least a portion of one of said separated blood components into two or more sub-components using the spinning membrane separator drive unit includes separating the platelet-rich plasma into plasma and platelet concentrate.

Aspect 107. The method of any of Aspects 105-106, further comprising providing a blood separation device including the centrifugal separator and the spinning membrane separator drive unit.

Aspect 108. The method of any of Aspects 105-107, wherein said separating at least a portion of the blood in the fluid flow circuit into two or more blood components using the centrifugal separator includes conveying a combination of the blood and a recirculated portion of one of said separated blood components into the centrifugal separator.

Aspect 109. The method of any of Aspects 105-108, wherein said separating at least a portion of the blood in the fluid flow circuit into two or more blood components using the centrifugal separator includes separating and collecting red blood cells from said at least a portion of the blood using the centrifugal separator, and said further separating at least a portion of one of said separated blood components into two or more sub-components using the spinning membrane separator drive unit includes separating and collecting plasma and platelet concentrate from platelet-rich plasma using the spinning membrane separator drive unit.

Aspect 110. The method of any of Aspects 105-109, wherein said conveying blood through the fluid flow circuit includes conveying a portion of the blood into a container and another portion of the blood into the centrifugal separator.

Aspect 111. The method of Aspect 110, further comprising conveying at least a portion of the blood in the container into the centrifugal separator, separating at least a portion of the blood from the container into said two or more blood components using the centrifugal separator, and further separating at least a portion of one of said blood components separated from the blood from the container into said two or more sub-components using the spinning membrane separator drive unit.

Aspect 112. The method of Aspect 111, wherein said separating at least a portion of the blood from the container into said two or more blood components using the centrifugal separator includes conveying a combination of the blood from the container and a recirculated portion of one of said blood components separated from the blood from the container into the centrifugal separator.

Aspect 113. The method of any of Aspects 111-112, wherein said separating at least a portion of the blood from the container into said two or more blood components using the centrifugal separator includes simultaneously conveying separated red blood cells out of the fluid flow circuit, and said further separating at least a portion of one of said blood components separated from the blood from the container into said two or more sub-components using the spinning membrane separator drive unit includes simultaneously collecting plasma and platelet concentrate.

Aspect 114. The method of any of Aspects 111-112, wherein said separating at least a portion of the blood from the container into said two or more blood components using the centrifugal separator includes simultaneously collecting separated red blood cells, and said further separating at least a portion of one of said blood components separated from the blood from the container into said two or more sub-components using the spinning membrane separator drive unit includes simultaneously collecting platelet concentrate and conveying plasma out of the fluid flow circuit.

Aspect 115. The method of any of Aspects 105-114, further comprising conveying an additive solution through a leukocyte removal filter, mixing separated red blood cells and the additive solution, and conveying the mixture of the red blood cells and the additive solution through the leukocyte removal filter.

Aspect 116. The method of any of Aspects 105-108, wherein said separating at least a portion of the blood in the fluid flow circuit into two or more blood components using the centrifugal separator includes separating red blood cells from said at least a portion of the blood using the centrifugal separator and conveying at least a portion of the separated red blood cells into a container, and said further separating at least a portion of one of said separated blood components into two or more sub-components using the spinning membrane separator drive unit includes separating plasma and platelet concentrate from platelet-rich plasma using the spinning membrane separator drive unit, collecting at least a portion of the separated platelet concentrate, and conveying at least a portion of the separated plasma into said container with the separated red blood cells.

Aspect 117. The method of Aspect 116, wherein said conveying blood through the fluid flow circuit includes conveying a portion of the blood into an in-process container and another portion of the blood into the centrifugal separator.

Aspect 118. The method of Aspect 117, further comprising conveying at least a portion of the blood in the in-process container into the centrifugal separator, separating at least a portion of the blood from the in-process container into said two or more blood components using the centrifugal separator, and further separating at least a portion of one of said blood components separated from the blood from the in-process container into said two or more sub-components using the spinning membrane separator drive unit.

Aspect 119. The method of Aspect 118, wherein said separating at least a portion of the blood from the in-process container into said two or more blood components using the centrifugal separator includes conveying a combination of the blood from the in-process container and a recirculated portion of one of said blood components separated from the blood from the in-process container into the centrifugal separator.

Aspect 120. The method of any of Aspects 118-119, wherein said separating at least a portion of the blood from the in-process container into said two or more blood components using the centrifugal separator includes simultaneously conveying separated red blood cells out of the fluid flow circuit, and said further separating at least a portion of one of said blood components separated from the blood from the in-process container into said two or more sub-components using the spinning membrane separator drive unit includes simultaneously collecting plasma and platelet concentrate.

Aspect 121. The method of any of Aspects 118-119, wherein said separating at least a portion of the blood from the in-process container into said two or more blood components using the centrifugal separator includes simultaneously conveying separated red blood cells out of the fluid flow circuit, and said further separating at least a portion of one of said blood components separated from the blood from the in-process container into said two or more sub-components using the spinning membrane separator drive unit includes simultaneously collecting platelet concentrate and conveying plasma out of the fluid flow circuit.

Aspect 122. The method of any of Aspects 105-108, wherein said separating at least a portion of the blood in the fluid flow circuit into two or more blood components using the centrifugal separator includes simultaneously conveying separated red blood cells out of the fluid flow circuit; and said further separating at least a portion of one of said separated blood components into two or more sub-components using the spinning membrane separator drive unit includes simultaneously collecting platelet concentrate and conveying plasma out of the fluid flow circuit.

Aspect 123. The method of any of Aspects 105-108, wherein said separating at least a portion of the blood in the fluid flow circuit into two or more blood components using the centrifugal separator includes simultaneously conveying separated red blood cells out of the fluid flow circuit; and said further separating at least a portion of one of said separated blood components into two or more sub-components using the spinning membrane separator drive unit includes simultaneously collecting platelet concentrate and plasma.

Aspect 124. The method of any of Aspects 105-123, further comprising conveying said at least a portion of one of said separated blood components from the centrifugal separator to the spinning membrane separator drive unit and optically detecting a characteristic of said at least a portion of one of said separated blood components.

Aspect 125. The method of Aspect 124, wherein the concentration of platelets in said at least a portion of one of said separated blood components is optically detected.

Aspect 126. The method of Aspect 125, further comprising conveying platelet concentrate out of the spinning membrane separator drive unit at a volumetric flow rate based at least in part on the concentration of platelets in said at least a portion of one of said separated blood components.

Aspect 127. The method of any of Aspects 105-126, wherein said further separating at least a portion of one of said separated blood components into two or more sub-components using the spinning membrane separator drive unit includes separating plasma from the at least a portion of one of said separated blood components using the spinning membrane separator drive unit, conveying at least a portion of the plasma out of the spinning membrane separator drive unit, and optically detecting a characteristic of the plasma.

Aspect 128. The method of Aspect 127, wherein said optically detecting a characteristic of the plasma includes determining whether the plasma is lipemic and/or hemolytic.

Aspect 129. The method of any of Aspects 105-128, wherein said further separating said at least a portion of one of said separated blood components into two or more sub-components using the spinning membrane separator drive unit includes simultaneously operating the centrifugal separator to separate said at least a portion of the blood in the fluid flow circuit into two or more blood components and operating the spinning membrane separator drive unit to further separate said at least a portion of one of said separated blood components into two or more sub-components.

Aspect 130. A method of controlling a blood separation procedure comprising: controlling a pump to convey blood through a fluid flow circuit; controlling a centrifugal separator to separate at least a portion of the blood in the fluid flow circuit into two or more blood components; and controlling a spinning membrane separator drive unit to further separate at least a portion of one of said separated blood components into two or more sub-components.

Aspect 131. The method of Aspect 130, wherein said controlling the centrifugal separator to separate at least a portion of the blood in the fluid flow circuit into two or more blood components includes separating the blood into red blood cells and platelet-rich plasma, and said controlling the spinning membrane separator drive unit to further separate at least a portion of one of said separated blood components into two or more sub-components includes separating the platelet-rich plasma into plasma and platelet concentrate.

Aspect 132. The method of any of Aspects 130-131, further comprising providing a blood separation device including the centrifugal separator and the spinning membrane separator drive unit.

Aspect 133. The method of any of Aspects 130-132, wherein controlling the centrifugal separator to separate at least a portion of the blood in the fluid flow circuit into two or more blood components includes conveying a combination of the blood and a recirculated portion of one of said separated blood components into the centrifugal separator.

Aspect 134. The method of any of Aspects 130-133, wherein said controlling the centrifugal separator to separate at least a portion of the blood in the fluid flow circuit into two or more blood components includes controlling the centrifugal separator to separate and collect red blood cells from said at least a portion of the blood, and said controlling the spinning membrane separator drive unit to further separate at least a portion of one of said separated blood components into two or more sub-components includes controlling the spinning membrane separator drive unit to separate and collect plasma and platelet concentrate from platelet-rich plasma.

Aspect 135. The method of any of Aspects 130-134, wherein said controlling the pump to convey blood through the fluid flow circuit includes controlling the pump to convey a portion of the blood into a container and another portion of the blood into the centrifugal separator.

Aspect 136. The method of Aspect 135, further comprising controlling the pump to convey at least a portion of the blood in the container into the centrifugal separator, controlling the centrifugal separator to separate at least a portion of the blood from the container into said two or more blood components, and controlling the spinning membrane separator drive unit to further separate at least a portion of one of said blood components separated from the blood from the container into said two or more sub-components.

Aspect 137. The method of Aspect 136, wherein said controlling the centrifugal separator to separate at least a portion of the blood from the container into said two or more blood components includes conveying a combination of the blood from the container and a recirculated portion of one of said blood components separated from the blood from the container into the centrifugal separator.

Aspect 138. The method of any of Aspects 136-137, wherein said controlling the centrifugal separator to separate at least a portion of the blood from the container into said two or more blood components includes simultaneously conveying separated red blood cells out of the fluid flow circuit, and said controlling the spinning membrane separator drive unit to further separate at least a portion of one of said blood components separated from the blood from the container into said two or more sub-components includes simultaneously collecting plasma and platelet concentrate.

Aspect 139. The method of any of Aspects 136-137, wherein said controlling the centrifugal separator to separate at least a portion of the blood from the container into said two or more blood components includes simultaneously collecting separated red blood cells, and said controlling the spinning membrane separator drive unit to further separate at least a portion of one of said blood components separated from the blood from the container into said two or more sub-components includes simultaneously collecting platelet concentrate and conveying plasma out of the fluid flow circuit.

Aspect 140. The method of any of Aspects 130-139, further comprising controlling a second pump to convey an additive solution through a leukocyte removal filter, mixing separated red blood cells and the additive solution, and controlling the second pump to convey the mixture of the red blood cells and the additive solution through the leukocyte removal filter.

Aspect 141. The method of any of Aspects 130-133, wherein said controlling the centrifugal separator to separate at least a portion of the blood in the fluid flow circuit into two or more blood components includes separating red blood cells from said at least a portion of the blood using the centrifugal separator and conveying at least a portion of the separated red blood cells into a container, and said controlling the spinning membrane separator drive unit to further separate at least a portion of one of said separated blood components into two or more sub-components includes separating plasma and platelet concentrate from platelet-rich plasma using the spinning membrane separator drive unit, collecting at least a portion of the separated platelet concentrate, and conveying at least a portion of the separated plasma into said container with the separated red blood cells.

Aspect 142. The method of Aspect 141, wherein said controlling the pump to convey blood through the fluid flow circuit includes controlling the pump to convey a portion of the blood into an in-process container and another portion of the blood into the centrifugal separator.

Aspect 143. The method of Aspect 142, further comprising controlling the pump to convey at least a portion of the blood in the in-process container into the centrifugal separator, controlling the centrifugal separator to separate at least a portion of the blood from the in-process container into said two or more blood components, and controlling the spinning membrane separator drive unit to further separate at least a portion of one of said blood components separated from the blood from the in-process container into said two or more sub-components.

Aspect 144. The method of Aspect 143, wherein said controlling the centrifugal separator to separate at least a portion of the blood from the in-process container into said two or more blood components includes conveying a combination of the blood from the in-process container and a recirculated portion of one of said blood components separated from the blood from the in-process container into the centrifugal separator.

Aspect 145. The method of any of Aspects 143-144, wherein said controlling the centrifugal separator to separate at least a portion of the blood from the in-process container into said two or more blood components includes simultaneously conveying separated red blood cells out of the fluid flow circuit, and said controlling the spinning membrane separator drive unit to further separate at least a portion of one of said blood components separated from the blood from the in-process container into said two or more sub-components includes simultaneously collecting plasma and platelet concentrate.

Aspect 146. The method of any of Aspects 143-144, wherein said controlling the centrifugal separator to separate at least a portion of the blood from the in-process container into said two or more blood components includes simultaneously conveying separated red blood cells out of the fluid flow circuit, and said controlling the spinning membrane separator drive unit to further separate at least a portion of one of said blood components separated from the blood from the in-process container into said two or more sub-components includes simultaneously collecting platelet concentrate and conveying plasma out of the fluid flow circuit.

Aspect 147. The method of any of Aspects 130-133, wherein said controlling the centrifugal separator to separate at least a portion of the blood in the fluid flow circuit into two or more blood components includes simultaneously conveying separated red blood cells out of the fluid flow circuit; and said controlling the spinning membrane separator drive unit to further separate at least a portion of one of said separated blood components into two or more sub-components includes simultaneously collecting platelet concentrate and conveying plasma out of the fluid flow circuit.

Aspect 148. The method of any of Aspects 130-133, wherein said controlling the centrifugal separator to separate at least a portion of the blood in the fluid flow circuit into two or more blood components includes simultaneously conveying separated red blood cells out of the fluid flow circuit; and said controlling the spinning membrane separator drive unit to further separate at least a portion of one of said separated blood components into two or more sub-components includes simultaneously collecting platelet concentrate and plasma.

Aspect 149. The method of any of Aspects 130-148, further comprising optically detecting a characteristic of said at least a portion of one of said separated blood components.

Aspect 150. The method of Aspect 149, wherein the concentration of platelets in said at least a portion of one of said separated blood components is optically detected.

Aspect 151. The method of Aspect 150, further comprising conveying platelet concentrate out of the spinning membrane separator drive unit at a volumetric flow rate based at least in part on the concentration of platelets in said at least a portion of one of said separated blood components.

Aspect 152. The method of any of Aspects 130-151, wherein said controlling the spinning membrane separator drive unit to further separate at least a portion of one of said separated blood components into two or more sub-components includes separating plasma from the at least a portion of one of said separated blood components using the spinning membrane separator drive unit, conveying at least a portion of the plasma out of the spinning membrane separator drive unit, and optically detecting a characteristic of the plasma.

Aspect 153. The method of Aspect 152, wherein said optically detecting a characteristic of the plasma includes determining whether the plasma is lipemic and/or hemolytic.

Aspect 154. The method of any of Aspects 130-153, wherein said controlling the spinning membrane separator drive unit to further separate said at least a portion of one of said separated blood components into two or more sub-components includes simultaneously controlling the centrifugal separator to separate said at least a portion of the blood in the fluid flow circuit into two or more blood components and controlling the spinning membrane separator drive unit to further separate said at least a portion of one of said separated blood components into two or more sub-components.

Aspect 155. A blood separation method comprising: mounting a fluid flow circuit to a blood separation device including a centrifugal separator and a spinning membrane separator drive unit; conveying blood through the fluid flow circuit; separating red blood cells from at least a portion of the blood in the fluid flow circuit using the spinning membrane separator drive unit; and collecting at least a portion of the separated red blood cells.

Aspect 156. The method of Aspect 155, wherein said separating red blood cells from at least a portion of the blood in the fluid flow circuit includes separating plasma from the blood and conveying at least a portion of the plasma into a return container.

Aspect 157. The method of Aspect 156, further comprising conveying at least a portion of the plasma in the return container out of the fluid flow circuit while separating red blood cells from blood using the spinning membrane separator drive unit.

Aspect 158. The method of any of Aspects 155-157, wherein said collecting at least a portion of the separated red blood cells includes conveying said at least a portion of the separated red blood cells through a leukocyte removal filter.

Aspect 159. The method of any of Aspects 155-158, wherein said conveying blood through the fluid flow circuit includes conveying a portion of the blood into an in-process container and another portion of the blood into the spinning membrane separator drive unit.

Aspect 160. The method of Aspect 159, further comprising conveying at least a portion of the blood in the in-process container into the spinning membrane separator drive unit, separating red blood cells from said at least a portion of the blood from the in-process container using the spinning membrane separator drive unit, and collecting at least a portion of the red blood cells separated from the blood from the in-process container.

Aspect 161. The method of Aspect 155, wherein said separating red blood cells from at least a portion of the blood in the fluid flow circuit includes separating plasma from the blood and conveying at least a portion of the plasma out of the fluid flow circuit.

Aspect 162. The method of any of Aspects 155-161, wherein said conveying blood through the fluid flow circuit includes optically detecting a characteristic of the blood.

Aspect 163. The method of Aspect 162, wherein a hematocrit of the blood is optically detected.

Aspect 164. The method of Aspect 163, further comprising conveying red blood cells out of the spinning membrane separator drive unit at a volumetric flow rate based at least in part on the hematocrit of the blood.

Aspect 165. The method of any of Aspects 155-164, wherein said separating red blood cells from at least a portion of the blood in the fluid flow circuit includes separating plasma from the blood using the spinning membrane separator drive unit, conveying at least a portion of the plasma out of the spinning membrane separator drive unit, and optically detecting a characteristic of the plasma.

Aspect 166. The method of Aspect 165, wherein said optically detecting a characteristic of the plasma includes determining whether the plasma is lipemic and/or hemolytic.

Aspect 167. The method of any of Aspects 155-166, wherein said separating red blood cells from said at least a portion of the blood in the fluid flow circuit using the spinning membrane separator drive unit includes separating red blood cells from said at least a portion of the blood in the fluid flow circuit using the spinning membrane separator drive unit and not the centrifugal separator.

Aspect 168. A method of controlling a blood separation procedure comprising: mounting a fluid flow circuit including a fluid container to a blood separation device including a plurality of pumps, a centrifugal separator, and a spinning membrane separator drive unit; controlling at least one of said pumps to convey blood through the fluid flow circuit; controlling the spinning membrane separator drive unit to separate red blood cells from at least a portion of the blood in the fluid flow circuit; and controlling at least one of said pumps to convey at least a portion of the separated red blood cells to the fluid container.

Aspect 169. The method of Aspect 168, wherein said controlling the spinning membrane separator drive unit to separate red blood cells from at least a portion of the blood in the fluid flow circuit includes controlling the spinning membrane separator drive unit to separate plasma from the blood and convey at least a portion of the plasma into a return container.

Aspect 170. The method of Aspect 169, further comprising controlling said at least one of said pumps to convey at least a portion of the plasma in the return container out of the fluid flow circuit while controlling the spinning membrane separator drive unit to separate red blood cells from blood.

Aspect 171. The method of any of Aspects 168-170, wherein said controlling said at least one of said pumps to convey said at least a portion of the separated red blood cells to the fluid container includes conveying said at least a portion of the separated red blood cells through a leukocyte removal filter.

Aspect 172. The method of any of Aspects 168-171, wherein said controlling said at least one of said pumps to convey blood through the fluid flow circuit includes conveying a portion of the blood into an in-process container and another portion of the blood into the spinning membrane separator drive unit.

Aspect 173. The method of Aspect 172, further comprising controlling said at least one of said pumps to convey at least a portion of the blood in the in-process container into the spinning membrane separator drive unit, controlling the spinning membrane separator drive unit to separate red blood cells from said at least a portion of the blood from the in-process container, and controlling said at least one of said pumps to convey at least a portion of the red blood cells separated from said at least a portion of the blood from the in-process container to the fluid container.

Aspect 174. The method of Aspect 168, wherein said controlling the spinning membrane separator drive unit to separate red blood cells from at least a portion of the blood in the fluid flow circuit includes separating plasma from the blood and conveying at least a portion of the plasma out of the fluid flow circuit.

Aspect 175. The method of any of Aspects 168-174, wherein said controlling said at least one of said pumps to convey blood through the fluid flow circuit includes optically detecting a characteristic of the blood.

Aspect 176. The method of Aspect 175, wherein a hematocrit of the blood is optically detected.

Aspect 177. The method of Aspect 176, further comprising controlling at least one of said pumps to convey red blood cells out of the spinning membrane separator drive unit at a volumetric flow rate based at least in part on the hematocrit of the blood.

Aspect 178. The method of any of Aspects 168-177, wherein said controlling the spinning membrane separator drive unit to separate red blood cells from said at least a portion of the blood in the fluid flow circuit includes controlling the spinning membrane separator drive unit to separate plasma from the blood, conveying at least a portion of the plasma out of the spinning membrane separator drive unit, and optically detecting a characteristic of the plasma.

Aspect 179. The method of Aspect 178, wherein said optically detecting a characteristic of the plasma includes determining whether the plasma is lipemic and/or hemolytic.

Aspect 180. The method of any of Aspects 168-179, wherein said controlling the spinning membrane separator drive unit to separate red blood cells from said at least a portion of the blood in the fluid flow circuit includes controlling the spinning membrane separator drive unit and not the centrifugal separator to separate red blood cells from at least a portion of the blood in the fluid flow circuit.

Aspect 181. A blood separation method comprising: mounting a fluid flow circuit to a blood separation device including a centrifugal separator and a spinning membrane separator drive unit; conveying blood through the fluid flow circuit; separating red blood cells and plasma from at least a portion of the blood in the fluid flow circuit using the spinning membrane separator drive unit and not the centrifugal separator; collecting at least a portion of the separated red blood cells; and collecting at least a portion of the separated plasma.

Aspect 182. The method of Aspect 181, wherein said separating red blood cells and plasma from at least a portion of the blood in the fluid flow circuit includes conveying at least a portion of the red blood cells into a return container.

Aspect 183. The method of Aspect 182, further comprising conveying at least a portion of the red blood cells in the return container out of the fluid flow circuit while separating red blood cells and plasma from blood using the spinning membrane separator drive unit.

Aspect 184. The method of any of Aspects 181-183, wherein said collecting at least a portion of the separated red blood cells includes conveying said at least a portion of the separated red blood cells through a leukocyte removal filter.

Aspect 185. The method of any of Aspects 181-184, wherein said conveying blood through the fluid flow circuit includes conveying a portion of the blood into an in-process container and another portion of the blood into the spinning membrane separator drive unit.

Aspect 186. The method of Aspect 185, further comprising conveying at least a portion of the blood in the in-process container into the spinning membrane separator drive unit, separating red blood cells and plasma from said at least a portion of the blood from the in-process container using the spinning membrane separator drive unit, and collecting at least a portion of the plasma separated from the blood from the in-process container.

Aspect 187. The method of Aspect 181, wherein said separating red blood cells and plasma from at least a portion of the blood in the fluid flow circuit includes conveying at least a portion of the red blood cells out of the fluid flow circuit.

Aspect 188. The method of any of Aspects 181-187, wherein said conveying blood through the fluid flow circuit includes optically detecting a characteristic of the blood.

Aspect 189. The method of Aspect 188, wherein a hematocrit of the blood is optically detected.

Aspect 190. The method of Aspect 189, further comprising conveying red blood cells out of the spinning membrane separator drive unit at a volumetric flow rate based at least in part on the hematocrit of the blood.

Aspect 191. The method of any of Aspects 181-190, wherein said separating red blood cells and plasma from at least a portion of the blood in the fluid flow circuit includes optically detecting a characteristic of the plasma.

Aspect 192. The method of Aspect 191, wherein said optically detecting a characteristic of the plasma includes determining whether the plasma is lipemic and/or hemolytic.

Aspect 193. The method of any of Aspects 181-192, wherein said separating red blood cells and plasma from said at least a portion of the blood in the fluid flow circuit using the spinning membrane separator drive unit includes separating red blood cells and plasma from said at least a portion of the blood in the fluid flow circuit using the spinning membrane separator drive unit and not the centrifugal separator.

Aspect 194. A method of controlling a blood separation procedure comprising: mounting a fluid flow circuit including a plurality of fluid containers to a blood separation device including a plurality of pumps, a centrifugal separator, and a spinning membrane separator drive unit; controlling at least one of said pumps to convey blood through the fluid flow circuit; controlling the spinning membrane separator drive unit to separate red blood cells and plasma from at least a portion of the blood in the fluid flow circuit; controlling at least one of said pumps to convey at least a portion of the separated red blood cells to one of said fluid containers; and conveying at least a portion of the separated plasma to one of said fluid containers.

Aspect 195. The method of Aspect 194, wherein controlling the spinning membrane separator drive unit to separate red blood cells and plasma from said at least a portion of the blood in the fluid flow circuit includes controlling at least one of said pumps to convey at least a portion of the red blood cells into a return container.

Aspect 196. The method of Aspect 195, further comprising controlling at least one of said pumps to convey at least a portion of the red blood cells in the return container out of the fluid flow circuit while controlling the spinning membrane separator drive unit to separate red blood cells and plasma from blood.

Aspect 197. The method of any of Aspects 194-196, wherein said controlling at least one of said pumps to convey at least a portion of the separated red blood cells to one of said fluid containers includes controlling said at least one of said pumps to convey said at least a portion of the separated red blood cells through a leukocyte removal filter.

Aspect 198. The method of any of Aspects 194-197, wherein said controlling at least one of said pumps to convey blood through the fluid flow circuit includes controlling said at least one of said pumps to convey a portion of the blood into an in-process container and another portion of the blood into the spinning membrane separator drive unit.

Aspect 199. The method of Aspect 198, further comprising controlling at least one of said pumps to convey at least a portion of the blood in the in-process container into the spinning membrane separator drive unit, controlling the spinning membrane separator drive unit to separate red blood cells and plasma from said at least a portion of the blood from the in-process container, and conveying at least a portion of the plasma separated from the blood from the in-process container to one of said fluid containers.

Aspect 200. The method of Aspect 194, wherein said controlling the spinning membrane separator to separate red blood cells and plasma from at least a portion of the blood in the fluid flow circuit includes controlling at least one of said pumps to convey at least a portion of the red blood cells out of the fluid flow circuit.

Aspect 201. The method of any of Aspects 194-200, wherein said controlling at least one of said pumps to convey blood through the fluid flow circuit includes optically detecting a characteristic of the blood.

Aspect 202. The method of Aspect 201, wherein a hematocrit of the blood is optically detected.

Aspect 203. The method of Aspect 202, wherein said controlling at least one of said pumps to convey at least a portion of the separated red blood cells to one of said fluid containers includes controlling said at least one of said pumps to conveying said at least a portion of the red blood cells out of the spinning membrane separator drive unit at a volumetric flow rate based at least in part on the hematocrit of the blood.

Aspect 204. The method of any of Aspects 194-203, wherein said conveying at least a portion of the separated plasma to one of said fluid containers includes optically detecting a characteristic of the plasma.

Aspect 205. The method of Aspect 204, wherein said optically detecting a characteristic of the plasma includes determining whether the plasma is lipemic and/or hemolytic.

Aspect 206. The method of any of Aspects 194-204, wherein said controlling the spinning membrane separator drive unit to separate red blood cells and plasma from said at least a portion of the blood in the fluid flow circuit includes controlling the spinning membrane separator drive unit and not the centrifugal separator to separate red blood cells and plasma from said at least a portion of the blood in the fluid flow circuit.

Aspect 207. A blood separation method comprising: mounting a fluid flow circuit to a blood separation device including a centrifugal separator and a spinning membrane separator drive unit; conveying blood through the fluid flow circuit; separating plasma from at least a portion of the blood in the fluid flow circuit using the spinning membrane separator drive unit; and collecting at least a portion of the separated plasma.

Aspect 208. The method of Aspect 207, wherein said separating plasma from said at least a portion of the blood in the fluid flow circuit includes separating red blood cells from said at least a portion of the blood in the fluid flow circuit using the spinning membrane separator drive unit and conveying at least a portion of the red blood cells into a return container.

Aspect 209. The method of Aspect 208, further comprising conveying at least a portion of the red blood cells in the return container out of the fluid flow circuit while separating plasma from blood using the spinning membrane separator drive unit.

Aspect 210. The method of any of Aspects 207-209, wherein said conveying blood through the fluid flow circuit includes conveying a portion of the blood into an in-process container and another portion of the blood into the spinning membrane separator drive unit.

Aspect 211. The method of Aspect 210, further comprising conveying at least a portion of the blood in the in-process container into the spinning membrane separator drive unit, separating plasma from said at least a portion of the blood from the in-process container using the spinning membrane separator drive unit, and collecting at least a portion of the plasma separated from the blood from the in-process container.

Aspect 212. The method of Aspect 207, wherein said separating plasma from said at least a portion of the blood in the fluid flow circuit includes separating red blood cells from said at least a portion of the blood in the fluid flow circuit using the spinning membrane separator drive unit and conveying at least a portion of the red blood cells out of the fluid flow circuit.

Aspect 213. The method of any of Aspects 207-212, wherein said conveying blood through the fluid flow circuit includes optically detecting a characteristic of the blood.

Aspect 214. The method of Aspect 213, wherein a hematocrit of the blood is optically detected.

Aspect 215. The method of Aspect 214, further comprising conveying red blood cells out of the spinning membrane separator drive unit at a volumetric flow rate based at least in part on the hematocrit of the blood.

Aspect 216. The method of any of Aspects 207-215, wherein said separating plasma from said at least a portion of the blood in the fluid flow circuit includes optically detecting a characteristic of the plasma.

Aspect 217. The method of Aspect 216, wherein said optically detecting a characteristic of the plasma includes determining whether the plasma is lipemic and/or hemolytic.

Aspect 218. The method of any of Aspects 207-217, wherein said separating plasma from said at least a portion of the blood in the fluid flow circuit using the spinning membrane separator drive unit includes separating plasma from said at least a portion of the blood in the fluid flow circuit using the spinning membrane separator drive unit and not the centrifugal separator.

Aspect 219. A method of controlling a blood separation procedure comprising: mounting a fluid flow circuit including a fluid container to a blood separation device including a plurality of pumps, a centrifugal separator, and a spinning membrane separator drive unit; controlling at least one of said pumps to convey blood through the fluid flow circuit; controlling the spinning membrane separator drive unit to separate plasma from at least a portion of the blood in the fluid flow circuit; and controlling at least one of said pumps to convey at least a portion of the separated plasma to the fluid container.

Aspect 220. The method of Aspect 219, wherein said controlling the spinning membrane separator drive unit to separate plasma from said at least a portion of the blood in the fluid flow circuit includes separating red blood cells from said at least a portion of the blood in the fluid flow circuit using the spinning membrane separator drive unit and controlling at least one of said pumps to convey at least a portion of the red blood cells into a return container.

Aspect 221. The method of Aspect 220, further comprising controlling at least one of said pumps to convey at least a portion of the red blood cells in the return container out of the fluid flow circuit while controlling the spinning membrane separator drive unit to separate plasma from blood.

Aspect 222. The method of any of Aspects 219-221, wherein said controlling at least one of said pumps to convey blood through the fluid flow circuit includes controlling said at least one of said pumps to convey a portion of the blood into an in-process container and another portion of the blood into the spinning membrane separator drive unit.

Aspect 223. The method of Aspect 222, further comprising controlling said at least one of said pumps to convey at least a portion of the blood in the in-process container into the spinning membrane separator drive unit, controlling the spinning membrane separator drive unit to separate plasma from said at least a portion of the blood from the in-process container, and controlling at least one of said pumps to convey at least a portion of the plasma separated from the blood from the in-process container to the fluid container.

Aspect 224. The method of Aspect 219, wherein said controlling the spinning membrane separator to separate plasma from said at least a portion of the blood in the fluid flow circuit includes controlling the spinning membrane separator to separate red blood cells from said at least a portion of the blood in the fluid flow circuit, and further comprising controlling at least one of said pumps to conveying at least a portion of the red blood cells out of the fluid flow circuit.

Aspect 225. The method of any of Aspects 219-224, wherein said controlling at least one of said pumps to convey blood through the fluid flow circuit includes optically detecting a characteristic of the blood.

Aspect 226. The method of Aspect 225, wherein a hematocrit of the blood is optically detected.

Aspect 227. The method of Aspect 226, further comprising controlling at least one of said pumps to convey red blood cells out of the spinning membrane separator drive unit at a volumetric flow rate based at least in part on the hematocrit of the blood.

Aspect 228. The method of any of Aspects 219-227, wherein said controlling the spinning membrane separator drive unit to separate plasma from said at least a portion of the blood in the fluid flow circuit includes optically detecting a characteristic of the plasma.

Aspect 229. The method of Aspect 228, wherein said optically detecting a characteristic of the plasma includes determining whether the plasma is lipemic and/or hemolytic.

Aspect 230. The method of any of Aspects 219-229, wherein said controlling the spinning membrane separator drive unit to separate plasma from said at least a portion of the blood in the fluid flow circuit includes controlling the spinning membrane separator drive unit and not the centrifugal separator to separate plasma from said at least a portion of the blood in the fluid flow circuit.

Aspect 231. A blood separation method comprising: conveying blood through a fluid flow circuit; separating at least a portion of the blood in the fluid flow circuit into first and second blood components; conveying at least a portion of the first blood component into a container; further separating at least a portion of the second blood component into first and second sub-components; conveying at least a portion of the first sub-component into the container to form a mixture with said at least a portion of the first blood component in the container; collecting at least a portion of the second sub-component; separating at least a portion of the mixture into said first and second blood components; further separating at least a portion of the second blood component separated from the mixture into said first and second sub-components; and collecting at least a portion of the second sub-component separated from said at least a portion of the second blood component separated from the mixture.

Aspect 232. The method of Aspect 231, wherein the first blood component comprises red blood cells, the second blood component comprises platelet-rich plasma, the first sub-component comprises plasma, and the second sub-component comprises platelet concentrate.

Aspect 233. The method of any of Aspects 231-232, wherein said separating at least a portion of the blood in the fluid flow circuit into first and second blood components includes using a first separator, and said further separating at least a portion of the second blood component into first and second sub-components includes using a second separator.

Aspect 234. The method of Aspect 233, wherein the first separator comprises a centrifugal separator and the second separator comprises a spinning membrane separator drive unit.

Aspect 235. The method of any of Aspects 233-234, further comprising providing a blood separation device including the first separator and the second separator.

Aspect 236. The method of any of Aspects 233-235, wherein said separating at least a portion of the mixture into said first and second blood components includes using the first separator, and said further separating at least a portion of the second blood component separated from the mixture into said first and second sub-components includes using the second separator.

Aspect 237. The method of any of Aspects 231-236, wherein said further separating at least a portion of the second blood component separated from the mixture into said first and second sub-components includes simultaneously conveying at least a portion of the first blood component separated from the mixture out of the fluid flow circuit.

Aspect 238. The method of any of Aspects 231-237, wherein said further separating at least a portion of the second blood component separated from the mixture into said first and second sub-components includes simultaneously collecting at least a portion of the first sub-component separated from the second component separated from the mixture.

Aspect 239. The method of any of Aspects 231-237, wherein said further separating at least a portion of the second blood component separated from the mixture into said first and second sub-components includes simultaneously conveying at least a portion of the first sub-component separated from the second component separated from the mixture out of the fluid flow circuit.

Aspect 240. The method of any of Aspects 231-239, wherein said separating at least a portion of the blood in the fluid flow circuit into first and second blood components includes flowing a combination of the blood and a recirculated portion of the second blood component separated from the blood into a first separator, and said separating at least a portion of the mixture into said first and second blood components includes flowing a combination of the mixture and a recirculated portion of the second blood component separated from the mixture into the first separator.

Aspect 241. The method of Aspect 240, wherein a hematocrit of the combination of the blood and the recirculated portion of the second blood component separated from the blood is the same as a hematocrit as the combination of the mixture and the recirculated portion of the second blood component separated from the mixture.

Aspect 242. The method of Aspect 240, wherein the volumetric flow rate of the combination of the blood and the recirculated portion of the second blood component separated from the blood into the first separator is the same as the volumetric flow rate of the combination of the mixture and the recirculated portion of the second blood component separated from the blood into the first separator.

Aspect 243. The method of Aspect 240, wherein a hematocrit of the combination of the blood and the recirculated portion of the second blood component separated from the blood is the same as a hematocrit as the combination of the mixture and the recirculated portion of the second blood component separated from the mixture, and the volumetric flow rate of the combination of the blood and the recirculated portion of the second blood component separated from the blood into the first separator is the same as the volumetric flow rate of the combination of the mixture and the recirculated portion of the second blood component separated from the blood into the first separator.

Aspect 244. The method of Aspect 243, wherein Qcent=Qin-wb+Qrecirc-wb=Qin-reproc+Qrecirc-reproc, Qrecirc-wb=((Qin-wb*Hdnr)/Hrecirc)−Qin-wb, Qin-reproc=(Qin-wb*Hdnr)/Hreproc, and Qrecirc-reproc=((Qin-reproc*Hreproc)/Hrecirc)−Qin-reproc, in which Qcent is the volumetric flow rate into the first separator, Qin-wb is the volumetric flow rate of the blood, Qrecirc-wb is the volumetric flow rate of the recirculated portion of the second blood component separated from the blood, Qin-reproc is the volumetric flow rate of the mixture, Qrecirc-reproc is the volumetric flow rate of the recirculated portion of the second blood component separated from the mixture, Hdnr is a hematocrit of the blood, Hrecirc is the hematocrit of the combination of the blood and the recirculated portion of the second blood component separated from the blood and the hematocrit of the combination of the mixture and the recirculated portion of the second blood component separated from the mixture, and Hreproc is a hematocrit of the mixture.

Aspect 245. The method of any of Aspects 231-244, further comprising optically detecting a characteristic of said at least a portion of the second blood component prior to said further separating said at least a portion of the second blood component into first and second sub-components.

Aspect 246. The method of Aspect 245, wherein the concentration of platelets in said at least a portion of one of the second blood component is optically detected.

Aspect 247. The method of Aspect 246, wherein said collecting said at least a portion of the second sub-component includes conveying said at least a portion of the second sub-component through the fluid flow circuit at a volumetric flow rate based at least in part on the concentration of platelets in said at least a portion of the second blood component.

Aspect 248. The method of any of Aspects 231-247, wherein said further separating said at least a portion of the second blood component into first and second sub-components includes separating plasma from the at least a portion of the second blood component, conveying at least a portion of the plasma through the fluid flow circuit, and optically detecting a characteristic of the plasma.

Aspect 249. The method of Aspect 248, wherein said optically detecting a characteristic of the plasma includes determining whether the plasma is lipemic and/or hemolytic.

Aspect 250. The method of any of Aspects 231-249, wherein said further separating said at least a portion of the second blood component into said first and second sub-components includes simultaneously separating said at least a portion of the blood in the fluid flow circuit into said first and second blood components and further separating said at least a portion of the second blood component into said first and second sub-components.

Aspect 251. The method of any of Aspects 231-250, wherein said further separating said at least a portion of the second blood component separated from the mixture into said first and second sub-components includes simultaneously separating said at least a portion of the mixture into said first and second blood components and further separating said at least a portion of the second blood component separated from the mixture into said first and second sub-components.

Aspect 252. A method of controlling a blood separation procedure comprising: controlling a pump to convey blood through a fluid flow circuit; controlling a first separator to separate at least a portion of the blood in the fluid flow circuit into first and second blood components; conveying at least a portion of the first blood component into a container; controlling a second separator to further separate at least a portion of the second blood component into first and second sub-components; controlling a second pump to convey at least a portion of the first sub-component into the container to form a mixture with said at least a portion of the first blood component in the container; collecting at least a portion of the second sub-component; controlling the first separator to separate at least a portion of the mixture into said first and second blood components; controlling the second separator to further separate at least a portion of the second blood component separated from the mixture into said first and second sub-components; and collecting at least a portion of the second sub-component separated from said at least a portion of the second blood component separated from the mixture.

Aspect 253. The method of Aspect 252, wherein the first blood component comprises red blood cells, the second blood component comprises platelet-rich plasma, the first sub-component comprises plasma, and the second sub-component comprises platelet concentrate.

Aspect 254. The method of any of Aspects 252-253, wherein the first separator comprises a centrifugal separator and the second separator comprises a spinning membrane separator drive unit.

Aspect 255. The method of any of Aspects 252-254, further comprising providing a blood separation device including the first separator and the second separator.

Aspect 256. The method of any of Aspects 252-255, wherein said controlling the second separator to further separate at least a portion of the second blood component separated from the mixture into said first and second sub-components includes simultaneously conveying at least a portion of the first blood component separated from the mixture out of the fluid flow circuit.

Aspect 257. The method of any of Aspects 252-256, wherein said controlling the second separator to further separate at least a portion of the second blood component separated from the mixture into said first and second sub-components includes simultaneously collecting at least a portion of the first sub-component separated from the second component separated from the mixture.

Aspect 258. The method of any of Aspects 252-256, wherein said controlling the second separator to further separate at least a portion of the second blood component separated from the mixture into said first and second sub-components includes simultaneously conveying at least a portion of the first sub-component separated from the second component separated from the mixture out of the fluid flow circuit.

Aspect 259. The method of any of Aspects 252-258, wherein said controlling the first separator to separate at least a portion of the blood in the fluid flow circuit into first and second blood components includes flowing a combination of the blood and a recirculated portion of the second blood component separated from the blood into the first separator, and said controlling the first separator to separate at least a portion of the mixture into said first and second blood components includes flowing a combination of the mixture and a recirculated portion of the second blood component separated from the mixture into the first separator.

Aspect 260. The method of Aspect 259, wherein a hematocrit of the combination of the blood and the recirculated portion of the second blood component separated from the blood is the same as a hematocrit as the combination of the mixture and the recirculated portion of the second blood component separated from the mixture.

Aspect 261. The method of Aspect 259, wherein the volumetric flow rate of the combination of the blood and the recirculated portion of the second blood component separated from the blood into the first separator is the same as the volumetric flow rate of the combination of the mixture and the recirculated portion of the second blood component separated from the blood into the first separator.

Aspect 262. The method of Aspect 259, wherein a hematocrit of the combination of the blood and the recirculated portion of the second blood component separated from the blood is the same as a hematocrit as the combination of the mixture and the recirculated portion of the second blood component separated from the mixture, and the volumetric flow rate of the combination of the blood and the recirculated portion of the second blood component separated from the blood into the first separator is the same as the volumetric flow rate of the combination of the mixture and the recirculated portion of the second blood component separated from the blood into the first separator.

Aspect 263. The method of Aspect 262, wherein Qcent=Qin-wb+Qrecirc-wb=Qin-reproc+Qrecirc-reproc, Qrecirc-wb=((Qin-wb*Hdnr)/Hrecirc)−Qin-wb, Qin-reproc=(Qin-wb*Hdnr)/Hreproc, and Qrecirc-reproc=((Qin-reproc*Hreproc)/Hrecirc)−Qin-reproc, in which Qcent is the volumetric flow rate into the first separator, Qin-wb is the volumetric flow rate of the blood, Qrecirc-wb is the volumetric flow rate of the recirculated portion of the second blood component separated from the blood, Qin-reproc is the volumetric flow rate of the mixture, Qrecirc-reproc is the volumetric flow rate of the recirculated portion of the second blood component separated from the mixture, Hdnr is a hematocrit of the blood, Hrecirc is the hematocrit of the combination of the blood and the recirculated portion of the second blood component separated from the blood and the hematocrit of the combination of the mixture and the recirculated portion of the second blood component separated from the mixture, and Hreproc is a hematocrit of the mixture.

Aspect 264. The method of any of Aspects 252-263, further comprising optically detecting a characteristic of said at least a portion of the second blood component prior to said controlling the second separator to further separate at least a portion of the second blood component into first and second sub-components.

Aspect 265. The method of Aspect 264, wherein the concentration of platelets in said at least a portion of the second blood component is optically detected.

Aspect 266. The method of Aspect 265, wherein said collecting said at least a portion of the second sub-component includes conveying said at least a portion of the second sub-component through the fluid flow circuit at a volumetric flow rate based at least in part on the concentration of platelets in said at least a portion of the second blood component.

Aspect 267. The method of any of Aspects 252-266, wherein said controlling the second separator to further separate said at least a portion of the second blood component into first and second sub-components includes separating plasma from the at least a portion of the second blood component, conveying at least a portion of the plasma through the fluid flow circuit, and optically detecting a characteristic of the plasma.

Aspect 268. The method of Aspect 267, wherein said optically detecting a characteristic of the plasma includes determining whether the plasma is lipemic and/or hemolytic.

Aspect 269. The method of any of Aspects 252-268, wherein said controlling the second separator to further separate said at least a portion of the second blood component into said first and second sub-components includes simultaneously controlling the first separator to separate said at least a portion of the blood in the fluid flow circuit into said first and second blood components and controlling the second separator to further separate said at least a portion of the second blood component into said first and second sub-components.

Aspect 270. The method of any of Aspects 252-269, wherein said controlling the second separator to further separate said at least a portion of the second blood component separated from the mixture into said first and second sub-components includes simultaneously controlling the first separator to separate said at least a portion of the mixture into said first and second blood components and controlling the second separator to further separate said at least a portion of the second blood component separated from the mixture into said first and second sub-components.

Aspect 271. A centrifugal separation chamber comprising: a body including a low-g side wall portion and a high-g side wall portion extending circumferentially about a rotational axis in a spaced apart relationship to define therebetween a generally annular channel; a plurality of interior radial walls defining an inlet and at least one outlet associated with the channel; and a ramp defined by one of the side wall portions and extending across at least a portion of the channel to display an interface between separated fluid components within the channel, wherein at least a portion of the ramp and at least a portion of the other side wall portion angularly aligned with the ramp are formed of a light-transmissive material.

Aspect 272. The centrifugal separation chamber of Aspect 271, wherein said light-transmissive material is generally rigid.

Aspect 273. The centrifugal separation chamber of any of Aspects 271-272, wherein the entire body is formed of said light-transmissive material.

Aspect 274. The centrifugal separation chamber of any of Aspects 271-273, wherein said plurality of interior radial walls define the inlet and first and second outlets.

Aspect 275. The centrifugal separation chamber of Aspect 274, wherein the first outlet is associated with the low-g side wall portion and configured to remove at least a portion of a separated fluid component positioned at the low-g side wall portion from the channel, and the second outlet is associated with the high-g side wall portion and configured to remove at least a portion of a separated fluid component positioned at the high-g side wall portion from the channel.

Aspect 276. The centrifugal separation chamber of any of Aspects 274-275, wherein the channel extends from an upstream end to a downstream end, the inlet and the first outlet are positioned adjacent to the upstream end of the channel, and the second outlet is positioned adjacent to the downstream end of the channel.

Aspect 277. The centrifugal separation chamber of any of Aspects 274-276, wherein the ramp is positioned in the path of fluid and/or a fluid component moving from the inlet to the first outlet.

Aspect 278. The centrifugal separation chamber of any of Aspects 274-277, further comprising first and second end wall portions spaced apart in a direction parallel to the rotational axis, wherein the first and second end wall portions cooperate with the side wall portions to define the channel, the first and second outlets open into the channel adjacent to the second end wall portion, and the inlet opens into the channel adjacent to the first end wall portion.

Aspect 279. The centrifugal separation chamber of any of Aspects 274-277, further comprising first and second end wall portions spaced apart in a direction parallel to the rotational axis, wherein the first and second end wall portions cooperate with the side wall portions to define the channel, and the inlet and the first and second outlets open into the channel adjacent to the second end wall portion.

Aspect 280. The centrifugal separation chamber of any of Aspects 274-277, further comprising first and second end wall portions spaced apart in a direction parallel to the rotational axis, wherein the first and second end wall portions cooperate with the side wall portions to define the channel, the first and second outlets open into the channel adjacent to the second end wall portion, and the inlet opens into the channel at an intermediate axial location spaced from the first and second end wall portions.

Aspect 281. The centrifugal separation chamber of any of Aspects 271-280, further comprising a reflector associated with the low-g side wall portion and configured to receive light passing through the ramp along an initial path and direct the light out of the centrifugal separation chamber at an angle to the initial path.

Aspect 282. The centrifugal separation chamber of Aspect 281, wherein the reflector is configured to direct the light out of the centrifugal separation chamber at an approximately 90° angle to the initial path.

Aspect 283. The centrifugal separation chamber of any of Aspects 281-282, wherein the reflector is separately formed from the body.

Aspect 284. The centrifugal separation chamber of any of Aspects 281-282, wherein the reflector is integrally formed with the body.

Aspect 285. The centrifugal separation chamber of any of Aspects 281-284, wherein the reflector is configured to diffuse the light directed out of the centrifugal separation chamber.

Aspect 286. The centrifugal separation chamber of any of Aspects 281-285, wherein the reflector comprises a prismatic reflector.

Aspect 287. A prismatic reflector for incorporation into a centrifugal separation chamber, comprising: inner and outer walls; and first and second end walls, wherein the prismatic reflector is formed of a light-transmissive material, the inner wall is configured to receive light traveling along an initial path and transmit the light to the first end wall, the first end wall is configured to receive the light transmitted through the inner wall and direct the light toward the second end wall in a direction that is angled with respect to the initial path, and the second end wall is configured to receive the light from the first end wall and transmit the light out of the prismatic reflector.

Aspect 288. The prismatic reflector of Aspect 287, wherein the first end wall is angled approximately 45° with respect to the second end wall.

Aspect 289. The prismatic reflector of any of Aspects 287-288, wherein first end wall and the inner and outer walls are configured to transmit the light from the first end wall to the second end wall by total internal reflection.

Aspect 290. The prismatic reflector of any of Aspects 287-289, wherein at least a portion of the second end wall is roughened to diffuse the light transmitted out of the prismatic reflector.

Aspect 291. An interface monitoring system for detecting the location of an interface between separated fluid components within a channel of a centrifugal separation chamber having a rotational axis, the interface monitoring system comprising: a light source configured to transmit a light along an initial path toward the rotational axis, into the centrifugal separation chamber, and through the channel of the centrifugal separation chamber; and a light detector configured to receive at least a portion of the light as the light exits the centrifugal separation chamber and generate a signal indicative of the location of the interface between separated fluid components within the channel of the centrifugal separation chamber, wherein the light detector is oriented to receive light traveling in a direction generally perpendicular to the initial path of the light.

Aspect 292. The interface monitoring system of Aspect 291, wherein the light detector is oriented to receive light traveling in a direction generally parallel to the rotational axis.

Aspect 293. The interface monitoring system of any of Aspects 291-292, wherein the light source comprises a laser.

Aspect 294. The interface monitoring system of any of Aspects 291-293, wherein the light source is configured to emit a red light.

Aspect 295. The interface monitoring system of any of Aspects 291-294, wherein the light source includes a lens configured to focus the light at a location within the centrifugal separation chamber.

Aspect 296. The interface monitoring system of any of Aspects 291-295, wherein the light detector is oriented to receive light that has passed through the channel only once.

Aspect 297. The interface monitoring system of any of Aspects 291-296, further comprising a controller configured and/or programmed to determine the location of the interface between the separated fluid components within the channel of the centrifugal separation chamber by comparing an actual pulse width of the signal to a target pulse width.

Aspect 298. A blood separation system, comprising: a blood separation device including a centrifugal separator and an interface monitoring system; and a fluid flow circuit including a centrifugal separation chamber comprising a channel defined between a low-g side wall portion and a high-g side wall portion and configured to be mounted to the centrifugal separator, wherein the interface monitoring system includes a light source configured to transmit a light along an initial path toward the rotational axis, into the centrifugal separation chamber, and through the channel of the centrifugal separation chamber, and a light detector configured to receive at least a portion of the light as the light exits the centrifugal separation chamber, wherein the light detector is oriented to receive light traveling in a direction generally perpendicular to the initial path of the light.

Aspect 299. The blood separation system of Aspect 298, wherein at least a portion of the side wall portions are formed of a generally rigid, light-transmissive material, and the light source is configured to transmit the light through the side wall portions.

Aspect 300. The blood separation system of Aspect 299, wherein the centrifugal separation chamber includes a ramp defined by one of the side wall portions and extending across at least a portion of the channel to display an interface between separated blood components within the channel, and the light source is configured to transmit the light through the ramp.

Aspect 301. The blood separation system of Aspect 300, wherein the centrifugal separation chamber includes a reflector associated with the low-g side wall portion and configured to receive light passing through the ramp and direct the light toward the light detector.

Aspect 302. The blood separation system of any of Aspects 298-301, wherein the centrifugal separation chamber includes a rotational axis, and the light detector is oriented to receive light traveling in a direction generally parallel to the rotational axis.

Aspect 303. The blood separation system of any of Aspects 298-302, wherein the light source comprises a laser.

Aspect 304. The blood separation system of any of Aspects 298-303, wherein the light source is configured to emit a red light.

Aspect 305. The blood separation system of any of Aspects 298-304, wherein the light source includes a lens configured to focus the light at a location within the centrifugal separation chamber.

Aspect 306. The blood separation system of any of Aspects 298-305, wherein the light detector is oriented to receive light that has passed through the channel only once.

Aspect 307. The blood separation system of any of Aspects 298-306, wherein the blood separation device includes a centrifuge compartment in which at least a portion of the centrifugal separator is positioned, and the light source and the light detector are mounted to stationary surfaces of the centrifuge compartment.

Aspect 308. The blood separation system of any of Aspects 298-307, wherein the light detector is configured to generate a signal indicative of the location of the interface between separated blood components within the channel of the centrifugal separation chamber, and the blood separation device further includes a controller configured and/or programmed to determine the location of the interface between the separated fluid components within the channel of the centrifugal separation chamber by comparing an actual pulse width of the signal to a target pulse width.

Aspect 309. A method of detecting the location of an interface between separated fluid components within a channel of a centrifugal separation chamber having a rotational axis, the method comprising: separating fluid in a channel of a centrifugal separation chamber into at least two fluid components; directing a light along an initial path through the channel so as to intersect at least one of the fluid components; directing the light exiting the channel out of the centrifugal separation chamber in a direction generally perpendicular to the initial path of the light; detecting at least a portion of the light exiting the centrifugal separation chamber; and generating a signal indicative of the location of an interface between the separated fluid components within the channel.

Aspect 310. The method of Aspect 309, wherein said directing the light along the initial path through the channel so as to intersect at least one of the fluid components includes directing the light through a ramp associated with the channel and configured to display the interface between the separated fluid components.

Aspect 311. The method of any of Aspects 309-310, wherein said directing the light exiting the channel out of the centrifugal separation chamber in a direction generally perpendicular to the initial path of the light includes directing the light through a prismatic reflector associated with the channel.

Aspect 312. The method of any of Aspects 309-311, wherein said directing the light exiting the channel out of the centrifugal separation chamber in a direction generally perpendicular to the initial path of the light includes diffusing the light exiting the centrifugal separation chamber.

Aspect 313. The method of any of Aspects 309-312, wherein said directing the light exiting the channel out of the centrifugal separation chamber in a direction generally perpendicular to the initial path of the light includes directing the light exiting the channel out of the centrifugal separation chamber in a direction generally parallel to the rotational axis.

Aspect 314. The method of any of Aspects 309-313, wherein said directing the light along an initial path through the channel so as to intersect at least one of the fluid components includes directing light from a laser through the channel.

Aspect 315. The method of any of Aspects 309-314, wherein said directing the light along an initial path through the channel so as to intersect at least one of the fluid components includes directing a red light through the channel.

Aspect 316. The method of any of Aspects 309-315, wherein said directing the light along an initial path through the channel so as to intersect at least one of the fluid components includes focusing the light at a location within the centrifugal separation chamber.

Aspect 317. The method of any of Aspects 309-316, wherein said detecting at least a portion of the light exiting the centrifugal separation chamber includes detecting light that has passed through the channel only once.

Aspect 318. The method of any of Aspects 309-317, wherein said directing the light along the initial path through the channel so as to intersect at least one of the fluid components includes emitting the light from a stationary location, and said detecting at least a portion of the light exiting the centrifugal separation chamber includes detecting said at least a portion of the light at a stationary location.

Aspect 319. The method of any of Aspects 309-318, further comprising determining the location of the interface between the separated fluid components within the channel by comparing an actual pulse width of the signal to a target pulse width.

Aspect 320. A method of controlling a fluid separation procedure comprising: controlling a pump to convey fluid into a channel of a centrifugal separation chamber; controlling a centrifugal separator to rotate the centrifugal separation chamber about a rotational axis to separate the fluid in the channel of the centrifugal separation chamber into at least two fluid components; controlling a light source to direct a light along an initial path through the channel so as to intersect at least one of the fluid components and direct the light exiting the channel out of the centrifugal separation chamber in a direction generally perpendicular to the initial path of the light; controlling a light detector to detect at least a portion of the light exiting the centrifugal separation chamber; and controlling the light detector to generate a signal indicative of the location of an interface between the separated fluid components within the channel.

Aspect 321. The method of Aspect 320, wherein said controlling the light source to direct the light along the initial path through the channel so as to intersect at least one of the fluid components includes directing the light through a ramp associated with the channel and configured to display the interface between the separated fluid components.

Aspect 322. The method of any of Aspects 320-321, wherein said controlling the light source to direct the light exiting the channel out of the centrifugal separation chamber in a direction generally perpendicular to the initial path of the light includes directing the light through a prismatic reflector associated with the channel.

Aspect 323. The method of any of Aspects 320-322, wherein said controlling the light source to direct the light exiting the channel out of the centrifugal separation chamber in a direction generally perpendicular to the initial path of the light includes diffusing the light exiting the centrifugal separation chamber.

Aspect 324. The method of any of Aspects 320-323, wherein said controlling the light source to direct the light exiting the channel out of the centrifugal separation chamber in a direction generally perpendicular to the initial path of the light includes directing the light exiting the channel out of the centrifugal separation chamber in a direction generally parallel to the rotational axis.

Aspect 325. The method of any of Aspects 320-324, wherein said controlling the light source to direct the light along an initial path through the channel so as to intersect at least one of the fluid components includes directing light from a laser through the channel.

Aspect 326. The method of any of Aspects 320-325, wherein said controlling the light source to direct the light along an initial path through the channel so as to intersect at least one of the fluid components includes directing a red light through the channel.

Aspect 327. The method of any of Aspects 320-326, wherein said controlling the light source to direct the light along an initial path through the channel so as to intersect at least one of the fluid components includes focusing the light at a location within the centrifugal separation chamber.

Aspect 328. The method of any of Aspects 320-327, wherein said controlling the light detector to detect at least a portion of the light exiting the centrifugal separation chamber includes detecting light that has passed through the channel only once.

Aspect 329. The method of any of Aspects 320-328, wherein said controlling the light source to direct the light along the initial path through the channel so as to intersect at least one of the fluid components includes emitting the light from a stationary location, and said controlling the light detector to detect at least a portion of the light exiting the centrifugal separation chamber includes detecting said at least a portion of the light at a stationary location.

Aspect 330. The method of any of Aspects 320-329, further determining the location of the interface between the separated fluid components within the channel by comparing an actual pulse width of the signal to a target pulse width.

It will be understood that the embodiments described above are illustrative of some of the applications of the principles of the present subject matter.

Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood separation device comprising:
a centrifugal separator;
a spinning membrane separator drive unit; and
a controller configured and/or programmed to control the operation of the centrifugal separator and the spinning membrane separator drive unit, wherein the centrifugal separator and the spinning membrane separator drive unit are incorporated into a case.

2. The blood separation device of claim 1, further comprising first and second pumps, wherein the controller is configured and/or programmed to control the centrifugal separator to separate blood into two or more blood components,
control the first pump to recirculate a portion of one of the blood components into the centrifugal separator with blood entering the centrifugal separator, and
control the second pump to convey another portion of said one of the blood components into the spinning membrane separator drive unit to separate said another portion of said one of the blood components into two or more sub-components.

3. The blood separation device of claim 1, further comprising an interface monitoring system associated with the centrifugal separator and including
a light source configured to emit light through separated blood components within the centrifugal separator, and
a light detector configured to receive at least a portion of the light emitted by the light source and cooperate with the controller to determine the location of an interface between two separated blood components within the centrifugal separator, wherein the light detector is positioned and oriented to receive light traveling in a direction that is generally perpendicular to the direction of the light emitted by the light source.

4. The blood separation device of claim 1, wherein the controller is configured and/or programmed to control only one of the centrifugal separator and the spinning membrane separator drive unit or both of the centrifugal separator and the spinning membrane separator drive unit to separate blood into two or more blood components or to separate a blood component into two or more sub-components.

5. A fluid flow circuit for use in combination with a blood separation device, comprising:
a centrifugal separation chamber configured for receipt by a centrifugal separator of the blood separation device; and
a spinning membrane separator in fluid communication with the centrifugal separation chamber and configured for receipt by a spinning membrane separator drive unit of the blood separation device.

6. The fluid flow circuit of claim 5, further comprising a reprocess container configured to receive at least a portion of at least one blood component separated from blood by the centrifugal separation chamber and/or the spinning membrane separator and to supply said at least a portion of said at least one blood component to the centrifugal separation chamber for separation of said at least a portion of said at least one blood component into two or more blood components.

7. The fluid flow circuit of claim 5, wherein the centrifugal separation chamber comprises
a body including a low-g side wall portion and a high-g side wall portion extending circumferentially about a rotational axis in a spaced apart relationship to define therebetween a generally annular channel;
a plurality of interior radial walls defining an inlet and at least one outlet associated with the channel; and
a ramp defined by one of the side wall portions and extending across at least a portion of the channel to display an interface between separated fluid components within the channel, wherein at least a portion of the ramp and at least a portion of the other side wall portion angularly aligned with the ramp are formed of a light-transmissive material.

8. The fluid flow circuit of claim 7, wherein said light-transmissive material is generally rigid.

9. The fluid flow circuit of claim 7, further comprising a reflector associated with the low-g side wall portion and configured to receive light passing through the ramp along an initial path and direct the light out of the centrifugal separation chamber at an angle to the initial path.

10. The fluid flow circuit of claim 9, wherein the reflector is configured to direct the light out of the centrifugal separation chamber at an approximately 90° angle to the initial path.

11. A blood separation method comprising:
conveying blood through a fluid flow circuit;
separating at least a portion of the blood in the fluid flow circuit into two or more blood components using a centrifugal separator of a blood separation device; and
further separating at least a portion of one of said separated blood components into two or more sub-components using a spinning membrane separator drive unit of the blood separation device.

12. The method of claim 11, wherein
said separating at least a portion of the blood in the fluid flow circuit into two or more blood components using the centrifugal separator includes separating the blood into red blood cells and platelet-rich plasma, and
said further separating at least a portion of one of said separated blood components into two or more sub-components using the spinning membrane separator drive unit includes separating the platelet-rich plasma into plasma and platelet concentrate.

13. The method of claim 11, wherein said separating at least a portion of the blood in the fluid flow circuit into two or more blood components using the centrifugal separator includes conveying a combination of the blood and a recirculated portion of one of said separated blood components into the centrifugal separator.

14. The method of claim 11, wherein
said separating at least a portion of the blood in the fluid flow circuit into two or more blood components using the centrifugal separator includes separating and collecting red blood cells from said at least a portion of the blood using the centrifugal separator, and
said further separating at least a portion of one of said separated blood components into two or more sub-components using the spinning membrane separator drive unit includes separating and collecting plasma and platelet concentrate from platelet-rich plasma using the spinning membrane separator drive unit.

15. The method of claim 11, further comprising
conveying an additive solution through a leukocyte removal filter,
mixing separated red blood cells and the additive solution, and
conveying the mixture of the red blood cells and the additive solution through the leukocyte removal filter.

16. The method of claim 11, wherein
said separating at least a portion of the blood in the fluid flow circuit into two or more blood components using the centrifugal separator includes separating red blood cells from said at least a portion of the blood using the centrifugal separator and conveying at least a portion of the separated red blood cells into a container, and
said further separating at least a portion of one of said separated blood components into two or more sub-components using the spinning membrane separator drive unit includes
separating plasma and platelet concentrate from platelet-rich plasma using the spinning membrane separator drive unit,
collecting at least a portion of the separated platelet concentrate, and
conveying at least a portion of the separated plasma into said container with the separated red blood cells.

17. The method of claim 11, wherein
said separating at least a portion of the blood in the fluid flow circuit into two or more blood components using the centrifugal separator includes simultaneously conveying separated red blood cells out of the fluid flow circuit and to a recipient; and
said further separating at least a portion of one of said separated blood components into two or more sub-components using the spinning membrane separator drive unit includes simultaneously collecting platelet concentrate and conveying plasma out of the fluid flow circuit and to the recipient.

18. The method of claim 11, wherein
said separating at least a portion of the blood in the fluid flow circuit into two or more blood components using the centrifugal separator includes simultaneously conveying separated red blood cells out of the fluid flow circuit and to a recipient; and
said further separating at least a portion of one of said separated blood components into two or more sub-components using the spinning membrane separator drive unit includes simultaneously collecting platelet concentrate and plasma.

19. A blood separation method comprising:
conveying blood through a fluid flow circuit;
separating at least a portion of the blood in the fluid flow circuit into two or more blood components using a centrifugal separator;
conveying at least a portion of one of said separated blood components from the centrifugal separator to a spinning membrane separator drive unit;
optically detecting the concentration of platelets in said at least a portion of one of said separated blood components;
further separating said at least a portion of one of said separated blood components into two or more sub-components using the spinning membrane separator drive unit; and
conveying platelet concentrate out of the spinning membrane separator drive unit at a volumetric flow rate based at least in part on the concentration of platelets in said at least a portion of one of said separated blood components.

20. A blood separation method comprising:
conveying blood through a fluid flow circuit;
separating at least a portion of the blood in the fluid flow circuit into two or more blood components using a centrifugal separator; and
further separating said at least a portion of one of said separated blood components into two or more sub-components using the spinning membrane separator drive unit, wherein said further separating said at least a portion of one of said separated blood components into two or more sub-components using the spinning membrane separator drive unit includes simultaneously operating the centrifugal separator to separate said at least a portion of the blood in the fluid flow circuit into two or more blood components and operating the spinning membrane separator drive unit to further separate said at least a portion of one of said separated blood components into two or more sub-components.

* * * * *